(12) United States Patent
Mendlein et al.

(10) Patent No.: US 11,767,520 B2
(45) Date of Patent: Sep. 26, 2023

(54) COMPOSITIONS AND METHODS FOR TREATING LUNG INFLAMMATION

(71) Applicant: aTyr Pharma, Inc., San Diego, CA (US)

(72) Inventors: John D. Mendlein, Encinitas, CA (US); Kathleen Ogilvie, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 659 days.

(21) Appl. No.: 16/499,979

(22) PCT Filed: Apr. 19, 2018

(86) PCT No.: PCT/US2018/028417
§ 371 (c)(1),
(2) Date: Oct. 1, 2019

(87) PCT Pub. No.: WO2018/195338
PCT Pub. Date: Oct. 25, 2018

(65) Prior Publication Data
US 2020/0377874 A1 Dec. 3, 2020

Related U.S. Application Data

(60) Provisional application No. 62/487,812, filed on Apr. 20, 2017.

(51) Int. Cl.
| | | |
|---|---|---|
| A61K 39/385 | (2006.01) |
| C07K 16/46 | (2006.01) |
| C07K 19/00 | (2006.01) |
| C12N 9/00 | (2006.01) |
| A61P 11/00 | (2006.01) |
| A61P 29/00 | (2006.01) |
| A61K 9/48 | (2006.01) |
| A61K 9/51 | (2006.01) |
| A61K 31/4418 | (2006.01) |
| A61K 31/496 | (2006.01) |
| A61K 38/53 | (2006.01) |
| A61M 5/178 | (2006.01) |

(52) U.S. Cl.
CPC ............... *C12N 9/93* (2013.01); *A61K 9/48* (2013.01); *A61K 9/5123* (2013.01); *A61K 31/4418* (2013.01); *A61K 31/496* (2013.01); *A61K 38/53* (2013.01); *A61P 11/00* (2018.01); *A61P 29/00* (2018.01); *C12Y 601/01021* (2013.01); *A61M 5/178* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,155,214 A | 10/1992 | Baird et al. |
| 5,370,995 A | 12/1994 | Hennecke et al. |
| 5,484,703 A | 1/1996 | Raben et al. |
| 5,556,645 A | 9/1996 | Bockman et al. |
| 5,641,867 A | 6/1997 | Stern et al. |
| 5,663,066 A | 9/1997 | Raben et al. |
| 5,665,066 A | 9/1997 | Fisher |
| 5,716,632 A * | 2/1998 | Margolin ............... A61P 27/06 |
| | | | 514/879 |
| 5,750,387 A | 5/1998 | Hodgson et al. |
| 5,753,480 A | 5/1998 | Lawlor |
| 5,756,327 A | 5/1998 | Sassanfar et al. |
| 5,759,833 A | 6/1998 | Shiba et al. |
| 5,776,749 A | 7/1998 | Hodgson et al. |
| 5,795,757 A | 8/1998 | Hodgson et al. |
| 5,798,240 A | 8/1998 | Martinis et al. |
| 5,801,013 A | 9/1998 | Tao et al. |
| 5,817,528 A | 10/1998 | Bohm et al. |
| 5,866,390 A | 2/1999 | Lawlor |
| 5,885,815 A | 3/1999 | Sassanfar et al. |
| 5,928,920 A | 7/1999 | Hodgson et al. |
| 5,939,298 A | 8/1999 | Brown et al. |
| 5,977,079 A | 11/1999 | Good et al. |
| 5,981,606 A | 11/1999 | Martin |
| 6,013,483 A | 1/2000 | Coleman et al. |
| 6,225,060 B1 | 5/2001 | Clark et al. |
| 6,228,837 B1 | 5/2001 | Stern et al. |

(Continued)

FOREIGN PATENT DOCUMENTS

| | | |
|---|---|---|
| CA | 2531146 | 3/2005 |
| CN | 1314486 A | 9/2001 |

(Continued)

OTHER PUBLICATIONS

Delgado et al. Analysis and review of patients with idiopathic pulmonary fibrosis treated with pirfenidone. International Journal of Clinical Pharmacy, (Feb. 2017) vol. 39, No. 1, pp. 333-334. Abstract No. PT034.Meeting Info: 45th ESCP-NSF Int. Sym. on Clin. Pharm Oct. 7, 2016 (Year: 2016).*

Tokuriki et al. Stability effects of mutations and protein evolvability, Current Opinion in Structural Biology, 19:596-604, (2009). (Year: 2009).*

Bhattacharya et al. Impact of genetic variation on three dimensional structure and function of proteins; PLOS One 12(3): e0171355, pp. 1-22, (Mar. 2017). (Year: 2017).*

(Continued)

*Primary Examiner* — Elizabeth C. Kemmerer
*Assistant Examiner* — Regina M DeBerry
(74) *Attorney, Agent, or Firm* — COOLEY LLP

(57) ABSTRACT

Provided are therapies, including combination therapies, for the treatment of lung inflammation, including interstitial lung diseases (ILDs), which include the use of at least one histidyl-tRNA synthetase (HRS) polypeptide or an expressible polynucleotide that encodes the HRS polypeptide, alone or in combination with at least one immunomodulatory agent.

12 Claims, 6 Drawing Sheets

Specification includes a Sequence Listing.

(56) References Cited

U.S. PATENT DOCUMENTS

| | | |
|---|---|---|
| 6,255,090 B1 | 7/2001 | Famodu et al. |
| 6,265,188 B1 | 7/2001 | Brown et al. |
| 6,428,960 B1 | 8/2002 | Clark et al. |
| 6,548,060 B1 | 4/2003 | Kim |
| 6,696,619 B1 | 2/2004 | Famodu et al. |
| 6,712,978 B2 | 3/2004 | Leinenbach et al. |
| 6,723,318 B1 | 4/2004 | Sandberg et al. |
| 6,743,619 B1 | 6/2004 | Tang et al. |
| 6,800,286 B1 | 10/2004 | Olwin et al. |
| 6,812,339 B1 | 11/2004 | Venter et al. |
| 6,852,512 B2 | 2/2005 | Choi et al. |
| 6,864,226 B1 | 3/2005 | Coleman et al. |
| 6,875,749 B2 | 4/2005 | Schwarz et al. |
| 6,903,189 B2 | 6/2005 | Schimmel et al. |
| 6,916,648 B2 | 7/2005 | Goddard et al. |
| 7,037,505 B2 | 5/2006 | Kim et al. |
| 7,045,301 B2 | 5/2006 | Coleman et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,282,208 B2 | 10/2007 | Kim |
| 7,413,885 B2 | 8/2008 | Schimmel et al. |
| 7,459,529 B2 | 12/2008 | Kim |
| 7,476,651 B2 | 1/2009 | Schimmel et al. |
| 7,482,326 B2 | 1/2009 | Coleman et al. |
| 7,521,215 B2 | 4/2009 | Schimmel et al. |
| 7,528,106 B2 | 5/2009 | Friedlander et al. |
| 7,572,452 B2 | 8/2009 | Kim |
| 7,745,391 B2 | 6/2010 | Mintz et al. |
| 7,842,467 B1 | 11/2010 | Heidbrink et al. |
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,014,957 B2 | 9/2011 | Radich et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,182,686 B2 | 5/2012 | Witthaus et al. |
| 8,318,163 B2 | 11/2012 | Appleton et al. |
| 8,404,242 B2 | 3/2013 | Zhou et al. |
| 8,404,471 B2 | 3/2013 | Greene et al. |
| 8,466,264 B2 | 6/2013 | Appleton et al. |
| 8,481,296 B2 | 7/2013 | Yang |
| 8,648,173 B2 | 2/2014 | Wu et al. |
| 8,722,043 B2 | 5/2014 | Borg et al. |
| 8,747,840 B2 | 6/2014 | Greene et al. |
| 8,753,638 B2 | 6/2014 | Zhou et al. |
| 8,828,395 B2 | 9/2014 | Watkins et al. |
| 8,835,387 B2 | 9/2014 | Chiang et al. |
| 8,920,805 B2 | 12/2014 | Wu et al. |
| 8,945,541 B2 | 2/2015 | Greene et al. |
| 8,946,157 B2 | 2/2015 | Greene et al. |
| 8,961,960 B2 | 2/2015 | Chiang et al. |
| 8,961,961 B2 | 2/2015 | Greene et al. |
| 8,962,560 B2 | 2/2015 | Greene et al. |
| 8,969,301 B2 | 3/2015 | Greene et al. |
| 8,980,253 B2 | 3/2015 | Greene et al. |
| 8,981,045 B2 | 3/2015 | Greene et al. |
| 8,986,680 B2 | 3/2015 | Greene et al. |
| 8,986,681 B2 | 3/2015 | Greene et al. |
| 8,993,723 B2 | 3/2015 | Greene et al. |
| 8,999,321 B2 | 4/2015 | Greene et al. |
| 9,029,506 B2 | 5/2015 | Greene et al. |
| 9,034,320 B2 | 5/2015 | Greene et al. |
| 9,034,321 B2 | 5/2015 | Greene et al. |
| 9,034,598 B2 | 5/2015 | Greene et al. |
| 9,062,301 B2 | 6/2015 | Greene et al. |
| 9,062,302 B2 | 6/2015 | Greene et al. |
| 9,068,177 B2 | 6/2015 | Greene et al. |
| 9,127,268 B2 | 9/2015 | Watkins et al. |
| 9,157,076 B2 | 10/2015 | Greene et al. |
| 9,273,302 B2 | 3/2016 | Chiang et al. |
| 9,296,803 B2 | 3/2016 | Kozbar |
| 9,315,794 B2 | 4/2016 | Greene et al. |
| 9,320,782 B2 | 4/2016 | Greene et al. |
| 9,328,340 B2 | 5/2016 | Watkins et al. |
| 9,347,053 B2 | 5/2016 | Greene et al. |
| 9,399,770 B2 | 7/2016 | Greene et al. |
| 9,404,104 B2 | 8/2016 | Greene et al. |
| 9,422,539 B2 | 8/2016 | Greene et al. |
| 9,428,743 B2 | 8/2016 | Greene et al. |
| 9,453,214 B2 | 9/2016 | Greene |
| 9,499,810 B2 | 11/2016 | Belani et al. |
| 9,528,103 B2 | 12/2016 | Greene et al. |
| 9,540,628 B2 | 1/2017 | Watkins et al. |
| 9,540,629 B2 | 1/2017 | Greene et al. |
| 9,556,425 B2 | 1/2017 | Greene et al. |
| 9,574,187 B2 | 2/2017 | Greene et al. |
| 9,585,946 B2 | 3/2017 | Greene et al. |
| 9,587,235 B2 | 3/2017 | Buechler et al. |
| 9,593,322 B2 | 3/2017 | Greene et al. |
| 9,593,323 B2 | 3/2017 | Greene et al. |
| 9,605,265 B2 | 3/2017 | Zhou et al. |
| 9,623,093 B2 | 4/2017 | Greene et al. |
| 9,637,730 B2 | 5/2017 | Greene et al. |
| 9,687,533 B2 | 6/2017 | Greene et al. |
| 9,943,577 B2 | 4/2018 | Watkins et al. |
| 10,017,582 B2 | 7/2018 | Zhou et al. |
| 10,093,915 B2 | 10/2018 | Wu et al. |
| 10,196,628 B2 | 2/2019 | Greene et al. |
| 10,472,618 B2 | 11/2019 | Wu et al. |
| 10,526,419 B2 | 1/2020 | Zhou et al. |
| 10,669,533 B2 | 6/2020 | Greene et al. |
| 10,711,260 B2 | 7/2020 | Wu et al. |
| 10,941,214 B2 | 3/2021 | Zhou et al. |
| 11,072,787 B2 * | 7/2021 | Wu ............... C12Y 601/01021 |
| 11,078,299 B2 | 8/2021 | Zhou et al. |
| 2002/0128187 A1 | 9/2002 | Tang et al. |
| 2002/0160957 A1 | 10/2002 | Stern et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0134301 A1 | 7/2003 | Brooksbank et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0119175 A1 | 6/2005 | Kim |
| 2005/0136513 A1 | 6/2005 | Zhang |
| 2005/0181375 A1 | 8/2005 | Aziz et al. |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0134663 A1 | 6/2006 | Harkin et al. |
| 2006/0160175 A1 | 7/2006 | Anderson et al. |
| 2006/0204508 A1 | 9/2006 | Champion et al. |
| 2006/0228715 A1 | 10/2006 | Shiffman et al. |
| 2006/0248617 A1 | 11/2006 | Imanaka et al. |
| 2006/0275794 A1 | 12/2006 | Carrino et al. |
| 2007/0037165 A1 | 2/2007 | Venter et al. |
| 2007/0042392 A1 | 2/2007 | Tang et al. |
| 2007/0048322 A1 | 3/2007 | Schimmel et al. |
| 2007/0054278 A1 | 3/2007 | Cargill |
| 2007/0061916 A1 | 3/2007 | Kovalic et al. |
| 2007/0072175 A1 | 3/2007 | Cooper et al. |
| 2007/0083334 A1 | 4/2007 | Mintz et al. |
| 2007/0093440 A1 | 4/2007 | Champion et al. |
| 2007/0111238 A1 | 5/2007 | Jamieson et al. |

(56) References Cited

U.S. PATENT DOCUMENTS

| | | |
|---|---|---|
| 2007/0154931 A1 | 7/2007 | Radich et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0202539 A1 | 8/2009 | You et al. |
| 2009/0221437 A1 | 9/2009 | Harkin et al. |
| 2009/0221794 A1 | 9/2009 | Kim et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0264453 A1 | 10/2009 | Shiffman et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0041608 A1 | 2/2010 | Kim |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0130904 A1 | 5/2010 | Kirber |
| 2010/0138941 A1 | 6/2010 | Kim et al. |
| 2010/0167997 A1 | 7/2010 | Kim |
| 2010/0172921 A1 | 7/2010 | Wu et al. |
| 2010/0209445 A1 | 8/2010 | Jahns et al. |
| 2010/0297149 A1 | 11/2010 | Zhou et al. |
| 2010/0310576 A1 | 12/2010 | Adams et al. |
| 2011/0086058 A1 | 4/2011 | Jiang et al. |
| 2011/0091377 A1 | 4/2011 | Alani et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0129486 A1* | 6/2011 | Meiron ............. C12N 5/0605 424/93.7 |
| 2011/0136119 A1 | 6/2011 | Kim et al. |
| 2011/0150885 A1 | 6/2011 | Watkins et al. |
| 2011/0183924 A1 | 7/2011 | Mintz et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0027779 A1 | 2/2012 | Borg et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0165484 A1* | 6/2013 | Radhakrishnan ......... A61P 9/10 514/345 |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0141994 A1 | 5/2014 | Wu et al. |
| 2014/0255375 A1 | 9/2014 | Belani et al. |
| 2014/0255378 A1 | 9/2014 | Watkins et al. |
| 2014/0302075 A1 | 10/2014 | Buechler et al. |
| 2014/0335087 A1 | 11/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0064188 A1 | 3/2015 | Greene |
| 2015/0093799 A1 | 4/2015 | Chiang et al. |
| 2015/0140072 A1 | 5/2015 | Watkins et al. |
| 2015/0159148 A1 | 6/2015 | Buechler et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290305 A1 | 10/2015 | Greene et al. |
| 2015/0344866 A1 | 12/2015 | Greene et al. |
| 2015/0353914 A1 | 12/2015 | Greene et al. |
| 2015/0361412 A1 | 12/2015 | Greene et al. |
| 2015/0361413 A1 | 12/2015 | Greene et al. |
| 2016/0175458 A1 | 6/2016 | Alvarez et al. |
| 2016/0369259 A1 | 12/2016 | Chiang et al. |
| 2017/0100456 A1 | 4/2017 | Briscoe et al. |
| 2017/0114148 A1 | 4/2017 | Zhou et al. |
| 2017/0202933 A1 | 7/2017 | Watkins et al. |
| 2017/0267990 A1 | 9/2017 | Wu et al. |
| 2017/0321206 A1 | 11/2017 | Greene et al. |
| 2018/0282402 A1 | 10/2018 | Adams et al. |
| 2019/0031775 A1 | 1/2019 | Zhou et al. |
| 2019/0062720 A1 | 2/2019 | Wu et al. |
| 2019/0264190 A1 | 8/2019 | Greene et al. |
| 2019/0309076 A1 | 10/2019 | Burman et al. |
| 2020/0085925 A1 | 3/2020 | Burkart et al. |
| 2020/0149028 A1 | 5/2020 | Wu et al. |
| 2020/0216564 A1 | 7/2020 | Zhou et al. |
| 2020/0231704 A1 | 7/2020 | Zhou et al. |
| 2020/0283751 A1 | 9/2020 | Wu et al. |
| 2020/0377874 A1 | 12/2020 | Mendlein et al. |
| 2022/0098327 A1 | 3/2022 | Zhou et al. |
| 2022/0098568 A1 | 3/2022 | Wu et al. |

FOREIGN PATENT DOCUMENTS

| | | |
|---|---|---|
| CN | 1331293 | 1/2002 |
| CN | 1341725 | 3/2002 |
| CN | 1341727 | 3/2002 |
| CN | 1352242 | 6/2002 |
| CN | 1352252 | 6/2002 |
| CN | 1519315 A | 8/2004 |
| CN | 101267810 A | 9/2008 |
| CN | 102821784 A | 12/2012 |
| CN | 104334196 A | 2/2015 |
| CN | 105378075 A | 3/2016 |
| EP | 0313378 | 10/1988 |
| EP | 0307247 | 3/1989 |
| EP | 0893494 | 1/1999 |
| EP | 0893496 | 1/1999 |
| EP | 0897004 | 2/1999 |
| EP | 0575484 | 9/2000 |
| EP | 1275720 | 1/2003 |
| EP | 1300468 | 4/2003 |
| EP | 1384486 | 1/2004 |
| EP | 1748063 | 1/2007 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| JP | 2013-513390 | 4/2013 |
| JP | 55-90540 | 9/2014 |

(56) References Cited

FOREIGN PATENT DOCUMENTS

| | | |
|---|---|---|
| KR | 10-2002-0092596 | 12/2002 |
| KR | 101067816 | 9/2011 |
| KR | 2015/0077770 A | 7/2015 |
| WO | WO 1991/008291 | 6/1991 |
| WO | WO 1996/039506 | 12/1996 |
| WO | WO 1997/025426 | 7/1997 |
| WO | WO 1997/026351 | 7/1997 |
| WO | WO 1997/039017 | 10/1997 |
| WO | WO 1998/014591 | 4/1998 |
| WO | WO 1998/050554 | 11/1998 |
| WO | WO 1999/029729 | 6/1999 |
| WO | WO 1999/029858 | 6/1999 |
| WO | WO 1999/045130 | 9/1999 |
| WO | WO 2000/055320 | 9/2000 |
| WO | WO 2000/073801 | 12/2000 |
| WO | WO 2001/007628 | 2/2001 |
| WO | WO 2001/019999 | 3/2001 |
| WO | WO 2001/057190 | 8/2001 |
| WO | WO 2001/064892 | 9/2001 |
| WO | WO 2001/074841 | 10/2001 |
| WO | WO 2001/075067 | 10/2001 |
| WO | WO 2001/075078 | 10/2001 |
| WO | WO 2001/088188 | 11/2001 |
| WO | WO 2001/090330 | 11/2001 |
| WO | WO 2001/094568 | 12/2001 |
| WO | WO 2001/095927 | 12/2001 |
| WO | WO 2002/044349 | 6/2002 |
| WO | WO 2002/055663 | 7/2002 |
| WO | WO 2002/059323 | 8/2002 |
| WO | WO 2002/067970 | 9/2002 |
| WO | WO 2002/068579 | 9/2002 |
| WO | WO 2003/009813 | 2/2003 |
| WO | WO 2003/051388 | 6/2003 |
| WO | WO 2003/080648 | 10/2003 |
| WO | WO 2003/094848 | 11/2003 |
| WO | WO 2003/094862 | 11/2003 |
| WO | WO 2004/023973 | 3/2004 |
| WO | WO 2004/030615 | 4/2004 |
| WO | WO 2004/060262 | 7/2004 |
| WO | WO 2004/063355 | 7/2004 |
| WO | WO 2004/064863 | 8/2004 |
| WO | WO 2004/087875 | 10/2004 |
| WO | WO 2005/019258 | 3/2005 |
| WO | WO 2005/019415 | 3/2005 |
| WO | WO 2005/073250 | 8/2005 |
| WO | WO 2005/087953 | 9/2005 |
| WO | WO 2005/102395 | 11/2005 |
| WO | WO 2005/113812 | 12/2005 |
| WO | WO 2005/117954 | 12/2005 |
| WO | WO 2006/016217 | 2/2006 |
| WO | WO 2006/048219 | 5/2006 |
| WO | WO 2006/057500 | 6/2006 |
| WO | WO 2006/083087 | 8/2006 |
| WO | WO 2007/020075 | 2/2007 |
| WO | WO 2007/064941 | 6/2007 |
| WO | WO 2007/083853 | 7/2007 |
| WO | WO 2007/091106 | 8/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/030558 | 3/2008 |
| WO | WO 2008/094012 | 8/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/032013 | 3/2011 |
| WO | WO 2011/035335 | 3/2011 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/149247 | 11/2012 |
| WO | WO 2012/149252 | 11/2012 |
| WO | WO 2012/149259 | 11/2012 |
| WO | WO 2012/149265 | 11/2012 |
| WO | WO 2012/149282 | 11/2012 |
| WO | WO 2012/149301 | 11/2012 |
| WO | WO 2012/149405 | 11/2012 |
| WO | WO 2012/149411 | 11/2012 |
| WO | WO 2012/158945 | 11/2012 |
| WO | WO 2013/022982 | 2/2013 |
| WO | WO 2013/036293 | 3/2013 |
| WO | WO 2013/036294 | 3/2013 |
| WO | WO 2013/036295 | 3/2013 |
| WO | WO 2013/036296 | 3/2013 |
| WO | WO 2013/036299 | 3/2013 |
| WO | WO 2013/036300 | 3/2013 |
| WO | WO 2013/036301 | 3/2013 |
| WO | WO 2013/036302 | 3/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |
| WO | WO 2014/145050 | 9/2014 |
| WO | WO 2016/172722 | 10/2016 |
| WO | WO 2018/102589 | 6/2018 |

OTHER PUBLICATIONS

Fenton et al. Rheostat positions: A new classification of protein positions relevant to pharmacogenomics Medicinal Chemistry Research 29:1133-1146; (2020). (Year: 2020).*

Dehouck, Y. et al., "Fast and accurate predictions of protein stability changes upon mutations using statistical potentials and neural networks:PoPMuSiC-2.0," Bioinformatics, 25(19):2537-2543 (2009).

Extended Supplementary European Search Report for European Application No. 18787408.6, dated Apr. 23, 2021, 20 pages.

Teng, S. et al., "Sequence feature-based prediction of protein stability changes upon amino acid substitutions," BMC Genomics, 11(Suppl 2):S5 (2010), 8 pages.

Teng, S. et al., "Structural Assessment of the Effects of Amino Acid Substitutions on Protein Stability and Protein-Protein Interaction," Int J Comput. Biol Drug Des., 3(4):334-349 (2010).

Yang, L. et al., "Relationship between the anti-inflammatory properties of salmeterol/fluticasone and the expression of CD4+CD25+ Foxp3+regulatory T cells in COPD," Respiratory Research, 12:142 (2011), 11 pages.

Noble, P. W. et al., "Pirfenidone in patients with idiopathic pulmonary fibrosis (Capacity): two randomised trials," The Lancet, May 2011, 377(9779):1760-1769.

(56) References Cited

OTHER PUBLICATIONS

Taniguchi, H. et al., "Pirfenidone in idiopathic pulmonary fibrosis," Eur. Respir. J., Dec. 2010, 35(4):821-829.
Cottin, V., "Interstitial lung disease," Eur. Respir. Rev., Feb. 2013, 22(127):26-32.
Hagmeyer, L. et al., "Successful Concomitant Therapy with Pirfenidone and Nintedanib in Idiopathic Pulmonary Fibrosis: A Case Report," Respiration, Apr. 2016, 91(4):327-332.
Partial Supplementary European Search Report for European Application No. 18787408.6, dated Dec. 2, 2020, 23 pages.
Extended European Search Report for European Application No. 10753998.3, dated Nov. 21, 2012.
International Search Report and Written Opinion for International Application No. PCT/US2010/027525, dated Jan. 10, 2011.
Extended European Search Report for European Application No. 17169885.5, dated Oct. 6, 2017, 6 pages.
Extended European Search Report and Written Opinion for European Application No. 13749967.9, dated Sep. 4, 2015, 11 pages.
International Search Report and Written Opinion for International Application No. PCT/US2013/026494, dated Aug. 21, 2013, 21 pages.
Extended European Search Report for European Application No. 17189334.0, dated Jan. 23, 2018, 9 pages.
Extended European Search Report for European Application No. 18194251.7, dated Jan. 8, 2019, 18 pages.
International Search Report and Written Opinion for International Application No. PCT/US2014/029699, dated Aug. 19, 2014, 16 pages.
Extended European Search Report for European Application No. 17876227.4, dated Jun. 3, 2020, 9 pages.
International Search Report and Written Opinion for International Application No. PCT/US2017/064025, dated Jul. 9, 2018, 18 pages.
International Search Report and Written Opinion for International Application No. PCT/US2018/028417, dated Sep. 11, 2018, 14 pages.
International Search Report and Written Opinion for International Application No. PCT/US2019/026128, dated Aug. 12, 2019, 12 pages.
International Search Report and Written Opinion for International Application No. PCT/US2019/043755, dated Dec. 6, 2019, 14 pages.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Almagro, J. C. et al., "Humanization of Antibodies," Frontiers in Bioscience, 13:1619-1633 (Jan. 2008).
Amaar, Y. G. et al., "Cloning and characterization of the *C.elegans* histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Belikov, V. G., "Dependency between the molecule structure of compounds and their effect on a body," Pharmaceutical Chemistry, In two parts, General Pharmaceutical Chemistry, Second Edition, Revised supplemented, Moscow, Vyshaya shkola, 1993.
Berger, T., "Is there a rationale for therapeutic immunoadsorption in multiple sclerosis?" Eur. J. Clin. Invest. 35(8):467-468 (2005).

Bergoin, C. et al., "The anti-synthetase syndrome," Rev. Mal. Respir. Jun. 2002; 19(3):371-374 (English Abstract).
Mahler, M. et al., "Idiopathic inflammatory myopathies and the anti-synthetase syndrome: A comprehensive review," Autoimmun. Rev. 2014; 13(0):367-371.
Bernstein, R. M. et al., "Anti-Jo-1 antibody: a marker for myositis with interstitial lung disease," British Medical Journal, 289:151-152 (1984).
Biesenbach, P. et al., "Immunoadsorption in SLE: Three different high affinity columns are adequately effective in removing autoantibodies and controlling disease activity," Atherosclerosis Supplements, 10:114-121 (2009).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Bohm, M. et al., "Longlasting effects of immunoadsorption in severe Sjögren's syndrome," Ann. Rheum. Dis., 63:214-215 (2004).
Branden et al., "Introduction to Protein Structure," Garland Publishing Inc., New York, p. 247 (1991).
Braun, N. et al., "Immunoadsorption onto protein A induces remission in severe systemic lupus erythematosus," Nephrol. Dial. Transplant, 15(9):1367-1372 (2000).
Braun, N. et al., "Immunoglobulin and circulating immune complex kinetics during immunoadsorption onto protein A sepharose," Transfus. Sci., 19(Suppl):25-31 (1998).
Brenner et al., "IG-therasorb immunoapheresis in orthotopic xenotransplantation of baboons with landrace pig hearts," Transplantation, 69:208-214 (2000) [Abstract].
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Carter, P. J., "Introduction to current and future protein therapeutics: A protein engineering perspective," Experimental Cell Research, 317(9):1261-1269 (2011).
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Diagnostic Automation / Cortez Diagnostics, Inc., "AccuDiag Jo-1 ELISA Kit," Cat# 2570-2, Sep. 14, 2014, XP055265960, Retrieved from the Internet: URL:http://www.rapidtest.com/pdf/Jo-1_2570-2(09-14-2015).pdf [retrieved on Apr. 15, 2016].
Chen et al., "Fusion protein linkers: Property, design and functionality," Adv. Drug Del. Rev., Oct. 15, 2013, vol. 65, No. 10, pp. 1357-1369.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms are Involved in 6-Hydroxydopamine-and MPP+-Induced Dopaminergic Neuronal Cell Death: Role of Caspases, ROS, and JNK," Journal of Neuroscience Research, 57(1):86-94 (1999).
"D-Lactic Acid Production by Metabolically Engineered *Saccharomyces cerevisiae*," JBB, 101(2):172-177 (2006).
Datson, N. A. et al., "Development of the first marmoset-specific DNA microarray (Eumama): a new genetic tool for large-scale expression profiling in a non-human primate," BMC Genomics, 8(190):1-9 (2007).
De Genst, E. D. et al., "Antibody Repertoire Development in Camelids," Developmental and Comparative Immunology, 30:187-198 (2006).

(56) References Cited

OTHER PUBLICATIONS

Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Dittrich et al., "Immunoadsorption and plasma exchange in pregnancy," Kidney Blood Press. Res., 25:232-239 (2002) [Abstract].
Dorffel et al., "Immunoadsorption in idiopathic dilated cardiomyopathy, a 3-year follow-up," Int. J. Cardiol., 97(3):529-534 (2004) [Abstract].
Eming, R. et al., "Prolonged clinical remission of patients with severe pemphigus upon rapid removal of desmoglein-reactive autoantibodies by immunoadsorption," Dermatology, 212(2):177-187 (2006).
Eriani, G. et al., "Cytoplasmic aspartyl-tRNA synthetase from *Saccharomyces cerevisiae*. Study of its functional organisation by deletion analysis," European Journal of Biochemistry, 200(2):337-343 (1991).
Esnault, V. L. M. et al., "Influence of immunoadsorption on the removal of immunoglobulin G autoantibodies in crescentic glomerulonephritis," Nephron, 65(2):180-184 (1993).
Ewalt, K. L. et al., "Activation of Angiogenic Signaling Pathways by Two Human tRNA Synthetases," Biochemistry, 41(45):13344-13349 (2002).
Felden, B. et al., "Resected RNA pseudoknots and their recognition by histidyl-tRNA synthetase," Proc. Natl. Acad. Sci. USA, 95:10431-10436 (1998).
Felix et al., "Hemodynamic effects of immunoadsorption and subsequent immunoglobulin substitution in dilated cardiomyopathy: three-month results from a randomized study," J. Am. Coll. Cardiol., 35:1590-1598 (2000) [Abstract].
Fowler, S. B. et al., "Rational design of aggregation-resistant bioactive peptides: Reengineering human calcitonin," PNAS, 102(29):10105-10110 (Jul. 19, 2005).
Francklyn, C. et al., "Histidyl-tRNA Synthetase," Eurekah Bioscience, 1(3):265-277 (2005).
Friedman, A. W. et al., "Interstitial lung disease with autoantibodies against aminoacyl-tRNA synthetases in the absence of clinically apparent myositis," Semin. Arthritis Rheum. vol. 26, No. 1, Aug. 1, 1996, pp. 459-467.
Fresenius Medical Care Deutschland GmbH, "Globaffin, First Synthetic Broadband-Immunoadsorber," (2006), 2 pages.
Fresenius Medical Care Deutschland GmbH, "Immunosorba, Protein A Column for Immunoadsorption," Therapeutic Apheresis, (2006), 12 pages.
Frommhold, D. et al., "Sialyltransferase ST3Gal-IV controls CXCR2-mediated firm leukocyte arrest during inflammation," Journal of Experimental Medicine, 205(6):1435-1446 (2008).
Frost, N. et al., "Treatment of pemphigus vulgaris with protein A immunoadsorption: case report of long-term history showing favorable outcome," Ann. N.Y. Acad. Sci., 1051:591-596 (2005).
GenBank Accession No. AA984229, published May 27, 1998.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK293531, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. BE872272, published Jan. 13, 2011.
GenBank Accession No. BF791754, published Jan. 13, 2011.
GenBank Accession No. BG108830, published Jun. 1, 2001.
GenBank Accession No. BP268250, published Feb. 10, 2011.
GenBank Accession No. DA083923, published Feb. 17, 2011.
GenBank Accession No. DB146646, published Feb. 16, 2011.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9W60, published May 1, 2000.
GenBank Accession No. Z11518, published Oct. 7, 2008.
GenBank Accession No. BC080514, "*Homo sapiens* histidyl-tRNA synthetase, mRNA (cDNA done MGC:99562 Image:2821065), complete cds," Jul. 15, 2006.
Goldgur, Y. et al., "The crystal structure of phenylalanyl-tRNA synthetase from Thermus thermophilus complexed with cognate tRNA," Structure, 5(1):59-68 (1997).
Graninger et al., "Immunoadsorption therapy (therasorb) in patients with severe lupus erythematosus," Acta Med. Austriaca, 29:26-29 (2002) [Abstract].
Grant, G. A., "Synthetic Peptides for Production of Antibodies that Recognize Intact Proteins," Unit 9.2, Current Protocols in Immunology (2003) Supplement 55, 9.2.1-9.2.19.
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Grundtman, C. et al., "Immune mechanisms in the pathogenesis of idiopathic inflammatory myopathies," Arthritis Research & Therapy, 9:208 (2007).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Gunther et al., Successful therapy of pemphigus vulgaris with immunoadsorption using the TheraSorb adsorber, J. Dtsch. Dermatol. Ges., 6:661-663 (2008) [Abstract].
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Guo, H. H., "Protein tolerance to random amino acid change," PNAS, 101(25):9205-9210 (Jun. 22, 2004).
Guzzo, C. M. et al., "Systematic analysis of fusion and affinity tags using human aspartyl-tRNA synthetase expressed in *E. coli*," Protein Expression and Purification, 54(1):166-175 (2007).
Haas et al., "Long-term treatment of myasthenia gravis with immunoadsorption," J. Clin. Apher., 17:84-87 (2002) [Abstract].
Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hartl, D. et al., "Infiltrated neutrophils acquire novel chemokine receptor expression and chemokine responsiveness in chronic inflammatory lung diseases," J. Immunol., 181:8053-8067 (2008).
Hausmann, C. D. et al., "Aminoacyl-tRNA synthetase complexes: molecular multitasking revealed," FEMS Microbiol. Rev., 32(4):705-721 (2008).
Haussermann, A. et al., "Das anti-Jo-1-Syndrom -eine Sonderform der Myositis mit interstitieller Lungenerkrankung," Pneumologie, 64(08):496-503 (2010).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hessel et al., "Economic evaluation and survival analysis of immunoglobulin adsorption in patients with idiopathic dilated cardiomyopathy," Eur. J. Health Econ., 5:58-63 (2004) [Abstract].
GenBank Accession No. AK303778, *Home sapiens* cDNA FLJ58562 complete cds, EC6.1.1.21, Jul. 24, 2008, www.ncbi.nlm.nih.gov/nuccore/AK303778, 2 pages.
Hou, Y-M. et al., "Sequence determination and modeling of structural motifs for the smallest monomeric aminoacyl-tRNA synthetase," Proc. Nat. Acad. Sci., 88(3):976-980 (1991).

(56) References Cited

OTHER PUBLICATIONS

Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3-and CRCR5-expressing lymphocytes and immature dendritic cells to migrate", Blood, 105(11) 4207-4214 (2005).
Hu, J. et al., "Matrix metalloproteinase inhibitors as therapy for inflammatory and vascular diseases," Nature Reviews, Drug Discovery, vol. 6, Jun. 2007, pp. 480-498.
Huang, C. et al., "Receptor-Fc fusion therapeutics, traps, and Mimetibody technology," Current Opinion in Biotechnology, 20(6):692-699 (2009).
Ito, H., "Anti-interleukin-6 therapy for Crohn's disease," Curr. Pharm. Des., 9(4):295-305 (2003) (Abstract).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jackson, N. E. et al., "Alternate mRNA Splicing in Multiple Human Tryptase Genes Is Predicted to Regulate Tetramer Formation," J. Biol. Chem., vol. 283, No. 49, pp. 34178-34187 (Dec. 2008).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jahns et al., "Direct evidence for a beta 1-adrenergic receptor-directed autoimmune attack as a cause of idiopathic dilated cardiomyopathy," J. Clin. Invest, 113:1419-1429 (2004) [Abstract].
Jansen et al., "Treatment of coagulation inhibitors with extracorporeal immunoadsorption (Ig-Therasorb)," Br. J. Haematol., 112:91-97 (2001) [Abstract].
Jia, J. et al., "WHEP Domains Direct Noncanonical Function of Glutamyl-Prolyl tRNA Synthetase in Translational Control of Gene Expression," Molecular Cell, 29(6):679-690 (2008).
Junemann, A. G. et al., "Stimulatory Autoantibodies against β2-adrenergic Receptors in Open-angle Glaucoma—Effect of Immunoadsorption on Antibody Level and Intraocular Pressure," Glaucoma Genetics and Proteomics, ARVO2011 Visionary Genomics, Fort Lauderdale, FL, May 2, 2011 3 pages.
Jura, M. et al., "Comprehensive Insight into human aminoacyl-tRNA synthetases as autoantigens in idiopathic inflammatory myopathies," Critical Reviews in Immunology, 27(6):559-572 (2007).
Kaczmarek et al., "Successful management of antibody-mediated cardiac allograft rejection with combined immunoadsorption and anti-CD20 monoclonal antibody treatment: case report and literature review," J. Heart Lung Transplant., 26:511-515 (2007) [Abstract].
Kajiura, S. et al., "Establishment and Characterization of Monoclonal and Polyclonal Antibodies Against Human Intestinal Fatty Acid-Binding Protein (I-FABP) using Synthetic Regional Peptides and Recombinant I-FABP," Journal of Immunoassay and Immunochemistry, 29(1):19-41 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Katsumata, Y. et al., "Attenuation of experimental autoimmune myositis by blocking ICOS-ICOS ligand interaction," J. Immunol., 179:3772-3779 (2007).
Kim, T. et al., "Catalytic Peptide of Human Glutaminyl-tRNA Synthetase Is Essential for Its Assembly to the Aminoacyl-tRNA Synthetase Complex," Journal of Biological Chemistry, 275(28):21768-21772 (2000).
Kimchi-Sarfaty, C. et al., "A 'Silent' polymorphism in the MDR1 gene changes substrate specificity," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Klingel, R. et al., "Plasma exchange and immunoadsorption for autoimmune neurologic diseases—current guidelines and future perspectives," Atherosclerosis Supplements, 10:129-132 (2009).
Knebel et al., "Reduction of morbidity by immunoadsorption therapy in patients with dilated cardiomyopathy," Int. J. Cardiol., 97:517-520 (2004) [Abstract].
Knobl et al., "Extracorporeal immunoadsorption for the treatment of haemophilic patients with inhibitors to factor VIII or IX," Vox Sang. 77 (suppl 1): 57-64 (1999) [Abstract].
Knobl, P. et al., "Immunoadsorption for the treatment of a patient with severe thrombotic thrombocytopenic purpura resistant to plasma exchange: kinetics of an inhibitor of ADAMTS13," J. Thromb. Haemost., 1:187-189 (2003).
Ko, Y-G. et al., "Glutamine-dependent Antiapoptotic Interaction of Human Glutaminyl-tRNA Synthetase with Apoptosis Signal-regulating Kinase 1," Journal of Biological Chemistry, 276(8):6030-6036 (2001).
Kochendoerfer, G. G., "Site-specific polymer modification of therapeutic proteins," Current Opinion in Chemical Biology, 9:555-560 (2005).
Koh, Y. T. et al., "Role of Nucleic Acid-Sensing TLR's in Diverse Autoantibody Specifics and Anti-Nuclear Antibody-Producing B Cells," J Immunol., vol. 190(10):4982-4990, May 15, 2013.
Kohler, W. et al., "A randomized and controlled study comparing immunoadsorption and plasma exchange in myasthenic crisis," Journal of Clinical Apheresis, 26(6):347-355 (2011).
Koll, "Ig-TheraSorb immunoadsorption for selective removal of human immunoglobulins in diseases associated with pathogenic antibodies of all classes and IgG subclasses, immune complexes, and fragments of immunoglobulins," Ther. Apher., 2:147-152 (1998) [Abstract].
Koller et al., "Clearance of C4d deposition after successful treatment of acute humoral rejection in follow-up biopsies: a report of three cases," Transpl. Int, 17:177-181 (2004) [Abstract].
Kovaleski, B. J. et al., "In vitro characterization of the interaction between HIV-1 Gag and human lysyl-tRNA synthetase," J. Bio. Chem., 281(28):19449-19456 (2006).
Kucharzik, T. et al., "Neutrophil transmigration in inflammatory bowel disease is associated with differential expression of epithelial intercellular junction proteins," American Journal of Pathology, 159(6):2001-2009 (2001).
Laczika et al., "Immunoadsorption in Goodpasture's syndrome," Am. J. Kidney Dis., 36:392-395 (2000) [Abstract].
Lagoumintzis, G. et al., "Recent approaches to the development of antigen-specific immunotherapies for myasthenia gravis," Autoimmunity, 43(5-6):436-445 (2010).
Kiely, P. D. W. et al., "Serum skeletal troponin I in inflammatory muscle disease: relation to creatine kinase, CKMB and cardiac troponin I," Letters to the Editor, Ann. Rheum. Dis., 2000;59:750-751.
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Li, H. et al., "Tumor Necrosis Factor-related Weak Inducer of Apoptosis Augments Matrix Metalloproteinase 9 (MMP-9) Production in Skeletal Muscle through the Activation of Nuclear Factor-kB-inducing Kinase and p38 Mitogen-activated Protein Kinase: A

(56) References Cited

OTHER PUBLICATIONS potential role of MMP-9 in Myopathy," Journal of Biological Chemistry, 284(7):4439-4450 (Feb. 2009).
Link, A. J. et al., "Discovery of aminoacyl-tRNA synthetase activity through cell-surface display of noncanonical amino acids," Proc. Nat. Acad. Sci., 103(27):10180-10185 (2006).
Magalhaes, P. O. et al., "Methods of endotoxin removal from biological preparations: a review," J. Pharm. Pharmaceut. Sci., 10(3):388-404 (2007).
Martin, A. et al., "Epitope studies indicate that histidyl-tRNA synthetase is a stimulating antigen in idiopathic myositis," The FASEB Journal, 9:1226-1233 (1995).
Matthews, B. W., "Structural and genetic analysis of protein stability," Annu. Rev. Biochem., 62:139-160 (1993).
Matic et al., "Three cases of C-ANCA-positive vasculitis treated with immunoadsorption: possible benefit in early treatment," Ther. Aph., 5:68-72 (2001) [Abstract].
Mertsching, E. et al., "Identification of a T cell immunomodulatory domain in histidyl-tRNA synthetase," Poster Presentation, aTyr Pharma, San Diego, CA, May 2, 2018, 1 page.
Mertsching, E. et al., "Identification of a T cell immunomodulatory domain in histidyl-tRNA synthetase," Journal of Immunology, vol. 200, No. 1, Supplement 1, 105th Annual Meeting of the American Association of Immunologists, Austin, TX, Abstract, May 2018, 1 page.
Mileti, L. M. et al., "Clinical Characteristics of Patients With Anti-Jo-1 Antibodies," Journal of Clinical Rheumatology, 15(5):254-255 (Aug. 2009).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Miller, F. W. et al., "The role of an autoantigen, histidyl-tRNA synthetase, in the induction and maintenance of autoimmunity," Proc. Natl. Acad. Sci. USA, 87:9933-9937 (1990).
Moldenhauer et al., "Immunoadsorption patients with multiple sclerosis: an open-label pilot study," Eur. J. Clin. Invest., 35:523-530 (2005) [Abstract].
Moldoveanu, B. et al., "Inflammatory mechanisms in the lung," Journal of Inflammation Research, 2:1-11 (2009).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Moore, B. A. et al., "Matrix Metalloproteinase-9 Inhibition Reduces Inflammation and Improves Motility in Murine Models of Postoperative Ileus," Gastroenterology, 141(4):1283-1292 (Jun. 2011).
Mozaffar, T. et al., "Myopathy with anti-Jo-1 antibodies: pathology in perimysium and neighbouring muscle fibres," J. Neurol. Neurosurg. Psychiatry, 68:472-478 (2000).
Mueller et al., "Immunoglobulin adsorption in patients with idiopathic dilated cardiomyopathy," Circulation, 101:385-391 (2000) [Abstract].
Mukhopadhyay, R. et al., "The GAIT System: a gatekeeper of inflammatory gene expression," Trends in Biochemical Sciences, 34(7):324-331 (2009).
Nackley, A. G. et al., "Human Caechol-O-Methytransferase haplotypes modulate protein expression by altering mRNA secondary structure," Science, 314:1930-1933 (2006).
Naito, Y. et al., "Neutrophil-dependent oxidative stress in ulcerative colitis," J. Clin. Biochem. Nutr., 41:18-26 (2007).
Nameki, N. et al., Accession 1X59, "Chain A, Solution Structures of the WHEP-TRS Domain of Human Histidyl-TRNA Synthetase," May 15, 2015, 2 pages.
Ng, P. C. et al., "Predicting the effects of amino acid substitutions on protein function," Annu. Rev. Genomics Hum. Genet, 7:61-80 (2006).
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
Nishimoto, N. et al., "2-3). Anticytokine therapy in autoimmune diseases," Internal Medicine, 38(2):178-182 (Feb. 1999).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Omotoso, B. A. et al., "Therapeutic Plasma Exchange in Antisynthetase Syndrome With Severe Interstitial Lung Disease," Journal of Clinical Apheresis (2015), 5 pages.
Oppenheim, J. J. et al., "Chemokine receptors on dendritic cells promote autoimmune reactions," Arthritis Res., 4(3):S183-S188 (2002).
Oppenheim, J. J. et al., "Autoantigens act as tissue-specific chemoattractants," Journal of Leukocyte Biology, 77:854-861 (2005).
Ogilvie, K. et al., "ATYR1923 ameliorates dermal and pulmonary fibrosis in a murine model of sclerodermatous chronic graft vs. host disease," Poster presented at the Scleroderma Foundation National Patient Education Conference, Jul. 27-29, 2018, Philadelphia, PA, 1 page.
Ogilvie et al., "Resokine modulates immune cell infiltration into the lung and provides therapeutic activity in a bleomycin-induced lung fibrosis model," American Journal of Respiratory and Critical Care Medicine, vol. 195, p. A6428 (May 2017).
Ogilvie, K. et al., "Preclinical Characterization of ATYR1923 (iMod.Fc), an Immune-Modulatory Therapeutic with Potentially Broad Application in Interstitial Lung Diseases," (May 2018), Retrieved from the Internet Sep. 28, 2019: <https://www.atyrpharma.com/wp-content/uploads/2019/01/Exh99.1-ATS-2018.pdf>, 1 page.
Paz, S. et al., "ATYR1923 reduces neutrophil infiltration in an acute lipopolysaccharide (LPS) lung injury model," Keystone Symposia 2019 Conference in Santa Fe, New Mexico, Feb. 24-28, 2019, 1 page.
Palmer, A. et al., "Treatment of rapidly progressive glomerulonephritis by extracorporeal immunoadsorption, prednisolone and cyclophosphamide," Nephrol Dial Transplant., 6(8):536-542 (1991).
Palmer, A. et al., "Treatment of systemic lupus erythematosus by extracorporeal immunoadsorption," Lancet, 2(8605):272 (1988).
Park, S. G., et al., "Aminoacyl tRNA synthetases and their connections to disease," PNAS, 105(32):11043-11049 (2008).
Park, C-K. et al., "Development of antisynthetase syndrome in a patient with rheumatoid arthritis," Rheumatol. Int, 31:529-532 (2011).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Pottle et al., "Management of acute antibody-mediated rejection after heart transplantation," Brit. J. Transplant, 2:10-15 (2007).
Prophet et al., "Two cases of refractory endocrine ophthalmopathy successfully treated with extracorporeal immunoadsorption," Ther. Apher., 5:142-146 (2001) [Abstract].

(56) References Cited

OTHER PUBLICATIONS

Puffenberger, E. G. et al., "Genetic mapping and exome sequencing identify variants associated with five novel diseases," PLoS, 7(1):e28936 (2012).
Quesniaux, V. F.J. et al., "Hematopoiesis, including lymphocyte development and maturation," Principles of Immunopharmacology, pp. 3-17 (2005).
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39):24277-24283 (1994).
Rabitsch et al., "Prolonged red cell aplasia after major ABO-incompatible allogeneic hematopoietic stem cell transplantation: removal of persisting isohemagglutinins with Ig-Therasorb immunoadsorption," Bone Marrow Transplant,. 32:1015-1019 (2003) [Abstract].
Rech, J. et al., "Immunoadsorption and CD20 antibody treatment in a patient with treatment resistant systemic lupus erythematosus and preterminal renal insufficiency," Ann Rheum Dis., 65(4):552-553 (2006).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Interaction between human tRNA synthetases involves repeated sequence elements," Proc. Natl. Acad. Sci. USA, 93(19):10128-10133 (1996).
Rho, S. B. et al., "A multifunctional repeated motif is present in human bifunctional tRNA synthetase," Journal of Biological Chemistry, 273(18):11267-11273 (1998).
Ribas de Pouplana, L. et al., "Not Just Because it is There: Aminoacyl-tRNA Synthetases Gain Control of the Cell," Molecular Cell, 30:3-4 (2008).
Richardson, R. M. et al., "Role of the cytoplasmic tails of CXCR1 and CXCR2 in mediating leukocyte migration, activation, and regulation," Journal of Immunology, 170(6):2904-2911 (2003).
Roguin, L. P. et al., "Monoclonal Antibodies Inducing Conformational Changes on the Antigen Molecule," Scand. J. Immunol., vol. 58, pp. 387-394 (2003).
Rosenbaum, R. S. et al., "Structure of a B2-Adrenergic Receptor," vol. 318, No. 5854, Nov. 23, 2007, Science Japanese Edition, [retrieved on Dec. 4, 2015], Retrieved from the Internet, URL: <http://www.sciencemag.jp/archive-2006-8/general/science/07/2007_11_23/sci_jap.html>.
Rosenberg, N. L. et al., "Experimental autoimmune myositis in SJL/J mice," Clin. Exp. Immunol., 68:117-129 (1987).
Rubtsov, A., et al., "TLR7 Drives Accumulation of ABC's and Autoantibody Production in Autoimmune-prone Mice," Immonol Res. Mar. 2013, vol. 55(0); 210-216, 12 pages.
Safdari, Y. et al., "Antibody humanization methods—a review and update," Biotechnology and Genetic Engineering Reviews, vol. 29, No. 2, pp. 175-186 (2013).
Sanchez, A. P. et al., "The selective therapeutic apheresis procedures," Journal of Clinical Apheresis, 28(1):20-29 (2013).
Sauna, Z. E. et al., "Silent polymorhisms speak: How they affect pharmacogenomics and the treatment of cancer," Cancer Res., 67(20):9609-9612 (2007).
Scheper, G. C. et al., "Mitochondrial aspartyl-tRNA synthetase deficiency causes leukoencephalopathy with brain stem and spinal cord involvement and lactate elevation," Nat. Genet., vol. 39, No. 4, pp. 534-539 (Apr. 2007).
Schmaldienst et al., "Treatment of systemic lupus erythematosus by immunoadsorption in a patient suffering from tuberculosis," Am. J. Kidney Dis., 39:415-418 (2002) [Abstract].
Schmidt, E. et al., "Immunoadsorption in dermatology," Arch. Dermatol. Res., 302:241-253 (2010).
Schmidt, E. et al., "Protein A immunoadsorption: a novel and effective adjuvant treatment of severe pemphigus," Br J Dermatol., 148(6):1222-1229 (2003).
Schmutz, J. et al., "The DNA sequence and comparative analysis of human chromosome 5," Nature, 431:268-274 (2004).
Schray, B. et al., "Glutaminyl-tRNA synthetase as a component of the high-molecular weight complex of human aminoacyl-tRNA synthetases. An immunological study," Biochimica et Biophysica Acta, 1087(2):226-234(1990).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Shiba, K., "Intron positions delineate the evolutionary path of a pervasively appended peptide in five human aminoacyl-tRNA synthetases," Journal of Molecular Evolution, 55:727-733 (2002).
Simpson, J. A. et al., "Differential detection of skeletal troponin I isoforms in serum of a patient with rhabdomyolysis: Markers of muscle injury?", Clinical Chemistry, 48(7):1112-1114 (Jul. 2002).
Smith, D. F. et al., "Leukocyte phosphoinositide-3 kinase γ is required for chemokine-induced, sustained adhesion underflow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Staudt et al., "Immunohistological changes in dilated cardiomyopathy induced by immunoadsorption therapy and subsequent immuno-globulin substitution," Circulation, 103:2681-2686 (2001) [Abstract].
Staudt et al., "Potential role of autoantibodies belonging to the immunoglobulin G-3 subclass in cardiac dysfunction among patients with dilated cardiomyopathy," Circulation, 106:2448-2453 (2002) [Abstract].
Sorichter, S. et al., "Skeletal troponin I as a marker of exercise-induced muscle damage," Journal of Applied Physiology, 83(4):1076-1082 (Jan. 1997).
Stone, K. D. et al., "Immunomodulatory therapy of eosinophil-associated gastrointestinal diseases," Clin. Exp. Allergy, 38(12):1858-1865 (2008).
Stummvoll, G. H., "Immunoadsorption (IAS) for systemic lupus erythematosus," Lupus, 20:115-119 (2011).
Stummvoll et al., "IgG immunoadsorption reduces systemic lupus erythematosus activity and proteinuria: a long term observational study," Ann. Rheum. Dis., 64:1015-1021 (2005) [Abstract].
Sultan, S. M. et al., "Re-classifiyng myositis," Rheumatology, 49:831-833 (2010).
Suzuki, K. et al., "Successful treatment of polymyositis by immunoadsorption in a patient with polymyositis-systemic sclerosis overlap," Japan J. Apheresis, 13(2):135-136 (1994).
Tarabishy, A. B. et al., "Retinal Vasculitis Associated with the Anti-Synthetase Syndrome," Ocular Immunology & Inflammation, 18(1):16-18 (2010).
Targoff, I. N. et al., "Reaction of Anti-OJ Autoantibodies with Components of the Multi-enzyme Complex of Aminoacyl-tRNA Synthetases in Addition to Isoleucyl-tRNA Synthetases in Addition to Isoleucyl-tRNA Synthetase," Journal of Clinical Investigation, 91:2556-2564 (1993).
Targoff, I. N., "Update on myositis-specific and myositis-associated autoantibodies," Current Opinion in Rheumatology, 12:475-481 (2000).
"Theoretical pI/Mw (average) for the user-entered sequence," ExPASy, Computepl/Mw tool, [retrieved on Jan. 27, 2016], [online], URL: <http://web.expasy.org/compute_pi/>.
Toepfer et al., "Successful management of polyneuropathy associated with IgM gammopathy of undetermined significance with antibody-based immunoadsorption," Clin. Nephrol., 53:404-407 (2000) [Abstract].
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. Nov. 1-5, 2001.

(56) References Cited

OTHER PUBLICATIONS

Vassallo, J. D. et al., "Biomarkers of Drug-Induced Skeletal Muscle Injury in the Rat: Troponin I and Myoglobin," Toxicological Sciences, 111(2):402-412 (Jul. 2009).
Vennepureddy, A. et al., "Novel drugs and combination therapies for the treatment of metastatic melanoma," J. Clin. Med. Res. 8(2):63-75 (2016).
Veronese, F. M. et al., "Preface: Introduction and overview of peptide and protein pegylation," Advanced Drug Delivery Reviews, 54:453-456 (2002).
Vestergaard, C. et al., "Expression of CCR2 on monocytes and macrophages in chronically inflamed skin in atopic dermatitis and psoriasis," Acta Derm. Venereol., 84:353-358 (2004).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dualspecificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Woolhouse, I. S. et al., "Endothelial interactions of neutrophils under flow in chronic obstructive pulmonary disease," Eur. Respir. J., 25:612-617 (2005).
Xie, W. et al., "Long-range structural effects of a Charcot-Marie-Tooth disease-causing mutation in human glycyl-tRNA synthetase," PNAS, 104(24):9976-9981 (2007).
Xu, Z. et al., "Internally deleted human tRNA synthetase suggest evolutionary pressure for repurposing," Structure, 20(9):1470-1477 (2012).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yoshinaga, K. et al., "Ig L-chain Shuffling for Affinity Maturation of Phage Library-derived Human Antihuman MCP-1 Antibody Blocking its Chemotactic Activity," J. Biochem., 143:593-601 (2008).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).
Zeitler et al., "Treatment of acquired hemophilia by the Bonn-Malmo Protocol: documentation of an in vivo immunomodulating concept," Blood, 105:2287-2293 (2005) [Abstract].
Zeitler et al., "Long-term effects of a multimodal approach including immunoadsorption for the treatment of myasthenic crisis," Artif. Organs, 30:597-605 (2006) [Abstract].
Zhang, L. et al., "Chemical activation of innate and specific immunity in contact dermatitis," J. Invest. Dermatol., 115:168-176 (2000).
Zhou, Q. et al., "Orthogonal use of a human tRNA synthetase active site to achieve multifunctionality," Nature Structural & Molecular Biology, 17(1):57-62 (2010).
Zhu, J., et al., "Toll-Like Receptor Signaling Pathways—Therapeutic Opportunities," Hindawa Publishing Corporation, Mediators of Inflammation, vol. 2010, Article ID 781235, Mar. 2010, 7 pages.
Zillikens et al., "Treatment of severe pemphigus with protein A immunoadsorption, rituximab and intravenous immunoglobulins," Br. J. Dermatol., 158:382-388 (2008) [Abstract].
Zillikens, "Recommendations for the use of immunoapheresis in the treatment of autoimmune bullous diseases," J. Dtsch. Dermatol. Ges., 5:881-817 (2007) [Abstract].
Zwijnenburg, P. J. G et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Gomard-Mennesson, E. et al., "Clinical significance of anti-histidyl-tRNAsynthetase (Jo1) autoantibodies," Ann N Y Acad Sci. Aug. 2007;1109:414-420.
GenBank: NP_002100.2; "Histidine—tRNA ligase, cytoplasmic isoform 1 [*Homo sapiens*]," Publication Date: Nov. 20, 2011.
Stone, K. B. et al., (2007). "Anti-Jo-1 antibody levels correlate with disease activity in idiopathic inflammatory myopathy," Arthritis and Rheumatism, 56(9), 3125-3131.
Artificial Organs, 1983, vol. 12, No. 5, pp. 895-907.
Oka, K. et al., "Development of specific immunoadsorbent containing immobilized synthetic peptide of acetylcholine receptor for treatment of myasthenia gravis," Jpn. J. Artificial Organs, 1983, vol. 22, No. 1, pp. 194-197 (with English Abstract).
Oka, K. et al., "Study on the characteristics of adsorption in a specific immunoadsorbent containing immobilized synthetic peptide of acetylcholine receptor," Jpn J. Artificial Organs, 1995, vol. 24, No. 3, pp. 788-791 (with English Abstract).
Von Luettichau, I. et al., "Rantes chemokine expression in diseased and normal human tissues," Cytokine, vol. 8, No. 1, pp. 89-98 (Jan. 1996).
Han, J-H et al., "Macrophage inflammatory protein-1α is an osteodastogenic factor in myeloma that is independent of receptor activator of nuclear factor kB ligand," Blood, vol. 97, No. 11 pp. 3349-3353 (Jun. 2001).
Hashimoto, T. et al., "Ability of myeloma cells to secrete macrophage inflammatory protein (MIP)-1α and MIP-1β correlates with lytic bone lesions in patients with multiple myeloma," British Journal of Haematology, vol. 125, No. 1, pp. 38-41 (Apr. 2004).
Doan, H. Q. et al., "Toll-like Receptor 4 Activation Increases Akt Phosphorylation in Colon Cancer Cells," Anticancer Research, vol. 29, No. 7, pp. 2473-2478 (Jul. 2009).
Appleton, B. A. et al., "Structural studies of neuropilin/antibody complexes provide insights into semaphorin and VEGF binding," The EMBO Journal, 26(23):4902-4912 (Nov. 2007).

* cited by examiner

SEQUENCE LISTING

```
<160> NUMBER OF SEQ ID NOS: 233

<210> SEQ ID NO 1
<211> LENGTH: 509
<212> TYPE: PRT
<213> ORGANISM: Homo sapiens

<400> SEQUENCE: 1

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125
```

```
Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
                180                 185                 190

Lys Ile Met Cys Glu Ile Leu Ser Ser Leu Gln Ile Gly Asp Phe Leu
                195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
                435                 440                 445

Leu Asn Gln Leu Gln Tyr Cys Glu Glu Ala Gly Ile Pro Leu Val Ala
            450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
                500                 505

<210> SEQ ID NO 2
<211> LENGTH: 500
<212> TYPE: PRT
<213> ORGANISM: Homo sapiens
```

```
<400> SEQUENCE: 2

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Leu Gln Ile Gly Asp Phe Leu
            195                 200                 205

Val Lys Val Asn Asp Arg Arg Ile Leu Asp Gly Met Phe Ala Ile Cys
            210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
            275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400
```

```
Glu Glu Lys Ile Arg Thr Thr Glu Thr Gln Val Leu Val Ala Ser Ala
            405                 410                 415

Gln Lys Lys Leu Leu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
            485                 490                 495

Glu Ile Lys Arg
            500

<210> SEQ ID NO 3
<211> LENGTH: 501
<212> TYPE: PRT
<213> ORGANISM: Homo sapiens

<400> SEQUENCE: 3

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
            85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
            130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
            165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
            210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
            245                 250                 255
```

-continued

```
Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg
                500

<210> SEQ ID NO 4
<211> LENGTH: 502
<212> TYPE: PRT
<213> ORGANISM: Homo sapiens

<400> SEQUENCE: 4

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110
```

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
            275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr
            500

<210> SEQ ID NO 5
<211> LENGTH: 503

<212> TYPE: PRT
<213> ORGANISM: Homo sapiens

<400> SEQUENCE: 5

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400
```

```
Glu Glu Lys Ile Arg Thr Thr Glu Thr Gln Val Leu Val Ala Ser Ala
            405                 410                 415

Gln Lys Lys Leu Leu Glu Arg Leu Lys Leu Val Ser Glu Leu Trp
        420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Val Asp Val Arg Arg Glu Asp Leu Val Glu
            485                 490                 495

Glu Ile Lys Arg Arg Thr Gly
            500

<210> SEQ ID NO 6
<211> LENGTH: 504
<212> TYPE: PRT
<213> ORGANISM: Homo sapiens

<400> SEQUENCE: 6

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255
```

```
Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Val Asp Val Arg Arg Glu Asp Leu Val Glu
                485                 490                 495

Glu Ile Lys Arg Arg Thr Gly Gln
                500

<210> SEQ ID NO 7
<211> LENGTH: 505
<212> TYPE: PRT
<213> ORGANISM: Homo sapiens

<400> SEQUENCE: 7

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110
```

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro
            500                 505

<210> SEQ ID NO 8
<211> LENGTH: 506

```
<212> TYPE: PRT
<213> ORGANISM: Homo sapiens

<400> SEQUENCE: 8

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400
```

```
Glu Glu Lys Ile Arg Thr Thr Glu Thr Gln Val Leu Val Ala Ser Ala
                405             410                 415

Gln Lys Lys Leu Leu Glu Arg Leu Lys Leu Val Ser Glu Leu Trp
        420             425                 430

Asp Ala Gly Ile Lys Ala Glu Leu Leu Tyr Lys Lys Asn Pro Lys Leu
        435             440                 445

Leu Asn Gln Leu Gln Tyr Cys Glu Ala Gly Ile Pro Leu Val Ala
    450             455                 460

Ile Ile Gly Glu Gln Glu Leu Lys Asp Gly Val Ile Lys Leu Arg Ser
465             470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 9
<211> LENGTH: 505
<212> TYPE: PRT
<213> ORGANISM: Homo sapiens

<400> SEQUENCE: 9

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
                20                  25                  30

Glu Val Ala Lys Leu Leu Lys Leu Lys Ala Gln Leu Gly Pro Asp Glu
            35                  40                  45

Ser Lys Gln Lys Phe Val Leu Lys Thr Pro Lys Gly Thr Arg Asp Tyr
    50                  55                  60

Ser Pro Arg Gln Met Ala Val Arg Glu Lys Val Phe Asp Val Ile Ile
65              70                  75                  80

Arg Cys Phe Lys Arg His Gly Ala Glu Val Ile Asp Thr Pro Val Phe
                85                  90                  95

Glu Leu Lys Glu Thr Leu Met Gly Lys Tyr Gly Glu Asp Ser Lys Leu
                100                 105                 110

Ile Tyr Asp Leu Lys Asp Gln Gly Gly Glu Leu Leu Ser Leu Arg Tyr
            115                 120                 125

Asp Leu Thr Val Pro Phe Ala Arg Tyr Leu Ala Met Asn Lys Leu Thr
    130                 135                 140

Asn Ile Lys Arg Tyr His Ile Ala Lys Val Tyr Arg Arg Asp Asn Pro
145             150                 155                 160

Ala Met Thr Arg Gly Arg Tyr Arg Glu Phe Tyr Gln Cys Asp Phe Asp
                165                 170                 175

Ile Ala Gly Asn Phe Asp Pro Met Ile Pro Asp Ala Glu Cys Leu Lys
            180                 185                 190

Ile Met Cys Glu Ile Leu Ser Ser Leu Gln Ile Gly Asp Phe Leu Val
        195                 200                 205

Lys Val Asn Asp Arg Arg Ile Leu Asp Gly Met Phe Ala Ile Cys Gly
    210                 215                 220

Val Ser Asp Ser Lys Phe Arg Thr Ile Cys Ser Ser Val Asp Lys Leu
225             230                 235                 240

Asp Lys Val Ser Trp Glu Glu Val Lys Asn Glu Met Val Gly Glu Lys
                245                 250                 255
```

```
Gly Leu Ala Pro Glu Val Ala Asp Arg Ile Gly Asp Tyr Val Gln Gln
                260                 265                 270

His Gly Gly Val Ser Leu Val Glu Gln Leu Gln Asp Pro Lys Leu
        275                 280                 285

Ser Gln Asn Lys Gln Ala Leu Glu Gly Leu Gly Asp Leu Lys Leu Leu
290                 295                 300

Phe Glu Tyr Leu Thr Leu Phe Gly Ile Asp Asp Lys Ile Ser Phe Asp
305                 310                 315                 320

Leu Ser Leu Ala Arg Gly Leu Asp Tyr Tyr Thr Gly Val Ile Tyr Glu
                325                 330                 335

Ala Val Leu Leu Gln Thr Pro Ala Gln Ala Gly Glu Glu Pro Leu Gly
                340                 345                 350

Val Gly Ser Val Ala Ala Gly Gly Arg Tyr Asp Gly Leu Val Gly Met
                355                 360                 365

Phe Asp Pro Lys Gly Arg Lys Val Pro Cys Val Gly Leu Ser Ile Gly
        370                 375                 380

Val Glu Arg Ile Phe Ser Ile Val Glu Gln Arg Leu Glu Ala Leu Glu
385                 390                 395                 400

Glu Lys Ile Arg Thr Thr Glu Thr Gln Val Leu Val Ala Ser Ala Gln
                405                 410                 415

Lys Lys Leu Leu Glu Glu Arg Leu Lys Leu Val Ser Glu Leu Trp Asp
                420                 425                 430

Ala Gly Ile Lys Ala Glu Leu Leu Tyr Lys Lys Asn Pro Lys Leu Leu
        435                 440                 445

Asn Gln Leu Gln Tyr Cys Glu Glu Ala Gly Ile Pro Leu Val Ala Ile
450                 455                 460

Ile Gly Glu Gln Glu Leu Lys Asp Gly Val Ile Lys Leu Arg Ser Val
465                 470                 475                 480

Thr Ser Arg Glu Glu Val Asp Val Arg Arg Glu Asp Leu Val Glu Glu
                485                 490                 495

Ile Lys Arg Arg Thr Gly Gln Pro Leu
                500                 505

<210> SEQ ID NO 10
<211> LENGTH: 507
<212> TYPE: PRT
<213> ORGANISM: Homo sapiens

<400> SEQUENCE: 10

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110
```

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
        210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys
            500                 505

<210> SEQ ID NO 11
<211> LENGTH: 508

<212> TYPE: PRT
<213> ORGANISM: Homo sapiens

<400> SEQUENCE: 11

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400
```

```
Glu Glu Lys Ile Arg Thr Thr Glu Thr Gln Val Leu Val Ala Ser Ala
                405                 410                 415

Gln Lys Lys Leu Leu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Val Asp Val Arg Arg Glu Asp Leu Val Glu
                485                 490                 495

Glu Ile Lys Arg Arg Thr Gly Gln Pro Leu Cys Ile
                500                 505

<210> SEQ ID NO 12
<211> LENGTH: 48
<212> TYPE: PRT
<213> ORGANISM: Homo sapiens

<400> SEQUENCE: 12

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

<210> SEQ ID NO 13
<211> LENGTH: 80
<212> TYPE: PRT
<213> ORGANISM: Homo sapiens

<400> SEQUENCE: 13

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

<210> SEQ ID NO 14
<211> LENGTH: 79
<212> TYPE: PRT
<213> ORGANISM: Homo sapiens

<400> SEQUENCE: 14

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45
```

Glu Ser Lys Gln Lys Phe Val Leu Lys Thr Pro Lys Gly Thr Arg Asp
            50                  55                  60

Tyr Ser Pro Arg Gln Met Ala Val Arg Glu Lys Val Phe Asp Val
65                  70                  75

<210> SEQ ID NO 15
<211> LENGTH: 78
<212> TYPE: PRT
<213> ORGANISM: Homo sapiens

<400> SEQUENCE: 15

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp
65                  70                  75

<210> SEQ ID NO 16
<211> LENGTH: 77
<212> TYPE: PRT
<213> ORGANISM: Homo sapiens

<400> SEQUENCE: 16

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe
65                  70                  75

<210> SEQ ID NO 17
<211> LENGTH: 76
<212> TYPE: PRT
<213> ORGANISM: Homo sapiens

<400> SEQUENCE: 17

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val
65                  70                  75

<210> SEQ ID NO 18
<211> LENGTH: 75
<212> TYPE: PRT

<213> ORGANISM: Homo sapiens

<400> SEQUENCE: 18

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys
65                  70                  75

<210> SEQ ID NO 19
<211> LENGTH: 74
<212> TYPE: PRT
<213> ORGANISM: Homo sapiens

<400> SEQUENCE: 19

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu
65                  70

<210> SEQ ID NO 20
<211> LENGTH: 73
<212> TYPE: PRT
<213> ORGANISM: Homo sapiens

<400> SEQUENCE: 20

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg
65                  70

<210> SEQ ID NO 21
<211> LENGTH: 72
<212> TYPE: PRT
<213> ORGANISM: Homo sapiens

<400> SEQUENCE: 21

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

```
Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala Val
65                  70
```

<210> SEQ ID NO 22
<211> LENGTH: 71
<212> TYPE: PRT
<213> ORGANISM: Homo sapiens

<400> SEQUENCE: 22

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala
65                  70
```

<210> SEQ ID NO 23
<211> LENGTH: 70
<212> TYPE: PRT
<213> ORGANISM: Homo sapiens

<400> SEQUENCE: 23

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
            50                  55                  60

Tyr Ser Pro Arg Gln Met
65                  70
```

<210> SEQ ID NO 24
<211> LENGTH: 69
<212> TYPE: PRT
<213> ORGANISM: Homo sapiens

<400> SEQUENCE: 24

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
            50                  55                  60

Tyr Ser Pro Arg Gln
65
```

<210> SEQ ID NO 25
<211> LENGTH: 68
<212> TYPE: PRT
<213> ORGANISM: Homo sapiens

<400> SEQUENCE: 25

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg
65

<210> SEQ ID NO 26
<211> LENGTH: 67
<212> TYPE: PRT
<213> ORGANISM: Homo sapiens

<400> SEQUENCE: 26

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro
65

<210> SEQ ID NO 27
<211> LENGTH: 66
<212> TYPE: PRT
<213> ORGANISM: Homo sapiens

<400> SEQUENCE: 27

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser
65

<210> SEQ ID NO 28
<211> LENGTH: 65
<212> TYPE: PRT
<213> ORGANISM: Homo sapiens

<400> SEQUENCE: 28

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr
65

<210> SEQ ID NO 29
<211> LENGTH: 64
<212> TYPE: PRT
<213> ORGANISM: Homo sapiens

<400> SEQUENCE: 29

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

<210> SEQ ID NO 30
<211> LENGTH: 63
<212> TYPE: PRT
<213> ORGANISM: Homo sapiens

<400> SEQUENCE: 30

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg
    50                  55                  60

<210> SEQ ID NO 31
<211> LENGTH: 62
<212> TYPE: PRT
<213> ORGANISM: Homo sapiens

<400> SEQUENCE: 31

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr
    50                  55                  60

<210> SEQ ID NO 32
<211> LENGTH: 61
<212> TYPE: PRT
<213> ORGANISM: Homo sapiens

<400> SEQUENCE: 32

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly
    50                  55                  60

<210> SEQ ID NO 33
<211> LENGTH: 60
<212> TYPE: PRT
<213> ORGANISM: Homo sapiens

<400> SEQUENCE: 33

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 34
<211> LENGTH: 59
<212> TYPE: PRT
<213> ORGANISM: Homo sapiens

<400> SEQUENCE: 34

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro
    50                  55

<210> SEQ ID NO 35
<211> LENGTH: 58
<212> TYPE: PRT
<213> ORGANISM: Homo sapiens

<400> SEQUENCE: 35

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr
    50                  55

<210> SEQ ID NO 36
<211> LENGTH: 57
<212> TYPE: PRT

<213> ORGANISM: Homo sapiens

<400> SEQUENCE: 36

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys
    50                  55

<210> SEQ ID NO 37
<211> LENGTH: 56
<212> TYPE: PRT
<213> ORGANISM: Homo sapiens

<400> SEQUENCE: 37

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu
    50                  55

<210> SEQ ID NO 38
<211> LENGTH: 55
<212> TYPE: PRT
<213> ORGANISM: Homo sapiens

<400> SEQUENCE: 38

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val
    50                  55

<210> SEQ ID NO 39
<211> LENGTH: 54
<212> TYPE: PRT
<213> ORGANISM: Homo sapiens

<400> SEQUENCE: 39

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe
    50

<210> SEQ ID NO 40
<211> LENGTH: 53

```
<212> TYPE: PRT
<213> ORGANISM: Homo sapiens

<400> SEQUENCE: 40

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys
    50

<210> SEQ ID NO 41
<211> LENGTH: 52
<212> TYPE: PRT
<213> ORGANISM: Homo sapiens

<400> SEQUENCE: 41

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln
    50

<210> SEQ ID NO 42
<211> LENGTH: 51
<212> TYPE: PRT
<213> ORGANISM: Homo sapiens

<400> SEQUENCE: 42

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys
    50

<210> SEQ ID NO 43
<211> LENGTH: 50
<212> TYPE: PRT
<213> ORGANISM: Homo sapiens

<400> SEQUENCE: 43

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser
    50

<210> SEQ ID NO 44
```

```
<211> LENGTH: 49
<212> TYPE: PRT
<213> ORGANISM: Homo sapiens

<400> SEQUENCE: 44

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu

<210> SEQ ID NO 45
<211> LENGTH: 48
<212> TYPE: PRT
<213> ORGANISM: Homo sapiens

<400> SEQUENCE: 45

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

<210> SEQ ID NO 46
<211> LENGTH: 47
<212> TYPE: PRT
<213> ORGANISM: Homo sapiens

<400> SEQUENCE: 46

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro
        35                  40                  45

<210> SEQ ID NO 47
<211> LENGTH: 46
<212> TYPE: PRT
<213> ORGANISM: Homo sapiens

<400> SEQUENCE: 47

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly
        35                  40                  45

<210> SEQ ID NO 48
<211> LENGTH: 45
<212> TYPE: PRT
<213> ORGANISM: Homo sapiens

<400> SEQUENCE: 48

Met Ala Glu Arg Ala Ala Leu Glu Glu Leu Val Lys Leu Gln Gly Glu
1               5                   10                  15
```

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu
            35                  40                  45

<210> SEQ ID NO 49
<211> LENGTH: 44
<212> TYPE: PRT
<213> ORGANISM: Homo sapiens

<400> SEQUENCE: 49

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln
            35                  40

<210> SEQ ID NO 50
<211> LENGTH: 43
<212> TYPE: PRT
<213> ORGANISM: Homo sapiens

<400> SEQUENCE: 50

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala
            35                  40

<210> SEQ ID NO 51
<211> LENGTH: 42
<212> TYPE: PRT
<213> ORGANISM: Homo sapiens

<400> SEQUENCE: 51

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys
            35                  40

<210> SEQ ID NO 52
<211> LENGTH: 41
<212> TYPE: PRT
<213> ORGANISM: Homo sapiens

<400> SEQUENCE: 52

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu
            35                  40

<210> SEQ ID NO 53
<211> LENGTH: 40
<212> TYPE: PRT
<213> ORGANISM: Homo sapiens

<400> SEQUENCE: 53

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys
        35                  40

<210> SEQ ID NO 54
<211> LENGTH: 79
<212> TYPE: PRT
<213> ORGANISM: Homo sapiens

<400> SEQUENCE: 54

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
            20                  25                  30

Glu Val Ala Lys Leu Leu Lys Leu Lys Ala Gln Leu Gly Pro Asp Glu
        35                  40                  45

Ser Lys Gln Lys Phe Val Leu Lys Thr Pro Lys Gly Thr Arg Asp Tyr
    50                  55                  60

Ser Pro Arg Gln Met Ala Val Arg Glu Lys Val Phe Asp Val Ile
65                  70                  75

<210> SEQ ID NO 55
<211> LENGTH: 78
<212> TYPE: PRT
<213> ORGANISM: Homo sapiens

<400> SEQUENCE: 55

Glu Arg Ala Ala Leu Glu Glu Leu Val Lys Leu Gln Gly Glu Arg Val
1               5                   10                  15

Arg Gly Leu Lys Gln Gln Lys Ala Ser Ala Glu Leu Ile Glu Glu Glu
            20                  25                  30

Val Ala Lys Leu Leu Lys Leu Lys Ala Gln Leu Gly Pro Asp Glu Ser
        35                  40                  45

Lys Gln Lys Phe Val Leu Lys Thr Pro Lys Gly Thr Arg Asp Tyr Ser
    50                  55                  60

Pro Arg Gln Met Ala Val Arg Glu Lys Val Phe Asp Val Ile
65                  70                  75

<210> SEQ ID NO 56
<211> LENGTH: 77
<212> TYPE: PRT
<213> ORGANISM: Homo sapiens

<400> SEQUENCE: 56

Arg Ala Ala Leu Glu Glu Leu Val Lys Leu Gln Gly Glu Arg Val Arg
1               5                   10                  15

Gly Leu Lys Gln Gln Lys Ala Ser Ala Glu Leu Ile Glu Glu Glu Val
            20                  25                  30

Ala Lys Leu Leu Lys Leu Lys Ala Gln Leu Gly Pro Asp Glu Ser Lys
        35                  40                  45

-continued

Gln Lys Phe Val Leu Lys Thr Pro Lys Gly Thr Arg Asp Tyr Ser Pro
 50                  55                  60

Arg Gln Met Ala Val Arg Glu Lys Val Phe Asp Val Ile
 65                  70                  75

<210> SEQ ID NO 57
<211> LENGTH: 76
<212> TYPE: PRT
<213> ORGANISM: Homo sapiens

<400> SEQUENCE: 57

Ala Ala Leu Glu Glu Leu Val Lys Leu Gln Gly Glu Arg Val Arg Gly
 1               5                  10                  15

Leu Lys Gln Gln Lys Ala Ser Ala Glu Leu Ile Glu Glu Val Ala
                 20                  25                  30

Lys Leu Leu Lys Leu Lys Ala Gln Leu Gly Pro Asp Glu Ser Lys Gln
             35                  40                  45

Lys Phe Val Leu Lys Thr Pro Lys Gly Thr Arg Asp Tyr Ser Pro Arg
 50                  55                  60

Gln Met Ala Val Arg Glu Lys Val Phe Asp Val Ile
 65                  70                  75

<210> SEQ ID NO 58
<211> LENGTH: 75
<212> TYPE: PRT
<213> ORGANISM: Homo sapiens

<400> SEQUENCE: 58

Ala Leu Glu Glu Leu Val Lys Leu Gln Gly Glu Arg Val Arg Gly Leu
 1               5                  10                  15

Lys Gln Gln Lys Ala Ser Ala Glu Leu Ile Glu Glu Val Ala Lys
                 20                  25                  30

Leu Leu Lys Leu Lys Ala Gln Leu Gly Pro Asp Glu Ser Lys Gln Lys
             35                  40                  45

Phe Val Leu Lys Thr Pro Lys Gly Thr Arg Asp Tyr Ser Pro Arg Gln
 50                  55                  60

Met Ala Val Arg Glu Lys Val Phe Asp Val Ile
 65                  70                  75

<210> SEQ ID NO 59
<211> LENGTH: 74
<212> TYPE: PRT
<213> ORGANISM: Homo sapiens

<400> SEQUENCE: 59

Leu Glu Glu Leu Val Lys Leu Gln Gly Glu Arg Val Arg Gly Leu Lys
 1               5                  10                  15

Gln Gln Lys Ala Ser Ala Glu Leu Ile Glu Glu Val Ala Lys Leu
                 20                  25                  30

Leu Lys Leu Lys Ala Gln Leu Gly Pro Asp Glu Ser Lys Gln Lys Phe
             35                  40                  45

Val Leu Lys Thr Pro Lys Gly Thr Arg Asp Tyr Ser Pro Arg Gln Met
 50                  55                  60

Ala Val Arg Glu Lys Val Phe Asp Val Ile
 65                  70

<210> SEQ ID NO 60
<211> LENGTH: 73

```
<212> TYPE: PRT
<213> ORGANISM: Homo sapiens

<400> SEQUENCE: 60

Glu Glu Leu Val Lys Leu Gln Gly Glu Arg Val Arg Gly Leu Lys Gln
1               5                   10                  15

Gln Lys Ala Ser Ala Glu Leu Ile Glu Glu Val Ala Lys Leu Leu
            20                  25                  30

Lys Leu Lys Ala Gln Leu Gly Pro Asp Glu Ser Lys Gln Lys Phe Val
            35                  40                  45

Leu Lys Thr Pro Lys Gly Thr Arg Asp Tyr Ser Pro Arg Gln Met Ala
        50                  55                  60

Val Arg Glu Lys Val Phe Asp Val Ile
65                  70

<210> SEQ ID NO 61
<211> LENGTH: 72
<212> TYPE: PRT
<213> ORGANISM: Homo sapiens

<400> SEQUENCE: 61

Glu Leu Val Lys Leu Gln Gly Glu Arg Val Arg Gly Leu Lys Gln Gln
1               5                   10                  15

Lys Ala Ser Ala Glu Leu Ile Glu Glu Val Ala Lys Leu Leu Lys
            20                  25                  30

Leu Lys Ala Gln Leu Gly Pro Asp Glu Ser Lys Gln Lys Phe Val Leu
            35                  40                  45

Lys Thr Pro Lys Gly Thr Arg Asp Tyr Ser Pro Arg Gln Met Ala Val
        50                  55                  60

Arg Glu Lys Val Phe Asp Val Ile
65                  70

<210> SEQ ID NO 62
<211> LENGTH: 71
<212> TYPE: PRT
<213> ORGANISM: Homo sapiens

<400> SEQUENCE: 62

Leu Val Lys Leu Gln Gly Glu Arg Val Arg Gly Leu Lys Gln Gln Lys
1               5                   10                  15

Ala Ser Ala Glu Leu Ile Glu Glu Val Ala Lys Leu Leu Lys Leu
            20                  25                  30

Lys Ala Gln Leu Gly Pro Asp Glu Ser Lys Gln Lys Phe Val Leu Lys
            35                  40                  45

Thr Pro Lys Gly Thr Arg Asp Tyr Ser Pro Arg Gln Met Ala Val Arg
        50                  55                  60

Glu Lys Val Phe Asp Val Ile
65                  70

<210> SEQ ID NO 63
<211> LENGTH: 70
<212> TYPE: PRT
<213> ORGANISM: Homo sapiens

<400> SEQUENCE: 63

Val Lys Leu Gln Gly Glu Arg Val Arg Gly Leu Lys Gln Gln Lys Ala
1               5                   10                  15

Ser Ala Glu Leu Ile Glu Glu Val Ala Lys Leu Leu Lys Leu Lys
            20                  25                  30
```

Ala Gln Leu Gly Pro Asp Glu Ser Lys Gln Lys Phe Val Leu Lys Thr
            35                  40                  45

Pro Lys Gly Thr Arg Asp Tyr Ser Pro Arg Gln Met Ala Val Arg Glu
        50                  55                  60

Lys Val Phe Asp Val Ile
65                  70

<210> SEQ ID NO 64
<211> LENGTH: 69
<212> TYPE: PRT
<213> ORGANISM: Homo sapiens

<400> SEQUENCE: 64

Lys Leu Gln Gly Glu Arg Val Arg Gly Leu Lys Gln Gln Lys Ala Ser
1               5                   10                  15

Ala Glu Leu Ile Glu Glu Val Ala Lys Leu Leu Lys Leu Lys Ala
            20                  25                  30

Gln Leu Gly Pro Asp Glu Ser Lys Gln Lys Phe Val Leu Lys Thr Pro
        35                  40                  45

Lys Gly Thr Arg Asp Tyr Ser Pro Arg Gln Met Ala Val Arg Glu Lys
    50                  55                  60

Val Phe Asp Val Ile
65

<210> SEQ ID NO 65
<211> LENGTH: 68
<212> TYPE: PRT
<213> ORGANISM: Homo sapiens

<400> SEQUENCE: 65

Leu Gln Gly Glu Arg Val Arg Gly Leu Lys Gln Gln Lys Ala Ser Ala
1               5                   10                  15

Glu Leu Ile Glu Glu Val Ala Lys Leu Leu Lys Leu Lys Ala Gln
            20                  25                  30

Leu Gly Pro Asp Glu Ser Lys Gln Lys Phe Val Leu Lys Thr Pro Lys
        35                  40                  45

Gly Thr Arg Asp Tyr Ser Pro Arg Gln Met Ala Val Arg Glu Lys Val
    50                  55                  60

Phe Asp Val Ile
65

<210> SEQ ID NO 66
<211> LENGTH: 67
<212> TYPE: PRT
<213> ORGANISM: Homo sapiens

<400> SEQUENCE: 66

Gln Gly Glu Arg Val Arg Gly Leu Lys Gln Gln Lys Ala Ser Ala Glu
1               5                   10                  15

Leu Ile Glu Glu Val Ala Lys Leu Leu Lys Leu Lys Ala Gln Leu
            20                  25                  30

Gly Pro Asp Glu Ser Lys Gln Lys Phe Val Leu Lys Thr Pro Lys Gly
        35                  40                  45

Thr Arg Asp Tyr Ser Pro Arg Gln Met Ala Val Arg Glu Lys Val Phe
    50                  55                  60

Asp Val Ile
65

<210> SEQ ID NO 67
<211> LENGTH: 66
<212> TYPE: PRT
<213> ORGANISM: Homo sapiens

<400> SEQUENCE: 67

Gly Glu Arg Val Arg Gly Leu Lys Gln Gln Lys Ala Ser Ala Glu Leu
1               5                   10                  15
Ile Glu Glu Val Ala Lys Leu Leu Lys Leu Lys Ala Gln Leu Gly
            20                  25                  30
Pro Asp Glu Ser Lys Gln Lys Phe Val Leu Lys Thr Pro Lys Gly Thr
                35                  40                  45
Arg Asp Tyr Ser Pro Arg Gln Met Ala Val Arg Glu Lys Val Phe Asp
    50                  55                  60
Val Ile
65

<210> SEQ ID NO 68
<211> LENGTH: 64
<212> TYPE: PRT
<213> ORGANISM: Homo sapiens

<400> SEQUENCE: 68

Arg Val Arg Gly Leu Lys Gln Gln Lys Ala Ser Ala Glu Leu Ile Glu
1               5                   10                  15
Glu Glu Val Ala Lys Leu Leu Lys Leu Lys Ala Gln Leu Gly Pro Asp
            20                  25                  30
Glu Ser Lys Gln Lys Phe Val Leu Lys Thr Pro Lys Gly Thr Arg Asp
        35                  40                  45
Tyr Ser Pro Arg Gln Met Ala Val Arg Glu Lys Val Phe Asp Val Ile
    50                  55                  60

<210> SEQ ID NO 69
<211> LENGTH: 63
<212> TYPE: PRT
<213> ORGANISM: Homo sapiens

<400> SEQUENCE: 69

Val Arg Gly Leu Lys Gln Gln Lys Ala Ser Ala Glu Leu Ile Glu Glu
1               5                   10                  15
Glu Val Ala Lys Leu Leu Lys Leu Lys Ala Gln Leu Gly Pro Asp Glu
            20                  25                  30
Ser Lys Gln Lys Phe Val Leu Lys Thr Pro Lys Gly Thr Arg Asp Tyr
        35                  40                  45
Ser Pro Arg Gln Met Ala Val Arg Glu Lys Val Phe Asp Val Ile
    50                  55                  60

<210> SEQ ID NO 70
<211> LENGTH: 62
<212> TYPE: PRT
<213> ORGANISM: Homo sapiens

<400> SEQUENCE: 70

Arg Gly Leu Lys Gln Gln Lys Ala Ser Ala Glu Leu Ile Glu Glu Glu
1               5                   10                  15
Val Ala Lys Leu Leu Lys Leu Lys Ala Gln Leu Gly Pro Asp Glu Ser
            20                  25                  30
Lys Gln Lys Phe Val Leu Lys Thr Pro Lys Gly Thr Arg Asp Tyr Ser
        35                  40                  45

```
Pro Arg Gln Met Ala Val Arg Glu Lys Val Phe Asp Val Ile
    50                  55                  60
```

<210> SEQ ID NO 71
<211> LENGTH: 61
<212> TYPE: PRT
<213> ORGANISM: Homo sapiens

<400> SEQUENCE: 71

```
Gly Leu Lys Gln Gln Lys Ala Ser Ala Glu Leu Ile Glu Glu Val
1               5                   10                  15

Ala Lys Leu Leu Lys Leu Lys Ala Gln Leu Gly Pro Asp Glu Ser Lys
            20                  25                  30

Gln Lys Phe Val Leu Lys Thr Pro Lys Gly Thr Arg Asp Tyr Ser Pro
        35                  40                  45

Arg Gln Met Ala Val Arg Glu Lys Val Phe Asp Val Ile
    50                  55                  60
```

<210> SEQ ID NO 72
<211> LENGTH: 60
<212> TYPE: PRT
<213> ORGANISM: Homo sapiens

<400> SEQUENCE: 72

```
Leu Lys Gln Gln Lys Ala Ser Ala Glu Leu Ile Glu Glu Val Ala
1               5                   10                  15

Lys Leu Leu Lys Leu Lys Ala Gln Leu Gly Pro Asp Glu Ser Lys Gln
            20                  25                  30

Lys Phe Val Leu Lys Thr Pro Lys Gly Thr Arg Asp Tyr Ser Pro Arg
        35                  40                  45

Gln Met Ala Val Arg Glu Lys Val Phe Asp Val Ile
    50                  55                  60
```

<210> SEQ ID NO 73
<211> LENGTH: 59
<212> TYPE: PRT
<213> ORGANISM: Homo sapiens

<400> SEQUENCE: 73

```
Lys Gln Gln Lys Ala Ser Ala Glu Leu Ile Glu Glu Val Ala Lys
1               5                   10                  15

Leu Leu Lys Leu Lys Ala Gln Leu Gly Pro Asp Glu Ser Lys Gln Lys
            20                  25                  30

Phe Val Leu Lys Thr Pro Lys Gly Thr Arg Asp Tyr Ser Pro Arg Gln
        35                  40                  45

Met Ala Val Arg Glu Lys Val Phe Asp Val Ile
    50                  55
```

<210> SEQ ID NO 74
<211> LENGTH: 58
<212> TYPE: PRT
<213> ORGANISM: Homo sapiens

<400> SEQUENCE: 74

```
Gln Gln Lys Ala Ser Ala Glu Leu Ile Glu Glu Val Ala Lys Leu
1               5                   10                  15

Leu Lys Leu Lys Ala Gln Leu Gly Pro Asp Glu Ser Lys Gln Lys Phe
            20                  25                  30
```

Val Leu Lys Thr Pro Lys Gly Thr Arg Asp Tyr Ser Pro Arg Gln Met
            35                  40                  45

Ala Val Arg Glu Lys Val Phe Asp Val Ile
    50                  55

<210> SEQ ID NO 75
<211> LENGTH: 57
<212> TYPE: PRT
<213> ORGANISM: Homo sapiens

<400> SEQUENCE: 75

Gln Lys Ala Ser Ala Glu Leu Ile Glu Glu Val Ala Lys Leu Leu
1               5                   10                  15

Lys Leu Lys Ala Gln Leu Gly Pro Asp Glu Ser Lys Gln Lys Phe Val
                20                  25                  30

Leu Lys Thr Pro Lys Gly Thr Arg Asp Tyr Ser Pro Arg Gln Met Ala
            35                  40                  45

Val Arg Glu Lys Val Phe Asp Val Ile
    50                  55

<210> SEQ ID NO 76
<211> LENGTH: 56
<212> TYPE: PRT
<213> ORGANISM: Homo sapiens

<400> SEQUENCE: 76

Lys Ala Ser Ala Glu Leu Ile Glu Glu Val Ala Lys Leu Leu Lys
1               5                   10                  15

Leu Lys Ala Gln Leu Gly Pro Asp Glu Ser Lys Gln Lys Phe Val Leu
                20                  25                  30

Lys Thr Pro Lys Gly Thr Arg Asp Tyr Ser Pro Arg Gln Met Ala Val
            35                  40                  45

Arg Glu Lys Val Phe Asp Val Ile
    50                  55

<210> SEQ ID NO 77
<211> LENGTH: 55
<212> TYPE: PRT
<213> ORGANISM: Homo sapiens

<400> SEQUENCE: 77

Ala Ser Ala Glu Leu Ile Glu Glu Val Ala Lys Leu Leu Lys Leu
1               5                   10                  15

Lys Ala Gln Leu Gly Pro Asp Glu Ser Lys Gln Lys Phe Val Leu Lys
                20                  25                  30

Thr Pro Lys Gly Thr Arg Asp Tyr Ser Pro Arg Gln Met Ala Val Arg
            35                  40                  45

Glu Lys Val Phe Asp Val Ile
    50                  55

<210> SEQ ID NO 78
<211> LENGTH: 54
<212> TYPE: PRT
<213> ORGANISM: Homo sapiens

<400> SEQUENCE: 78

Ser Ala Glu Leu Ile Glu Glu Val Ala Lys Leu Leu Lys Leu Lys
1               5                   10                  15

Ala Gln Leu Gly Pro Asp Glu Ser Lys Gln Lys Phe Val Leu Lys Thr
            20                  25                  30

Pro Lys Gly Thr Arg Asp Tyr Ser Pro Arg Gln Met Ala Val Arg Glu
        35                  40                  45

Lys Val Phe Asp Val Ile
        50

<210> SEQ ID NO 79
<211> LENGTH: 53
<212> TYPE: PRT
<213> ORGANISM: Homo sapiens

<400> SEQUENCE: 79

Ala Glu Leu Ile Glu Glu Val Ala Lys Leu Leu Lys Leu Lys Ala
1               5                   10                  15

Gln Leu Gly Pro Asp Glu Ser Lys Gln Lys Phe Val Leu Lys Thr Pro
            20                  25                  30

Lys Gly Thr Arg Asp Tyr Ser Pro Arg Gln Met Ala Val Arg Glu Lys
        35                  40                  45

Val Phe Asp Val Ile
        50

<210> SEQ ID NO 80
<211> LENGTH: 52
<212> TYPE: PRT
<213> ORGANISM: Homo sapiens

<400> SEQUENCE: 80

Glu Leu Ile Glu Glu Val Ala Lys Leu Leu Lys Leu Lys Ala Gln
1               5                   10                  15

Leu Gly Pro Asp Glu Ser Lys Gln Lys Phe Val Leu Lys Thr Pro Lys
            20                  25                  30

Gly Thr Arg Asp Tyr Ser Pro Arg Gln Met Ala Val Arg Glu Lys Val
        35                  40                  45

Phe Asp Val Ile
        50

<210> SEQ ID NO 81
<211> LENGTH: 51
<212> TYPE: PRT
<213> ORGANISM: Homo sapiens

<400> SEQUENCE: 81

Leu Ile Glu Glu Val Ala Lys Leu Leu Lys Leu Lys Ala Gln Leu
1               5                   10                  15

Gly Pro Asp Glu Ser Lys Gln Lys Phe Val Leu Lys Thr Pro Lys Gly
            20                  25                  30

Thr Arg Asp Tyr Ser Pro Arg Gln Met Ala Val Arg Glu Lys Val Phe
        35                  40                  45

Asp Val Ile
        50

<210> SEQ ID NO 82
<211> LENGTH: 50
<212> TYPE: PRT
<213> ORGANISM: Homo sapiens

```
<400> SEQUENCE: 82

Ile Glu Glu Val Ala Lys Leu Leu Lys Leu Lys Ala Gln Leu Gly
1               5                   10                  15

Pro Asp Glu Ser Lys Gln Lys Phe Val Leu Lys Thr Pro Lys Gly Thr
            20                  25                  30

Arg Asp Tyr Ser Pro Arg Gln Met Ala Val Arg Glu Lys Val Phe Asp
        35                  40                  45

Val Ile
    50

<210> SEQ ID NO 83
<211> LENGTH: 49
<212> TYPE: PRT
<213> ORGANISM: Homo sapiens

<400> SEQUENCE: 83

Glu Glu Glu Val Ala Lys Leu Leu Lys Leu Lys Ala Gln Leu Gly Pro
1               5                   10                  15

Asp Glu Ser Lys Gln Lys Phe Val Leu Lys Thr Pro Lys Gly Thr Arg
            20                  25                  30

Asp Tyr Ser Pro Arg Gln Met Ala Val Arg Glu Lys Val Phe Asp Val
        35                  40                  45

Ile

<210> SEQ ID NO 84
<211> LENGTH: 48
<212> TYPE: PRT
<213> ORGANISM: Homo sapiens

<400> SEQUENCE: 84

Glu Glu Val Ala Lys Leu Leu Lys Leu Lys Ala Gln Leu Gly Pro Asp
1               5                   10                  15

Glu Ser Lys Gln Lys Phe Val Leu Lys Thr Pro Lys Gly Thr Arg Asp
            20                  25                  30

Tyr Ser Pro Arg Gln Met Ala Val Arg Glu Lys Val Phe Asp Val Ile
        35                  40                  45

<210> SEQ ID NO 85
<211> LENGTH: 47
<212> TYPE: PRT
<213> ORGANISM: Homo sapiens

<400> SEQUENCE: 85

Glu Val Ala Lys Leu Leu Lys Leu Lys Ala Gln Leu Gly Pro Asp Glu
1               5                   10                  15

Ser Lys Gln Lys Phe Val Leu Lys Thr Pro Lys Gly Thr Arg Asp Tyr
            20                  25                  30

Ser Pro Arg Gln Met Ala Val Arg Glu Lys Val Phe Asp Val Ile
        35                  40                  45

<210> SEQ ID NO 86
<211> LENGTH: 46
<212> TYPE: PRT
<213> ORGANISM: Homo sapiens

<400> SEQUENCE: 86

Val Ala Lys Leu Leu Lys Leu Lys Ala Gln Leu Gly Pro Asp Glu Ser
1               5                   10                  15
```

-continued

Lys Gln Lys Phe Val Leu Lys Thr Pro Lys Gly Thr Arg Asp Tyr Ser
            20                  25                  30

Pro Arg Gln Met Ala Val Arg Glu Lys Val Phe Asp Val Ile
            35                  40                  45

<210> SEQ ID NO 87
<211> LENGTH: 45
<212> TYPE: PRT
<213> ORGANISM: Homo sapiens

<400> SEQUENCE: 87

Ala Lys Leu Leu Lys Leu Lys Ala Gln Leu Gly Pro Asp Glu Ser Lys
1               5                   10                  15

Gln Lys Phe Val Leu Lys Thr Pro Lys Gly Thr Arg Asp Tyr Ser Pro
            20                  25                  30

Arg Gln Met Ala Val Arg Glu Lys Val Phe Asp Val Ile
        35                  40                  45

<210> SEQ ID NO 88
<211> LENGTH: 44
<212> TYPE: PRT
<213> ORGANISM: Homo sapiens

<400> SEQUENCE: 88

Lys Leu Leu Lys Leu Lys Ala Gln Leu Gly Pro Asp Glu Ser Lys Gln
1               5                   10                  15

Lys Phe Val Leu Lys Thr Pro Lys Gly Thr Arg Asp Tyr Ser Pro Arg
            20                  25                  30

Gln Met Ala Val Arg Glu Lys Val Phe Asp Val Ile
        35                  40

<210> SEQ ID NO 89
<211> LENGTH: 43
<212> TYPE: PRT
<213> ORGANISM: Homo sapiens

<400> SEQUENCE: 89

Leu Leu Lys Leu Lys Ala Gln Leu Gly Pro Asp Glu Ser Lys Gln Lys
1               5                   10                  15

Phe Val Leu Lys Thr Pro Lys Gly Thr Arg Asp Tyr Ser Pro Arg Gln
            20                  25                  30

Met Ala Val Arg Glu Lys Val Phe Asp Val Ile
        35                  40

<210> SEQ ID NO 90
<211> LENGTH: 42
<212> TYPE: PRT
<213> ORGANISM: Homo sapiens

<400> SEQUENCE: 90

Leu Lys Leu Lys Ala Gln Leu Gly Pro Asp Glu Ser Lys Gln Lys Phe
1               5                   10                  15

Val Leu Lys Thr Pro Lys Gly Thr Arg Asp Tyr Ser Pro Arg Gln Met
            20                  25                  30

Ala Val Arg Glu Lys Val Phe Asp Val Ile
        35                  40

<210> SEQ ID NO 91
<211> LENGTH: 41
<212> TYPE: PRT
<213> ORGANISM: Homo sapiens

```
<400> SEQUENCE: 91

Lys Leu Lys Ala Gln Leu Gly Pro Asp Glu Ser Lys Gln Lys Phe Val
1               5                   10                  15

Leu Lys Thr Pro Lys Gly Thr Arg Asp Tyr Ser Pro Arg Gln Met Ala
            20                  25                  30

Val Arg Glu Lys Val Phe Asp Val Ile
        35                  40

<210> SEQ ID NO 92
<211> LENGTH: 40
<212> TYPE: PRT
<213> ORGANISM: Homo sapiens

<400> SEQUENCE: 92

Leu Lys Ala Gln Leu Gly Pro Asp Glu Ser Lys Gln Lys Phe Val Leu
1               5                   10                  15

Lys Thr Pro Lys Gly Thr Arg Asp Tyr Ser Pro Arg Gln Met Ala Val
            20                  25                  30

Arg Glu Lys Val Phe Asp Val Ile
        35                  40

<210> SEQ ID NO 93
<211> LENGTH: 141
<212> TYPE: PRT
<213> ORGANISM: Homo sapiens

<400> SEQUENCE: 93

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met
    130                 135                 140

<210> SEQ ID NO 94
<211> LENGTH: 408
<212> TYPE: PRT
<213> ORGANISM: Homo sapiens

<400> SEQUENCE: 94

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30
```

Glu Glu Val Ala Lys Leu Leu Lys Leu Lys Ala Gln Leu Gly Pro Asp
             35                  40                  45

Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
                115                 120                 125

Tyr Asp Leu Thr Val Pro Phe Ala Arg Tyr Leu Ala Met Asn Lys Leu
            130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
            210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
            275                 280                 285

Leu Ser Gln Asn Lys Gln Ala Leu Glu Gly Leu Gly Asp Leu Lys Leu
            290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
            370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu
                405

<210> SEQ ID NO 95
<211> LENGTH: 113
<212> TYPE: PRT
<213> ORGANISM: Homo sapiens

<400> SEQUENCE: 95

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Asp Ser Lys
            100                 105                 110

Leu

<210> SEQ ID NO 96
<211> LENGTH: 60
<212> TYPE: PRT
<213> ORGANISM: Homo sapiens

<400> SEQUENCE: 96

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
50                  55                  60

<210> SEQ ID NO 97
<211> LENGTH: 270
<212> TYPE: PRT
<213> ORGANISM: Homo sapiens

<400> SEQUENCE: 97

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

```
Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Gly Tyr Pro Trp Trp Asn Ser Cys Ser Arg Ile Leu
                245                 250                 255

Asn Tyr Pro Lys Thr Ser Arg Pro Trp Arg Ala Trp Glu Thr
            260                 265                 270

<210> SEQ ID NO 98
<211> LENGTH: 105
<212> TYPE: PRT
<213> ORGANISM: Homo sapiens

<400> SEQUENCE: 98

Arg Thr Thr Glu Thr Gln Val Leu Val Ala Ser Ala Gln Lys Lys Leu
1               5                   10                  15

Leu Glu Glu Arg Leu Lys Leu Val Ser Glu Leu Trp Asp Ala Gly Ile
                20                  25                  30

Lys Ala Glu Leu Leu Tyr Lys Lys Asn Pro Lys Leu Leu Asn Gln Leu
            35                  40                  45

Gln Tyr Cys Glu Glu Ala Gly Ile Pro Leu Val Ala Ile Ile Gly Glu
        50                  55                  60

Gln Glu Leu Lys Asp Gly Val Ile Lys Leu Arg Ser Val Thr Ser Arg
65                  70                  75                  80

Glu Glu Val Asp Val Arg Arg Glu Asp Leu Val Glu Glu Ile Lys Arg
                85                  90                  95

Arg Thr Gly Gln Pro Leu Cys Ile Cys
            100                 105

<210> SEQ ID NO 99
<211> LENGTH: 395
<212> TYPE: PRT
<213> ORGANISM: Homo sapiens

<400> SEQUENCE: 99

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Asp Phe Asp Ile
        50                  55                  60

Ala Gly Asn Phe Asp Pro Met Ile Pro Asp Ala Glu Cys Leu Lys Ile
65                  70                  75                  80

Met Cys Glu Ile Leu Ser Ser Leu Gln Ile Gly Asp Phe Leu Val Lys
                85                  90                  95
```

Val Asn Asp Arg Arg Ile Leu Asp Gly Met Phe Ala Ile Cys Gly Val
            100                 105                 110

Ser Asp Ser Lys Phe Arg Thr Ile Cys Ser Ser Val Asp Lys Leu Asp
            115                 120                 125

Lys Val Ser Trp Glu Glu Val Lys Asn Glu Met Val Gly Glu Lys Gly
130                 135                 140

Leu Ala Pro Glu Val Ala Asp Arg Ile Gly Asp Tyr Val Gln Gln His
145                 150                 155                 160

Gly Gly Val Ser Leu Val Glu Gln Leu Leu Gln Asp Pro Lys Leu Ser
            165                 170                 175

Gln Asn Lys Gln Ala Leu Glu Gly Leu Gly Asp Leu Lys Leu Leu Phe
            180                 185                 190

Glu Tyr Leu Thr Leu Phe Gly Ile Asp Asp Lys Ile Ser Phe Asp Leu
            195                 200                 205

Ser Leu Ala Arg Gly Leu Asp Tyr Tyr Thr Gly Val Ile Tyr Glu Ala
            210                 215                 220

Val Leu Leu Gln Thr Pro Ala Gln Ala Gly Glu Glu Pro Leu Gly Val
225                 230                 235                 240

Gly Ser Val Ala Ala Gly Gly Arg Tyr Asp Gly Leu Val Gly Met Phe
            245                 250                 255

Asp Pro Lys Gly Arg Lys Val Pro Cys Val Gly Leu Ser Ile Gly Val
            260                 265                 270

Glu Arg Ile Phe Ser Ile Val Glu Gln Arg Leu Glu Ala Leu Glu Glu
            275                 280                 285

Lys Ile Arg Thr Thr Glu Thr Gln Val Leu Val Ala Ser Ala Gln Lys
290                 295                 300

Lys Leu Leu Glu Glu Arg Leu Lys Leu Val Ser Glu Leu Trp Asp Ala
305                 310                 315                 320

Gly Ile Lys Ala Glu Leu Leu Tyr Lys Lys Asn Pro Lys Leu Leu Asn
            325                 330                 335

Gln Leu Gln Tyr Cys Glu Glu Ala Gly Ile Pro Leu Val Ala Ile Ile
            340                 345                 350

Gly Glu Gln Glu Leu Lys Asp Gly Val Ile Lys Leu Arg Ser Val Thr
            355                 360                 365

Ser Arg Glu Glu Val Asp Val Arg Arg Glu Asp Leu Val Glu Glu Ile
            370                 375                 380

Lys Arg Arg Thr Gly Gln Pro Leu Cys Ile Cys
385                 390                 395

<210> SEQ ID NO 100
<211> LENGTH: 359
<212> TYPE: PRT
<213> ORGANISM: Homo sapiens

<400> SEQUENCE: 100

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Val Asn Asp Arg
50                  55                  60

```
Arg Ile Leu Asp Gly Met Phe Ala Ile Cys Gly Val Ser Asp Ser Lys
 65                  70                  75                  80

Phe Arg Thr Ile Cys Ser Ser Val Asp Lys Leu Asp Lys Val Ser Trp
                 85                  90                  95

Glu Glu Val Lys Asn Glu Met Val Gly Glu Lys Gly Leu Ala Pro Glu
            100                 105                 110

Val Ala Asp Arg Ile Gly Asp Tyr Val Gln Gln His Gly Gly Val Ser
            115                 120                 125

Leu Val Glu Gln Leu Leu Gln Asp Pro Lys Leu Ser Gln Asn Lys Gln
        130                 135                 140

Ala Leu Glu Gly Leu Gly Asp Leu Lys Leu Leu Phe Glu Tyr Leu Thr
145                 150                 155                 160

Leu Phe Gly Ile Asp Asp Lys Ile Ser Phe Asp Leu Ser Leu Ala Arg
                165                 170                 175

Gly Leu Asp Tyr Tyr Thr Gly Val Ile Tyr Glu Ala Val Leu Leu Gln
            180                 185                 190

Thr Pro Ala Gln Ala Gly Glu Glu Pro Leu Gly Val Gly Ser Val Ala
        195                 200                 205

Ala Gly Gly Arg Tyr Asp Gly Leu Val Gly Met Phe Asp Pro Lys Gly
210                 215                 220

Arg Lys Val Pro Cys Val Gly Leu Ser Ile Gly Val Glu Arg Ile Phe
225                 230                 235                 240

Ser Ile Val Glu Gln Arg Leu Glu Ala Leu Glu Glu Lys Ile Arg Thr
                245                 250                 255

Thr Glu Thr Gln Val Leu Val Ala Ser Ala Gln Lys Lys Leu Leu Glu
            260                 265                 270

Glu Arg Leu Lys Leu Val Ser Glu Leu Trp Asp Ala Gly Ile Lys Ala
        275                 280                 285

Glu Leu Leu Tyr Lys Lys Asn Pro Lys Leu Leu Asn Gln Leu Gln Tyr
            290                 295                 300

Cys Glu Glu Ala Gly Ile Pro Leu Val Ala Ile Ile Gly Glu Gln Glu
305                 310                 315                 320

Leu Lys Asp Gly Val Ile Lys Leu Arg Ser Val Thr Ser Arg Glu Glu
                325                 330                 335

Val Asp Val Arg Arg Glu Asp Leu Val Glu Glu Ile Lys Arg Arg Thr
            340                 345                 350

Gly Gln Pro Leu Cys Ile Cys
        355

<210> SEQ ID NO 101
<211> LENGTH: 399
<212> TYPE: PRT
<213> ORGANISM: Homo sapiens

<400> SEQUENCE: 101

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60
```

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Val Asn Asp Arg Arg Ile Leu Asp Gly Met Phe Ala
            100                 105                 110

Ile Cys Gly Val Ser Asp Ser Lys Phe Arg Thr Ile Cys Ser Ser Val
        115                 120                 125

Asp Lys Leu Asp Lys Val Ser Trp Glu Glu Val Lys Asn Glu Met Val
130                 135                 140

Gly Glu Lys Gly Leu Ala Pro Glu Val Ala Asp Arg Ile Gly Asp Tyr
145                 150                 155                 160

Val Gln Gln His Gly Gly Val Ser Leu Val Glu Gln Leu Leu Gln Asp
                165                 170                 175

Pro Lys Leu Ser Gln Asn Lys Gln Ala Leu Glu Gly Leu Gly Asp Leu
            180                 185                 190

Lys Leu Leu Phe Glu Tyr Leu Thr Leu Phe Gly Ile Asp Asp Lys Ile
        195                 200                 205

Ser Phe Asp Leu Ser Leu Ala Arg Gly Leu Asp Tyr Tyr Thr Gly Val
210                 215                 220

Ile Tyr Glu Ala Val Leu Leu Gln Thr Pro Ala Gln Ala Gly Glu Glu
225                 230                 235                 240

Pro Leu Gly Val Gly Ser Val Ala Ala Gly Arg Tyr Asp Gly Leu
                245                 250                 255

Val Gly Met Phe Asp Pro Lys Gly Arg Lys Val Pro Cys Val Gly Leu
            260                 265                 270

Ser Ile Gly Val Glu Arg Ile Phe Ser Ile Val Glu Gln Arg Leu Glu
        275                 280                 285

Ala Leu Glu Glu Lys Ile Arg Thr Thr Glu Thr Gln Val Leu Val Ala
        290                 295                 300

Ser Ala Gln Lys Lys Leu Leu Glu Glu Arg Leu Lys Leu Val Ser Glu
305                 310                 315                 320

Leu Trp Asp Ala Gly Ile Lys Ala Glu Leu Leu Tyr Lys Lys Asn Pro
            325                 330                 335

Lys Leu Leu Asn Gln Leu Gln Tyr Cys Glu Glu Ala Gly Ile Pro Leu
            340                 345                 350

Val Ala Ile Ile Gly Glu Gln Glu Leu Lys Asp Gly Val Ile Lys Leu
        355                 360                 365

Arg Ser Val Thr Ser Arg Glu Glu Val Asp Val Arg Arg Glu Asp Leu
370                 375                 380

Val Glu Glu Ile Lys Arg Arg Thr Gly Gln Pro Leu Cys Ile Cys
385                 390                 395

<210> SEQ ID NO 102
<211> LENGTH: 473
<212> TYPE: PRT
<213> ORGANISM: Homo sapiens

<400> SEQUENCE: 102

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

```
Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Val Asn
                165                 170                 175

Asp Arg Arg Ile Leu Asp Gly Met Phe Ala Ile Cys Gly Val Ser Asp
                180                 185                 190

Ser Lys Phe Arg Thr Ile Cys Ser Ser Val Asp Lys Leu Asp Lys Val
            195                 200                 205

Ser Trp Glu Glu Val Lys Asn Glu Met Val Gly Glu Lys Gly Leu Ala
        210                 215                 220

Pro Glu Val Ala Asp Arg Ile Gly Asp Tyr Val Gln Gln His Gly Gly
225                 230                 235                 240

Val Ser Leu Val Glu Gln Leu Leu Gln Asp Pro Lys Leu Ser Gln Asn
                245                 250                 255

Lys Gln Ala Leu Glu Gly Leu Gly Asp Leu Lys Leu Leu Phe Glu Tyr
                260                 265                 270

Leu Thr Leu Phe Gly Ile Asp Asp Lys Ile Ser Phe Asp Leu Ser Leu
            275                 280                 285

Ala Arg Gly Leu Asp Tyr Tyr Thr Gly Val Ile Tyr Glu Ala Val Leu
        290                 295                 300

Leu Gln Thr Pro Ala Gln Ala Gly Glu Glu Pro Leu Gly Val Gly Ser
305                 310                 315                 320

Val Ala Ala Gly Gly Arg Tyr Asp Gly Leu Val Gly Met Phe Asp Pro
                325                 330                 335

Lys Gly Arg Lys Val Pro Cys Val Gly Leu Ser Ile Gly Val Glu Arg
                340                 345                 350

Ile Phe Ser Ile Val Glu Gln Arg Leu Glu Ala Leu Glu Glu Lys Ile
            355                 360                 365

Arg Thr Thr Glu Thr Gln Val Leu Val Ala Ser Ala Gln Lys Lys Leu
        370                 375                 380

Leu Glu Glu Arg Leu Lys Leu Val Ser Glu Leu Trp Asp Ala Gly Ile
385                 390                 395                 400

Lys Ala Glu Leu Leu Tyr Lys Lys Asn Pro Lys Leu Leu Asn Gln Leu
                405                 410                 415

Gln Tyr Cys Glu Glu Ala Gly Ile Pro Leu Val Ala Ile Ile Gly Glu
                420                 425                 430

Gln Glu Leu Lys Asp Gly Val Ile Lys Leu Arg Ser Val Thr Ser Arg
            435                 440                 445
```

```
Glu Glu Val Asp Val Arg Arg Glu Asp Leu Val Glu Ile Lys Arg
450                 455                 460

Arg Thr Gly Gln Pro Leu Cys Ile Cys
465                 470

<210> SEQ ID NO 103
<211> LENGTH: 469
<212> TYPE: PRT
<213> ORGANISM: Homo sapiens

<400> SEQUENCE: 103

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Ala Gln Leu Gly Pro Asp
        35                  40                  45

Glu Ser Lys Gln Lys Phe Val Leu Lys Thr Pro Lys Glu Thr Leu Met
50                  55                  60

Gly Lys Tyr Gly Glu Asp Ser Lys Leu Ile Tyr Asp Leu Lys Asp Gln
65                  70                  75                  80

Gly Gly Glu Leu Leu Ser Leu Arg Tyr Asp Leu Thr Val Pro Phe Ala
            85                  90                  95

Arg Tyr Leu Ala Met Asn Lys Leu Thr Asn Ile Lys Arg Tyr His Ile
        100                 105                 110

Ala Lys Val Tyr Arg Arg Asp Asn Pro Ala Met Thr Arg Gly Arg Tyr
    115                 120                 125

Arg Glu Phe Tyr Gln Cys Asp Phe Asp Ile Ala Gly Asn Phe Asp Pro
130                 135                 140

Met Ile Pro Asp Ala Glu Cys Leu Lys Ile Met Cys Glu Ile Leu Ser
145                 150                 155                 160

Ser Leu Gln Ile Gly Asp Phe Leu Val Lys Val Asn Asp Arg Arg Ile
            165                 170                 175

Leu Asp Gly Met Phe Ala Ile Cys Gly Val Ser Asp Ser Lys Phe Arg
        180                 185                 190

Thr Ile Cys Ser Ser Val Asp Lys Leu Asp Lys Val Ser Trp Glu Glu
    195                 200                 205

Val Lys Asn Glu Met Val Gly Glu Lys Gly Leu Ala Pro Glu Val Ala
210                 215                 220

Asp Arg Ile Gly Asp Tyr Val Gln Gln His Gly Gly Val Ser Leu Val
225                 230                 235                 240

Glu Gln Leu Leu Gln Asp Pro Lys Leu Ser Gln Asn Lys Gln Ala Leu
            245                 250                 255

Glu Gly Leu Gly Asp Leu Lys Leu Leu Phe Glu Tyr Leu Thr Leu Phe
        260                 265                 270

Gly Ile Asp Asp Lys Ile Ser Phe Asp Leu Ser Leu Ala Arg Gly Leu
    275                 280                 285

Asp Tyr Tyr Thr Gly Val Ile Tyr Glu Ala Val Leu Leu Gln Thr Pro
290                 295                 300

Ala Gln Ala Gly Glu Glu Pro Leu Gly Val Gly Ser Val Ala Ala Gly
305                 310                 315                 320

Gly Arg Tyr Asp Gly Leu Val Gly Met Phe Asp Pro Lys Gly Arg Lys
            325                 330                 335

Val Pro Cys Val Gly Leu Ser Ile Gly Val Glu Arg Ile Phe Ser Ile
        340                 345                 350
```

```
Val Glu Gln Arg Leu Glu Ala Leu Glu Glu Lys Ile Arg Thr Thr Glu
            355                 360                 365

Thr Gln Val Leu Val Ala Ser Ala Gln Lys Lys Leu Leu Glu Glu Arg
        370                 375                 380

Leu Lys Leu Val Ser Glu Leu Trp Asp Ala Gly Ile Lys Ala Glu Leu
385                 390                 395                 400

Leu Tyr Lys Lys Asn Pro Lys Leu Leu Asn Gln Leu Gln Tyr Cys Glu
                405                 410                 415

Glu Ala Gly Ile Pro Leu Val Ala Ile Ile Gly Glu Gln Glu Leu Lys
            420                 425                 430

Asp Gly Val Ile Lys Leu Arg Ser Val Thr Ser Arg Glu Glu Val Asp
            435                 440                 445

Val Arg Arg Glu Asp Leu Val Glu Glu Ile Lys Arg Arg Thr Gly Gln
        450                 455                 460

Pro Leu Cys Ile Cys
465

<210> SEQ ID NO 104
<211> LENGTH: 435
<212> TYPE: PRT
<213> ORGANISM: Homo sapiens

<400> SEQUENCE: 104

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
            85                  90                  95

Phe Glu Leu Lys Asp Phe Asp Ile Ala Gly Asn Phe Asp Pro Met Ile
            100                 105                 110

Pro Asp Ala Glu Cys Leu Lys Ile Met Cys Glu Ile Leu Ser Ser Leu
        115                 120                 125

Gln Ile Gly Asp Phe Leu Val Lys Val Asn Asp Arg Arg Ile Leu Asp
    130                 135                 140

Gly Met Phe Ala Ile Cys Gly Val Ser Asp Ser Lys Phe Arg Thr Ile
145                 150                 155                 160

Cys Ser Ser Val Asp Lys Leu Asp Lys Val Ser Trp Glu Glu Val Lys
            165                 170                 175

Asn Glu Met Val Gly Glu Lys Gly Leu Ala Pro Glu Val Ala Asp Arg
        180                 185                 190

Ile Gly Asp Tyr Val Gln Gln His Gly Gly Val Ser Leu Val Glu Gln
    195                 200                 205

Leu Leu Gln Asp Pro Lys Leu Ser Gln Asn Lys Gln Ala Leu Glu Gly
    210                 215                 220

Leu Gly Asp Leu Lys Leu Leu Phe Glu Tyr Leu Thr Leu Phe Gly Ile
225                 230                 235                 240
```

```
Asp Asp Lys Ile Ser Phe Asp Leu Ser Leu Ala Arg Gly Leu Asp Tyr
                245                 250                 255

Tyr Thr Gly Val Ile Tyr Glu Ala Val Leu Leu Gln Thr Pro Ala Gln
            260                 265                 270

Ala Gly Glu Glu Pro Leu Gly Val Gly Ser Val Ala Ala Gly Gly Arg
        275                 280                 285

Tyr Asp Gly Leu Val Gly Met Phe Asp Pro Lys Gly Arg Lys Val Pro
    290                 295                 300

Cys Val Gly Leu Ser Ile Gly Val Glu Arg Ile Phe Ser Ile Val Glu
305                 310                 315                 320

Gln Arg Leu Glu Ala Leu Glu Glu Lys Ile Arg Thr Thr Glu Thr Gln
                325                 330                 335

Val Leu Val Ala Ser Ala Gln Lys Lys Leu Leu Glu Glu Arg Leu Lys
            340                 345                 350

Leu Val Ser Glu Leu Trp Asp Ala Gly Ile Lys Ala Glu Leu Leu Tyr
        355                 360                 365

Lys Lys Asn Pro Lys Leu Leu Asn Gln Leu Gln Tyr Cys Glu Glu Ala
    370                 375                 380

Gly Ile Pro Leu Val Ala Ile Ile Gly Glu Gln Glu Leu Lys Asp Gly
385                 390                 395                 400

Val Ile Lys Leu Arg Ser Val Thr Ser Arg Glu Val Asp Val Arg
                405                 410                 415

Arg Glu Asp Leu Val Glu Glu Ile Lys Arg Arg Thr Gly Gln Pro Leu
            420                 425                 430

Cys Ile Cys
        435

<210> SEQ ID NO 105
<211> LENGTH: 171
<212> TYPE: PRT
<213> ORGANISM: Homo sapiens

<400> SEQUENCE: 105

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Ala Leu Glu Glu
        50                  55                  60

Lys Ile Arg Thr Thr Glu Thr Gln Val Leu Val Ala Ser Ala Gln Lys
65                  70                  75                  80

Lys Leu Leu Glu Glu Arg Leu Lys Leu Val Ser Glu Leu Trp Asp Ala
                85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
        115                 120                 125

Gly Glu Gln Glu Leu Lys Asp Gly Val Ile Lys Leu Arg Ser Val Thr
    130                 135                 140
```

```
Ser Arg Glu Glu Val Asp Val Arg Arg Glu Asp Leu Val Glu Ile
145                 150                 155                 160

Lys Arg Arg Thr Gly Gln Pro Leu Cys Ile Cys
                165                 170
```

<210> SEQ ID NO 106
<211> LENGTH: 211
<212> TYPE: PRT
<213> ORGANISM: Homo sapiens

<400> SEQUENCE: 106

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Ala Leu Glu Glu Lys Ile Arg Thr Thr Glu Thr Gln
                100                 105                 110

Val Leu Val Ala Ser Ala Gln Lys Lys Leu Leu Glu Glu Arg Leu Lys
            115                 120                 125

Leu Val Ser Glu Leu Trp Asp Ala Gly Ile Lys Ala Glu Leu Leu Tyr
130                 135                 140

Lys Lys Asn Pro Lys Leu Leu Asn Gln Leu Gln Tyr Cys Glu Glu Ala
145                 150                 155                 160

Gly Ile Pro Leu Val Ala Ile Ile Gly Glu Gln Glu Leu Lys Asp Gly
                165                 170                 175

Val Ile Lys Leu Arg Ser Val Thr Ser Arg Glu Glu Val Asp Val Arg
            180                 185                 190

Arg Glu Asp Leu Val Glu Ile Lys Arg Arg Thr Gly Gln Pro Leu
                195                 200                 205

Cys Ile Cys
    210
```

<210> SEQ ID NO 107
<211> LENGTH: 141
<212> TYPE: PRT
<213> ORGANISM: Homo sapiens

<400> SEQUENCE: 107

```
Met Phe Asp Pro Lys Gly Arg Lys Val Pro Cys Val Gly Leu Ser Ile
1               5                   10                  15

Gly Val Glu Arg Ile Phe Ser Ile Val Glu Gln Arg Leu Glu Ala Leu
                20                  25                  30

Glu Glu Lys Ile Arg Thr Thr Glu Thr Gln Val Leu Val Ala Ser Ala
            35                  40                  45

Gln Lys Lys Leu Leu Glu Glu Arg Leu Lys Leu Val Ser Glu Leu Trp
50                  55                  60

Asp Ala Gly Ile Lys Ala Glu Leu Leu Tyr Lys Lys Asn Pro Lys Leu
65                  70                  75                  80
```

```
Leu Asn Gln Leu Gln Tyr Cys Glu Glu Ala Gly Ile Pro Leu Val Ala
                85                  90                  95

Ile Ile Gly Glu Gln Glu Leu Lys Asp Gly Val Ile Lys Leu Arg Ser
            100                 105                 110

Val Thr Ser Arg Glu Glu Val Asp Val Arg Arg Glu Asp Leu Val Glu
        115                 120                 125

Glu Ile Lys Arg Arg Thr Gly Gln Pro Leu Cys Ile Cys
130                 135                 140

<210> SEQ ID NO 108
<211> LENGTH: 143
<212> TYPE: PRT
<213> ORGANISM: Homo sapiens

<400> SEQUENCE: 108

Cys Leu Lys Ile Met Cys Glu Ile Leu Ser Leu Gln Ile Gly Asp
1               5                   10                  15

Phe Leu Val Lys Val Asn Asp Arg Arg Ile Leu Asp Gly Met Phe Ala
            20                  25                  30

Ile Cys Gly Val Ser Asp Ser Lys Phe Arg Thr Ile Cys Ser Ser Val
        35                  40                  45

Asp Lys Leu Asp Lys Val Ser Trp Glu Glu Val Lys Asn Glu Met Val
50                  55                  60

Gly Glu Lys Gly Leu Ala Pro Glu Val Ala Asp Arg Ile Gly Asp Tyr
65                  70                  75                  80

Val Gln Gln His Gly Gly Val Ser Leu Val Glu Gln Leu Leu Gln Asp
                85                  90                  95

Pro Lys Leu Ser Gln Asn Lys Gln Ala Leu Glu Gly Leu Gly Asp Leu
            100                 105                 110

Lys Leu Leu Phe Glu Tyr Leu Thr Leu Phe Gly Ile Asp Asp Lys Ile
        115                 120                 125

Ser Phe Asp Leu Ser Leu Ala Arg Gly Leu Asp Tyr Tyr Thr Gly
130                 135                 140

<210> SEQ ID NO 109
<211> LENGTH: 506
<212> TYPE: PRT
<213> ORGANISM: Homo sapiens

<400> SEQUENCE: 109

Met Pro Leu Leu Gly Leu Leu Pro Arg Arg Ala Trp Ala Ser Leu Leu
1               5                   10                  15

Ser Gln Leu Leu Arg Pro Pro Cys Ala Ser Cys Thr Gly Ala Val Arg
            20                  25                  30

Cys Gln Ser Gln Val Ala Glu Ala Val Leu Thr Ser Gln Leu Lys Ala
        35                  40                  45

His Gln Glu Lys Pro Asn Phe Ile Ile Lys Thr Pro Lys Gly Thr Arg
    50                  55                  60

Asp Leu Ser Pro Gln His Met Val Val Arg Glu Lys Ile Leu Asp Leu
65                  70                  75                  80

Val Ile Ser Cys Phe Lys Arg His Gly Ala Lys Gly Met Asp Thr Pro
                85                  90                  95

Ala Phe Glu Leu Lys Glu Thr Leu Thr Glu Lys Tyr Gly Glu Asp Ser
            100                 105                 110

Gly Leu Met Tyr Asp Leu Lys Asp Gln Gly Gly Glu Leu Leu Ser Leu
        115                 120                 125
```

Arg Tyr Asp Leu Thr Val Pro Phe Ala Arg Tyr Leu Ala Met Asn Lys
130                 135                 140

Val Lys Lys Met Lys Arg Tyr His Val Gly Lys Val Trp Arg Arg Glu
145                 150                 155                 160

Ser Pro Thr Ile Val Gln Gly Arg Tyr Arg Glu Phe Cys Gln Cys Asp
                165                 170                 175

Phe Asp Ile Ala Gly Gln Phe Asp Pro Met Ile Pro Asp Ala Glu Cys
                180                 185                 190

Leu Lys Ile Met Cys Glu Ile Leu Ser Gly Leu Gln Leu Gly Asp Phe
                195                 200                 205

Leu Ile Lys Val Asn Asp Arg Arg Ile Val Asp Gly Met Phe Ala Val
210                 215                 220

Cys Gly Val Pro Glu Ser Lys Phe Arg Ala Ile Cys Ser Ser Ile Asp
225                 230                 235                 240

Lys Leu Asp Lys Met Ala Trp Lys Asp Val Arg His Glu Met Val Val
                245                 250                 255

Lys Lys Gly Leu Ala Pro Glu Val Ala Asp Arg Ile Gly Asp Tyr Val
                260                 265                 270

Gln Cys His Gly Gly Val Ser Leu Val Glu Gln Met Phe Gln Asp Pro
                275                 280                 285

Arg Leu Ser Gln Asn Lys Gln Ala Leu Glu Gly Leu Gly Asp Leu Lys
290                 295                 300

Leu Leu Phe Glu Tyr Leu Thr Leu Phe Gly Ile Ala Asp Lys Ile Ser
305                 310                 315                 320

Phe Asp Leu Ser Leu Ala Arg Gly Leu Asp Tyr Tyr Thr Gly Val Ile
                325                 330                 335

Tyr Glu Ala Val Leu Leu Gln Thr Pro Thr Gln Ala Gly Glu Glu Pro
                340                 345                 350

Leu Asn Val Gly Ser Val Ala Ala Gly Gly Arg Tyr Asp Gly Leu Val
                355                 360                 365

Gly Met Phe Asp Pro Lys Gly His Lys Val Pro Cys Val Gly Leu Ser
370                 375                 380

Ile Gly Val Glu Arg Ile Phe Tyr Ile Val Glu Gln Arg Met Lys Thr
385                 390                 395                 400

Lys Gly Glu Lys Val Arg Thr Thr Glu Thr Gln Val Phe Val Ala Thr
                405                 410                 415

Pro Gln Lys Asn Phe Leu Gln Glu Arg Leu Lys Leu Ile Ala Glu Leu
                420                 425                 430

Trp Asp Ser Gly Ile Lys Ala Glu Met Leu Tyr Lys Asn Asn Pro Lys
                435                 440                 445

Leu Leu Thr Gln Leu His Tyr Cys Glu Ser Thr Gly Ile Pro Leu Val
                450                 455                 460

Val Ile Ile Gly Glu Gln Glu Leu Lys Glu Gly Val Ile Lys Ile Arg
465                 470                 475                 480

Ser Val Ala Ser Arg Glu Glu Val Ala Ile Lys Arg Glu Asn Phe Val
                485                 490                 495

Ala Glu Ile Gln Lys Arg Leu Ser Glu Ser
                500                 505

<210> SEQ ID NO 110
<211> LENGTH: 509
<212> TYPE: PRT
<213> ORGANISM: Mus musculus

```
<400> SEQUENCE: 110

Met Ala Asp Arg Ala Ala Leu Glu Glu Leu Val Arg Leu Gln Gly Ala
1               5                   10                  15

His Val Arg Gly Leu Lys Glu Gln Lys Ala Ser Ala Glu Gln Ile Glu
            20                  25                  30

Glu Glu Val Thr Lys Leu Leu Lys Leu Lys Ala Gln Leu Gly Gln Asp
            35                  40                  45

Glu Gly Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Lys Ile Met Cys Glu Ile Leu Ser Ser Leu Gln Ile Gly Asn Phe Leu
        195                 200                 205

Val Lys Val Asn Asp Arg Arg Ile Leu Asp Gly Met Phe Ala Val Cys
210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Val Glu Gly Leu Gly Asp Leu Lys Leu
290                 295                 300

Leu Phe Glu Tyr Leu Ile Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
            340                 345                 350

Gly Val Gly Ser Ile Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Ser
385                 390                 395                 400

Glu Glu Lys Val Arg Thr Thr Glu Thr Gln Val Leu Val Ala Ser Ala
                405                 410                 415
```

```
Gln Lys Lys Leu Leu Glu Glu Arg Leu Lys Leu Val Ser Glu Leu Trp
            420                 425                 430

Asp Ala Gly Ile Lys Ala Glu Leu Tyr Lys Lys Asn Pro Lys Leu
            435                 440                 445

Leu Asn Gln Leu Gln Tyr Trp Glu Glu Ala Gly Ile Pro Leu Val Ala
450                 455                 460

Ile Ile Gly Glu Gln Glu Leu Arg Asp Gly Val Ile Lys Leu Arg Ser
465                 470                 475                 480

Val Ala Ser Arg Glu Glu Val Asp Val Arg Arg Glu Asp Leu Val Glu
                485                 490                 495

Glu Ile Arg Arg Arg Thr Asn Gln Pro Leu Ser Thr Cys
                500                 505

<210> SEQ ID NO 111
<211> LENGTH: 509
<212> TYPE: PRT
<213> ORGANISM: Canis lupus familiaris

<400> SEQUENCE: 111

Met Ala Glu Arg Ala Ala Leu Glu Glu Leu Val Arg Leu Gln Gly Glu
1               5                   10                  15

Arg Val Arg Gly Leu Lys Gln Gln Lys Ala Ser Ala Glu Gln Ile Glu
            20                  25                  30

Glu Glu Val Ala Lys Leu Leu Lys Leu Ala Gln Leu Gly Pro Asp
        35                  40                  45

Glu Gly Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Glu Ile Met Cys Glu Ile Leu Arg Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp His Ile Gly Asp Tyr Val Gln
            260                 265                 270
```

```
Gln His Gly Gly Ile Ser Leu Val Glu Gln Leu Leu Gln Asp Pro Glu
        275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Ala Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Val Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
        370                 375                 380

Gly Val Glu Arg Ile Phe Ser Ile Val Glu Gln Arg Leu Glu Ala Thr
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
        420                 425                 430

Asn Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Ala Ser Arg Glu Glu Val Asp Val Pro Arg Glu Asp Leu Val Glu
                485                 490                 495

Glu Ile Lys Arg Arg Thr Ser Gln Pro Phe Cys Ile Cys
                500                 505

<210> SEQ ID NO 112
<211> LENGTH: 509
<212> TYPE: PRT
<213> ORGANISM: Bos taurus

<400> SEQUENCE: 112

Met Ala Asp Arg Ala Ala Leu Glu Asp Leu Val Arg Val Gln Gly Glu
1               5                   10                  15

Arg Val Arg Gly Leu Lys Gln Gln Lys Ala Ser Ala Glu Gln Ile Glu
                20                  25                  30

Glu Glu Val Ala Lys Leu Leu Lys Leu Lys Ala Gln Leu Gly Pro Asp
            35                  40                  45

Glu Gly Lys Pro Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125
```

Tyr Asp Leu Thr Val Pro Phe Ala Arg Tyr Leu Ala Met Asn Lys Leu
            130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Leu Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Ala Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Pro Pro Ala Arg Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Ile Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Thr Gly Ile Pro Leu Val Ala
    450                 455                 460

Ile Ile Gly Glu Gln Glu Leu Lys Asp Gly Val Ile Lys Leu Arg Ser
465                 470                 475                 480

Val Ala Ser Arg Glu Glu Val Asp Val Arg Arg Glu Asp Leu Val Glu
                485                 490                 495

Glu Ile Lys Arg Arg Thr Ser Gln Pro Leu Cys Ile Cys
            500                 505

<210> SEQ ID NO 113
<211> LENGTH: 508
<212> TYPE: PRT
<213> ORGANISM: Rattus norvegicus

```
<400> SEQUENCE: 113

Met Ala Asp Arg Ala Ala Leu Glu Glu Leu Val Arg Leu Gln Gly Ala
1               5                   10                  15

His Val Arg Gly Leu Lys Glu Gln Lys Ala Ser Ala Glu Gln Ile Glu
                20                  25                  30

Glu Glu Val Thr Lys Leu Leu Lys Leu Lys Ala Gln Leu Gly His Asp
            35                  40                  45

Glu Gly Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Lys Ile Met Cys Glu Ile Leu Ser Ser Leu Gln Ile Gly Asn Phe Gln
        195                 200                 205

Val Lys Val Asn Asp Arg Arg Ile Leu Asp Gly Met Phe Ala Val Cys
210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Val Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
            340                 345                 350

Gly Val Gly Ser Ile Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Lys Leu Glu Ala Ser
385                 390                 395                 400

Glu Glu Lys Val Arg Thr Thr Glu Thr Gln Val Leu Val Ala Ser Ala
                405                 410                 415
```

-continued

```
Gln Lys Lys Leu Leu Glu Glu Arg Leu Lys Leu Ile Ser Glu Leu Trp
            420                 425                 430

Asp Ala Gly Ile Lys Ala Glu Leu Tyr Lys Lys Asn Pro Lys Leu
            435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
            485                 490                 495

Glu Ile Arg Arg Arg Thr Ser Gln Pro Leu Ser Met
            500                 505

<210> SEQ ID NO 114
<211> LENGTH: 500
<212> TYPE: PRT
<213> ORGANISM: Gallus gallus

<400> SEQUENCE: 114

Met Ala Asp Glu Ala Ala Val Arg Gln Gln Ala Glu Val Val Arg Arg
1               5                   10                  15

Leu Lys Gln Asp Lys Ala Glu Pro Asp Glu Ile Ala Lys Glu Val Ala
            20                  25                  30

Lys Leu Leu Glu Met Lys Ala His Leu Gly Gly Asp Glu Gly Lys His
            35                  40                  45

Lys Phe Val Leu Lys Thr Pro Lys Gly Thr Arg Asp Tyr Gly Pro Lys
            50                  55                  60

Gln Met Ala Ile Arg Glu Arg Val Phe Ser Ala Ile Ala Cys Phe
65                  70                  75                  80

Lys Arg His Gly Ala Glu Val Ile Asp Thr Pro Val Phe Glu Leu Lys
            85                  90                  95

Glu Thr Leu Thr Gly Lys Tyr Gly Glu Asp Ser Lys Leu Ile Tyr Asp
            100                 105                 110

Leu Lys Asp Gln Gly Gly Glu Leu Leu Ser Leu Arg Tyr Asp Leu Thr
            115                 120                 125

Val Pro Phe Ala Arg Tyr Leu Ala Met Asn Lys Ile Thr Asn Ile Lys
130                 135                 140

Arg Tyr His Ile Ala Lys Val Tyr Arg Arg Asp Asn Pro Ala Met Thr
145                 150                 155                 160

Arg Gly Arg Tyr Arg Glu Phe Tyr Gln Cys Asp Phe Asp Ile Ala Gly
            165                 170                 175

Gln Phe Asp Pro Met Ile Pro Asp Ala Glu Cys Leu Lys Ile Val Gln
            180                 185                 190

Glu Ile Leu Ser Asp Leu Gln Leu Gly Asp Phe Leu Ile Lys Val Asn
            195                 200                 205

Asp Arg Arg Ile Leu Asp Gly Met Phe Ala Val Cys Gly Val Pro Asp
            210                 215                 220

Ser Lys Phe Arg Thr Ile Cys Ser Ser Val Asp Lys Leu Asp Lys Met
225                 230                 235                 240

Pro Trp Glu Glu Val Arg Asn Glu Met Val Gly Glu Lys Gly Leu Ser
            245                 250                 255

Pro Glu Ala Ala Asp Arg Ile Gly Glu Tyr Val Gln Leu His Gly Gly
            260                 265                 270
```

```
Met Asp Leu Ile Glu Gln Leu Gln Asp Pro Lys Leu Ser Gln Asn
            275                 280                 285

Lys Leu Val Lys Glu Gly Leu Gly Asp Met Lys Leu Leu Phe Glu Tyr
290                 295                 300

Leu Thr Leu Phe Gly Ile Thr Gly Lys Ile Ser Phe Asp Leu Ser Leu
305                 310                 315                 320

Ala Arg Gly Leu Asp Tyr Tyr Thr Gly Val Ile Tyr Glu Ala Val Leu
                325                 330                 335

Leu Gln Gln Asn Asp His Gly Glu Ser Val Ser Val Gly Ser Val
                340                 345                 350

Ala Gly Gly Gly Arg Tyr Asp Gly Leu Val Gly Met Phe Asp Pro Lys
                355                 360                 365

Gly Arg Lys Val Pro Cys Val Gly Ile Ser Ile Gly Ile Glu Arg Ile
370                 375                 380

Phe Ser Ile Leu Glu Gln Arg Val Glu Ala Ser Glu Glu Lys Ile Arg
385                 390                 395                 400

Thr Thr Glu Thr Gln Val Leu Val Ala Ser Ala Gln Lys Lys Leu Leu
                405                 410                 415

Glu Glu Arg Leu Lys Leu Ile Ser Glu Leu Trp Asp Ala Gly Ile Lys
                420                 425                 430

Ala Glu Val Leu Tyr Lys Lys Asn Pro Lys Leu Leu Asn Gln Leu Gln
                435                 440                 445

Tyr Cys Glu Asp Thr Gly Ile Pro Leu Val Ala Ile Val Gly Glu Gln
                450                 455                 460

Glu Leu Lys Asp Gly Val Val Lys Leu Arg Val Val Ala Thr Gly Glu
465                 470                 475                 480

Glu Val Asn Ile Arg Arg Glu Ser Leu Val Glu Ile Arg Arg Arg
                485                 490                 495

Thr Asn Gln Leu
            500

<210> SEQ ID NO 115
<211> LENGTH: 437
<212> TYPE: PRT
<213> ORGANISM: Danio rerio

<400> SEQUENCE: 115

Met Ala Ala Leu Gly Leu Val Ser Met Arg Leu Cys Ala Gly Leu Met
1               5                   10                  15

Gly Arg Arg Ser Ala Val Arg Leu His Ser Leu Arg Val Cys Ser Gly
                20                  25                  30

Met Thr Ile Ser Gln Ile Asp Glu Glu Val Ala Arg Leu Leu Gln Leu
            35                  40                  45

Lys Ala Gln Leu Gly Gly Asp Glu Gly Lys His Val Phe Val Leu Lys
        50                  55                  60

Thr Ala Lys Gly Thr Arg Asp Tyr Asn Pro Lys Gln Met Ala Ile Arg
65                  70                  75                  80

Glu Lys Val Phe Asn Ile Ile Asn Cys Phe Lys Arg His Gly Ala
                85                  90                  95

Glu Thr Ile Asp Ser Pro Val Phe Glu Leu Lys Glu Thr Leu Thr Gly
                100                 105                 110

Lys Tyr Gly Glu Asp Ser Lys Leu Ile Tyr Asp Leu Lys Asp Gln Gly
            115                 120                 125
```

Gly Glu Leu Leu Ser Leu Arg Tyr Asp Leu Thr Val Pro Phe Ala Arg
    130                 135                 140

Tyr Leu Ala Met Asn Lys Ile Thr Asn Ile Lys Arg Tyr His Ile Ala
145                 150                 155                 160

Lys Val Tyr Arg Arg Asp Asn Pro Ala Met Thr Arg Gly Arg Tyr Arg
                165                 170                 175

Glu Phe Tyr Gln Cys Asp Phe Asp Ile Ala Gly Gln Tyr Asp Ala Met
            180                 185                 190

Ile Pro Asp Ala Glu Cys Leu Lys Leu Val Tyr Glu Ile Leu Ser Glu
        195                 200                 205

Leu Asp Leu Gly Asp Phe Arg Ile Lys Val Asn Asp Arg Arg Ile Leu
    210                 215                 220

Asp Gly Met Phe Ala Ile Cys Gly Val Pro Asp Glu Lys Phe Arg Thr
225                 230                 235                 240

Ile Cys Ser Thr Val Asp Lys Leu Asp Lys Leu Ala Trp Glu Glu Val
                245                 250                 255

Lys Lys Glu Met Val Asn Glu Lys Gly Leu Ser Glu Val Ala Asp
            260                 265                 270

Arg Ile Arg Asp Tyr Val Ser Met Gln Gly Gly Lys Asp Leu Ala Glu
        275                 280                 285

Arg Leu Leu Gln Asp Pro Lys Leu Ser Gln Ser Lys Gln Ala Cys Ala
    290                 295                 300

Gly Ile Thr Asp Met Lys Leu Leu Phe Ser Tyr Leu Glu Leu Phe Gln
305                 310                 315                 320

Ile Thr Asp Lys Val Val Phe Asp Leu Ser Leu Ala Arg Gly Leu Asp
                325                 330                 335

Tyr Tyr Thr Gly Val Ile Tyr Glu Ala Ile Leu Thr Gln Ala Asn Pro
            340                 345                 350

Ala Pro Ala Ser Thr Pro Ala Glu Gln Asn Gly Ala Glu Asp Ala Gly
        355                 360                 365

Val Ser Val Gly Ser Val Ala Gly Gly Arg Tyr Asp Gly Leu Val
    370                 375                 380

Gly Met Phe Asp Pro Lys Ala Gly Lys Cys Pro Val Trp Gly Ser Ala
385                 390                 395                 400

Leu Ala Leu Arg Gly Ser Ser Pro Ser Trp Ser Arg Arg Gln Ser Cys
                405                 410                 415

Leu Gln Arg Arg Cys Ala Pro Leu Lys Leu Lys Cys Leu Trp Leu Gln
            420                 425                 430

His Arg Arg Thr Phe
        435

<210> SEQ ID NO 116
<211> LENGTH: 435
<212> TYPE: PRT
<213> ORGANISM: Macaca fascicularis

<400> SEQUENCE: 116

Met Ala Glu Arg Ala Ala Leu Glu Glu Leu Val Lys Leu Gln Gly Glu
1               5                   10                  15

Arg Val Arg Gly Leu Lys Gln Gln Gln Ala Ser Ala Glu Leu Ile Glu
            20                  25                  30

Glu Glu Val Gly Lys Leu Leu Lys Leu Lys Ala Gln Leu Gly Pro Asp
        35                  40                  45

```
Glu Ser Lys Gln Lys Phe Val Leu Lys Thr Pro Lys Gly Thr Arg Asp
     50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Asp Phe Asp Ile Ala Gly Asn Phe Asp Pro Met Ile
            100                 105                 110

Pro Asp Ala Glu Cys Leu Lys Ile Met Cys Glu Ile Leu Ser Ser Leu
            115                 120                 125

Gln Ile Gly Asp Phe Leu Val Lys Val Asn Asp Arg Arg Ile Leu Asp
130                 135                 140

Gly Met Phe Ala Ile Cys Gly Val Ser Asp Ser Lys Phe Arg Thr Ile
145                 150                 155                 160

Cys Ser Ser Val Asp Lys Leu Asp Lys Val Ser Trp Glu Glu Val Lys
                165                 170                 175

Asn Glu Met Val Gly Glu Lys Gly Leu Ala Pro Glu Val Ala Asp Arg
            180                 185                 190

Ile Gly Asp Tyr Val Gln Gln His Gly Gly Val Ser Leu Val Glu Gln
            195                 200                 205

Leu Leu Gln Asp Pro Lys Leu Ser Gln Asn Lys Gln Ala Leu Glu Gly
210                 215                 220

Leu Gly Asp Leu Lys Leu Leu Phe Glu Tyr Leu Thr Leu Phe Gly Ile
225                 230                 235                 240

Asp Asp Lys Ile Ser Phe Asp Leu Ser Leu Ala Arg Gly Leu Asp Tyr
                245                 250                 255

Tyr Thr Gly Val Ile Tyr Glu Ala Val Leu Leu Gln Thr Pro Ala Gln
            260                 265                 270

Ala Gly Glu Glu Pro Leu Gly Val Gly Ser Val Ala Ala Gly Gly Arg
            275                 280                 285

Tyr Asp Gly Leu Val Gly Met Phe Asp Pro Lys Gly Arg Lys Val Pro
290                 295                 300

Cys Val Gly Leu Ser Ile Gly Val Glu Arg Ile Phe Ser Ile Val Glu
305                 310                 315                 320

Gln Arg Leu Glu Ala Leu Glu Glu Lys Val Arg Thr Thr Glu Thr Gln
                325                 330                 335

Val Leu Val Ala Ser Ala Gln Lys Lys Leu Leu Glu Glu Arg Leu Lys
            340                 345                 350

Leu Val Ser Glu Leu Trp Asp Ala Gly Ile Lys Ala Glu Leu Leu Tyr
            355                 360                 365

Lys Lys Asn Pro Lys Leu Leu Asn Gln Leu Gln Tyr Cys Glu Glu Ala
370                 375                 380

Gly Ile Pro Leu Val Ala Ile Ile Gly Glu Gln Glu Leu Lys Asp Gly
385                 390                 395                 400

Val Ile Lys Leu Arg Ser Val Thr Ser Arg Glu Val Asn Val Arg
                405                 410                 415

Arg Glu Asp Leu Val Glu Glu Ile Lys Arg Arg Thr Gly Gln Leu Leu
            420                 425                 430

Arg Ile Cys
435

<210> SEQ ID NO 117
<211> LENGTH: 138
```

```
<212> TYPE: PRT
<213> ORGANISM: Artificial Sequence
<220> FEATURE:
<223> OTHER INFORMATION: Consensus HRS WHEP sequence
<220> FEATURE:
<221> NAME/KEY: MOD_RES
<222> LOCATION: (1)..(50)
<223> OTHER INFORMATION: Xaa is any amino acid or absent
<220> FEATURE:
<221> NAME/KEY: misc_feature
<222> LOCATION: (52)..(56)
<223> OTHER INFORMATION: Xaa can be any naturally occurring amino acid
<220> FEATURE:
<221> NAME/KEY: MOD_RES
<222> LOCATION: (57)..(58)
<223> OTHER INFORMATION: Xaa is any amino acid or absent
<220> FEATURE:
<221> NAME/KEY: MOD_RES
<222> LOCATION: (61)..(62)
<223> OTHER INFORMATION: Xaa is any amino acid
<220> FEATURE:
<221> NAME/KEY: MOD_RES
<222> LOCATION: (65)..(65)
<223> OTHER INFORMATION: Xaa is any amino acid
<220> FEATURE:
<221> NAME/KEY: MOD_RES
<222> LOCATION: (68)..(69)
<223> OTHER INFORMATION: Xaa is any amino acid
<220> FEATURE:
<221> NAME/KEY: misc_feature
<222> LOCATION: (72)..(78)
<223> OTHER INFORMATION: Xaa can be any naturally occurring amino acid
<220> FEATURE:
<221> NAME/KEY: MOD_RES
<222> LOCATION: (79)..(80)
<223> OTHER INFORMATION: Xaa is any amino acid or absent
<220> FEATURE:
<221> NAME/KEY: MOD_RES
<222> LOCATION: (82)..(83)
<223> OTHER INFORMATION: Xaa is any amino acid
<220> FEATURE:
<221> NAME/KEY: MOD_RES
<222> LOCATION: (86)..(86)
<223> OTHER INFORMATION: Xaa is any amino acid
<220> FEATURE:
<221> NAME/KEY: MOD_RES
<222> LOCATION: (89)..(138)
<223> OTHER INFORMATION: Xaa is any amino acid or absent

<400> SEQUENCE: 117

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Leu Xaa Xaa Xaa Xaa Xaa Xaa Xaa Gln Gly Xaa Xaa Val Arg
    50                  55                  60

Xaa Leu Lys Xaa Xaa Lys Ala Xaa Xaa Xaa Xaa Xaa Xaa Xaa Xaa
65                  70                  75                  80

Val Xaa Xaa Leu Leu Xaa Leu Lys Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa
    130                 135
```

```
<210> SEQ ID NO 118
<211> LENGTH: 61
<212> TYPE: PRT
<213> ORGANISM: Artificial Sequence
<220> FEATURE:
<223> OTHER INFORMATION: Made in Lab:  cysteine modified HRS polypeptide

<400> SEQUENCE: 118

Met Cys Ala Glu Arg Ala Ala Leu Glu Glu Leu Val Lys Leu Gln Gly
1               5                   10                  15

Glu Arg Val Arg Gly Leu Lys Gln Gln Lys Ala Ser Ala Glu Leu Ile
            20                  25                  30

Glu Glu Glu Val Ala Lys Leu Leu Lys Leu Lys Ala Gln Leu Gly Pro
        35                  40                  45

Asp Glu Ser Lys Gln Lys Phe Val Leu Lys Thr Pro Lys
    50                  55                  60

<210> SEQ ID NO 119
<211> LENGTH: 60
<212> TYPE: PRT
<213> ORGANISM: Artificial Sequence
<220> FEATURE:
<223> OTHER INFORMATION: Made in Lab:  cysteine modified HRS polypeptide

<400> SEQUENCE: 119

Met Ala Glu Arg Ala Ala Leu Glu Glu Leu Val Lys Leu Gln Gly Glu
1               5                   10                  15

Arg Val Arg Gly Leu Lys Gln Gln Lys Cys Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 120
<211> LENGTH: 61
<212> TYPE: PRT
<213> ORGANISM: Artificial Sequence
<220> FEATURE:
<223> OTHER INFORMATION: Made in Lab:  cysteine modified HRS polypeptide

<400> SEQUENCE: 120

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Cys
    50                  55                  60

<210> SEQ ID NO 121
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 121

Met Ala Glu Arg Ala Ala Leu Glu Glu Leu Val Lys Leu Gln Gly Glu
1               5                   10                  15
```

```
Arg Val Arg Gly Leu Lys Gln Gln Lys Ala Ser Ala Glu Leu Ile Glu
             20                  25                  30

Glu Glu Val Ala Lys Leu Leu Lys Leu Lys Ala Gln Leu Gly Pro Asp
         35                  40                  45

Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Glu Thr Leu Met Gly Lys Tyr Gly Glu Asp Ser Lys
             100                 105                 110

Leu Ile Tyr Asp Leu Lys Asp Gln Gly Gly Glu Leu Leu Ser Leu Arg
         115                 120                 125

Tyr Asp Leu Thr Val Pro Phe Ala Arg Tyr Leu Ala Met Asn Lys Leu
 130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Ala Asp Phe
                165                 170                 175

Asp Ile Ala Gly Asn Phe Asp Pro Met Ile Pro Asp Ala Glu Cys Leu
             180                 185                 190

Lys Ile Met Cys Glu Ile Leu Ser Ser Leu Gln Ile Gly Asp Phe Leu
         195                 200                 205

Val Lys Val Asn Asp Arg Arg Ile Leu Asp Gly Met Phe Ala Ile Cys
 210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
             260                 265                 270

Gln His Gly Gly Val Ser Leu Val Glu Gln Leu Leu Gln Asp Pro Lys
         275                 280                 285

Leu Ser Gln Asn Lys Gln Ala Leu Glu Gly Leu Gly Asp Leu Lys Leu
 290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
             340                 345                 350

Gly Val Gly Ser Val Ala Ala Gly Gly Arg Tyr Asp Gly Leu Val Gly
         355                 360                 365

Met Phe Asp Pro Lys Gly Arg Lys Val Pro Cys Val Gly Leu Ser Ile
 370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
             420                 425                 430
```

```
Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 122
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 122

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Val Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270
```

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
                435                 440                 445

Leu Asn Gln Leu Gln Tyr Cys Glu Glu Ala Gly Ile Pro Leu Val Ala
                450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 123
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 123

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
                115                 120                 125

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ala Leu
                180                 185                 190

Lys Ile Met Cys Glu Ile Leu Ser Ser Leu Gln Ile Gly Asp Phe Leu
                195                 200                 205

Val Lys Val Asn Asp Arg Arg Ile Leu Asp Gly Met Phe Ala Ile Cys
        210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
        370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 124
<211> LENGTH: 506

```
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 124
```

| | | | | | | | | | | | | | | |
|---|---|---|---|---|---|---|---|---|---|---|---|---|---|---|
|Met|Ala|Glu|Arg|Ala|Leu|Glu|Glu|Leu|Val|Lys|Leu|Gln|Gly|Glu|
|1| | | |5| | | | |10| | | | |15|

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Glu Leu Leu Ser Leu Arg
                115                 120                 125

Tyr Asp Leu Thr Val Pro Phe Ala Arg Tyr Leu Ala Met Asn Lys Leu
 130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ser Leu
                180                 185                 190

Lys Ile Met Cys Glu Ile Leu Ser Ser Leu Gln Ile Gly Asp Phe Leu
                195                 200                 205

Val Lys Val Asn Asp Arg Arg Ile Leu Asp Gly Met Phe Ala Ile Cys
 210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
                290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
                370                 375                 380

```
Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 125
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 125

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Val Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
            210                 215                 220
```

```
Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
            245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
            275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 126
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 126

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60
```

```
Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Glu Thr Leu Met Gly Lys Tyr Gly Asp Ser Lys
            100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Ser
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
            275                 280                 285

Leu Ser Gln Asn Lys Gln Ala Leu Glu Gly Leu Gly Asp Leu Lys Leu
            290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
            450                 455                 460

Ile Ile Gly Glu Gln Glu Leu Lys Asp Gly Val Ile Lys Leu Arg Ser
465                 470                 475                 480
```

```
Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505

<210> SEQ ID NO 127
<211> LENGTH: 506
<212> TYPE: PRT
<213> ORGANISM: Artificial Sequence
<220> FEATURE:
<223> OTHER INFORMATION: Made in Lab: modified HRS polypeptide to remove
      surface exposed cysteines

<400> SEQUENCE: 127

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Ser Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335
```

```
Glu Ala Val Leu Leu Gln Thr Pro Ala Gln Ala Gly Glu Glu Pro Leu
                340                 345                 350

Gly Val Gly Ser Val Ala Ala Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
                500                 505

<210> SEQ ID NO 128
<211> LENGTH: 19
<212> TYPE: PRT
<213> ORGANISM: Homo sapiens

<400> SEQUENCE: 128

Val Pro Ser Thr Pro Pro Thr Pro Ser Pro Ser Thr Pro Pro Thr Pro
1               5                   10                  15

Ser Pro Ser

<210> SEQ ID NO 129
<211> LENGTH: 101
<212> TYPE: PRT
<213> ORGANISM: Homo sapiens

<400> SEQUENCE: 129

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Val Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Glu Pro Trp Asn His Gly Lys Thr
65                  70                  75                  80

Phe Thr Cys Thr Ala Ala Tyr Pro Glu Ser Lys Thr Pro Leu Thr Ala
                85                  90                  95

Thr Leu Ser Lys Ser
            100

<210> SEQ ID NO 130
<211> LENGTH: 131
```

```
<212> TYPE: PRT
<213> ORGANISM: Homo sapiens

<400> SEQUENCE: 130

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
            115                 120                 125

Thr Cys Tyr
    130

<210> SEQ ID NO 131
<211> LENGTH: 6
<212> TYPE: PRT
<213> ORGANISM: Homo sapiens

<400> SEQUENCE: 131

Val Pro Pro Pro Pro Pro
1               5

<210> SEQ ID NO 132
<211> LENGTH: 101
<212> TYPE: PRT
<213> ORGANISM: Homo sapiens

<400> SEQUENCE: 132

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Ala Thr Phe Thr Trp Thr Pro Ser Ser Gly Lys Ser
            35                  40                  45

Ala Val Gln Gly Pro Pro Glu Arg Asp Leu Cys Gly Cys Tyr Ser Val
50                  55                  60

Ser Ser Val Leu Pro Gly Cys Ala Gln Pro Trp Asn His Gly Glu Thr
65                  70                  75                  80

Phe Thr Cys Thr Ala Ala His Pro Glu Leu Lys Thr Pro Leu Thr Ala
                85                  90                  95

Asn Ile Thr Lys Ser
            100

<210> SEQ ID NO 133
<211> LENGTH: 131
<212> TYPE: PRT
<213> ORGANISM: Homo sapiens
```

<400> SEQUENCE: 133

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
        115                 120                 125

Thr Cys Tyr
    130

<210> SEQ ID NO 134
<211> LENGTH: 58
<212> TYPE: PRT
<213> ORGANISM: Homo sapiens

<400> SEQUENCE: 134

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
50                  55

<210> SEQ ID NO 135
<211> LENGTH: 108
<212> TYPE: PRT
<213> ORGANISM: Homo sapiens

<400> SEQUENCE: 135

Glu Cys Pro Ser His Thr Gln Pro Leu Gly Val Tyr Leu Leu Thr Pro
1               5                   10                  15

Ala Val Gln Asp Leu Trp Leu Arg Asp Lys Ala Thr Phe Thr Cys Phe
            20                  25                  30

Val Val Gly Ser Asp Leu Lys Asp Ala His Leu Thr Trp Glu Val Ala
        35                  40                  45

Gly Lys Val Pro Thr Gly Gly Val Glu Glu Gly Leu Leu Glu Arg His
50                  55                  60

Ser Asn Gly Ser Gln Ser Gln His Ser Arg Leu Thr Leu Pro Arg Ser
65                  70                  75                  80

Leu Trp Asn Ala Gly Thr Ser Val Thr Cys Thr Leu Asn His Pro Ser
                85                  90                  95

Leu Pro Pro Gln Arg Leu Met Ala Leu Arg Glu Pro
            100                 105

<210> SEQ ID NO 136
<211> LENGTH: 117
<212> TYPE: PRT
<213> ORGANISM: Homo sapiens

<400> SEQUENCE: 136

```
Ala Ala Gln Ala Pro Val Lys Leu Ser Leu Asn Leu Leu Ala Ser Ser
1               5                   10                  15

Asp Pro Pro Glu Ala Ala Ser Trp Leu Leu Cys Glu Val Ser Gly Phe
            20                  25                  30

Ser Pro Pro Asn Ile Leu Leu Met Trp Leu Glu Asp Gln Arg Glu Val
        35                  40                  45

Asn Thr Ser Gly Phe Ala Pro Ala Arg Pro Pro Gln Pro Arg Ser
    50                  55                  60

Thr Thr Phe Trp Ala Trp Ser Val Leu Arg Val Pro Ala Pro Pro Ser
65                  70                  75                  80

Pro Gln Pro Ala Thr Tyr Thr Cys Val Val Ser His Glu Asp Ser Arg
                85                  90                  95

Thr Leu Leu Asn Ala Ser Arg Ser Leu Glu Val Ser Tyr Val Thr Asp
                100                 105                 110

His Gly Pro Met Lys
            115
```

<210> SEQ ID NO 137
<211> LENGTH: 107
<212> TYPE: PRT
<213> ORGANISM: Homo sapiens

<400> SEQUENCE: 137

```
Val Cys Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala
                100                 105
```

<210> SEQ ID NO 138
<211> LENGTH: 108
<212> TYPE: PRT
<213> ORGANISM: Homo sapiens

<400> SEQUENCE: 138

```
Asp Ser Asn Pro Arg Gly Val Ser Ala Tyr Leu Ser Arg Pro Ser Pro
1               5                   10                  15

Phe Asp Leu Phe Ile Arg Lys Ser Pro Thr Ile Thr Cys Leu Val Val
            20                  25                  30

Asp Leu Ala Pro Ser Lys Gly Thr Val Asn Leu Thr Trp Ser Arg Ala
        35                  40                  45
```

Ser Gly Lys Pro Val Asn His Ser Thr Arg Lys Glu Glu Lys Gln Arg
        50                  55                  60

Asn Gly Thr Leu Thr Val Thr Ser Thr Leu Pro Val Gly Thr Arg Asp
65                  70                  75                  80

Trp Ile Glu Gly Glu Thr Tyr Gln Cys Arg Val Thr His Pro His Leu
                85                  90                  95

Pro Arg Ala Leu Met Arg Ser Thr Thr Lys Thr Ser
            100                 105

<210> SEQ ID NO 139
<211> LENGTH: 110
<212> TYPE: PRT
<213> ORGANISM: Homo sapiens

<400> SEQUENCE: 139

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
                20                  25                  30

Met Pro Glu Asp Ile Ser Val Gln Trp Leu His Asn Glu Val Gln Leu
            35                  40                  45

Pro Asp Ala Arg His Ser Thr Thr Gln Pro Arg Lys Thr Lys Gly Ser
        50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 140
<211> LENGTH: 15
<212> TYPE: PRT
<213> ORGANISM: Homo sapiens

<400> SEQUENCE: 140

Glu Pro Lys Ser Cys Asp Lys Thr His Thr Cys Pro Pro Cys Pro
1               5                   10                  15

<210> SEQ ID NO 141
<211> LENGTH: 11
<212> TYPE: PRT
<213> ORGANISM: Homo sapiens

<400> SEQUENCE: 141

Ser Asp Lys Thr His Thr Cys Pro Pro Cys Pro
1               5                   10

<210> SEQ ID NO 142
<211> LENGTH: 110
<212> TYPE: PRT
<213> ORGANISM: Homo sapiens

<400> SEQUENCE: 142

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 143
<211> LENGTH: 107
<212> TYPE: PRT
<213> ORGANISM: Homo sapiens

<400> SEQUENCE: 143

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 144
<211> LENGTH: 229
<212> TYPE: PRT
<213> ORGANISM: Homo sapiens

<400> SEQUENCE: 144

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Glu Glu Met Thr Lys Asn Gln
            130                 135                 140

```
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
                195                 200                 205

Val Met His Glu Ala Leu His Asn His Tyr Thr Gln Lys Ser Leu Ser
210                 215                 220

Leu Ser Pro Gly Lys
225
```

<210> SEQ ID NO 145
<211> LENGTH: 12
<212> TYPE: PRT
<213> ORGANISM: Homo sapiens

<400> SEQUENCE: 145

```
Glu Arg Lys Cys Cys Val Glu Cys Pro Pro Cys Pro
1               5                   10
```

<210> SEQ ID NO 146
<211> LENGTH: 109
<212> TYPE: PRT
<213> ORGANISM: Homo sapiens

<400> SEQUENCE: 146

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
                100                 105
```

<210> SEQ ID NO 147
<211> LENGTH: 107
<212> TYPE: PRT
<213> ORGANISM: Homo sapiens

<400> SEQUENCE: 147

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Met Leu Asp Ser Asp Gly Ser Phe
        50                  55                  60
```

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 148
<211> LENGTH: 62
<212> TYPE: PRT
<213> ORGANISM: Homo sapiens

<400> SEQUENCE: 148

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 149
<211> LENGTH: 110
<212> TYPE: PRT
<213> ORGANISM: Homo sapiens

<400> SEQUENCE: 149

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 150
<211> LENGTH: 107
<212> TYPE: PRT
<213> ORGANISM: Homo sapiens

<400> SEQUENCE: 150

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Ile Phe Ser Cys Ser Val Met His Glu Ala Leu His Asn Arg Phe
                 85                  90                  95

Thr Gln Lys Ser Leu Ser Leu Ser Pro Gly Lys
            100                 105

<210> SEQ ID NO 151
<211> LENGTH: 12
<212> TYPE: PRT
<213> ORGANISM: Homo sapiens

<400> SEQUENCE: 151

Glu Ser Lys Tyr Gly Pro Pro Cys Pro Ser Cys Pro
1               5                   10

<210> SEQ ID NO 152
<211> LENGTH: 110
<212> TYPE: PRT
<213> ORGANISM: Homo sapiens

<400> SEQUENCE: 152

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 153
<211> LENGTH: 107
<212> TYPE: PRT
<213> ORGANISM: Homo sapiens

<400> SEQUENCE: 153

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 154
<211> LENGTH: 112
<212> TYPE: PRT
<213> ORGANISM: Homo sapiens

<400> SEQUENCE: 154

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110

<210> SEQ ID NO 155
<211> LENGTH: 106
<212> TYPE: PRT
<213> ORGANISM: Homo sapiens

<400> SEQUENCE: 155

Asp Gln Asp Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
        35                  40                  45

Glu Ala Val Lys Thr His Thr Asn Ile Ser Glu Ser His Pro Asn Ala
    50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105

<210> SEQ ID NO 156
<211> LENGTH: 131
<212> TYPE: PRT
<213> ORGANISM: Homo sapiens

<400> SEQUENCE: 156

Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
    50                  55                  60

```
Gln Ala Pro Gly Arg Tyr Phe Ala His Ser Ile Leu Thr Val Ser Glu
 65                  70                  75                  80

Glu Glu Trp Asn Thr Gly Glu Thr Tyr Thr Cys Val Val Ala His Glu
                 85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
        115                 120                 125

Thr Cys Tyr
        130

<210> SEQ ID NO 157
<211> LENGTH: 287
<212> TYPE: PRT
<213> ORGANISM: Artificial Sequence
<220> FEATURE:
<223> OTHER INFORMATION: Made in Lab: HRS-Fc fusion protein

<400> SEQUENCE: 157

Met Asp Lys Thr His Thr Cys Pro Pro Cys Pro Ala Pro Glu Leu Leu
  1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Ala Glu Arg Ala Ala Leu Glu Glu Leu Val Lys Leu
225                 230                 235                 240

Gln Gly Glu Arg Val Arg Gly Leu Lys Gln Lys Ala Ser Ala Glu
                245                 250                 255

Leu Ile Glu Glu Glu Val Ala Lys Leu Leu Lys Leu Lys Ala Gln Leu
            260                 265                 270

Gly Pro Asp Glu Ser Lys Gln Lys Phe Val Leu Lys Thr Pro Lys
        275                 280                 285
```

<210> SEQ ID NO 158
<211> LENGTH: 288
<212> TYPE: PRT
<213> ORGANISM: Artificial Sequence
<220> FEATURE:
<223> OTHER INFORMATION: Made in Lab: HRS-Fc fusion protein

<400> SEQUENCE: 158

```
Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285
```

<210> SEQ ID NO 159
<211> LENGTH: 288
<212> TYPE: PRT
<213> ORGANISM: Artificial Sequence
<220> FEATURE:
<223> OTHER INFORMATION: Made in Lab: HRS-Fc fusion protein

<400> SEQUENCE: 159

```
Met Ala Glu Arg Ala Ala Leu Glu Glu Leu Val Lys Leu Gln Gly Glu
1               5                   10                  15
```

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Ser Asp Lys Thr
50                      55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
            115                 120                 125

Lys Thr Lys Pro Arg Glu Glu Gln Tyr Asn Ser Thr Tyr Arg Val Val
130                     135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
            195                 200                 205

Leu Val Lys Gly Phe Tyr Pro Ser Asp Ile Ala Val Glu Trp Glu Ser
            210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
            275                 280                 285

<210> SEQ ID NO 160
<211> LENGTH: 288
<212> TYPE: PRT
<213> ORGANISM: Artificial Sequence
<220> FEATURE:
<223> OTHER INFORMATION: Made in Lab: HRS-Fc fusion protein

<400> SEQUENCE: 160

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
        50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

```
Asn Gly Lys Glu Tyr Lys Cys Lys Val Ser Asn Lys Ala Leu Pro Ala
                100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
    195                 200                 205

Val Met His Glu Ala Leu His Asn His Tyr Thr Gln Lys Ser Leu Ser
210                 215                 220

Leu Ser Pro Gly Lys Ala Glu Arg Ala Ala Leu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
    275                 280                 285

<210> SEQ ID NO 161
<211> LENGTH: 288
<212> TYPE: PRT
<213> ORGANISM: Artificial Sequence
<220> FEATURE:
<223> OTHER INFORMATION: Made in Lab: HRS-Fc fusion protein

<400> SEQUENCE: 161

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ser Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175
```

```
Ile Ser Lys Ala Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
            195                 200                 205

Leu Val Lys Gly Phe Tyr Pro Ser Asp Ile Ala Val Glu Trp Glu Ser
            210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                    245                 250                 255

Arg Trp Gln Gln Gly Asn Val Phe Ser Cys Ser Val Met His Glu Ala
                    260                 265                 270

Leu His Asn His Tyr Thr Gln Lys Ser Leu Ser Leu Ser Pro Gly Lys
                    275                 280                 285

<210> SEQ ID NO 162
<211> LENGTH: 268
<212> TYPE: PRT
<213> ORGANISM: Artificial Sequence
<220> FEATURE:
<223> OTHER INFORMATION: Made in Lab: HRS-Fc fusion protein

<400> SEQUENCE: 162

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
        50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                    85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                    165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
        210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                    245                 250                 255
```

Glu Leu Ile Glu Glu Glu Val Ala Lys Leu Leu Lys
                260                 265

<210> SEQ ID NO 163
<211> LENGTH: 273
<212> TYPE: PRT
<213> ORGANISM: Artificial Sequence
<220> FEATURE:
<223> OTHER INFORMATION: Made in Lab: HRS-Fc fusion protein

<400> SEQUENCE: 163

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu

<210> SEQ ID NO 164
<211> LENGTH: 278
<212> TYPE: PRT
<213> ORGANISM: Artificial Sequence
<220> FEATURE:
<223> OTHER INFORMATION: Made in Lab: HRS-Fc fusion protein

<400> SEQUENCE: 164

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu Gly Pro Asp Glu Ser
            275

<210> SEQ ID NO 165
<211> LENGTH: 283
<212> TYPE: PRT
<213> ORGANISM: Artificial Sequence
<220> FEATURE:
<223> OTHER INFORMATION: Made in Lab: HRS-Fc fusion protein

<400> SEQUENCE: 165

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

```
Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Val Ala Lys Leu Leu Lys Leu Lys Ala Gln
            260                 265                 270

Leu Gly Pro Asp Glu Ser Lys Gln Lys Phe Val
            275                 280

<210> SEQ ID NO 166
<211> LENGTH: 294
<212> TYPE: PRT
<213> ORGANISM: Artificial Sequence
<220> FEATURE:
<223> OTHER INFORMATION: Made in Lab: HRS-Fc fusion protein

<400> SEQUENCE: 166

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

```
Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Val Ala Lys Leu Leu Lys Leu Lys Ala Gln
                260                 265                 270

Leu Gly Pro Asp Glu Ser Lys Gln Lys Phe Val Leu Lys Thr Pro Lys
                275                 280                 285

Gly Thr Arg Asp Tyr Ser
            290

<210> SEQ ID NO 167
<211> LENGTH: 268
<212> TYPE: PRT
<213> ORGANISM: Artificial Sequence
<220> FEATURE:
<223> OTHER INFORMATION: Made in Lab: HRS-Fc fusion protein

<400> SEQUENCE: 167

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Val Ala Lys Leu Leu Lys Ser Asp Lys Thr His Thr Cys Pro
            35                  40                  45

Pro Cys Pro Ala Pro Glu Leu Leu Gly Gly Pro Ser Val Phe Leu Phe
        50                  55                  60

Pro Pro Lys Pro Lys Asp Thr Leu Met Ile Ser Arg Thr Pro Glu Val
65                  70                  75                  80

Thr Cys Val Val Val Asp Val Ser His Glu Asp Pro Glu Val Lys Phe
                85                  90                  95

Asn Trp Tyr Val Asp Gly Val Glu Val His Asn Ala Lys Thr Lys Pro
            100                 105                 110

Arg Glu Glu Gln Tyr Asn Ser Thr Tyr Arg Val Val Ser Val Leu Thr
        115                 120                 125

Val Leu His Gln Asp Trp Leu Asn Gly Lys Glu Tyr Lys Cys Lys Val
130                 135                 140

Ser Asn Lys Ala Leu Pro Ala Pro Ile Glu Lys Thr Ile Ser Lys Ala
145                 150                 155                 160

Lys Gly Gln Pro Arg Glu Pro Gln Val Tyr Thr Leu Pro Pro Ser Arg
                165                 170                 175

Glu Glu Met Thr Lys Asn Gln Val Ser Leu Thr Cys Leu Val Lys Gly
            180                 185                 190

Phe Tyr Pro Ser Asp Ile Ala Val Glu Trp Glu Ser Asn Gly Gln Pro
        195                 200                 205

Glu Asn Asn Tyr Lys Thr Thr Pro Pro Val Leu Asp Ser Asp Gly Ser
210                 215                 220

Phe Phe Leu Tyr Ser Lys Leu Thr Val Asp Lys Ser Arg Trp Gln Gln
225                 230                 235                 240
```

Gly Asn Val Phe Ser Cys Ser Val Met His Glu Ala Leu His Asn His
                245                 250                 255

Tyr Thr Gln Lys Ser Leu Ser Leu Ser Pro Gly Lys
            260                 265

<210> SEQ ID NO 168
<211> LENGTH: 273
<212> TYPE: PRT
<213> ORGANISM: Artificial Sequence
<220> FEATURE:
<223> OTHER INFORMATION: Made in Lab: HRS-Fc fusion protein

<400> SEQUENCE: 168

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Ser Asp Lys
        35                  40                  45

Thr His Thr Cys Pro Pro Cys Pro Ala Pro Glu Leu Leu Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser His Glu Asp
                85                  90                  95

Pro Glu Val Lys Phe Asn Trp Tyr Val Asp Gly Val Glu Val His Asn
            100                 105                 110

Ala Lys Thr Lys Pro Arg Glu Glu Gln Tyr Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Ala Leu Pro Ala Pro Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Arg Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Lys Leu Thr Val Asp Lys
225                 230                 235                 240

Ser Arg Trp Gln Gln Gly Asn Val Phe Ser Cys Ser Val Met His Glu
                245                 250                 255

Ala Leu His Asn His Tyr Thr Gln Lys Ser Leu Ser Leu Ser Pro Gly
            260                 265                 270

Lys

<210> SEQ ID NO 169
<211> LENGTH: 278
<212> TYPE: PRT
<213> ORGANISM: Artificial Sequence
<220> FEATURE:
<223> OTHER INFORMATION: Made in Lab: HRS-Fc fusion protein

<400> SEQUENCE: 169

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Ser Asp Lys Thr His Thr Cys Pro Pro Cys Pro Ala Pro Glu
    50                  55                  60

Leu Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Lys Phe Asn Trp Tyr Val Asp Gly
            100                 105                 110

Val Glu Val His Asn Ala Lys Thr Lys Pro Arg Glu Glu Gln Tyr Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Ala Lys Gly Gln Pro Arg Glu
                165                 170                 175

Pro Gln Val Tyr Thr Leu Pro Pro Ser Arg Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Lys
225                 230                 235                 240

Leu Thr Val Asp Lys Ser Arg Trp Gln Gln Gly Asn Val Phe Ser Cys
                245                 250                 255

Ser Val Met His Glu Ala Leu His Asn His Tyr Thr Gln Lys Ser Leu
            260                 265                 270

Ser Leu Ser Pro Gly Lys
        275
```

<210> SEQ ID NO 170
<211> LENGTH: 283
<212> TYPE: PRT
<213> ORGANISM: Artificial Sequence
<220> FEATURE:
<223> OTHER INFORMATION: Made in Lab: HRS-Fc fusion protein

<400> SEQUENCE: 170

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Ser Asp Lys Thr His Thr Cys Pro Pro
    50                  55                  60
```

Cys Pro Ala Pro Glu Leu Leu Gly Gly Pro Ser Val Phe Leu Phe Pro
65                  70                  75                  80

Pro Lys Pro Lys Asp Thr Leu Met Ile Ser Arg Thr Pro Glu Val Thr
            85                  90                  95

Cys Val Val Val Asp Val Ser His Glu Asp Pro Glu Val Lys Phe Asn
            100                 105                 110

Trp Tyr Val Asp Gly Val Glu Val His Asn Ala Lys Thr Lys Pro Arg
            115                 120                 125

Glu Glu Gln Tyr Asn Ser Thr Tyr Arg Val Val Ser Val Leu Thr Val
            130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
            165                 170                 175

Gly Gln Pro Arg Glu Pro Gln Val Tyr Thr Leu Pro Pro Ser Arg Glu
            180                 185                 190

Glu Met Thr Lys Asn Gln Val Ser Leu Thr Cys Leu Val Lys Gly Phe
            195                 200                 205

Tyr Pro Ser Asp Ile Ala Val Glu Trp Glu Ser Asn Gly Gln Pro Glu
            210                 215                 220

Asn Asn Tyr Lys Thr Thr Pro Pro Val Leu Asp Ser Asp Gly Ser Phe
225                 230                 235                 240

Phe Leu Tyr Ser Lys Leu Thr Val Asp Lys Ser Arg Trp Gln Gln Gly
            245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
            275                 280

<210> SEQ ID NO 171
<211> LENGTH: 294
<212> TYPE: PRT
<213> ORGANISM: Artificial Sequence
<220> FEATURE:
<223> OTHER INFORMATION: Made in Lab: HRS-Fc fusion protein

<400> SEQUENCE: 171

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Ser Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
            85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
            115                 120                 125

Val Glu Val His Asn Ala Lys Thr Lys Pro Arg Glu Glu Gln Tyr Asn
            130                 135                 140

-continued

```
Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
            165                 170                 175

Ala Pro Ile Glu Lys Thr Ile Ser Lys Ala Lys Gly Gln Pro Arg Glu
        180                 185                 190

Pro Gln Val Tyr Thr Leu Pro Pro Ser Arg Glu Glu Met Thr Lys Asn
    195                 200                 205

Gln Val Ser Leu Thr Cys Leu Val Lys Gly Phe Tyr Pro Ser Asp Ile
210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
            245                 250                 255

Leu Thr Val Asp Lys Ser Arg Trp Gln Gln Gly Asn Val Phe Ser Cys
        260                 265                 270

Ser Val Met His Glu Ala Leu His Asn His Tyr Thr Gln Lys Ser Leu
    275                 280                 285

Ser Leu Ser Pro Gly Lys
    290

<210> SEQ ID NO 172
<211> LENGTH: 347
<212> TYPE: PRT
<213> ORGANISM: Artificial Sequence
<220> FEATURE:
<223> OTHER INFORMATION: Made in Lab: HRS-Fc fusion protein

<400> SEQUENCE: 172

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205
```

```
Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285

Ala Glu Arg Ala Ala Leu Glu Glu Leu Val Lys Leu Gln Gly Glu Arg
    290                 295                 300

Val Arg Gly Leu Lys Gln Gln Lys Ala Ser Ala Glu Leu Ile Glu Glu
305                 310                 315                 320

Glu Val Ala Lys Leu Leu Lys Leu Lys Ala Gln Leu Gly Pro Asp Glu
                325                 330                 335

Ser Lys Gln Lys Phe Val Leu Lys Thr Pro Lys
            340                 345

<210> SEQ ID NO 173
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 173

Gly Ser Gly Ser
1

<210> SEQ ID NO 174
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 174

Gly Gly Ser Gly
1

<210> SEQ ID NO 175
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 175

Gly Gly Gly Ser
1

<210> SEQ ID NO 176
<211> LENGTH: 5
<212> TYPE: PRT
<213> ORGANISM: Artificial Sequence
<220> FEATURE:
<223> OTHER INFORMATION: Made in Lab: peptide linker sequence

<400> SEQUENCE: 176

Gly Gly Gly Gly Ser
1               5
```

```
<210> SEQ ID NO 177
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 177

Gly Asn Gly Asn
1

<210> SEQ ID NO 178
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 178

Gly Gly Asn Gly
1

<210> SEQ ID NO 179
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 179

Gly Gly Gly Asn
1

<210> SEQ ID NO 180
<211> LENGTH: 5
<212> TYPE: PRT
<213> ORGANISM: Artificial Sequence
<220> FEATURE:
<223> OTHER INFORMATION: Made in Lab: peptide linker sequence

<400> SEQUENCE: 180

Gly Gly Gly Gly Asn
1               5

<210> SEQ ID NO 181
<211> LENGTH: 15
<212> TYPE: PRT
<213> ORGANISM: Artificial Sequence
<220> FEATURE:
<223> OTHER INFORMATION: Made in Lab: peptide linker sequence

<400> SEQUENCE: 181

Gly Gly Gly Gly Ser Gly Gly Gly Gly Ser Gly Gly Gly Gly Ser
1               5                   10                  15

<210> SEQ ID NO 182
<211> LENGTH: 22
<212> TYPE: PRT
<213> ORGANISM: Artificial Sequence
<220> FEATURE:
<223> OTHER INFORMATION: Made in Lab: peptide linker sequence
```

<400> SEQUENCE: 182

Gly Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 183
<211> LENGTH: 30
<212> TYPE: PRT
<213> ORGANISM: Artificial Sequence
<220> FEATURE:
<223> OTHER INFORMATION: Made in Lab: peptide linker sequence

<400> SEQUENCE: 183

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 184
<211> LENGTH: 25
<212> TYPE: PRT
<213> ORGANISM: Artificial Sequence
<220> FEATURE:
<223> OTHER INFORMATION: Made in Lab: peptide linker sequence

<400> SEQUENCE: 184

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 185
<211> LENGTH: 14
<212> TYPE: PRT
<213> ORGANISM: Artificial Sequence
<220> FEATURE:
<223> OTHER INFORMATION: Made in Lab: peptide linker sequence

<400> SEQUENCE: 185

Asn Val Asp His Lys Pro Ser Asn Thr Lys Val Asp Lys Arg
1               5                   10

<210> SEQ ID NO 186
<211> LENGTH: 5
<212> TYPE: PRT
<213> ORGANISM: Artificial Sequence
<220> FEATURE:
<223> OTHER INFORMATION: Made in Lab: peptide linker sequence

<400> SEQUENCE: 186

Asp Gly Gly Gly Ser
1               5

<210> SEQ ID NO 187
<211> LENGTH: 5
<212> TYPE: PRT
<213> ORGANISM: Artificial Sequence
<220> FEATURE:
<223> OTHER INFORMATION: Made in Lab: peptide linker sequence

<400> SEQUENCE: 187

Thr Gly Glu Lys Pro
1               5

```
<210> SEQ ID NO 188
<211> LENGTH: 4
<212> TYPE: PRT
<213> ORGANISM: Artificial Sequence
<220> FEATURE:
<223> OTHER INFORMATION: Made in Lab: peptide linker sequence

<400> SEQUENCE: 188

Gly Gly Arg Arg
1

<210> SEQ ID NO 189
<211> LENGTH: 14
<212> TYPE: PRT
<213> ORGANISM: Artificial Sequence
<220> FEATURE:
<223> OTHER INFORMATION: Made in Lab: peptide linker sequence

<400> SEQUENCE: 189

Glu Gly Lys Ser Ser Gly Ser Gly Ser Glu Ser Lys Val Asp
1               5                   10

<210> SEQ ID NO 190
<211> LENGTH: 18
<212> TYPE: PRT
<213> ORGANISM: Artificial Sequence
<220> FEATURE:
<223> OTHER INFORMATION: Made in Lab: peptide linker sequence

<400> SEQUENCE: 190

Lys Glu Ser Gly Ser Val Ser Ser Glu Gln Leu Ala Gln Phe Arg Ser
1               5                   10                  15

Leu Asp

<210> SEQ ID NO 191
<211> LENGTH: 8
<212> TYPE: PRT
<213> ORGANISM: Artificial Sequence
<220> FEATURE:
<223> OTHER INFORMATION: Made in Lab: peptide linker sequence

<400> SEQUENCE: 191

Gly Gly Arg Arg Gly Gly Gly Ser
1               5

<210> SEQ ID NO 192
<211> LENGTH: 9
<212> TYPE: PRT
<213> ORGANISM: Artificial Sequence
<220> FEATURE:
<223> OTHER INFORMATION: Made in Lab: peptide linker sequence

<400> SEQUENCE: 192

Leu Arg Gln Arg Asp Gly Glu Arg Pro
1               5

<210> SEQ ID NO 193
<211> LENGTH: 12
<212> TYPE: PRT
<213> ORGANISM: Artificial Sequence
<220> FEATURE:
<223> OTHER INFORMATION: Made in Lab: peptide linker sequence
```

<400> SEQUENCE: 193

Leu Arg Gln Lys Asp Gly Gly Gly Ser Glu Arg Pro
1               5                   10

<210> SEQ ID NO 194
<211> LENGTH: 16
<212> TYPE: PRT
<213> ORGANISM: Artificial Sequence
<220> FEATURE:
<223> OTHER INFORMATION: Made in Lab: peptide linker sequence

<400> SEQUENCE: 194

Leu Arg Gln Lys Asp Gly Gly Gly Ser Gly Gly Gly Ser Glu Arg Pro
1               5                   10                  15

<210> SEQ ID NO 195
<211> LENGTH: 19
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 195

Leu Leu Asn Phe Asp Leu Leu Lys Leu Ala Gly Asp Val Glu Ser Asn
1               5                   10                  15

Pro Gly Pro

<210> SEQ ID NO 196
<211> LENGTH: 19
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 196

Thr Leu Asn Phe Asp Leu Leu Lys Leu Ala Gly Asp Val Glu Ser Asn
1               5                   10                  15

Pro Gly Pro

<210> SEQ ID NO 197
<211> LENGTH: 14
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 197

Leu Leu Lys Leu Ala Gly Asp Val Glu Ser Asn Pro Gly Pro
1               5                   10

<210> SEQ ID NO 198
<211> LENGTH: 17
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 198

Asn Phe Asp Leu Leu Lys Leu Ala Gly Asp Val Glu Ser Asn Pro Gly
1               5                   10                  15

Pro

<210> SEQ ID NO 199
<211> LENGTH: 20
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 199

Gln Leu Leu Asn Phe Asp Leu Leu Lys Leu Ala Gly Asp Val Glu Ser
1               5                   10                  15

Asn Pro Gly Pro
            20

<210> SEQ ID NO 200
<211> LENGTH: 24
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 200

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 201
<211> LENGTH: 40
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 201

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 202
<211> LENGTH: 18
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 202

Leu Asn Phe Asp Leu Leu Lys Leu Ala Gly Asp Val Glu Ser Asn Pro
1               5                   10                  15

Gly Pro

```
<210> SEQ ID NO 203
<211> LENGTH: 40
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 203

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 204
<211> LENGTH: 33
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 204

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 205
<211> LENGTH: 7
<212> TYPE: PRT
<213> ORGANISM: Tobacco etch virus
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (7)..(7)
<223> OTHER INFORMATION: Xaa is either Gly or Ser

<400> SEQUENCE: 205

Glu Xaa Xaa Tyr Xaa Gln Xaa
1               5

<210> SEQ ID NO 206
<211> LENGTH: 7
<212> TYPE: PRT
<213> ORGANISM: Tobacco etch virus

<400> SEQUENCE: 206

Glu Asn Leu Tyr Phe Gln Gly
1               5

<210> SEQ ID NO 207
<211> LENGTH: 7
```

```
<212> TYPE: PRT
<213> ORGANISM: Tabacco etch virus

<400> SEQUENCE: 207

Glu Asn Leu Tyr Phe Gln Ser
1               5

<210> SEQ ID NO 208
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 208

Gly Arg Gly Asp
1

<210> SEQ ID NO 209
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 209

Gly Arg Gly Asp Asn Pro
1               5

<210> SEQ ID NO 210
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 210

Gly Arg Gly Asp Ser
1               5

<210> SEQ ID NO 211
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 211

Gly Arg Gly Asp Ser Pro Lys
1               5

<210> SEQ ID NO 212
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 212

Ala Ala Pro Val
1

<210> SEQ ID NO 213
<211> LENGTH: 4
<212> TYPE: PRT
<213> ORGANISM: Artificial Sequence
<220> FEATURE:
```

```
<223> OTHER INFORMATION: Elastase cleavable linker

<400> SEQUENCE: 213

Ala Ala Pro Leu
1

<210> SEQ ID NO 214
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 214

Ala Ala Pro Phe
1

<210> SEQ ID NO 215
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 215

Ala Ala Pro Ala
1

<210> SEQ ID NO 216
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 216

Ala Tyr Leu Val
1

<210> SEQ ID NO 217
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 217

Gly Pro Xaa Gly Pro Xaa
1               5

<210> SEQ ID NO 218
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid
```

```
<400> SEQUENCE: 218

Leu Gly Pro Xaa
1

<210> SEQ ID NO 219
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 219

Gly Pro Ile Gly Pro Xaa
1               5

<210> SEQ ID NO 220
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 220

Ala Pro Gly Leu Xaa
1               5

<210> SEQ ID NO 221
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 221

Pro Leu Gly Pro Asp Arg Xaa
1               5

<210> SEQ ID NO 222
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 222

Pro Leu Gly Leu Leu Gly Xaa
1               5

<210> SEQ ID NO 223
<211> LENGTH: 7
<212> TYPE: PRT
<213> ORGANISM: Artificial Sequence
<220> FEATURE:
```

```
<223> OTHER INFORMATION: Collagenase cleavable linker

<400> SEQUENCE: 223

Pro Gln Gly Ile Ala Gly Trp
1               5

<210> SEQ ID NO 224
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 224

Pro Leu Gly Cys His
1               5

<210> SEQ ID NO 225
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 225

Pro Leu Gly Leu Tyr Ala
1               5

<210> SEQ ID NO 226
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 226

Pro Leu Ala Leu Trp Ala Arg
1               5

<210> SEQ ID NO 227
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 227

Pro Leu Ala Tyr Trp Ala Arg
1               5

<210> SEQ ID NO 228
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 228

Pro Tyr Ala Tyr Tyr Met Arg
1               5

<210> SEQ ID NO 229
<211> LENGTH: 7
<212> TYPE: PRT
<213> ORGANISM: Artificial Sequence
<220> FEATURE:
<223> OTHER INFORMATION: Gelatinase cleavable linker
```

```
<400> SEQUENCE: 229

Pro Leu Gly Met Tyr Ser Arg
1               5

<210> SEQ ID NO 230
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 230

Gly Asp Lys Pro
1

<210> SEQ ID NO 231
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 231

Gly Ser Asp Lys Pro
1               5

<210> SEQ ID NO 232
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 232

Ala Leu Ala Leu
1

<210> SEQ ID NO 233
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 233

Gly Phe Leu Gly
1
```

COMPOSITIONS AND METHODS FOR TREATING LUNG INFLAMMATION

CROSS-REFERENCE TO RELATED APPLICATIONS

This application claims priority under 35 U.S.C. § 119(e) to U.S. Application No. 62/487,812, filed Apr. 20, 2017, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_131_01 WO_ST25.txt. The text file is about 276 KB, was created on Apr. 18, 2018, and is being submitted electronically via EFS-Web.

BACKGROUND

Technical Field

Embodiments of the present disclosure relate to therapies, including combination therapies, for the treatment of lung inflammation, including interstitial lung diseases (ILDs), which include the use of at least one histidyl-tRNA synthetase (HRS) polypeptide or an expressible polynucleotide that encodes the HRS polypeptide, alone or in combination with at least one immunomodulatory agent.

Description of the Related Art

Interstitial lung diseases (ILDs) are group of heterogeneous disorders that primarily affect the lung interstitium in which inflammation is a predominant underlying mechanism. Within the ILD designation, there are a number of fibrotic lung conditions that are generally recognized as having a measurable inflammatory component involving both innate and adaptive immune mechanisms that contribute to pathogenesis at several levels.

Patients with ILD often suffer from progressive, debilitating respiratory symptoms, and experience significant morbidity and increased mortality compared to the general population. As a group, these conditions constitute a high unmet medical need, for which there are few effective treatments which don't have significant unwanted side effects.

BRIEF SUMMARY

Embodiments of the present disclosure relate, in pertinent part, to therapeutic compositions, comprising:
(a) a histidyl-tRNA synthetase (HRS) polypeptide, or an expressible polynucleotide that encodes the HRS polypeptide; and
(b) an immunomodulatory agent.

In some embodiments, the HRS polypeptide comprises, consists, or consists essentially of an amino acid sequence that is at least 80%, 85%, 90%, 95%, 96%, 97%, 98%, 99%, or 100% identical to a sequence selected from Table H1, Table H2, and Table H4.

In some embodiments, the HRS polypeptide is 500-506 amino acids in length and is at least 90% identical to SEQ ID NO:8 (HRS(1-506)) or 9 (HRS(2-506)) and lacks residues 507-509 of SEQ ID NO:1. In some embodiments, the HRS polypeptide comprises, consists, or consists essentially of SEQ ID NO:8 (HRS(1-506)). In some embodiments, the HRS polypeptide comprises, consists, or consists essentially of SEQ ID NO:9 (HRS(2-506)).

In some embodiments, the HRS polypeptide is fused to a heterologous polypeptide. In some embodiments, the heterologous polypeptide comprises an Fc region, to form an HRS-Fc fusion polypeptide.

In some embodiments, the HRS-Fc fusion polypeptide comprises, consists, or consists essentially of an amino acid sequence that is at least 80%, 85%, 90%, 95%, 96%, 97%, 98%, 99%, or 100% identical to a sequence selected from Table H8. In some embodiments, the HRS polypeptide at least about 80%, 85%, 90%, or 95% pure on a protein basis and less than about 5% aggregated.

In some embodiments, (a) is an expressible polynucleotide that encodes the HRS polypeptide, optionally a modified mRNA polynucleotide, which optionally comprises one or more non-natural basis and/or non-natural internucleotide linkages.

In some embodiments, the HRS polypeptide has a non-canonical activity, optionally an anti-inflammatory activity.

In some embodiments, the immunomodulatory agent is selected from one or more of pirfenidone, nintedanib, a sphingosine-1-phosphate (S1P) and/or S1P receptor (S1PR) modulator, a steroid optionally a glucocorticoid, a calcineurin inhibitor, a mechanistic target of rapamycin (mTOR) inhibitor, an indoleamine-pyrrole 2,3-dioxygenase (IDO) inhibitor, an inosine-5'-monophosphate dehydrogenase (IMPDH) inhibitor, a cytokine and/or cytokine receptor inhibitor, a B cell receptor inhibitor, a kinase inhibitor, and a cytostatic agent optionally methotrexate.

In some embodiments, the S1P and/or S1PR modulator is selected from amiselimod (S1PR antagonist), fingolimod (S1PR$_1$ functional antagonist), sonepcizumab (S1P-specific monoclonal antibody), KRP203 (S1PR$_1$ agonist), SEW2871 (S1PR$_1$ agonist), siponimod (S1PR$_1$ and S1PR$_5$ modulator), RPC1063 (S1PR$_1$ modulator), ONO-4641 (S1PR$_1$ and S1PR$_5$ agonist), JTE-013 (S1PR$_2$ antagonist), GSK2018682 (S1PR$_1$ agonist), ponesimod (S1PR$_1$ agonist), suramin (selective S1PR$_3$ and S1PR$_5$ antagonist), VPC23019 (arylamide analogs; competitive S1PR$_1$ and S1PR$_3$ antagonists); and W146 (selective S1PR$_1$ antagonist), an antisense or RNAi agent targeted against an S1PR, and an antibody or antigen-binding fragment or small molecule that specifically binds S1P and/or an S1PR, optionally wherein the amiselimod is at a dosage unit that ranges from about 0.1 mg to about 10 mg, or a dosage unit of about, no more than about, or at least about 0.1, 0.2, 0.3, 0.337, 0.4, 0.5, 0.6, 0.7, 0.8, 0.9, 1, 2, 3, 4, 5, 6, 7, 8, 9, 10 mg, or optionally wherein the amiselimod is at a dosage unit that ranges from about 0.1 mg/kg to about 10 mg/kg, or a dosage unit of about, no more than about, or at least about 0.1, 0.2, 0.3, 0.337, 0.4, 0.5, 0.6, 0.7, 0.8, 0.9, 1, 2, 3, 4, 5, 6, 7, 8, 9, 10 mg/kg.

In some embodiments, the steroid is selected from betamethasone, budesonide, cortisol (hydrocortisone), cortisone, deflazacort, deoxycorticosterone, dexamethasone, fludrocortisone, hydrocortisone, methylprednisolone, prednisone, prednisolone, and triamcinolone.

In some embodiments, the calcineurin inhibitor is selected from cyclosporin, pimecrolimus, tacrolimus, an antisense or RNAi agent targeted against calcineurin or a subunit thereof, and an antibody or antigen-binding fragment or small molecule that specifically binds calcineurin or a subunit thereof.

In some embodiments, the mTOR inhibitor is an ATP-competitive mTOR kinase inhibitor, an mTORC1/mTORC2 dual inhibitor, and/or an mTOR/PI3K dual inhibitor, or wherein the mTOR inhibitor is selected from one or more of everolimus, rapamycin, deforolimus, temsirolimus, dactolisib, BGT226, SF1126, PKI-587, NVPBE235, sapanisertib, AZD8055, AZD2014, antisense or RNAi agent targeted against mTOR, and an antibody or antigen-binding fragment or small molecule that specifically binds mTOR.

In some embodiments, the IDO inhibitor is selected from indoximod (NLG-8189), 1-methyl-tryptophan (1MT), β-Carboline (norharmane; 9H-pyrido[3,4-b]indole), rosmarinic acid, and epacadostat, an antisense or RNAi agent targeted against IDO, and an antibody or antigen-binding fragment or small molecule that specifically binds IDO.

In some embodiments, the IMPDH inhibitor is selected from one or more of mycophenolic acid (mycophenolate mofetil), ribavirin, and 6TGMP (6-thioguanine monophosphate), an antisense or RNAi agent targeted against IMPDH, and an antibody or antigen-binding fragment or small molecule that specifically binds IMPDH.

In some embodiments, the cytokine inhibitor is an inhibitor of a cytokine selected from one or more of interleukin-1 (IL-1) including IL-1α and IL-1β, interleukin-5 (IL-5), interleukin-6 (IL-6), interleukin-8 (IL-8), interleukin-11 (IL-11), interleukin-12 (IL-12), interleukin-17 (IL-17), interleukin-18 (IL-18), interleukin-20 (IL-20), interleukin-33 (IL-33), tumor necrosis factor (TNF), interferon gamma (IFN-gamma), transforming growth factor-β (TGF-β), and granulocyte-macrophage colony stimulating factor (GM-CSF), and/or a cytokine receptor selected from one or more of IL-1R, IL-6R, IL-8R, IL-11R, IL-12R, IL-17R, IL-18R, IL-20R, ST2 (Interleukin 1 receptor-like 1, IL1RL1), a TNFR such as TNFR1, interferon-gamma receptor (IFNGR), and a TGF-β receptor such as TGFβR1 (ALK5) or TGFβR2, and further wherein the cytokine and/or cytokine receptor inhibitor is selected from an antisense or RNAi agent targeted against the cytokine and/or cytokine receptor, and an antibody or antigen-binding fragment or small molecule that specifically binds the cytokine or cytokine receptor.

In some embodiments, the cytokine and/or cytokine receptor inhibitor is selected from one or more of adalimumab, anakinra, basiliximab, canakinumab, certolizumab, daclizumab, etanercept, golimumab, infliximab, ixekizumab, mepolizumab, reslizumab, rilonacept, secukinumab, serilumab, sirukumab, tocilizumab, and ustekinumab.

In some embodiments, the kinase inhibitor is an inhibitor of a kinase selected from one or more of a Janus kinase (JAK, including JAK1, JAK2, JAK3, TYK2), epidermal growth factor receptor (EGFR), a receptor tyrosine-protein kinase erbB-2 (Her2/neu, or ERBB2), Bcr-Abl, c-SRC, a Mitogen-activated protein kinase (MAP) kinase, anaplastic lymphoma kinase (ALK), spleen tyrosine kinase (SYK), Bruton's tyrosine kinase (BTK), a vascular endothelial growth factor (VEGF), a vascular endothelial growth factor receptor (VEGFR, including VEGFR1, VEGFR2, VEGFR3), a fibroblast growth factor receptor (FGFR), B-Raf, RET proto-oncogene, a platelet-derived growth factor receptor (PDGF-R), a tropomyosin receptor kinase (Trk, including TrkA, TrkB, TrkC), and c-Met, and further wherein the kinase inhibitor is selected from an antisense or RNAi agent targeted against the kinase, and an antibody or antigen-binding fragment or small molecule that specifically binds the kinase.

In some embodiments, the kinase inhibitor is selected from or more of nintedanib, baricitinib, fedratinib, filgotinib, gandotinib, lestaurtinib, momelotinib, pacritinib, peficitinib, ruxolitinib, tofacitinib, padacitinib, afatinib, axitinib, bosutinib, cetuximab, cobimetinib, crizotinib, cabozantinib, dasatinib, entrectinib, erlotinib, fostamatinib, gefitinib, ibrutinib, imatinib, lapatinib, lenvatinib, mubritinib, neratinib, nilotinib, pazopanib, pegaptanib, sorafenib, sunitinib, SU6656, toceranib, vandetanib, vatalanib, and vemurafenib.

In some embodiments, the B cell receptor inhibitor is selected from an antisense or RNAi agent targeted against CD20, and an antibody or antigen-binding fragment or small molecule that specifically binds CD20, or wherein the B cell receptor inhibitor is optionally selected from one or more of ibritumomab tiuxetan, obinutuzumab, ocaratuzumab, ocrelizumab, rituximab, tositumomab, and veltuzumab.

In some embodiments, the antisense agent is about 10-40 bases in length, and is optionally selected from a morpholino oligonucleotide (PMO), a peptide nucleic acid (PNA), a 2' O-methyl phosphorothioate oligonucleotide, a tricyclophosphorothioate oligonucleotide, and a locked nucleic acid (LNA).

In some embodiments, the antisense agent specifically hybridizes to a target region within a pre-mRNA or mRNA target sequence that encodes the target protein, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence.

In some embodiments, the RNAi agent comprises a sense strand that is substantially identical to an mRNA target sequence that encodes the target protein, and optionally an antisense strand that is complementary or substantially complementary to the mRNA target sequence that encodes the target protein, and optionally wherein the RNAi agent is a double-stranded short-interfering RNA (siRNA) oligonucleotide, or optionally wherein the RNAi agent, optionally an siRNA oligonucleotide, is encoded by a viral vector.

In some embodiments, the antibody or antigen-binding fragment thereof is a monoclonal antibody, optionally a humanized antibody, or optionally an Fv fragment or a single chain Fv (sFv) polypeptide.

In some embodiments, the composition has a purity of at least about 80%, 85%, 90%, 95%, 98%, or 99% on a protein basis or a weight-weight basis and is substantially aggregate-free.

In some embodiments, the composition is substantially endotoxin-free.

Certain compositions comprise lipid nanoparticles.

In some embodiments, the composition is in a syringe, optionally an injectable syringe. In some embodiments, the composition is a capsule, for example, an oral capsule.

Also included are methods of treating lung inflammation in a subject in need thereof, comprising administering to the subject
 (a) a histidyl-tRNA synthetase (HRS) polypeptide, or an expressible polynucleotide that encodes the HRS polypeptide; and
 (b) an immunomodulatory agent.

In some embodiments, (a) and (b) are administered separately, and are optionally defined according as described herein. In some embodiments, (a) and (b) are administered together, optionally as a therapeutic composition described herein.

In some embodiments, the HRS polypeptide comprises an Fc region, to form an HRS-Fc fusion polypeptide, for example, wherein the HRS-Fc fusion polypeptide comprises, consists, or consists essentially of an amino acid sequence that is at least 80%, 85%, 90%, 95%, 96%, 97%, 98%, 99%, or 100% identical to a sequence selected from Table H8. In some embodiments, the HRS polypeptide comprises, consists, or consists essentially of SEQ ID NO:157 (Fc-HRS(2-60) or HRS$^{FC1}$).

In some embodiments, the immunomodulatory agent alters one or more pharmacokinetic characteristics of the HRS polypeptide relative to the HRS polypeptide alone. In certain embodiments, the one or more altered pharmacokinetic characteristics of the HRS polypeptide are increased serum half-life, increased bioavailability, increased exposure (AUC), increased serum concentration, and/or decreased clearance.

In some embodiments, the immunomodulatory agent is pirfenidone or nintedanib.

In some embodiments, the HRS polypeptide comprises, consists, or consists essentially of SEQ ID NO:157 (Fc-HRS (2-60) or HRSF$^{C1}$, and the immunomodulatory agent is pirfenidone. In some embodiments, the pirfenidone increases the serum concentration of the HRS polypeptide in the subject by at least about 10, 20, 30, 40, 50, 60, 70, 80, 90, 100, 150, or 200% or more relative to the HRS polypeptide alone In some embodiments, the pirfenidone is administered at an individual dosage unit that ranges from about 50 to about 1000 mg, or an individual dosage unit of about no more than about, or at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg, optionally in 1, 2, or 3 capsules for oral dosing.

In some embodiments, the dosage of pirfenidone is administered at a daily dosage unit that ranges from about 100 to about 4000 mg/day, or a daily dosage unit of about, no more than about, or at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1200, 1300, 1400, 1500, 1600, 1700, 1800, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day, optionally in about 1, 2, 3, 4, 5, 6, 7, 8, 9 capsules for oral dosing.

In some embodiments, the pirfenidone is administered at an individual dosage unit of about 800 mg (e.g., 801 mg), optionally as three ~267 mg capsules for oral dosing, taken as three capsules per individual dosage. In some embodiments, the pirfenidone is administered at daily dosage unit of about 2400 mg/day (e.g., 2403 mg/day), optionally as nine ~267 mg capsules for oral dosing three times daily, taken as three capsules per individual dosage.

In some embodiments, the nintedanib is administered at an individual dosage unit that ranges from about 10 to about 500 mg, or an individual dosage unit of about, no more than about, or at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg, optionally in about 1, 2, or 3 capsules.

In some embodiments, the nintedanib is administered at a daily dosage unit that ranges from about 20 to about 1000 mg/day, or a daily dosage unit of about, no more than about, or at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg/day, optionally in about 1, 2, 3, 4, 5, or 6 capsules.

In some embodiments, the nintedanib is administered at a daily dosage unit that ranges from about 100 to 150 mg, or ranges from about 200 to 300 mg/day, optionally for a once or twice daily dosage. In some embodiments, the nintedanib is administered at a daily dosage unit of about 100 or 150 mg, or about 200 to 300 mg/day, optionally for a once or twice daily dosage.

In some embodiments, the subject has or is risk for having an interstitial lung disease (ILD). In some embodiments, the ILD is idiopathic or associated with a connective tissue disease, an autoimmune disease, exposure to inhaled substances or drug(s), an infection, or a malignancy.

In some embodiments, the ILD is selected from or is associated with one or more of idiopathic interstitial pneumonia, idiopathic pulmonary fibrosis, sarcoidosis, Hammann-Rich syndrome, Antisynthetase syndrome, idiopathic eosinophilic pneumonia, alveolar hemorrhage syndrome, pulmonary alveolar proteinosis, asbestosis, silicosis, berylliosis, rheumatoid arthritis, lupus erythematosus, chronic graft vs host disease with pulmonary involvement, sclerosis (systemic) or scleroderma, polymyositis, dermatomyositis, chronic pulmonary disease, asthma, bronchitis (respiratory bronchitis), pneumonia, hypersensitivity pneumonitis, chronic hypersensitivity pneumonia, respiratory distress syndrome, Still's disease, acute lung injury, microscopic polyangitis, pulmonary edema, pulmonary Langerhans cell histiocytosis, acute inhalational exposures, drug-induced lung disease, desquamative interstitial pneumonia, and/or cystic fibrosis.

In some embodiments, the ILD is associated with one or more of Surfactant-Protein-B Deficiency (Mutations in SFTPB), Surfactant-Protein-C Deficiency (Mutations in SFTPC), ABCA3-Deficiency (Mutations in ABCA3), Brain Lung Thyroid Syndrome (Mutations in TTF1), or Congenital Pulmonary Alveolar Proteinosis (Mutations in CSFR2A, CSFR2B), Alveolar Capillary Dysplasia (Mutations in FoxF1), Mutations in telomerase reverse transcriptase (PERT), Mutations in telomerase RNA component (TERC), Mutations in the regulator of telomere elongation helicase 1 (RIEL1), and/or Mutations in poly(A)-specific ribonuclease (PARN).

In some embodiments, the drug(s) are selected from one or more of antibiotics, chemotherapeutic agents, antiarrhythmic agents, and statins. In some embodiments, the infection is selected from one or more of atypical pneumonia, pneumocystis pneumonia (PCP), tuberculosis, *Chlamydia trachomatis*, and Respiratory Syncytial Virus (RSV), cryptogenic organizing pneumonia. In some embodiments, the malignancy is lymphangitic carcinomatosis or lymphoma.

In some embodiments, the subject in need thereof has a condition selected from one or more of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema.

In some embodiments, the subject in need thereof has an obstructive or inflammatory airway disease. In some embodiments, the obstructive or inflammatory airways disease is selected from one or more of chronic eosinophilic pneumonia, chronic obstructive pulmonary disease (COPD), COPD that includes chronic bronchitis, pulmonary emphysema or dyspnea, COPD that is characterized by irreversible, progressive airways obstruction, and acute respiratory distress syndrome (ARDS).

In some embodiments, the subject in need thereof has a condition related to exacerbation of airways hyper-reactivity consequent to other drug therapy, airway disease that is associated with pulmonary hypertension, bronchitis or acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis, vesicular bronchitis, acute lung injury, bronchiectasis or cylindric bronchiectasis, sacculated bronchiectasis, fusiform bronchiectasis, capillary bronchiectasis, cystic bronchiectasis, dry bronchiectasis, or follicular bronchiectasis.

In some embodiments, the subject in need thereof has an Ashcroft score of 1, 2, 3, 4, 5, 6, 7, or 8.

Certain embodiments increase the life expectancy of the subject in need thereof, optionally by about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more years.

Certain embodiments improve one or more of the clinical symptoms or parameters of the lung inflammation in the subject in need thereof.

In some embodiments, the one or more clinical symptoms or parameters are selected from one or more of lung fibrosis, inflammatory cell infiltrates in the lung, respiratory function, and body weight.

Certain embodiments improve lung fibrosis in the subject in need thereof by about or at least about 10, 20, 30, 40, 50, 60, 70, 80, 90, 100, 200, 300, 400, 500, 600, 700, 800, 900, 1000% or more, optionally as measured over a period of about 1, 2, 3, 4, 5, 6, 7, 8, 9, 10, 11, 12, 13, 14, 15, 16, 17, 18, 19, 20, 21, 22, 23, or 24 months or more.

Certain embodiments improve lung fibrosis in the subject in need thereof as measured by a reduced Ashcroft score, optionally an Ashcroft score that is reduced by 1, 2, 3, 4, 5, 6, 7, or 8 grades relative to an earlier score.

Certain embodiments reduce inflammatory cell infiltrates in the lung by about or at least about 10, 20, 30, 40, 50, 60, 70, 80, 90, 100, 200, 300, 400, 500, 600, 700, 800, 900, 1000% or more, optionally as measured over a period of about 1, 2, 3, 4, 5, 6, 7, 8, 9, 10, 11, 12, 13, 14, 15, 16, 17, 18, 19, 20, 21, 22, 23, or 24 months or more.

Certain embodiments improve respiratory function by about or at least about 10, 20, 30, 40, 50, 60, 70, 80, 90, 100, 200, 300, 400, 500, 600, 700, 800, 900, 1000% or more, optionally as measured over a period of about 1, 2, 3, 4, 5, 6, 7, 8, 9, 10, 11, 12, 13, 14, 15, 16, 17, 18, 19, 20, 21, 22, 23, or 24 months or more. In some embodiments, the improved respiratory function is selected from one or more of increased expiration time, increased inspiration time, decreased peak expiratory flow, decreased peak inspiratory flow, decreased respiratory minute volume (RMV), and decreased respiratory rate.

Also included are patient care kits, comprising:
(a) a histidyl-tRNA synthetase (HRS) polypeptide, or an expressible polynucleotide that encodes the HRS polypeptide; and
(b) an immunomodulatory agent.

In certain patient care kits, (a) and (b) are in separate compositions, and are optionally defined as described herein. In some patient care kits, (a) and (b) are in the same composition, optionally as a therapeutic composition as described herein.

In some embodiments, the immunomodulatory agent is pirfenidone or nintedanib.

In some embodiments, the pirfenidone is at an individual dosage unit that ranges from about 50 to about 1000 mg (optionally in about 1, 2, or 3 capsules for oral dosing), or an individual dosage unit of about no more than about, or at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg (optionally in 1, 2, or 3 capsules for oral dosing).

In some embodiments, the pirfenidone is at a daily dosage unit that ranges from about 100 to about 4000 mg/day (optionally in about 3, 4, 5, 6, 7, 8, 9 capsules for oral dosing), or a daily dosage unit of about, no more than about, or at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1200, 1300, 1400, 1500, 1600, 1700, 1800, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day (optionally in about 3, 4, 5, 6, 7, 8, 9 capsules for oral dosing).

In specific embodiments, the pirfenidone is at an individual dosage unit of about 800 mg (e.g., 801 mg), for example, as three ~267 mg capsules for oral dosing, taken as three capsules per individual dosage. In specific embodiments, the pirfenidone is at daily dosage unit of about 2400 mg/day (e.g., 2403 mg/day), for example, as nine ~267 mg capsules for oral dosing three times daily, taken as three capsules per individual dosage.

In some embodiments, the nintedanib is at an individual dosage unit that ranges from about 10 to about 500 mg (optionally in about 1, 2, or 3 capsules), or an individual dosage unit of about, no more than about, or at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg (optionally in about 1, 2, or 3 capsules).

In some embodiments, the nintedanib is at a daily dosage unit that ranges from about 20 to about 1000 mg/day (optionally in about 1, 2, 3, 4, 5, or 6 capsules), or a daily dosage unit of about, no more than about, or at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg/day (optionally in about 1, 2, 3, 4, 5, or 6 capsules).

In some embodiments, the nintedanib is at a daily dosage unit that ranges from about 100 to 150 mg, or ranges from about 200 to 300 mg/day, optionally for a once or twice daily dosage. In some embodiments, the nintedanib is at a dosage unit of about 100 or 150 mg, or about 200 to 300 mg/day, optionally for a once or twice daily dosage.

Also included are methods of altering one or more pharmacokinetic characteristics of an HRS-Fc fusion polypeptide in a subject, comprising administering to the subject the HRS-Fc fusion polypeptide, or an expressible polynucleotide that encodes the HRS-Fc fusion polypeptide, in combination with pirfenidone. In some embodiments, HRS-Fc fusion polypeptide comprises, consists, or consists essentially of an amino acid sequence that is at least 80%, 85%, 90%, 95%, 96%, 97%, 98%, 99%, or 100% identical to a sequence selected from Table H8. In some embodiments, the HRS polypeptide comprises, consists, or consists essentially of SEQ ID NO:157 (Fc-HRS(2-60) or $HRS^{FC1}$).

Also included are methods of treating lung inflammation (as described herein) in a subject in need thereof, comprising administering to the subject an HRS-Fc fusion polypeptide, or an expressible polynucleotide that encodes the HRS-Fc fusion polypeptide. In some embodiments, the HRS-Fc fusion polypeptide comprises, consists, or consists essentially of an amino acid sequence that is at least 80%, 85%, 90%, 95%, 96%, 97%, 98%, 99%, or 100% identical to a sequence selected from Table H8. In some embodiments, the HRS polypeptide comprises, consists, or consists essentially of SEQ ID NO:157 (Fc-HRS(2-60) or $HRS^{FC1}$).

DETAILED DESCRIPTION

Figure 1:
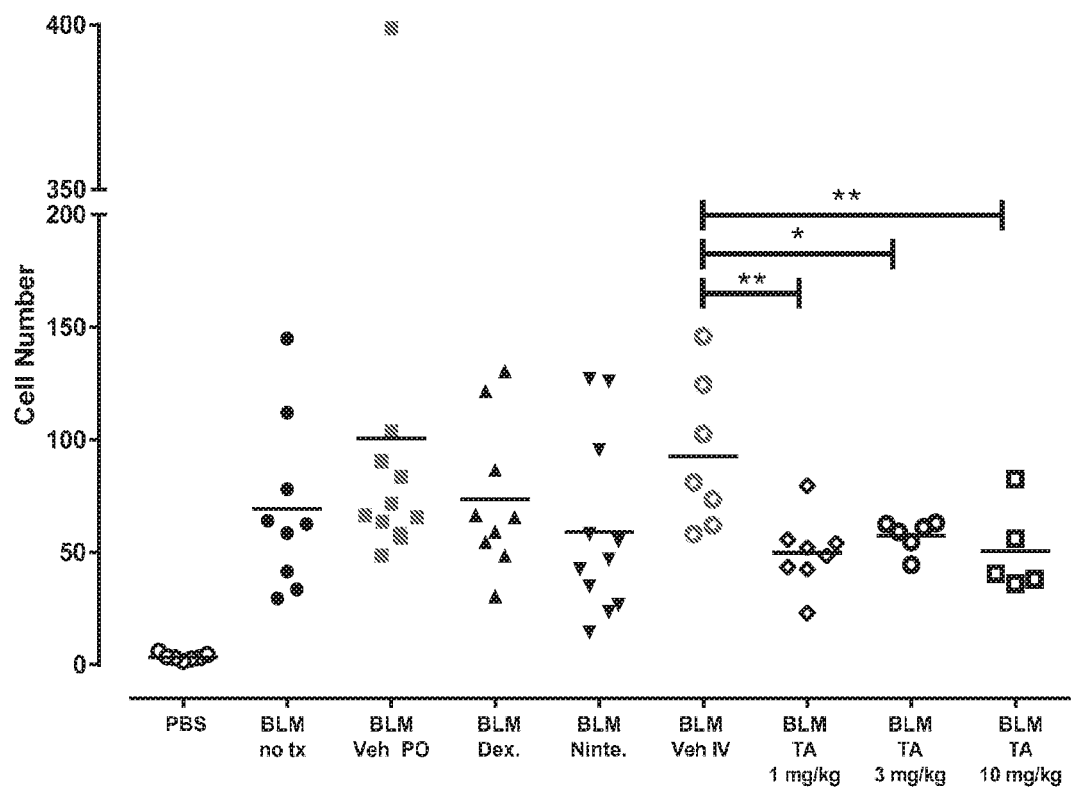
FIG. 1 shows BAL Fluid Cell Counts. Individual cell counts are shown with a line indicating the group mean: "no tx" indicates no treatment, "Veh" indicates treatment with Vehicle, "Dex." indicates treatment with dexamethasone, "Ninte." indicates treatment with Nintedanib, and "TA" indicates treatment with Test Article. Statistical comparisons were conducted by 1-way ANOVA within PO or IV treatment groups followed by Dunnett's post-hoc test. $*p<0.05$, $**p<0.01$ vs. IV Vehicle.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005). Poly(ethylene glycol), Chemistry and Biological Applications, ACS, Washington, 1997; Veronese, F., and J. M. Harris, Eds., Peptide and protein PEGylation, Advanced Drug Delivery Reviews, 54(4) 453-609 (2002); Zalipsky, S., et al., "Use of functionalized Poly(Ethylene Glycols) for modification of polypeptides" in Polyethylene Glycol Chemistry: Biotechnical and Biomedical Applications.

Definitions

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "antagonist" or "inhibitor" refers to biological structure or chemical agent that interferes with or otherwise reduces the physiological action of another agent or molecule. In some instances, the antagonist specifically binds to the other agent or molecule. Included are full and partial antagonists.

An "agonist" refers to biological structure or chemical agent that increases or enhances the physiological action of another agent or molecule. In some instances, the agonist specifically binds to the other agent or molecule. Included are full and partial agonists.

The term "anergy" refers to the functional inactivation of a T cell, or B cell response to re-stimulation by antigen.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, a subject "at risk" of developing a disease, or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

The term "binding" refers to a direct association between two molecules, due to, for example, covalent, electrostatic, hydrophobic, and ionic and/or hydrogen-bond interactions, including interactions such as salt bridges and water bridges.

The term "clonal deletion" refers to the deletion (e.g., loss, or death) of auto-reactive T-cells. Clonal deletion can be achieved centrally in the thymus, or in the periphery, or both.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligosaccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

As used herein, the terms "contacting a cell", "introducing" or "delivering" include delivery of the agents described herein (e.g., polypeptide agents, polynucleotide agents) into a cell by methods routine in the art, e.g., transfection (e.g., liposome, calcium-phosphate, polyethyleneimine), electroporation (e.g., nucleofection), microinjection) or administration to a subject.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains" In some embodiments, the peptides have the capability of inducing cell (e.g., muscle cell) penetration within about or at least about 30%, 40%, 50%, 60%, 70%, 80%, 90%, or 100% of cells of a given cell culture population and allow macromolecular translocation within multiple tissues (e.g., muscle tissues) in vivo upon systemic or other form of administration. In some embodiments, the CPPs are of the formula —[(C(O)CHR'NH)$_m$]R" wherein R' is a side chain of a naturally occurring amino acid or a one- or two-carbon homolog thereof, R" is selected from Hydrogen or acyl, and m is an integer up to 50. Additional CPPs are well-known in the art and are disclosed, for example, in U.S. Application No. 2010/0016215, which is incorporated by reference in its entirety. In some embodiments, m is an integer selected from 1 to 50 where, when m is 1, the moiety is a single amino acid or derivative thereof. Any of the polynucleotide agents (e.g., antisense, RNAi agents) described herein can be conjugated to a CPP, for example, to improve uptake into target cells, e.g., muscle cells.

The term "half maximal effective concentration" or "EC50" refers to the concentration of an agent (e.g., HRS polypeptide, or other agent) as described herein at which it induces a response halfway between the baseline and maximum after some specified exposure time; the EC50 of a graded dose response curve therefore represents the concentration of a compound at which 50% of its maximal effect is observed. EC50 also represents the plasma concentration required for obtaining 50% of a maximum effect in vivo. Similarly, the "EC90" refers to the concentration of an agent or composition at which 90% of its maximal effect is observed. The "EC90" can be calculated from the "EC50" and the Hill slope, or it can be determined from the data directly, using routine knowledge in the art. In some embodiments, the EC50 of an agent is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a biotherapeutic composition will have an EC50 value of about 1 nM or less.

"Homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The term "innate immune response" refers to the responses of immune cells (including macrophages, and natural killer cells (NK)) and the associated mechanisms of modulating cytokine expression and release (e.g., interferons and interferon-signaling), inducing cell death, and inhibiting protein synthesis, which defend the host from infection by pathogens.

By "isolated" is meant material that is substantially or essentially free from components that normally accompany it in its native state. For example, an "isolated polynucleotide," "isolated oligonucleotide," or "isolated oligonucleotide" as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The terms "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more agents or compositions to produce or cause a greater physiological response (i.e., downstream effects) in a cell or a subject relative to the response caused by either no agent/compound or a control compound. Relevant physiological or cellular responses (in vivo or in vitro) will be apparent to persons skilled in the art, and may include increases in skeletal muscle mass in a tissue or subject in need thereof. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7, 1.8), the amount produced by no agent/compound (the absence of an agent) or a control compound. The term "reduce" or "inhibit" may relate generally to the ability of one or more agents or compositions to "decrease" a relevant physiological or cellular response, such as expression of a target gene or a symptom of a disease or condition described herein, as measured according to routine techniques in the diagnostic art. Relevant physiological or cellular responses (in vivo or in vitro) will be apparent to persons skilled in the art, and may include reductions or improvements in the symptoms or pathology of lung inflammation or an ILD, as described herein. A "decrease" in a response may be "statistically significant" as compared to the response produced by no agent or composition or a control agent or composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

In certain embodiments, the "purity" of any given agent in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high performance liquid chromatography (HPLC), a well-known form of column chromatography used frequently in biochemistry and analytical chemistry to separate, identify, and quantify compounds.

A "lipid nanoparticle" or "solid lipid nanoparticle" refers to one or more spherical nanoparticles with an average diameter of between about 10 to about 1000 nanometers, and which comprise a solid lipid core matrix that can solubilize lipophilic molecules. The lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, which are incorporated by reference in their entireties.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligonucleotide. Exemplary analogs include hypoxanthine (the base component of the nucleoside inosine); 2, 6-diaminopurine; 5-methyl cytosine; C5-propynyl-modified pyrimidines; 9-(aminoethoxy)phenoxazine (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glen-research.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligonucleotides described herein. Examples of expanded-size nucleobases are shown below:

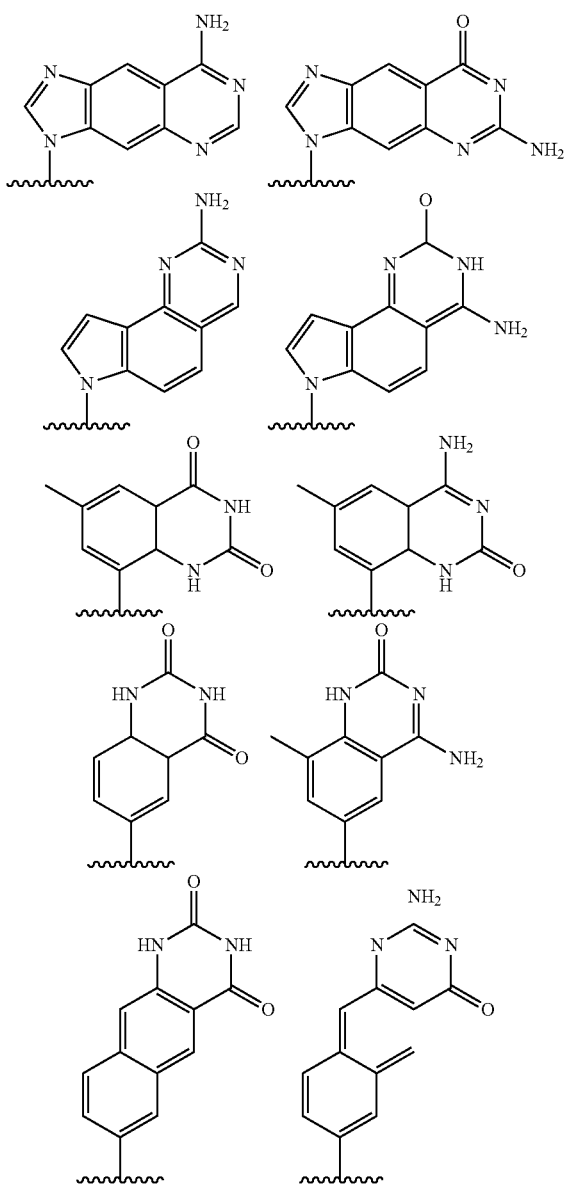

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligonucleotide.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "polynucleotide" and "nucleic acid" includes mRNA, RNA, cRNA, cDNA, and DNA. The term typically refers to polymeric form of nucleotides of at least 10 bases in length, either ribonucleotides or deoxynucleotides or a modified form of either type of nucleotide. The term includes single and double stranded forms of DNA. The terms "isolated DNA" and "isolated polynucleotide" and "isolated nucleic acid" refer to a molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode a polypeptide. Also included are recombinant vectors, including, for example, expression vectors, viral vectors, plasmids, cosmids, phagemids, phage, viruses, and the like.

Additional coding or non-coding sequences may, but need not, be present within a polynucleotide described herein, and a polynucleotide may, but need not, be linked to other molecules and/or support materials. Hence, a polynucleotide or expressible polynucleotides, regardless of the length of the coding sequence itself, may be combined with other sequences, for example, expression control sequences.

"Expression control sequences" include regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, which have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease 51) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-REx™ system (Invitrogen Carlsbad, Calif.), LacSwitch® (Stratagene, (San Diego, Calif.) and the Cre-ERT tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

An "expressible polynucleotide" includes a cDNA, RNA, mRNA or other polynucleotide that comprises at least one coding sequence and optionally at least one expression control sequence, for example, a transcriptional and/or translational regulatory element, and which can express an encoded polypeptide (for example, an HRS polypeptide) upon introduction into a cell, for example, a cell in a subject.

In some embodiments, the expressible polynucleotide is a modified RNA or modified mRNA polynucleotide, for example, a non-naturally occurring RNA analog. In certain embodiments, the modified RNA or mRNA polypeptide comprises one or more modified or non-natural bases, for example, a nucleotide base other than adenine (A), guanine (G), cytosine (C), thymine (T), and/or uracil (U). In some embodiments, the modified mRNA comprises one or more modified or non-natural internucleotide linkages. Expressible RNA polynucleotides for delivering an encoded therapeutic polypeptide are described, for example, in Kormann et al., Nat Biotechnol. 29:154-7, 2011; and U.S. Application Nos. 2015/0111248; 2014/0243399; 2014/0147454; and 2013/0245104, which are incorporated by reference in their entireties.

In some embodiments, various viral vectors that can be utilized to deliver an expressible polynucleotide include adenoviral vectors, herpes virus vectors, vaccinia virus vectors, adeno-associated virus (AAV) vectors, and retroviral vectors. In some instances, the retroviral vector is a derivative of a murine or avian retrovirus, or is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein. Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector.

In certain instances, the expressible polynucleotides described herein are engineered for localization within a cell, potentially within a specific compartment such as the nucleus, or are engineered for secretion from the cell or translocation to the plasma membrane of the cell. In exemplary embodiments, the expressible polynucleotides are engineered for nuclear localization.

Also included are biologically active "variants" and "fragments" of the polypeptides described herein, and the polynucleotides that encode the same. "Variants" contain one or more substitutions, additions, deletions, and/or insertions relative to a reference polypeptide or polynucleotide (see, e.g., the Tables and the Sequence Listing). A variant polypeptide or polynucleotide comprises an amino acid or polynucleotide sequence with at least about 50%, 55%, 60%, 65%, 70%, 75%, 80%, 85%, 90%, 91%, 92%, 93%, 94%, 95%, 96%, 97%, 98%, 99% or more sequence identity or similarity or homology to a reference sequence, as described herein, and substantially retains the activity of that reference sequence. Also included are sequences that consist of or differ from a reference sequences by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids or nucleotides and which substantially retain the activity of that reference sequence. In certain embodiments, the additions or deletions include C-terminal and/or N-terminal additions and/or deletions.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an agent provided herein to dissolve in a liquid solvent and form a homogenous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" includes a mammalian subject such as a human subject.

"Substantially" or "essentially" means nearly totally or completely, for instance, 95% or greater of some given quantity.

"Therapeutic response" refers to improvement of symptoms (whether or not sustained) based on the administration of the therapeutic response.

As used herein, the term "target" refers to a RNA region, and specifically, to a RNA region of a target gene described herein. The target can include coding and non-coding sequences, 5' upstream sequences, 3' downstream sequences, and other RNA sequences described herein.

The term "target sequence" refers to a portion of the target RNA against which the antisense or RNAi agent is directed, for example, the sequence to which the antisense oligonucleotide will hybridize by Watson-Crick base pairing of a complementary sequence, or the sequence that corresponds to the sense strand of the RNAi agent.

As used herein, the term "quantifying", "quantification" or other related words refer to determining the quantity, mass, or concentration in a unit volume, of a nucleic acid, polynucleotide, oligonucleotide, peptide, polypeptide, or protein.

As used herein, the terms "therapeutically effective amount", "therapeutic dose," "prophylactically effective amount," or "diagnostically effective amount" is the amount of an agent needed to elicit the desired biological response following administration. Similarly the term "antisense therapy" or "RNAi therapy" includes a therapy that maintains the average steady state concentration of an antisense or RNAi agent in the patient's plasma or other tissue compartment (e.g., muscle tissue) above the minimum effective therapeutic level.

As used herein, "treatment" of a subject (e g a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Histidyl-tRNA Synthetase (HRS) Polypeptides and Polynucleotides

Certain embodiments include histidyl-tRNA synthetase polypeptides ("HRS" or "HisRS" polypeptides), including conjugates (e.g., Fc conjugates), variants, and fragments thereof, and expressible polynucleotides that encode the HRS polypeptides. Histidyl-tRNA synthetases belong to the class II tRNA synthetase family, which has three highly conserved sequence motifs. Class I and II tRNA synthetases are widely recognized as being responsible for the specific attachment of an amino acid to its cognate tRNA in a two-step reaction: the amino acid (AA) is first activated by ATP to form AA-AMP and then transferred to the acceptor end of the tRNA. The full-length histidyl-tRNA synthetases typically exist either as a cytosolic homodimer, or an alternatively spliced mitochondrial form.

Certain biological fragments or alternatively spliced isoforms of eukaryotic histidyl-tRNA synthetases, or in some contexts the intact full-length synthetase, modulate certain therapeutically relevant cell-signaling pathways and/or have anti-inflammatory properties. These activities, which are distinct from the classical role of tRNA synthetases in protein synthesis, are referred to herein as "non-canonical activities." For example, as provided herein, HRS polypeptides such as the N-terminal fragment of histidyl-tRNA synthetase (e.g., HRS 1-48, HRS 1-60) are capable, inter alis, of exerting an anti-inflammatory signal by blocking the migration, activation, or differentiation of inflammatory cells (e.g., monocytes, macrophages, T cells, B cells, NK cells, dendritic cells) associated with the sites of active inflammation in vivo. In addition, certain mutations or deletions (e.g., HRS 1-506, HRS 1-60) relative to the full-length HRS polypeptide sequence confer increased activities and/or improved pharmacological properties. The sequences of certain exemplary HRS polypeptides are provided in Table H1 below.

TABLE H1

Exemplary HRS polypeptides

| Name | Residues | Sequence | SEQ ID NO: |
|---|---|---|---|
| FL cytosolic wild type | 1-509 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQPLCIC | 1 |
| HRS(1-500) | 1-500 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKR | 2 |
| HRS(1-501) | 1-501 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRR | 3 |
| HRS(1-502) | 1-502 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK | 4 |

TABLE H1-continued

Exemplary HRS polypeptides

| Name | Residues | Sequence | SEQ ID NO: |
|---|---|---|---|
| | | KLLEERLKLVSELWDAGIKAELLYKKNPKLLNQLQYCE EAGIPLVAIIGEQELKDGVIKLRSVTSREEVDVRREDL VEEIKRRT | |
| HRS(1-503) | 1-503 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTG | 5 |
| HRS(1-504) | 1-504 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQ | 6 |
| HRS(1-505) | 1-505 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQP | 7 |
| HisRS1[N8] HRS(1-506) | 1-506 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQPL | 8 |
| HRS(2-506) | 2-506 | AERAALEELVKLQGERVRGLKQQKASAELIEEEVAKLL KLKAQLGPDESKQKFVLKTPKGTRDYSPRQMAVREKVF DVIIRCFKRHGAEVIDTPVFELKETLMGKYGEDSKLIY DLKDQGGELLSLRYDLTVPFARYLAMNKLTNIKRYHIA KVYRRDNPAMTRGRYREFYQCDFDIAGNFDPMIPDAEC LKIMCEILSSLQIGDFLVKVNDRRILDGMFAICGVSDS KFRTICSSVDKLDKVSWEEVKNEMVGEKGLAPEVADRI GDYVQQHGGVSLVEQLLQDPKLSQNKQALEGLGDLKLL FEYLTLFGIDDKISFDLSLARGLDYYTGVIYEAVLLQT PAQAGEEPLGVGSVAAGGRYDGLVGMFDPKGRKVPCVG LSIGVERIFSIVEQRLEALEEKIRTTETQVLVASAQKK | 9 |

TABLE H1-continued

Exemplary HRS polypeptides

| Name | Residues | Sequence | SEQ ID NO: |
|---|---|---|---|
| | | LLEERLKLVSELWDAGIKAELLYKKNPKLLNQLQYCEE AGIPLVAIIGEQELKDGVIKLRSVTSREEVDVRREDLV EEIKRRTGQPL | |
| HRS(1-507) | 1-507 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQPLC | 10 |
| HRS(1-508) | 1-508 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQPLCI | 11 |
| HisRS1[N6] HRS(1-48) | 1-48 | MAERAALEELVKLQGERVRGLKQQKASAELIEEEVAKL LK LKAQLGPD | 12 |
| | 1-80 | MAERAALEELVKLQGERVRGLKQQKASAELIEEEVAKL LKLKAQLGPDESKQKFVLKTPKGTRDYSPRQMAVREKV FDVI | 13 |
| | 1-79 | MAERAALEELVKLQGERVRGLKQQKASAELIEEEVAKL LK LKAQLGPDESKQKFVLKTPKGTRDYSPRQMAVREKVFD V | 14 |
| | 1-78 | MAERAALEELVKLQGERVRGLKQQKASAELIEEEVAKL LKLKAQLGPDESKQKFVLKTPKGTRDYSPRQMAVREKV FD | 15 |
| | 1-77 | MAERAALEELVKLQGERVRGLKQQKASAELIEEEVAKL LKLKAQLGPDESKQKFVLKTPKGTRDYSPRQMAVREKV F | 16 |
| | 1-76 | MAERAALEELVKLQGERVRGLKQQKASAELIEEEVAKL LKLKAQLGPDESKQKFVLKTPKGTRDYSPRQMAVREKV | 17 |
| | 1-75 | MAERAALEELVKLQGERVRGLKQQKASAELIEEEVAKL LKLKAQLGPDESKQKFVLKTPKGTRDYSPRQMAVREK | 18 |
| | 1-74 | MAERAALEELVKLQGERVRGLKQQKASAELIEEEVAKL LKLKAQLGPDESKQKFVLKTPKGTRDYSPRQMAVRE | 19 |
| | 1-73 | MAERAALEELVKLQGERVRGLKQQKASAELIEEEVAKL LKLKAQLGPDESKQKFVLKTPKGTRDYSPRQMAVR | 20 |
| | 1-72 | MAERAALEELVKLQGERVRGLKQQKASAELIEEEVAKL LKLKAQLGPDESKQKFVLKTPKGTRDYSPRQMAV | 21 |
| | 1-71 | MAERAALEELVKLQGERVRGLKQQKASAELIEEEVAKL LKLKAQLGPDESKQKFVLKTPKGTRDYSPRQMA | 22 |
| | 1-70 | MAERAALEELVKLQGERVRGLKQQKASAELIEEEVAKL LKLKAQLGPDESKQKFVLKTPKGTRDYSPRQM | 23 |

TABLE H1-continued

Exemplary HRS polypeptides

| Name | Residues | Sequence | SEQ ID NO: |
|---|---|---|---|
| | 1-69 | MAERAALEELVKLQGERVRGLKQQKASAELIEEEVAKL LKLKAQLGPDESKQKFVLKTPKGTRDYSPRQ | 24 |
| | 1-68 | MAERAALEELVKLQGERVRGLKQQKASAELIEEEVAKL LKLKAQLGPDESKQKFVLKTPKGTRDYSPR | 25 |
| | 1-67 | MAERAALEELVKLQGERVRGLKQQKASAELIEEEVAKL LKLKAQLGPDESKQKFVLKTPKGTRDYSP | 26 |
| | 1-66 | MAERAALEELVKLQGERVRGLKQQKASAELIEEEVAKL LKLKAQLGPDESKQKFVLKTPKGTRDYS | 27 |
| | 1-65 | MAERAALEELVKLQGERVRGLKQQKASAELIEEEVAKL LKLKAQLGPDESKQKFVLKTPKGTRDY | 28 |
| | 1-64 | MAERAALEELVKLQGERVRGLKQQKASAELIEEEVAKL LKLKAQLGPDESKQKFVLKTPKGTRD | 29 |
| | 1-63 | MAERAALEELVKLQGERVRGLKQQKASAELIEEEVAKL LKLKAQLGPDESKQKFVLKTPKGTR | 30 |
| | 1-62 | MAERAALEELVKLQGERVRGLKQQKASAELIEEEVAKL LKLKAQLGPDESKQKFVLKTPKGT | 31 |
| | 1-61 | MAERAALEELVKLQGERVRGLKQQKASAELIEEEVAKL LKLKAQLGPDESKQKFVLKTPKG | 32 |
| | 1-60 | MAERAALEELVKLQGERVRGLKQQKASAELIEEEVAKL LKLKAQLGPDESKQKFVLKTPK | 33 |
| | 1-59 | MAERAALEELVKLQGERVRGLKQQKASAELIEEEVAKL LKLKAQLGPDESKQKFVLKTP | 34 |
| | 1-58 | MAERAALEELVKLQGERVRGLKQQKASAELIEEEVAKL LKLKAQLGPDESKQKFVLKT | 35 |
| | 1-57 | MAERAALEELVKLQGERVRGLKQQKASAELIEEEVAKL LKLKAQLGPDESKQKFVLK | 36 |
| | 1-56 | MAERAALEELVKLQGERVRGLKQQKASAELIEEEVAKL LKLKAQLGPDESKQKFVL | 37 |
| | 1-55 | MAERAALEELVKLQGERVRGLKQQKASAELIEEEVAKL LKLKAQLGPDESKQKFV | 38 |
| | 1-54 | MAERAALEELVKLQGERVRGLKQQKASAELIEEEVAKL LKLKAQLGPDESKQKF | 39 |
| | 1-53 | MAERAALEELVKLQGERVRGLKQQKASAELIEEEVAKL LKLKAQLGPDESKQK | 40 |
| | 1-52 | MAERAALEELVKLQGERVRGLKQQKASAELIEEEVAKL LKLKAQLGPDESKQ | 41 |
| | 1-51 | MAERAALEELVKLQGERVRGLKQQKASAELIEEEVAKL LKLKAQLGPDESK | 42 |
| | 1-50 | MAERAALEELVKLQGERVRGLKQQKASAELIEEEVAKL LKLKAQLGPDES | 43 |
| | 1-49 | MAERAALEELVKLQGERVRGLKQQKASAELIEEEVAKL LKLKAQLGPDE | 44 |
| | 1-48 | MAERAALEELVKLQGERVRGLKQQKASAELIEEEVAKL LKLKAQLGPD | 45 |
| | 1-47 | MAERAALEELVKLQGERVRGLKQQKASAELIEEEVAKL LKLKAQLGP | 46 |
| | 1-46 | MAERAALEELVKLQGERVRGLKQQKASAELIEEEVAKL LKLKAQLG | 47 |
| | 1-45 | MAERAALEELVKLQGERVRGLKQQKASAELIEEEVAKL LKLKAQL | 48 |

TABLE H1-continued

Exemplary HRS polypeptides

| Name | Residues | Sequence | SEQ ID NO: |
|---|---|---|---|
| | 1-44 | MAERAALEELVKLQGERVRGLKQQKASAELIEEEVAKL LKLKAQ | 49 |
| | 1-43 | MAERAALEELVKLQGERVRGLKQQKASAELIEEEVAKL LK LKA | 50 |
| | 1-42 | MAERAALEELVKLQGERVRGLKQQKASAELIEEEVAKL LK LK | 51 |
| | 1-41 | MAERAALEELVKLQGERVRGLKQQKASAELIEEEVAKL LK L | 52 |
| | 1-40 | MAERAALEELVKLQGERVRGLKQQKASAELIEEEVAKL LK | 53 |
| | 2-80 | AERAALEELVKLQGERVRGLKQQKASAELIEEEVAKLL KLKAQLGPDESKQKFVLKTPKGTRDYSPRQMAVREKVF DVI | 54 |
| | 3-80 | ERAALEELVKLQGERVRGLKQQKASAELIEEEVAKLLK LKAQLGPDESKQKFVLKTPKGTRDYSPRQMAVREKVFD VI | 55 |
| | 4-80 | RAALEELVKLQGERVRGLKQQKASAELIEEEVAKLLKL KAQLGPDESKQKFVLKTPKGTRDYSPRQMAVREKVFDV I | 56 |
| | 5-80 | AALEELVKLQGERVRGLKQQKASAELIEEEVAKLLKLK AQLGPDESKQKFVLKTPKGTRDYSPRQMAVREKVFDVI | 57 |
| | 6-80 | ALEELVKLQGERVRGLKQQKASAELIEEEVAKLLKLKA QLGPDESKQKFVLKTPKGTRDYSPRQMAVREKVFDVI | 58 |
| | 7-80 | LEELVKLQGERVRGLKQQKASAELIEEEVAKLLKLKAQ LGPDESKQKFVLKTPKGTRDYSPRQMAVREKVFDVI | 59 |
| | 8-80 | EELVKLQGERVRGLKQQKASAELIEEEVAKLLKLKAQL GPDESKQKFVLKTPKGTRDYSPRQMAVREKVFDVI | 60 |
| | 9-80 | ELVKLQGERVRGLKQQKASAELIEEEVAKLLKLKAQLG PDESKQKFVLKTPKGTRDYSPRQMAVREKVFDVI | 61 |
| | 10-80 | LVKLQGERVRGLKQQKASAELIEEEVAKLLKLKAQLGP DESKQKFVLKTPKGTRDYSPRQMAVREKVFDVI | 62 |
| | 11-80 | VKLQGERVRGLKQQKASAELIEEEVAKLLKLKAQLGPD ESKQKFVLKTPKGTRDYSPRQMAVREKVFDVI | 63 |
| | 12-80 | KLQGERVRGLKQQKASAELIEEEVAKLLKLKAQLGPDE SKQKFVLKTPKGTRDYSPRQMAVREKVFDVI | 64 |
| | 13-80 | LQGERVRGLKQQKASAELIEEEVAKLLKLKAQLGPDES KQKFVLKTPKGTRDYSPRQMAVREKVFDVI | 65 |
| | 14-80 | QGERVRGLKQQKASAELIEEEVAKLLKLKAQLGPDESK QKFVLKTPKGTRDYSPRQMAVREKVFDVI | 66 |
| | 15-80 | GERVRGLKQQKASAELIEEEVAKLLKLKAQLGPDESKQ KFVLKTPKGTRDYSPRQMAVREKVFDVI | 67 |
| | 16-80 | RVRGLKQQKASAELIEEEVAKLLKLKAQLGPDESKQKF VLKTPKGTRDYSPRQMAVREKVFDVI | 68 |
| | 17-80 | VRGLKQQKASAELIEEEVAKLLKLKAQLGPDESKQKFV LKTPKGTRDYSPRQMAVREKVFDVI | 69 |
| | 18-80 | RGLKQQKASAELIEEEVAKLLKLKAQLGPDESKQKFVL KTPKGTRDYSPRQMAVREKVFDVI | 70 |
| | 19-80 | GLKQQKASAELIEEEVAKLLKLKAQLGPDESKQKFVLK TPKGTRDYSPRQMAVREKVFDVI | 71 |

TABLE H1-continued

Exemplary HRS polypeptides

| Name | Residues | Sequence | SEQ ID NO: |
|---|---|---|---|
| | 20-80 | LKQQKASAELIEEEVAKLLKLKAQLGPDESKQKFVLKT PKGTRDYSPRQMAVREKVFDVI | 72 |
| | 21-80 | KQQKASAELIEEEVAKLLKLKAQLGPDESKQKFVLKTP KGTRDYSPRQMAVREKVFDVI | 73 |
| | 22-80 | QQKASAELIEEEVAKLLKLKAQLGPDESKQKFVLKTPK GTRDYSPRQMAVREKVFDVI | 74 |
| | 23-80 | QKASAELIEEEVAKLLKLKAQLGPDESKQKFVLKTPKG TRDYSPRQMAVREKVFDVI | 75 |
| | 24-80 | KASAELIEEEVAKLLKLKAQLGPDESKQKFVLKTPKGT RDYSPRQMAVREKVFDVI | 76 |
| | 25-80 | ASAELIEEEVAKLLKLKAQLGPDESKQKFVLKTPKGTR DYSPRQMAVREKVFDVI | 77 |
| | 26-80 | SAELIEEEVAKLLKLKAQLGPDESKQKFVLKTPKGTRD YSPRQMAVREKVFDVI | 78 |
| | 27-80 | AELIEEEVAKLLKLKAQLGPDESKQKFVLKTPKGTRDY SPRQMAVREKVFDVI | 79 |
| | 28-80 | ELIEEEVAKLLKLKAQLGPDESKQKFVLKTPKGTRDYS PRQMAVREKVFDVI | 80 |
| | 29-80 | LIEEEVAKLLKLKAQLGPDESKQKFVLKTPKGTRDYSP RQMAVREKVFDVI | 81 |
| | 30-80 | IEEEVAKLLKLKAQLGPDESKQKFVLKTPKGTRDYSPR QMAVREKVFDVI | 82 |
| | 31-80 | EEEVAKLLKLKAQLGPDESKQKFVLKTPKGTRDYSPRQ MAVREKVFDVI | 83 |
| | 32-80 | EEVAKLLKLKAQLGPDESKQKFVLKTPKGTRDYSPRQM AVREKVFDVI | 84 |
| | 33-80 | EVAKLLKLKAQLGPDESKQKFVLKTPKGTRDYSPRQMA VREKVFDVI | 85 |
| | 34-80 | VAKLLKLKAQLGPDESKQKFVLKTPKGTRDYSPRQMAV REKVFDVI | 86 |
| | 35-80 | AKLLKLKAQLGPDESKQKFVLKTPKGTRDYSPRQMAVR EKVFDVI | 87 |
| | 36-80 | KLLKLKAQLGPDESKQKFVLKTPKGTRDYSPRQMAVRE KVFDVI | 88 |
| | 37-80 | LLKLKAQLGPDESKQKFVLKTPKGTRDYSPRQMAVREK VFDVI | 89 |
| | 38-80 | LKLKAQLGPDESKQKFVLKTPKGTRDYSPRQMAVREKVFD VI | 90 |
| | 39-80 | KLKAQLGPDESKQKFVLKTPKGTRDYSPRQMAVREKVFD VI | 91 |
| | 40-80 | LKAQLGPDESKQKFVLKTPKGTRDYSPRQMAVREKVFD VI | 92 |
| HisRS1$^{N2}$ | 1-141 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAM | 93 |
| HisRS1$^{N2}$ | 1-408 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE | 94 |

TABLE H1-continued

Exemplary HRS polypeptides

| Name | Residues | Sequence | SEQ ID NO: |
|---|---|---|---|
| | | CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTE | |
| HisRS1$^{N3}$ | 1-113 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKL | 95 |
| HisRS1$^{N4}$ | 1-60 | MAERAALEELVKLQGERVRGLKQQKASAELIEEEVAKL LKLKAQLGPDESKQKFVLKTPK | 96 |
| HisRS1$^{N5}$ | 1-243 + 27aa | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVGYPWWNSCSRILNYPKTSRPWR AWET | 97 |
| HisRS1$^{C1}$ | 405-509 | RTTETQVLVASAQKKLLEERLKLVSELWDAGIKAELLY KKNPKLLNQLQYCEEAGIPLVAIIGEQELKDGVIKLRS VTSREEVDVRREDLVEEIKRRTGQPLCIC | 98 |
| HisRS1$^{C2}$ | 1-60 + 175-509 | MAERAALEELVKLQGERVRGLKQQKASAELIEEEVAKL LKLKAQLGPDESKQKFVLKTPKDFDIAGNFDPMIPDAE CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTGVIYEAVLLQ TPAQAGEEPLGVGSVAAGGRYDGLVGMFDPKGRKVPCV GLSIGVERIFSIVEQRLEALEEKIRTTETQVLVASAQK KLLEERLKLVSELWDAGIKAELLYKKNPKLLNQLQYCE EAGIPLVAIIGEQELKDGVIKLRSVTSREEVDVRREDL VEEIKRRTGQPLCIC | 99 |
| HisRS1$^{C3}$ | 1-60 + 211-509 | MAERAALEELVKLQGERVRGLKQQKASAELIEEEVAKL LKLKAQLGPDESKQKFVLKTPKVNDRRILDGMFAICGV SDSKFRTICSSVDKLDKVSWEEVKNEMVGEKGLAPEVA DRIGDYVQQHGGVSLVEQLLQDPKLSQNKQALEGLGDL KLLFEYLTLFGIDDKISFDLSLARGLDYYTGVIYEAVL LQTPAQAGEEPLGVGSVAAGGRYDGLVGMFDPKGRKVP CVGLSIGVERIFSIVEQRLEALEEKIRTTETQVLVASA QKKLLEERLKLVSELWDAGIKAELLYKKNPKLLNQLQY CEEAGIPLVAIIGEQELKDGVIKLRSVTSREEVDVRRE DLVEEIKRRTGQPLCIC | 100 |
| HisRS1$^{C4}$ | 1-100 + 211-509 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKVNDRRILDGMFAIC GVSDSKFRTICSSVDKLDKVSWEEVKNEMVGEKGLAPE VADRIGDYVQQHGGVSLVEQLLQDPKLSQNKQALEGLG DLKLLFEYLTLFGIDDKISFDLSLARGLDYYTGVIYEA VLLQTPAQAGEEPLGVGSVAAGGRYDGLVGMFDPKGRK VPCVGLSIGVERIFSIVEQRLEALEEKIRTTETQVLVA SAQKKLLEERLKLVSELWDAGIKAELLYKKNPKLLNQL QYCEEAGIPLVAIIGEQELKDGVIKLRSVTSREEVDVR REDLVEEIKRRTGQPLCIC | 101 |
| HisRS1$^{C5}$ | 1-174 + 211-509 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKETLMGKYGEDSKLI YDLKDQGGELLSLRYDLTVPFARYLAMNKLTNIKRYHI AKVYRRDNPAMTRGRYREFYQCVNDRRILDGMFAICGV SDSKFRTICSSVDKLDKVSWEEVKNEMVGEKGLAPEVA DRIGDYVQQHGGVSLVEQLLQDPKLSQNKQALEGLGDL KLLFEYLTLFGIDDKISFDLSLARGLDYYTGVIYEAVL LQTPAQAGEEPLGVGSVAAGGRYDGLVGMFDPKGRKVP CVGLSIGVERIFSIVEQRLEALEEKIRTTETQVLVASA QKKLLEERLKLVSELWDAGIKAELLYKKNPKLLNQLQY CEEAGIPLVAIIGEQELKDGVIKLRSVTSREEVDVRRE DLVEEIKRRTGQPLCIC | 102 |

TABLE H1-continued

Exemplary HRS polypeptides

| Name | Residues | Sequence | SEQ ID NO: |
|---|---|---|---|
| HisRS1$^{C6}$ | 1-60 + 101-509 | MAERAALEELVKLQGERVRGLKQQKASAELIEEEVAKL LKLKAQLGPDESKQKFVLKTPKETLMGKYGEDSKLIYD LKDQGGELLSLRYDLTVPFARYLAMNKLTNIKRYHIAK VYRRDNPAMTRGRYREFYQCDFDIAGNFDPMIPDAECL KIMCEILSSLQIGDFLVKVNDRRILDGMFAICGVSDSK FRTICSSVDKLDKVSWEEVKNEMVGEKGLAPEVADRIG DYVQQHGGVSLVEQLLQDPKLSQNKQALEGLGDLKLLF EYLTLFGIDDKISFDLSLARGLDYYTGVIYEAVLLQTP AQAGEEPLGVGSVAAGGRYDGLVGMFDPKGRKVPCVGL SIGVERIFSIVEQRLEALEEKIRTTETQVLVASAQKKL LEERLKLVSELWDAGIKAELLYKKNPKLLNQLQYCEEA GIPLVAIIGEQELKDGVIKLRSVTSREEVDVRREDLVE EIKRRTGQPLCIC | 103 |
| HisRS1$^{C7}$ | P1-100 + 175-509 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKDFDIAGNFDPMIPD AECLKIMCEILSSLQIGDFLVKVNDRRILDGMFAICGV SDSKFRTICSSVDKLDKVSWEEVKNEMVGEKGLAPEVA DRIGDYVQQHGGVSLVEQLLQDPKLSQNKQALEGLGDL KLLFEYLTLFGIDDKISFDLSLARGLDYYTGVIYEAVL LQTPAQAGEEPLGVGSVAAGGRYDGLVGMFDPKGRKVP CVGLSIGVERIFSIVEQRLEALEEKIRTTETQVLVASA QKKLLEERLKLVSELWDAGIKAELLYKKNPKLLNQLQY CEEAGIPLVAIIGEQELKDGVIKLRSVTSREEVDVRRE DLVEEIKRRTGQPLCIC | 104 |
| HisRS1$^{C8}$ | 1-60 + 399-509 | MAERAALEELVKLQGERVRGLKQQKASAELIEEEVAKL LKLKAQLGPDESKQKFVLKTPKALEEKIRTTETQVLVA SAQKKLLEERLKLVSELWDAGIKAELLYKKNPKLLNQL QYCEEAGIPLVAIIGEQELKDGVIKLRSVTSREEVDVR REDLVEEIKRRTGQPLCIC | 105 |
| HisRS1$^{c9}$ | 1-100 + 399-509 | MAERAALEELVKLQGERVRGLKQQKASAELIEEEVAKL LKLKAQLGPDESKQKFVLKTPKGTRDYSPRQMAVREKV FDVIIRCFKRHGAEVIDTPVFELKALEEKIRTTETQVL VASAQKKLLEERLKLVSELWDAGIKAELLYKKNPKLLN QLQYCEEAGIPLVAIIGEQELKDGVIKLRSVTSREEVD VRREDLVEEIKRRTGQPLCIC | 106 |
| HisRS1$^{C10}$ | 369-509 | MFDPKGRKVPCVGLSIGVERIFSIVEQRLEALEEKIRT TETQVLVASAQKKLLEERLKLVSELWDAGIKAELLYKK NPKLLNQLQYCEEAGIPLVAIIGEQELKDGVIKLRSVT SREEVDVRREDLVEEIKRRTGQPLCIC | 107 |
| HisRS1$^{J1}$ | 191-333 | CLKIMCEILSSLQIGDFLVKVNDRRILDGMFAICGVSD SKFRTICSSVDKLDKVSWEEVKNEMVGEKGLAPEVADR IGDYVQQHGGVSLVEQLLQDPKLSQNKQALEGLGDLKL LFEYLTLFGIDDKISFDLSLARGLDYYTG | 108 |
| FL mito. wild type | 1-506 | MPLLGLLPRRAWASLLSQLLRPPCASCTGAVRCQSQVA EAVLTSQLKAHQEKPNFIIKTPKGTRDLSPQHMVVREK ILDLVISCFKRHGAKGMDTPAFELKETLTEKYGEDSGL MYDLKDQGGELLSLRYDLTVPFARYLAMNKVKKMKRYH VGKVWRRESPTIVQGRYREFCQCDFDIAGQFDPMIPDA ECLKIMCEILSGLQLGDFLIKVNDRRIVDGMFAVCGVP ESKFRAICSSIDKLDKMAWKDVRHEMVVKKGLAPEVAD RIGDYVQCHGGVSLVEQMFQDPRLSQNKQALEGLGDLK LLFEYLTLFGIADKISFDLSLARGLDYYTGVIYEAVLL QTPTQAGEEPLNVGSVAAGGRYDGLVGMFDPKGHKVPC VGLSIGVERIFYIVEQRMKTKGEKVRTTETQVFVATPQ KNFLQERLKIAELWDSGIKAEMLYKNNPKLLTQLHYC ESTGIPLVVIIGEQELKEGVIKIRSVASREEVAIKREN FVAEIQKRLSES | 109 |
| Mus musculus | FL | MADRAALEELVRLQGAHVRGLKEQKASAEQIEEEVTKL LKLKAQLGQDEGKQKFVLKTPKGTRDYSPRQMAVREKV FDVIIRCFKRHGAEVIDTPVFELKETLTGKYGEDSKLI YDLKDQGGELLSLRYDLTVPFARYLAMNKLTNIKRYHI AKVYRRDNPAMTRGRYREFYQCDFDIAGQFDPMIPDAE CLKIMCEILSSLQIGNFLVKVNDRRILDGMFAVCGVPD SKFRTICSSVDKLDKVSWEEVKNEMVGEKGLAPEVADR IGDYVQQHGGVSLVEQLLQDPKLSQNKQAVEGLGDKL LFEYLILFGIDDKISFDLSLARGLDYYTGVIYEAVLLQ | 110 |

TABLE H1-continued

Exemplary HRS polypeptides

| Name | Residues | Sequence | SEQ ID NO: |
|---|---|---|---|
| | | MPTQAGEEPLGVGSIAAGGRYDGLVGMFDPKGRKVPCV GLSIGVERIFSIVEQRLEAS EEKVRTTETQVLVASAQKKLLEERLKLVSELWDAGIKA ELLYKKNPKLLNQLQYWEEAGIPLVAIIGEQELRDGVI KLRSVASREEVDVRREDLVEEIRRRTNQPLSTC | |
| Canis lupus familiaris | FL | MAERAALEELVRLQGERVRGLKQQKASAEQIEEEVAKL LKLKAQLGPDEGKQKFVLKTPKGTRDYSPRQMAVREKV FDVIISCFKRHGAEVIDTPVFELKETLTGKYGEDSKLI YDLKDQGGELLSLRYDLTVPFARYLAMNKLTNIKRYHI AKVYRRDNPAMTRGRYREFYQCDFDIAGQFDPMIPDAE CLEIMCEILR SLQIGDFLVKVNDRRILDGMFAICGVPDSKFRTICSSV DKLDKVSWEEVKNEMVGEKGLAPEVADHIGDYVQQHGG ISLVEQLLQDPELSQNKQALEGLGDLKLLFEYLTLFGI ADKISFDLSLARGLDYYTGVIYEAVLLQTPVQAGEEPL GVGSVAAGGRYDGLVGMFDPKGRKVPCVGLSIGVERIF SIVEQRLEATEEKVRTTETQVLVASAQKKLLEERLKLV SELWNAGIKAELLYKKNPKLLNQLQYCEEAGIPLVAII GEQELKDGVIKLRSVASREEVDVPREDLVEEIKRRTSQ PFCIC | 111 |
| Bos taurus | FL | MADRAALEDLVRVQGERVRGLKQQKASAEQIEEEVAKL LKLKAQLGPDEGKPKFVLKTPKGTRDYSPRQMAVREKV FDVIISCFKRHGAEVIDTPVFELKETLTGKYGEDSKLI YDLKDQGGELLSLRYDLTVPFARYLAMNKLTNIKRYHI AKVYRRDNPAMTRGRYREFYQCDFDIAGQFDPMLPDAE CLKIMCEILSSLQIGDFLVKVNDRRILDGMFAICGVPD SKFRTICSSVDKLDKVSWEEVKNEMVGEKGLAPEVADR IGDYVQQHGGVSLVEQLLQDPKLSQNKQALEGLGDLKL LFEYLTLFGIADKISFDLSLARGLDYYTGVIYEAVLLQ PPARAGEEPLGVGSVAAGGRYDGLVGMFDPKGRKVPCV GLSIGVERIFSIVEQRLEALEEKVRTTETQVLVASAQK KLLEERLKLISELWDAGIKAELLYKKNPKLLNQLQYCE ETGIPLVAIIGEQELKDGVIKLRSVASREEVDVR REDLVEEIKR RTSQPLCIC | 112 |
| Rattus norvegicus | FL | MADRAALEELVRLQGAHVRGLKEQKASAEQIEEEVTKL LKLKAQLGHDEGKQKFVLKTPKGTRDYSPRQMAVREKV FDVIIRCFKRHGAEVIDTPVFELKETLTGKYGEDSKLI YDLKDQGGELLSLRYDLTVPFARYLAMNKLTNIKRYHI AKVYRRDNPAMTRGRYREFYQCDFDIAGQFDPMIPDAE CLKIMCEILSSLQIGNFQVKVNDRRILDGMFAVCGVPD SKFRTICSSVDKLDKVSWEEVKNEMVGEKGLAPEVADR IGDYVQQHGGVSLVEQLLQDPKLSQNKQAVEGLGDLKL LFEYLTLFGIDDKISFDLSLARGLDYYTGVIYEAVLLQ MPTQAGEEPLGVGSIAAGGRYDGLVGMFDPKGRKVPCV GLSIGVERIFSIVEQKLEASEEKVRTTETQVLVASAQK KLLEERLKLISELWDAGIKAELLYKKNPKLLNQLQYCE EAGI PLVAIIGEQE LKDGVIKLRSVTSREEVDVR REDLVEEIRR RTSQPLSM | 113 |
| Gallus gallus | FL | MADEAAVRQQAEVVRRLKQDKAEPDEIAKEVAKLLEMK AHLGGDEGKHKFVLKTPKGTRDYGPKQMAIRERVFSAI IACFKRHGAEVIDTPVFELKETLTGKYGEDSKLIYDLK DQGGELLSLRYDLTVPFARYLAMNKITNIKRYHIAKVY RRDNPAMTRGRYREFYQCDFDIAGQFDPMIPDAECLKI VQEILSDLQLGDFLIKVNDRRILDGMFAVCGVPDSKFR TICSSVDKLDKMPWEEVRNEMVGEKGLSPEAADRIGEY VQLHGGMDLIEQLLQDPKLSQNKLVKEGLGDMKLLFEY LTLFGITGKISFDLSLARGLDYYTGVIYEAVLLQQNDH GEESVSVGSVAGGGRYDGLVGMFDPKGR KVPCVGISIGIERIFSILEQRVEASEEKIR TTETQVLVASAQKKLLEERLKLISELWDAGIKAEVLYK KNPKLLNQLQYCEDTGIPLVAIVGEQELKDGVVKLRVV ATGEEVNIRRESLVEEIRRRTNQL | 114 |
| Danio rerio | FL | MAALGLVSMRLCAGLMGRRSAVRLHSLRVCSGMTISQI DEEVARLLQLKAQLGGDEGKHVFVLKTAKGTRDYNPKQ MAIREKVFNIIINCFKRHGAETIDSPVFELKETLTGKY GEDSKLIYDLKDQGGELLSLRYDLTVPFARYLAMNKIT NIKRYHIAKVYRRDNPAMTRGRYREFYQCDFDIAGQYD AMIPDAECLKLVYEILSELDLGDFRIKVNDRRILDGMF AICGVPDEKFRTICSTVDKLDKLAWEEVKKEMVNEKGL SEEVADRIRDYVSMQGGKDLAERLLQDPKLSQSKQACA | 115 |

TABLE H1-continued

Exemplary HRS polypeptides

| Name | Residues | Sequence | SEQ ID NO: |
|---|---|---|---|
| | | GITDMKLLFSYLELFQITDKVVFDLSLARGLDYYTGVI YEAILTQANPAPASTPAEQNGAEDAGVSVGSVAGGGRY DGLVGMFDPKAGKCPVWGSALALRGSSPSWSRRQSCLQ RRCAPLKLKCLWLQHRRTF | |
| Macaca fascicularis | FL | MAERAALEELVKLQGERVRGLKQQKASAELIEEEVGKL LKLKAQLGPDESKQKFVLKTPKGTRDYSPRQMAVREKV FDVIIRCFKRHGAEVIDTPVFELKETLMGKYGEDSKLI YDLKDQGGELLSLRHDLTVPFARYLAMNKLTNIKRYHI AKVYRRDNPAMTRGRYREFYQCDFDIAGNFDPMIPDAE CLKIMCEILSSLQIGDFLVKVNDRRILDGMFAICGVSD SKFRTICSSVDKLDKVSWEEVKNEAVLLQTPAQAGEEP LGVGSVAAGGRYDGLVGMFDPKGRKVPCVGLSIGVERI FSIVEQ RLEALEEKVRTTETQVLVASAQKKLLEERLKLVSELWD AGIKAELLYKKNPKLLNQLQYCEEAGIPLVAIIGEQEL KDGVIKLRSVTSREEVNVRREDLKTGQNGDFNFYYGYF IDYYWQKWPDTTPFSYKALGA | 116 |
| HRS WHEP consensus | | $X_A$-L-$X_B$-Q-G-X-X-V-R-X-L-K-X-X-K-A-$X_C$-V-X-X-L-L-X-L-K-$X_D$ Where: X is any amino acid $X_A$ is 0-50 amino acids $X_B$ is about 5-7 amino acids, preferably 6 amino acids $X_C$ is about 7-9 amino acids, preferably 8 amino acids $X_D$ is 0-50 amino acids | 117 |

Accordingly, in certain embodiments, the HRS polypeptide comprises, consists, or consists essentially of a mammalian HRS amino acid sequence in Table H1 (e.g., SEQ ID NOs:1-117), or an active variant or fragment thereof. In some embodiments, the HRS polypeptide comprises, consists, or consists essentially of a human HRS amino acid sequence in Table H1 (e.g., SEQ ID NOs:1-109), or an active variant or fragment thereof. In some embodiments, the expressible polynucleotide encodes an HRS polypeptide that comprises consists, or consists essentially of an amino acid sequence in Table H1 (e.g., SEQ ID NO:1-117), for example, a human HRS sequence in Table H1 SEQ ID NOs:1-109), or an active variant or fragment thereof.

As noted herein, a HRS polypeptide may be altered in various ways including amino acid substitutions, deletions, truncations, additions, and insertions. Methods for such manipulations are generally known in the art. For example, amino acid sequence variants of a HRS reference polypeptide can be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873, 192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant HRS polypeptides may contain conservative amino acid substitutions at various locations along their sequence, relative to a reference HRS amino acid residue. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i e, glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (Science, 256: 14430-1445, 1992), however, include proline in the same group as glycine, serine, alanine and threonine. Accordingly, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant HRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser, Ala, Leu, Val | Ser, Ala |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, Wm.C. Brown Publishers (1993).

In some embodiments, HRS polypeptides have one or more cysteine insertions or substitutions, for example, where one or more non-cysteine residues are substituted with a cysteine residue (e.g., to alter stability, to facilitate thiol-based conjugation of an Fc fragment, to facilitate thiol-based attachment of PEG or other molecules). In some embodiments, the one or more cysteine substitutions are near the N-terminus and/or C-terminus of the HRS polypeptide, or other surface exposed regions of a HRS polypeptide. Particular embodiments include where one or more of residues within 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of an HRS polypeptide are substituted with a cysteine residue. In some embodiments, cysteine residues may be added to the HRS polypeptide through the creation of N, or C-terminal fusion proteins. Such fusion proteins may be of any length, but will typically be about 1-5, or about 5-10, about 10 to 20, or about 20 to 30 amino acids in length.

Specific examples of cysteine modified proteins are shown in Table H2, which are based on the HRS polypeptide HRS(1-60). This approach can be applied to the HRS polypeptides of Table H1 and other HRS nolvnentides described herein.

TABLE H2

Exemplary cysteine modified HRS polypeptides

| Name | Protein Sequences | SEQ ID NO: |
|---|---|---|
| HRS(1-60)-M1MC- | MCAERAALEELVKLQGERVRGLKQQKASAELIEEEVAKLLKLKAQLGPDESKQKFVLKTPK | 118 |
| HRS(1-60)-A26C- | MAERAALEELVKLQGERVRGLKQQKCSAELIEEEVAKLLKLKAQLGPDESKQKFVLKTPK | 119 |
| HRS(1-60)-C61 | MAERAALEELVKLQGERVRGLKQQKASAELIEEEVAKLLKLKAQLGPDESKQKFVLKTPKC | 120 |

Accordingly, in certain embodiments, the HRS polypeptide comprises, consists, or consists essentially of an amino acid sequence in Table H2 (SEQ ID NO:118-120) or an active variant or fragment thereof. In some embodiments, the expressible polynucleotide encodes an HRS polypeptide that comprises consists, or consists essentially of an amino acid sequence in Table H2 (e.g., SEQ ID NO:118-120) or an active variant or fragment thereof.

In some embodiments, the HRS polypeptide have mutations in which the endogenous or naturally-occurring cysteine residues are mutated to alternative amino acids, or deleted. In some embodiments, the insertion or substitution of cysteine residue(s) into the HRS polypeptide is combined with the elimination of other surface exposed reactive cysteine residues. Accordingly, in some embodiments, an HRS polypeptide comprises one or more substitutions and/or deletions at any one or more of Cys83, Cys174, Cys191, Cys196, Cys224, Cys235, Cys379, Cys455, Cys507, and/or Cys509 (as defined by SEQ ID NO:1), for instance, to remove naturally-occurring cysteine residues, including combinations thereof.

Specific embodiments include an HRS polypeptide of Table H1 having a mutation or deletion of any one or more of Cys83, Cys174, Cys191, Cys196, Cys224, Cys235, Cys379, Cys455, or the deletion of Cys507 and Cys509, for instance, by the deletion of the C-terminal 3 amino acids (4507-509). Exemplary mutations at these positions include for example the mutation of cysteine to serine, alanine, leucine, valine or glycine. In certain embodiments, amino acid residues for specific cysteine substitutions can be selected from naturally-occurring substitutions that are found in HRS orthologs from other species and organisms. Exemplary substitutions of this type are presented in

TABLE H3

Table H3. Naturally-occurring sequence variation at positions occupied by cysteine residues in human HRS

| H. sapiens cysteine residue # | P. troglodyte | M. mulatta | B. taurus | M. musculus | R. norvegicus | G. gallus |
|---|---|---|---|---|---|---|
| 83 | C | C | C | C | C | C |
| 174 | C | C | C | C | C | C |
| 191 | C | C | C | C | C | C |
| 196 | C | C | C | C | C | Q |
| 224 | C | C | C | C | C | C |
| 235 | C | C | C | C | C | C |
| 379 | C | C | C | C | C | C |
| 455 | C | C | C | C | C | C |
| 507 | C | R | C | S | S | — |
| 509 | C | C | C | C | — | — |

| H. sapiens cysteine residue # | X. laevis | D. rerio | D. melanogaster | C. elegans | S. cerevisiae | E. coli |
|---|---|---|---|---|---|---|
| 83 | C | C | V | T | L | V |
| 174 | C | C | C | C | C | L |
| 191 | C | C | C | V | C | A/L |
| 196 | H | Y | S | M | V | L/A |
| 224 | C | C | C | S | A | A |
| 235 | C | C | C | C | S | E |
| 379 | C | V | C | C | C | A |
| 455 | C | — | C | C | A | A |
| 507 | — | — | — | S/Q | S/E | — |
| 509 | — | — | — | I | I/G | — |

In some embodiments, the naturally-occurring cysteines selected for mutagenesis are selected based on their surface exposure. Accordingly, in one aspect the cysteine residues selected for substitution are selected from Cys224, Cys235, Cys507 and Cys509. In some embodiments, the last three (C-terminal) residues of SEQ ID NO:1 are deleted so as to delete residues 507 to 509. In some embodiments, the cysteines are selected for mutation or deletion so as to eliminate an intramolecular cysteine pair, for example Cys174 and Cys191.

Specific examples of cysteine mutations/substitutions (indicated in bold underline) to reduce surface exposed cysteine residues include those listed below in Table H4.

TABLE H4

| \multicolumn{3}{c}{Exemplary HRS polypeptides with substitutions to remove surface exposed cysteines} |

| Name | Protein Sequence | SEQ ID NO: |
|---|---|---|
| HRS(1-506) C174A | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQADFDIAGNFDPMIPDAECLKIMCEILSSLQI GDFLVKVNDRRILDGMFAICGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 121 |
| HRS(1-506) C174V | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQVDFDIAGNFDPMIPDAECLKIMCEILSSLQI GDFLVKVNDRRILDGMFAICGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 122 |
| HRS(1-506) C191A | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQCDFDIAGNFDPMIPDAEALKIMCEILSSLQI GDFLVKVNDRRILDGMFAICGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 123 |
| HRS(1-506) C191S | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQCDFDIAGNFDPMIPDAESLKIMCEILSSLQI GDFLVKVNDRRILDGMFAICGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 124 |
| HRS(1-506) C191V | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQCDFDIAGNFDPMIPDAEVLKIMCEILSSLQI GDFLVKVNDRRILDGMFAICGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 125 |
| HRS(1-506) C224S | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQCDFDIAGNFDPMIPDAECLKIMCEILSSLQI GDFLVKVNDRRILDGMFAISGVSDSKFRTICSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 126 |

TABLE H4-continued

Exemplary HRS polypeptides with substitutions to remove surface exposed cysteines

| Name | Protein Sequence | SEQ ID NO: |
|---|---|---|
| HRS(1-506) C2355 | MAERAALEELVKLQGERVRGLKQQKASAELIEEEVAKLLKLKAQLGPDESK QKFVLKTPKGTRDYSPRQMAVREKVFDVIIRCFKRHGAEVIDTPVFELKET LMGKYGEDSKLIYDLKDQGGELLSLRYDLTVPFARYLAMNKLTNIKRYHIA KVYRRDNPAMTRGRYREFYQCDFDIAGNFDPMIPDAECLKIMCEILSSLQI GDFLVKVNDRRILDGMFAICGVSDSKFRTISSSVDKLDKVSWEEVKNEMVG EKGLAPEVADRIGDYVQQHGGVSLVEQLLQDPKLSQNKQALEGLGDLKLLF EYLTLFGIDDKISFDLSLARGLDYYTGVIYEAVLLQTPAQAGEEPLGVGSV AAGGRYDGLVGMFDPKGRKVPCVGLSIGVERIFSIVEQRLEALEEKIRTTE TQVLVASAQKKLLEERLKLVSELWDAGIKAELLYKKNPKLLNQLQYCEEAG IPLVAIIGEQELKDGVIKLRSVTSREEVDVRREDLVEEIKRRTGQPL | 127 |

Accordingly, in certain embodiments, the HRS polypeptide comprises, consists, or consists essentially of an amino acid sequence in Table H4 (SEQ ID NO:121-127) or an active variant or fragment thereof. In some embodiments, the expressible polynucleotide encodes an HRS polypeptide that comprises consists, or consists essentially of an amino acid sequence in Table H4 (e.g., SEQ ID NO:121-127) or an active variant or fragment thereof.

In some embodiments, such cysteine substituted mutants are modified to engineer-in, insert, or otherwise introduce a new surface exposed cysteine residue at a defined surface exposed position, where the introduced residue does not substantially interfere with the non-canonical activity of the HRS polypeptide. Specific examples include for example the insertion (or re-insertion back) of additional cysteine residues at the N- or C-terminus of any of the reduced cysteine HRS polypeptides described above. In some embodiments, the insertion of such N- or C-terminal surface exposed cysteines involves the re-insertion of the last 1, last 2, or last 3 naturally occurring C-terminal amino acids of the full length human HRS to a reduced cysteine variant of a HRS polypeptide e.g., the re-insertion of all or part of the sequence CIC (Cys Ile Cys). Exemplary reduced cysteine mutants include for example any combination of mutations (or the deletion of) at residues Cys174, Cys191, Cys224, and Cys235, and or the deletion or substitution of Cys507 and Cys509 (based on the numbering of full length human cytosolic HRS (SEQ ID NO:1) in any of the HRS polypeptides of Table H1.

For some types of site-specific conjugation or attachment to heterologous molecules such as Fc regions or PEG or other heterologous molecules, HRS polypeptides may have one or more glutamine substitutions, where one or more naturally-occurring (non-glutamine) residues are substituted with glutamine, for example, to facilitate transglutaminase-catalyzed attachment of the molecule(s) to the glutamine's amide group. In some embodiments, glutamine substitutions are introduced near the N-terminus and/or C-terminus of the HRS polypeptide. Particular embodiments include where one or more of residues within 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of an HRS polypeptide are substituted with a glutamine residue. These and related HRS polypeptides can also include substitutions (e.g., conservative substitutions) to remove any naturally-occurring glutamine residues, if desired, and thereby regulate the degree of site-specific conjugation or attachment.

For certain types of site-specific conjugation or attachment to heterologous molecules such as Fc regions or PEG or other heterologous molecules, HRS polypeptides may have one or more lysine substitutions, where one or more naturally-occurring (non-lysine) residues are substituted with lysine, for example, to facilitate acylation or alkylation-based attachment of molecule(s) to the lysine's amino group. These methods also typically result in attachment of molecule(s) to the N-terminal residue. In some embodiments, lysine substations are near the N-terminus and/or C-terminus of the HRS polypeptide. Particular embodiments include where one or more of residues within 1, 2, 3, 4, 5, 6, 7, 8, 9, 10, 11, 12, 13, 14, 15, 16, 17, 18, 19, 20, 21, 22, 23, 24 or 25 amino acids to the N-terminus and/or C-terminus of an HRS polypeptide are substituted with a lysine residue. These and related HRS polypeptides can also include substitutions (e.g., conservative substitutions) to remove any naturally-occurring lysine residues, if desired, and thereby regulate the degree of site-specific conjugation or attachment.

Site-specific conjugation to HRS polypeptides may also be performed by substituting one or more solvent accessible surface amino acids of a HRS polypeptide. For example, suitable solvent accessible amino acids may be determined based on the predicted solvent accessibility using the SPIDDER server (http://sppider.cchmc.org/) using the published crystal structure of an exemplary HRS polypeptide (see Xu et al., Structure. 20:1470-7, 2012; and U.S. Application No. 61/674,639). Based on this analysis several amino acids on the surface may potentially be used as mutation sites to introduce functional groups suitable for conjugation or attachment. The surface accessibility score of amino acids based on the crystal structure can be calculated, where the higher scores represent better accessibility. In particular embodiments, higher scores (for example, >40) are preferred. Accordingly in some embodiments an amino acid position have a surface accessibility score of greater than 40 may be used to introduce a cysteine, lysine, glutamine, or other non-naturally-occurring amino acid.

In particular embodiments, a solvent accessible surface amino acid is selected from the group consisting of: alanine, glycine, and serine, and can be substituted with naturally occurring amino acids including, but not limited to, cysteine, glutamine, or lysine, or a non-naturally occurring amino acid that is optimized for site specific conjugation or attachment.

Certain embodiments include site-specific conjugation or attachment to an HRS polypeptide at any amino acid position by virtue of substituting a non-naturally-occurring amino acid comprising a functional group that will form a covalent bond with the functional group attached to a heterologous molecules such as an Fc region or PEG or other heterologous molecule. Non-natural amino acids can be inserted or substituted at, for example, one or more of residues within 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus, at the N-terminus and/or C-terminus, or at a solvent accessible surface amino acid residue of an HRS polypeptide described herein.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

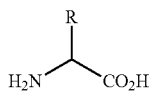

A non-natural amino acid is typically any structure having the foregoing formula wherein the R group is any substituent other than one used in the twenty natural amino acids. See, e.g., biochemistry texts such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxyl amide, or organosilane group, or the like or any combination thereof.

Specific examples of unnatural amino acids include, but are not limited to, p-acetyl-L-phenylalanine, O-methyl-L-tyrosine, an L-3-(2-naphthy)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Accordingly, one may select a non-naturally occurring amino acid comprising a functional group that forms a covalent bond with any preferred functional group of a desired molecule (e.g., Fc region, PEG). Non-natural amino acids, once selected, can either be purchased from vendors, or chemically synthesized. Any number of non-natural amino acids may be incorporated into the target molecule and may vary according to the number of desired molecules that are to be attached. The molecules may be attached to all or only some of the non-natural amino acids. Further, the same or different non-natural amino acids may be incorporated into a HRS polypeptide, depending on the desired outcome. In certain embodiments, about 1, 2, 3, 4, 5, 6, 7, 8, 9, 10 or more non-natural amino acids are incorporated into a HRS polypeptide any or all of which may be conjugated to a molecule comprising a desired functional group.

In certain aspects, the use of non-natural amino acids can be utilized to modify (e.g., increase) a selected non-canonical activity of an HRS polypeptide, or to alter the in vivo or in vitro half-life of the protein. Non-natural amino acids can also be used to facilitate (selective) chemical modifications (e.g., pegylation) of an HRS polypeptide, as described herein. For instance, certain non-natural amino acids allow selective attachment of polymers such as an Fc region or PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the HRS polypeptides can be composed of naturally occurring and non-naturally occurring amino acids as well as amino acid analogs and mimetics.

In certain embodiments, a HRS polypeptide comprises, consists, or consists essentially of the minimal active fragment of a full-length HRS polypeptide capable of modulating an anti-inflammatory activity in vivo or having antibody or auto-reactive T-cell blocking activities. In some embodiments, such a minimal active fragment comprises, consists, or consists essentially of the WHEP domain (e.g., about amino acids 1-43 of SEQ ID NO:1) or an active variant or fragment thereof. In some aspects, the minimal active fragment comprises, consists, or consists essentially of the aminoacylation domain, (e.g., about amino acids 54-398 of SEQ ID NO:1) or an active variant or fragment thereof. In some aspects, the minimal active fragment comprises, consists, or consists essentially of the anticodon binding domain (e.g., about amino acids 406-501 of SEQ ID NO:1) or an active variant or fragment thereof.

In certain embodiments, the HRS polypeptide is about, at least about, and/or up to about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 501, 502, 503, 504, 505, 506, 507, 508, or 509 amino acids in length, including all integers ranges in between, and comprises, consists, or consists essentially of an amino acid sequence in Table H1, Table H2, or Table H4.

In certain embodiments, the HRS polypeptide possesses at least one non-canonical activity, for example, an anti-inflammatory activity or cross-reactivity with auto-antibody or auto reactive T-cell from a subject with a disease associated with autoantibodies (e.g., Jo-1 antibodies) to a histidyl-tRNA synthetase. Assays to determine anti-inflammatory activity, including routine measurements of cytokine release from in vitro cell based, and animal studies are well established in the art (see, for example, Wittmann et al., J Vis Exp. (65):e4203. doi: 10.3791/4203, 2012; Feldman et al., Mol Cell. 47:585-95, 2012; Clutterbuck et al., J Proteomics. 74:704-15, 2011, Giddings and Maitra, J Biomol Screen. 15:1204-10, 2010; Wijnhoven et al., Glycoconj J. 25:177-85, 2008; and Frow et al., Med Res Rev. 24:276-98, 2004) and can be readily used to profile and optimize anti-inflammatory activity. An exemplary in vivo experimental system is also described in the accompanying Examples.

In some embodiments, the HRS polypeptide does not significantly compete for disease associated auto-antibody binding (e.g., Jo-1 antibody) to wild type histidyl-tRNA synthetase in a competitive ELISA up to a concentration of about 1 to 5×10−7M, or higher. Accordingly, in some embodiments, the HRS polypeptide has a lower affinity to disease associated auto-antibody than wild type histidyl-tRNA synthetase (SEQ ID NO:1) as measured in a competitive ELISA. In some embodiments, the HRS polypeptide has an apparent affinity for the disease associated auto-antibody (e.g., Jo-1 antibody) which is at least about 10 fold less, or at least about 20 fold less, or at least about 50 fold less, or at least about 100 fold less than the affinity of the disease associated auto-antibody to wild type human (SEQ ID NO:1).

It will be appreciated that in any of the HRS polypeptides, the N-terminal acid of the HRS polypeptide (for example, the N-terminal Met) may be deleted.

In other embodiments, fusion proteins of HRS polypeptide to other (non HARS) proteins (e.g. heterologous proteins or polypeptides) are also included, and these fusion proteins may modulate the HRS polypeptide's biological activity, secretion, antigenicity, targeting, biological life, ability to penetrate cellular membranes, or the blood brain barrier, or pharmacokinetic properties. Examples of fusion proteins that improve pharmacokinetic properties ("PK modifiers") include without limitation, fusions to human albumin (Osborn et al.: Eur. J. Pharmacol. 456(1-3): 149-158, (2002)), antibody Fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the HRS polypeptide. This additional extension adopts a bulky random structure, which significantly increases the size of the resulting fusion protein. By this means the typically rapid clearance of smaller HRS polypeptides via kidney filtration is retarded by several orders of magnitude. Additionally use of Ig G fusion proteins has also been shown to enable some fusion protein proteins to penetrate the blood brain barrier (Fu et al., (2010) Brain Res. 1352:208-13).

Examples of fusion proteins that modulate the antigenicity, or immunomodulatory properties of the HRS polypeptide include fusions to T cell binding ligands, including for example, MHC Class I and II proteins, b-2 microglobulin, portions of LFA-3, portions of the Fc region of the heavy chain, and conjugates and derivatives thereof; Examples of such fusion proteins are described in for example EP 1 964 854, U.S. Pat. Nos. 5,468,481; 5,130,297; 5,635,363; 6,451, 314 and US 2009/0280135.

Additionally in some embodiments, the HRS polypeptide can include synthetic, or naturally occurring secretion signal sequences, derived from other well characterized secreted proteins. In some embodiments such proteins, may be processed by proteolytic cleavage to form the HRS polypeptide in situ. In some embodiments the HRS polypeptide can comprise heterologous proteolytic cleavage sites, to enable the in situ expression, and production of the HRS polypeptide either at an intracellular, or an extracellular location. Other fusions proteins may also include for example fusions of HRS polypeptide to ubiquitin to provide a new N-terminal amino acid, or the use of a secretion signal to mediate high level secretion of the HRS polypeptide into the extracellular medium, or N, or C-terminal epitope tags to improve purification or detection, and fusions to cell penetrating peptides.

In certain aspects, the use of non-natural amino acids can be utilized to modify (e.g., increase) a selected non-canonical activity of a HRS polypeptide, or to alter the in vivo or in vitro half-life of the protein. Non-natural amino acids can also be used to facilitate (selective) chemical modifications (e.g., pegylation) of a HRS protein, as described elsewhere herein. For instance, certain non-natural amino acids allow selective attachment of polymers such as PEG to a given protein, and thereby improve their pharmacokinetic properties.

Certain embodiments include HRS-Fc conjugates, which comprise at least one Fc region that is covalently attached to one or more HRS polypeptides. Examples of HRS-Fc conjugates include fusion proteins and various forms of chemically cross-linked proteins. A wide variety of Fc region sequences may be employed in the HRS-Fc conjugates, including wild-type sequences from any number of species, as well as variants, fragments, hybrids, and chemically modified forms thereof. The HRS-Fc polypeptides may also (optionally) comprise one or more linkers, which typically separate the Fc region(s) from the HRS polypeptide(s), including peptide linkers and chemical linkers, as described herein and known in the art. It will be appreciated that in any of these HRS-Fc conjugates the native N or C terminal amino acid of the HRS polypeptides, or native N or C-amino acid in the Fc domain, may be deleted and/or replaced with non-native amino acid(s), for example, to facilitate expression and or cloning or to serve as a linker sequence between the two proteins.

HRS-Fc conjugate polypeptides can provide a variety of advantages relative to un-conjugated or unmodified HRS polypeptides, e.g., corresponding HRS polypeptides of the same or similar sequence having no Fc region(s) attached thereto. Merely by way of illustration, the covalent attachment of one or more Fc regions can alter (e.g., increase, decrease) the HRS polypeptide's solubility, half-life (e.g., in serum, in a selected tissue, in a test tube under storage conditions, for example, at room temperature or under refrigeration), dimerization or multimerization properties, biological activity or activities, for instance, by providing Fc-region-associated effector functions (e.g., activation of the classical complement cascade, interaction with immune effector cells via the Fc receptor (FcR), compartmentalization of immunoglobulins), cellular uptake, intracellular transport, tissue distribution, and/or bioavailability, relative to an unmodified HRS polypeptide having the same or similar sequence. In certain aspects, Fc regions can confer effector functions relating to complement-dependent cytotoxicity (CDC), antibody-dependent cell-mediated cytotoxicity (ADCC), and/or antibody-dependent cell-mediated phagocytocis (ADCP), which are believed to play a role in clearing specific target cells such as tumor cells and infected cells.

Certain embodiments employ HRS-Fc fusion proteins. "Fusion proteins" are defined elsewhere herein and well known in the art, as are methods of making fusion proteins (see, e.g., U.S. Pat. Nos. 5,116,964; 5,428,130; 5,455,165; 5,514,582; 6,406,697; 6,291,212; and 6,300,099 for general disclosure and methods related to Fc fusion proteins). In a HRS-Fc fusion protein, the Fc region can be fused to the N-terminus of the HRS polypeptide, the C-terminus, or both. In some embodiments, one or more Fc regions can be fused internally relative to HRS sequences, for instance, by placing an Fc region between a first HRS sequence (e.g., domain) and a second HRS sequence (e.g., domain), where the first HRS sequence is fused to the N-terminus of the Fc region and the second HRS sequence is fused to the C-terminus of the Fc region. In specific embodiments, the first and second HRS sequences are identical. In other embodiments, the first and second HRS sequences are different (e.g., they include different functional domains of the HRS polypeptide). Certain HRS-Fc fusion proteins can also include additional heterologous protein sequences, that is, non-Fc region and non-HRS polypeptide sequences.

The term "HRS-Fc" can indicate, but does not necessarily indicate, the N-terminal or C-terminal attachment of the Fc region to the HRS polypeptide. For instance, in certain instances the term "Fc-HRS" indicates fusion of the Fc region to the N-terminus of the HRS polypeptide, and the term "HRS-Fc" indicates fusion of the Fc region to the C-terminus of the HRS polypeptide. However, either term can be used more generally to refer to any fusion protein or conjugate of an Fc region and a HRS polypeptide.

In some embodiments the HRS-Fc fusion proteins may comprise tandemly repeated copies of the HRS polypeptide coupled to a single Fc domain, optionally separated by linker peptides. Exemplary tandemly repeated HRS-Fc fusion proteins are provided in Table H5. The preparation and sequences for specific tandemly repeated HRS-Fc conjugates are illustrated in the Examples.

TABLE H5

Exemplary Tandem HRS-Fc conjugates

HRS polypeptide-L-HRS-polypeptide-L-Fc
HRS-polypeptide-L-HRS-polypeptide-L-HRS-polypeptide-L-Fc TABLE H5-continued Exemplary Tandem HRS-Fc conjugates HRS-polypeptide-L-HRS-polypeptide-L-HRS-polypeptide-L-HRS-polypeptide-L-Fc
Fc-L-HRS-polypeptide-L-HRS-polypeptide
Fc-L-HRS-polypeptide-L-HRS-L-HRS-polypeptide
Fc-L-HRS-polypeptide-L-HRS-L-HRS-L-HRS-polypeptide
Where:
"Fc" is an Fc domain as described herein
"HRS-polypeptide" is an HRS polypeptide as described herein
"L" is an optional peptide linker Certain embodiments relate to HRS-Fc conjugates, where, for instance, one or more Fc regions are chemically conjugated or cross-linked to the HRS polypeptide(s). In these and related aspects, the Fc region can be conjugated to the HRS polypeptide at the N-terminal region (e.g., within the first 10, 20, 30, 40, 50, 60, 70, 80, 90, 100 or so amino acids), the internal region (between the N-terminal and C-terminal regions), and/or the C-terminal region (e.g., within the last 10, 20, 30, 40, 50, 60, 70, 80, 90, 100 or so amino acids). Polypeptides can be conjugated or cross-linked to other polypeptides according to a variety of routine techniques in the art. For instance, certain techniques employ the carboxyl-reactive carbodiimide crosslinker EDC (or EDAC), which covalently attaches via D, E, and C-terminal carboxyl groups. Other techniques employ activated EDC, which covalently attaches via K and N-terminal amino groups). Still other techniques employ m-maleimidobenzoyl-N-hydoxysuccinimide ester (MBS) or Sulfo-MBS, which covalently attach via the thiol group of a cysteine residue (see also U.S. Application No. 2007/0092940 for cysteine engineered Ig regions that can be used for thiol conjugation). Such cross-linked proteins can also comprise linkers, including cleavable or otherwise releasable linkers (e.g., enzymatically cleavable linkers, hydrolysable linkers), and non-cleavable linkers (i.e., physiologically-stable linkers). Certain embodiments may employ non-peptide polymers (e.g., PEG polymers; HRS-N-PEG-N-Fc conjugate) as a cross-linker between the Fc region(s) and the HRS polypeptide(s), as described, for example, in U.S. Application No. 2006/0269553. See also US Application No. 2007/0269369 for exemplary descriptions of Fc region conjugation sites.

In certain embodiments, discussed in greater detail below, variant or otherwise modified Fc regions can be employed, including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylation/sialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb, FcRn), its pharmacokinetic properties (e.g., stability or half-life, bioavailability, tissue distribution, volume of distribution, concentration, elimination rate constant, elimination rate, area under the curve (AUC), clearance, $C_{max}$, $t_{max}$, $C_{min}$, fluctuation), its immunogenicity, its complement fixation or activation, and/or the CDC/ADCC/ADCP-related activities of the Fc region, among other properties described herein, relative to a corresponding wild-type Fc sequence.

The "Fc region" of a HRS-Fc conjugate provided herein is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region, the latter being found only in IgG, IgA, and IgD immunoglobulins. The Fd region comprises the variable ($V_H$) and constant ($CH_1$) domains of the heavy chains, and together with the variable ($V_L$) and constant ($C_L$) domains of the light chains forms the antigen-binding fragment or Fab region.

The Fc region of IgG, IgA, and IgD immunoglobulins comprises the heavy chain constant domains 2 and 3, designated respectively as $CH_2$ and $CH_3$ regions; and the Fc region of IgE and IgM immunoglobulins comprises the heavy chain constant domains 2, 3, and 4, designated respectively as $CH_2$, $CH_3$, and $CH_4$ regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses. The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the $CH_2$ domain can also influence the specificity of the interaction between an immunoglobulin and its respective Fc receptor(s) (see, e.g., Shin et al., *Intern. Rev. Immunol.* 10:177-186, 1993).

The term "Fc region" or "Fc fragment" or "Fc" as used herein, thus refers to a protein that contains one or more of a $CH_2$ region, a $CH_3$ region, and/or a $CH_4$ region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the $CH_1$, $C_L$, $V_L$, and/or $V_H$ regions of an immunoglobulin.

The Fc region can be derived from the $CH_2$ region, $CH_3$ region, $CH_4$ region, and/or hinge region(s) of any one or more immunoglobulin classes, including but not limited to IgA, IgD, IgE, IgG, IgM, including subclasses and combinations thereof. In some embodiments, the Fc region is derived from an IgA immunoglobulin, including subclasses IgA1 and/or IgA2. In certain embodiments, the Fc region is derived from an IgD immunoglobulin. In particular embodiments, the Fc region is derived from an IgE immunoglobulin. In some embodiments, the Fc region is derived from an IgG immunoglobulin, including subclasses IgG1, IgG2, IgG2, IgG3, and/or IgG4. In certain embodiments, the Fc region is derived from an IgM immunoglobulin.

Certain Fc regions demonstrate specific binding for one or more Fc-receptors (FcRs). Examples of classes of Fc receptors include Fcγ receptors (FcγR), Fcα receptors (FcαR), Fcε receptors (FcεR), and the neonatal Fc receptor (FcRn). For instance, certain Fc regions have increased binding to (or affinity for) one or more FcγRs, relative to FcαRs, FcαRs, and/or FcRn. In some embodiments, Fc regions have increased binding to FcαRs, relative to one or more FcγRs, FcαRs, and/or FcRn. In other embodiments, Fc regions have increased binding to FcαRs (e.g., FcαRI), relative to one or more FcγRs, FcαRs, and/or FcRn. In particular embodiments, Fc regions have increased binding to FcRn, relative to one or more FcγRs, FcαRs, and/or FcαRs. In certain embodiments, the binding (or affinity) of an Fc region to one or more selected FcR(s) is increased relative to its binding to (or affinity for) one or more different FcR(s), typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

Examples of FcγRs include FcγRI, FcγRIIa, FcγRIIb, FcγRIIc, FcγRIIIa, and FcγRIIIb. FcγRI (CD64) is expressed on macrophages and dendritic cells and plays a role in phagocytosis, respiratory burst, cytokine stimulation, and dendritic cell endocytic transport. Expression of FcγRI is upregulated by both GM-CSF and γ-interferon (γ-IFN) and downregulated by interleukin-4 (IL-4). FcγRIIa is expressed on polymorphonuclear leukocytes (PMN), macrophages, dendritic cells, and mast cells. FcγRIIa plays a role in phagocytosis, respiratory burst, and cytokine stimulation. Expression of FcγRIIa is upregulated by GM-CSF and γ-IFN, and decreased by IL-4. FcγIIb is expressed on B cells, PMN, macrophages, and mast cells. FcγIIb inhibits immunoreceptor tyrosine-based activation motif (ITAM) mediated responses, and is thus an inhibitory receptor. Expression of FcγRIIc is upregulated by intravenous immunoglobulin (IVIG) and IL-4 and decreased by γ-IFN. FcγRIIc is expressed on NK cells. FcγRIIIa is expressed on natural killer (NK) cells, macrophages, mast cells, and platelets. This receptor participates in phagocytosis, respiratory burst, cytokine stimulation, platelet aggregation and degranulation, and NK-mediated ADCC. Expression of FcγRIII is upregulated by C5a, TGF-β, and γ-IFN and downregulated by IL-4. Fc γ RIIIb is a GPI-linked receptor expressed on PMN.

Certain Fc regions have increased binding to FcγRI, relative to FcγRIIa, FcγRIIb, FcγRIIc, FcγRIIIa, and/or FcγRIIIb. Some embodiments have increased binding to FcγRIIa, relative to FcγRI, FcγRIIb, FcγRIIc, FcγRIIIa, and/or FcγRIIIb. Particular Fc regions have increased binding to FcγRIIb, relative to FcγRI, FcγRIIa, FcγRIIc, FcγRIIIa, and/or FcγRIIIb. Certain Fc regions have increased binding to FcγRIIc, relative to FcγRI, FcγRIIa, FcγRIIb, FcγRIIIa, and/or FcγRIIIb. Some Fc regions have increased binding to FcγRIIIa, relative to FcγRI, FcγRIIa, FcγRIIb, FcγRIIc, and/or FcγRIIIb. Specific Fc regions have increased binding to FcγRIIIb, relative to FcγRI, FcγRIIa, FcγRIIb, FcγRIIc, and/or FcγRIIIa.

FcαRs include FcαRI (CD89). FcαRI is found on the surface of neutrophils, eosinophils, monocytes, certain macrophages (e.g., Kupffer cells), and certain dendritic cells. FcαRI is composed of two extracellular Ig-like domains, is a member of both the immunoglobulin superfamily and the multi-chain immune recognition receptor (MIRR) family, and signals by associating with two FcRγ signaling chains.

FcεRs include FcεRI and FcεRII. The high-affinity receptor FcεRI is a member of the immunoglobulin superfamily, is expressed on epidermal Langerhans cells, eosinophils, mast cells and basophils, and plays a major role in controlling allergic responses. FcεRI is also expressed on antigen-presenting cells, and regulates the production pro-inflammatory cytokines. The low-affinity receptor FcεRII (CD23) is a C-type lectin that can function as a membrane-bound or soluble receptor. FcεRII regulates B cell growth and differentiation, and blocks IgE-binding of eosinophils, monocytes, and basophils. Certain Fc regions have increased binding to FcεRI, relative to FcεRII. Other Fc regions have increased binding to FcεRII, relative to FcεRI.

TABLE H6

Exemplary Fc-Receptors

| Receptor | Primary Antibody Ligand | Ligand Affinity | Cell Distribution | Exemplary Effects Following Binding to Fc Ligand |
|---|---|---|---|---|
| FcγRI (CD64) | IgG1 and IgG3 | High (Kd ~$10^{-9}$ M) | Macrophages Neutrophils Eosinophils Dendritic cells | Phagocytosis Cell activation Activation of respiratory burst Induction of microbe killing |
| FcγRIIa (CD32) | IgG | Low (Kd > $10^{-7}$ M) | Macrophages Neutrophils Eosinophils Platelets Langerhans cells | Phagocytosis Degranulation (eosinophils) |
| FcγRIIb1 (CD32) | IgG | Low (Kd > $10^{-7}$ M) | B Cells Mast cells | No phagocytosis Inhibition of cell activity |
| FcγRIIb2 (CD32) | IgG | Low (Kd > $10^{-7}$ M) | Macrophages Neutrophils Eosinophils | Phagocytosis Inhibition of cell activity |
| FcγRIIIa (CD16a) | IgG | Low (Kd > $10^{-6}$ M) | NK cells Macrophages (certain tissues) | Induction of antibody-dependent cell-mediated cytotoxicity (ADCC) Induction of cytokine release by macrophages |
| FcγRIIIb (CD16b) | IgG | Low (Kd > $10^{-6}$ M) | Eosinophils Macrophages Neutrophils Mast cells Follicular dendritic cells | Induction of microbe killing |
| FcεRI | IgE | High (Kd ~$10^{-10}$ M) | Mast cells Eosinophils Basophils Langerhans cells | Degranulation |
| FcεRII (CD23) | IgE | Low (Kd > $10^{-7}$ M) | B cells Eosinophils Langerhans cells | Possible adhesion molecule |
| FcαRI (CD89) | IgA | Low (Kd > $10^{-6}$ M) | Monocytes Macrophages Neutrophils Eosinophils | Phagocytosis Induction of microbe killing |
| Fcα/μR | IgA and IgM | High for IgM, Moderate for IgA | B cells Mesangial cells Macrophages | Endocytosis Induction of microbe killing |
| FcRn | IgG | | Monocytes Macrophages Dendrite cells Epithelial cells Endothelial cells Hepatocytes | Transfers IgG from a mother to fetus through the placenta Transfers IgG from a mother to infant in milk Protects IgG from degradation |

Fc regions can be derived from the immunoglobulin molecules of any animal, including vertebrates such as mammals such cows, goats, swine, dogs, mice, rabbits, hamsters, rats, guinea pigs, non-human primates, and humans. The amino acid sequences of $CH_2$, $CH_3$, $CH_4$, and hinge regions from exemplary, wild-type human IgA1, IgA2, IgD, IgE, IgG1, IgG2, IgG3, IgG4, and IgM immunoglobulins are shown in Table H7.

TABLE H7

Exemplary Fc sequences

| Name | Sequence | SEQ ID NO: |
|---|---|---|
| IgA1 hinge | VPSTPPTPSPSTPPTPSPS | 128 |
| IgA1 CH2 | CCHPRLSLHRPALEDLLLGSEANLTCTLTGLRDASGVTFTWTPSSGKSAVQ GPPERDLCGCYSVSSVLPGCAEPWNHGKTFTCTAAYPESKTPLTATLSKS | 129 |
| IgA1 CH3 | GNTFRPEVHLLPPPSEELALNELVTLTCLARGFSPKDVLVRWLQGSQELPR EKYLTWASRQEPSQGTTTFAVTSILRVAAEDWKKGDTFSCMVGHEALPLAF TQKTIDRLAGKPTHVNVSVVMAEVDGTCY | 130 |
| IgA2 hinge | VPPPPP | 131 |
| IgA2 CH2 | CCHPRLSLHRPALEDLLLGSEANLTCTLTGLRDASGATFTWTPSSGKSAVQ GPPERDLCGCYSVSSVLPGCAQPWNHGETFTCTAAHPELKTPLTANITKS | 132 |
| IgA2 CH3 | GNTFRPEVHLLPPPSEELALNELVTLTCLARGFSPKDVLVRWLQGSQELPR EKYLTWASRQEPSQGTTTFAVTSILRVAAEDWKKGDTFSCMVGHEALPLAF TQKTIDRLAGKPTHVNVSVVMAEVDGTCY | 133 |
| IgD hinge | ESPKAQASSVPTAQPQAEGSLAKATTAPATTRNTGRGGEEKKKEKEKEEQE ERETKTP | 134 |
| IgD CH2 | ECPSHTQPLGVYLLTPAVQDLWLRDKATFTCFVVGSDLKDAHLTWEVAGKV PTGGVEEGLLERHSNGSQSQHSRLTLPRSLWNAGTSVTCTLNHPSLPPQRL MALREP | 135 |
| IgD CH3 | AAQAPVKLSLNLLASSDPPEAASWLLCEVSGFSPPNILLMWLEDQREVNTS GFAPARPPPQPRSTTFWAWSVLRVPAPPSPQPATYTCVVSHEDSRTLLNAS RSLEVSYVTDHGPMK | 136 |
| IgE CH2 | VCSRDFTPPTVKILQSSCDGGGHFPPTIQLLCLVSGYTPGTINITWLEDGQ VMDVDLSTASTTQEGELASTQSELTLSQKHWLSDRTYTCQVTYQGHTFEDS TKKCA | 137 |
| IgE CH3 | DSNPRGVSAYLSRPSPFDLFIRKSPTITCLVVDLAPSKGTVNLTWSRASGK PVNHSTRKEEKQRNGTLTVTSTLPVGTRDWIEGETYQCRVTHPHLPRALMR STTKTS | 138 |
| IgE CH4 | GPRAAPEVYAFATPEWPGSRDKRTLACLIQNFMPEDISVQWLHNEVQLPDA RHSTTQPRKTKGSGFFVFSRLEVTRAEWEQKDEFICRAVHEAASPSQTVQR AVSVNPGK | 139 |
| IgG1 hinge | EPKSCDKTHTCPPCP | 140 |
| modified human IgG1 hinge | SDKTHTCPPCP | 141 |
| IgG1 CH2 | APELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPI EKTISKAK | 142 |
| IgG1 CH3 | GQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLS LSPGK | 143 |
| IgG1 heavy chain | MSDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNV FSCSVMHEALHNHYTQKSLSLSPGK | 144 |
| IgG2 hinge | ERKCCVECPPCP | 145 |
| IgG2 CH2 | APPVAGPSVFLFPPKPKDTLMISRTPEVTCVVVDVSHEDPEVQFNWYVDGV EVHNAKTKPREEQFNSTFRVVSVLTVVHQDWLNGKEYKCKVSNKGLPAPIE KTISKTK | 146 |

TABLE H7-continued

Exemplary Fc sequences

| Name | Sequence | SEQ ID NO: |
|---|---|---|
| IgG2 CH3 | GQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK | 147 |
| IgG3 hinge | ELKTPLGDTTHTCPRCPEPKSCDTPPPCPRCPEPKSCDTPPPCPRCPEPKSCDTPPPCPRCP | 148 |
| IgG3 CH2 | APELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTK | 149 |
| IgG3 CH3 | GQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPGK | 150 |
| IgG4 hinge | ESKYGPPCPSCP | 151 |
| IgG4 CH2 | APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAK | 152 |
| IgG4 CH3 | GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 153 |
| IgM CH2 | VIAELPPKVSVFVPPRDGFFGNPRKSKLICQATGFSPRQIQVSWLREGKQVGSGVTTDQVQAEAKESGPTTYKVTSTLTIKESDWLGQSMFTCRVDHRGLTFQQNASSMCVP | 154 |
| IgM CH3 | DQDTAIRVFAIPPSFASIFLTKSTKLTCLVTDLTTYDSVTISWTRQNGEAVKTHTNISESHPNATRSAVGEASICEDDWNSGERFTCTVTHTDLPSPLKQTISRPK | 155 |
| IgM CH4 | GVALHRPDVYLLPPAREQLNLRESATITCLVTGFSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY | 156 |

An Fc region of an HRS-Fc conjugate can thus comprise, consist of, or consist essentially of one or more of the human Fc region amino acid sequences of Table H7, including variants, fragments, homologs, orthologs, paralogs, and combinations thereof. Certain illustrative embodiments comprise an Fc region that ranges in size from about 20-50, 20-100, 20-150, 20-200, 20-250, 20-300, 20-400, 50-100, 50-150, 50-200, 50-250, 50-300, 50-400, 100-150, 100-200, 100-250, 100-300, 100-350, 100-400, 200-250, 200-300, 200-350, or 200-400 amino acids in length, and optionally comprises, consists of, or consists essentially of any one or more of the sequences in Table H7. Certain embodiments comprise an Fc region of up to about 50, 60, 70, 80, 90, 100, 110, 120, 130, 140, 150, 160, 170, 180, 190, 200, 210, 220, 230, 240, 250, 300, 350, 400 or more amino acids, which optionally comprises, consists of, or consists essentially of any one or more of the amino acid sequences of Table H7.

Certain Fc regions comprise, consist of, or consist essentially of human IgA1 sequences of Table H7, in any order reading from N-terminus to C-terminus, including combinations thereof, and variants and fragments thereof. Certain Fc regions comprise, consist of, or consist essentially of human the IgA1 sequence of Table H7. Certain Fc regions comprise, consist of, or consist essentially of the human IgA1 sequence of Table H7. Certain Fc regions comprise, consist of, or consist essentially of the human IgA1 sequence of Table H7.

Some Fc regions comprise, consist of, or consist essentially of human IgA2 sequences of Table H7, in any order reading from N-terminus to C-terminus, including combinations thereof, and variants and fragments thereof. Certain Fc regions comprise, consist of, or consist essentially of human the IgA2 sequence of Table H7. Certain Fc regions comprise, consist of, or consist essentially of the human IgA2 sequence of Table H7. Certain Fc regions comprise, consist of, or consist essentially of the human IgA2 sequence of Table H7.

Certain Fc regions comprise, consist of, or consist essentially of human IgD sequences of Table H7, in any order reading from N-terminus to C-terminus, including combinations thereof, and variants and fragments of these sequences and combinations. Certain Fc regions comprise, consist of, or consist essentially of human IgE sequences of Table H7, in any order reading from N-terminus to C-terminus, including combinations thereof, and variants and fragments of these sequences and combinations. Certain Fc regions comprise, consist of, or consist essentially of human IgG1 sequences of Table H7, in any order reading from N-terminus to C-terminus, including combinations thereof, and variants and fragments of these sequences and combinations. Certain Fc regions comprise, consist of, or consist essentially of human IgG2 sequences of Table H7, in any order reading from N-terminus to C-terminus, including combinations thereof. Certain Fc regions comprise, consist of, or consist essentially of human IgG3 sequences of Table H7, in any order reading from N-terminus to C-terminus, including combinations thereof. Certain Fc regions comprise, consist of, or consist essentially of human IgG4 sequences of Table H7, in any order reading from N-terminus to C-terminus, including combinations thereof Certain Fc regions comprise, consist of, or consist essentially of human IgM sequences of Table H7, in any order reading from N-terminus to C-terminus, including combinations thereof, and variants and fragments of these sequences and combinations.

Exemplary HRS-Fc fusion conjugates are provided in Table H8 below.

TABLE H8

Exemplary HRS-Fc fusion proteins

| Name | Sequence | SEQ ID NO: |
|---|---|---|
| Fc-HRS(2-60) HRS$^{FC1}$ | MDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLN GKEYKCKVSNKALPAPIEKTISKAKGQPREPQVYTLPPSRDELTKNQV SLTCLVKGFYPSDIAVEWESNGQPENNYKTTPPVLDSDGSFFLYSKLT VDKSRWQQGNVFSCSVMHEALHNHYTQKSLSLSPGKAERAALEELVKL QGERVRGLKQQKASAELIEEEVAKLLKLKAQLGPDESKQKFVLKTPK | 157 |
| Fc-HRS(2-60) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLKLKAQLGPDESKQKFVLKTPK | 158 |
| HRS(1-60)-Fc | MAERAALEELVKLQGERVRGLKQQKASAELIEEEVAKLLKLKAQLGPD ESKQKFVLKTPKSDKTHTCPPCPAPELLGGPSVFLFPPKPKDTLMISR TPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTL PPSREEMTKNQVSLTCLVKGFYPSDIAVEWESNGQPENNYKTTPPVLD SDGSFFLYSKLTVDKSRWQQGNVFSCSVMHEALHNHYTQKSLSLSPGK | 159 |
| Fc-HRS(2-60) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLKLKAQLGPDESKQKFVLKTPK | 160 |
| HRS(1-60)-Fc | MAERAALEELVKLQGERVRGLKQQKASAELIEEEVAKLLKLKAQLGPD ESKQKFVLKTPKSDKTHTCPPCPAPELLGGPSVFLFPPKPKDTLMISR TPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTL PPSREEMTKNQVSLTCLVKGFYPSDIAVEWESNGQPENNYKTTPPVLD SDGSFFLYSKLTVDKSRWQQGNVFSCSVMHEALHNHYTQKSLSLSPGK | 161 |
| Fc-HRS (2-40) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLK | 162 |
| Fc-HRS (2-45) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLKLKAQL | 163 |
| Fc-HRS (2-50) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLKLKAQLGPDES | 164 |
| Fc-HRS (2-55) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK LQGERVRGLKQQKASAELIEEEVAKLLKLKAQLGPDESKQKFV | 165 |
| Fc-HRS (2-66) | MSDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGKAERAALEELVK | 166 |

TABLE H8-continued

Exemplary HRS-Fc fusion proteins

| Name | Sequence | SEQ ID NO: |
|---|---|---|
| | LQGERVRGLKQQKASAELIEEEVAKLLKLKAQLGPDESKQKFVLKTPK<br>GTRDYS | |
| HRS(1-40)-Fc | MAERAALEELVKLQGERVRGLKQQKASAELIEEEVAKLLKSDKTHTCP<br>PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQ<br>GNVFSCSVMHEALHNHYTQKSLSLSPGK | 167 |
| HRS(1-45)-Fc | MAERAALEELVKLQGERVRGLKQQKASAELIEEEVAKLLKLKAQLSDK<br>THTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKE<br>YKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDK<br>SRWQQGNVFSCSVMHEALHNHYTQKSLSLSPGK | 168 |
| HRS(1-50)-Fc | MAERAALEELVKLQGERVRGLKQQKASAELIEEEVAKLLKLKAQLGPD<br>ESSDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSK<br>LTVDKSRWQQGNVFSCSVMHEALHNHYTQKSLSLSPGK | 169 |
| HRS(1-55)-Fc | MAERAALEELVKLQGERVRGLKQQKASAELIEEEVAKLLKLKAQLGPD<br>ESKQKFVSDKTHTCPPCPAPELLGGPSVFLFPPKPKDTLMISRTPEVT<br>CVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSF<br>FLYSKLTVDKSRWQQGNVFSCSVMHEALHNHYTQKSLSLSPGK | 170 |
| HRS(1-66)-Fc | MAERAALEELVKLQGERVRGLKQQKASAELIEEEVAKLLKLKAQLGPD<br>ESKQKFVLKTPKGTRDYSSDKTHTCPPCPAPELLGGPSVFLFPPKPKD<br>TLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPRE<br>PQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSL<br>SLSPGK | 171 |
| Fc-HRS(2-60)<br>HRS(2-60) | MSDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWL<br>NGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKL<br>TVDKSRWQQGNVFSCSVMHEALHNHYTQKSLSLSPGKAERAALEELVK<br>LQGERVRGLKQQKASAELIEEEVAKLLKLKAQLGPDESKQKFVLKTPK<br>AERAALEELVKLQGERVRGLKQQKASAELIEEEVAKLLKLKAQLGPDE<br>SKQKFVLKTPK | 172 |

Accordingly, in certain embodiments, the HRS polypeptide is fused or otherwise conjugated to an Fc region and comprises, consists, or consists essentially of an amino acid sequence in Table H8 (SEQ ID NO:157-172) or an active variant or fragment thereof. In some embodiments, the expressible polynucleotide encodes an HRS polypeptide that comprises consists, or consists essentially of an amino acid sequence in Table H8 (e.g., SEQ ID NO: 157-172) or an active variant or fragment thereof.

As noted above, certain embodiments employ variants, fragments, hybrids, and/or otherwise modified forms an Fc region described herein and known in the art. Included are variants having one or more amino acid substitutions, insertions, deletions, and/or truncations relative to a reference sequence, such as any one or more of the reference sequences of Table H7 or Table H8. Polypeptide and polynucleotide variants are described elsewhere herein.

Also included are hybrid Fc regions, for example, Fc regions that comprise a combination of Fc domains (e g., hinge, $CH_2$, $CH_3$, $CH_4$) from immunoglobulins of different species, different Ig classes, and/or different Ig subclasses. General examples include hybrid Fc regions that comprise, consist of, or consist essentially of the following combination of $CH_2/CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgE/IgA1, IgE/IgA2, IgE/IgD, IgE/IgE, IgE/IgG1, IgE/IgG2, IgE/IgG3, IgE/IgG4, IgE/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM, IgM/IgA1, IgM/IgA2, IgM/IgD, IgM/IgE, IgM/IgG1, IgM/IgG2, IgM/IgG3, IgM/IgG4, IgM/IgM (or fragments or variants thereof), and optionally include a hinge from one or more of IgA1, IgA2, IgD, IgG1, IgG2, IgG3, or IgG4, and/or a $CH_4$ domain from IgE and/or IgM. In specific embodiments, the hinge, CH$_2$, CH$_3$, and CH$_4$ domains are from human Ig.

Additional examples include hybrid Fc regions that comprise, consist of, or consist essentially of the following combination of CH$_2$/CH$_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a CH$_3$ domain from one or more of IgA1, IgA2, IgD, IgE, IgG1, IgG2, IgG3, IgG4, or IgM. In specific embodiments, the hinge, CH$_2$, CH$_3$, and CH$_4$ domains are from human Ig.

Certain examples include hybrid Fc regions that comprise, consist of, or consist essentially of the following combination of CH$_3$/CH$_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a CH$_2$ domain from one or more of IgA1, IgA2, IgD, IgE, IgG1, IgG2, IgG3, IgG4, or IgM. In specific embodiments, the hinge, CH$_2$, CH$_3$, and CH$_4$ domains are from human Ig.

Particular examples include hybrid Fc regions that comprise, consist of, or consist essentially of the following combination of hinge/CH$_2$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a CH$_3$ domain from one or more of IgA1, IgA2, IgD, IgE, IgG1, IgG2, IgG3, IgG4, or IgM, and/or a CH$_4$ domain from IgE and/or IgM. In specific embodiments, the hinge, CH$_2$, CH$_3$, and CH$_4$ domains are from human Ig.

Certain examples include hybrid Fc regions that comprise, consist of, or consist essentially of the following combination of hinge/CH$_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a CH$_2$ domain from one or more of IgA1, IgA2, IgD, IgE, IgG1, IgG2, IgG3, IgG4, or IgM, and/or a CH$_4$ domain from IgE and/or IgM. In specific embodiments, the hinge, CH$_2$, CH$_3$, and CH$_4$ domains are from human Ig.

Some examples include hybrid Fc regions that comprise, consist of, or consist essentially of the following combination of hinge/CH$_4$ domains: IgA1/IgE, IgA1/IgM, IgA2/IgE, IgA2/IgM, IgD/IgE, IgD/IgM, IgG1/IgE, IgG1/IgM, IgG2/IgE, IgG2/IgM, IgG3/IgE, IgG3/IgM, IgG4/IgE, IgG4/IgM (or fragments or variants thereof), and optionally include a CH$_2$ domain from one or more of IgA1, IgA2, IgD, IgE, IgG1, IgG2, IgG3, IgG4, or IgM, and/or a CH$_3$ domain from one or more of IgA1, IgA2, IgD, IgE, IgG1, IgG2, IgG3, IgG4, or IgM.

Specific examples of hybrid Fc regions can be found, for example, in WO 2008/147143, which are derived from combinations of IgG subclasses or combinations of human IgD and IgG.

Also included are derivatized or otherwise modified Fc regions. In certain aspects, the Fc region may be modified by phosphorylation, sulfation, acrylation, glycosylation, methylation, farnesylation, acetylation, amidation, and the like, for instance, relative to a wild-type or naturally-occurring Fc region. In certain embodiments, the Fc region may comprise wild-type or native glycosylation patterns, or alternatively, it may comprise increased glycosylation relative to a native form, decreased glycosylation relative to a native form, or it may be entirely deglycosylated. As one example of a modified Fc glycoform, decreased glycosylation of an Fc region reduces binding to the Clq region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform can be generated by substituting the Q295 position with a cysteine residue (see, e.g., U.S. Application No. 2010/0080794), according to the Kabat et al. numbering system. Certain embodiments may include Fc regions where about 80-100% of the glycoprotein in Fc region comprises a mature core carbohydrate structure that lacks fructose (see, e.g., U.S. Application No. 2010/0255013). Some embodiments may include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region may comprise oligomannose-type N-glycans, and optionally have one or more of the following: increased ADCC activity, increased binding affinity for FcγRIIIA (and certain other FcRs), similar or increased binding specificity for the target of the HRS polypeptide, similar or higher binding affinity for the target of the HRS polypeptide, and/or similar or lower binding affinity for mannose receptor, relative to a corresponding Fc region or HRS-Fc conjugate that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., *Nat Biotechnol.* 17:176-180, 1999; Davies et al., *Biotechnol Bioeng.* 74:288-294, 2001; Shields et al., *J Biol Chem.* 277:26733-26740, 2002; Shinkawa et al., 2003, *J Biol Chem.* 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions may have altered binding to one or more FcRs, relative to a corresponding, wild-type Fc sequence (e.g., same species, same Ig class, same Ig subclass). For instance, such Fc regions may have increased binding to one or more of Fcγ receptors, Fcα receptors, Fcε receptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, Fcε receptors, and/or the neonatal Fc receptor, relative to a corresponding, wild-type Fc sequence. Specific FcRs are described elsewhere herein.

Specific examples of Fc variants having altered (e.g., increased, decreased) FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/E333A/K334A triple mutant, which has increased binding to FcγRIIIa, decreased binding to FcγRIIb, and increased ADCC (see, e.g., Shields et al., *J Biol Chem.* 276:6591-6604, 2001; and Presta et al., *Biochem Soc Trans.* 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/434S, and 428L/434S (see U.S. Application Nos. 2009/0163699 and 20060173170), based on the EU index of Kabat et al.

Certain variant, fragment, hybrid, or modified Fc regions may have altered effector functions, relative to a corresponding, wild-type Fc sequence. For example, such Fc regions may have increased complement fixation or activation, increased C1q binding affinity, increased CDC-related activity, increased ADCC-related activity, and/or increased ADCP-related activity, relative to a corresponding, wild-type Fc sequence. In other embodiments, such Fc regions may have decreased complement fixation or activation, decreased C1q binding affinity, decreased CDC-related activity, decreased ADCC-related activity, and/or decreased ADCP-related activity, relative to a corresponding, wild-type Fc sequence. As merely one illustrative example, an Fc region may comprise a deletion or substitution in a complement-binding site, such as a C1q-binding site, and/or a deletion or substitution in an ADCC site. Examples of such deletions/substitutions are described, for example, in U.S. Pat. No. 7,030,226. Many Fc effector functions, such as ADCC, can be assayed according to routine techniques in the art. (see, e.g., Zuckerman et al., *CRC Crit Rev Microbiol.* 7:1-26, 1978). Useful effector cells for such assays includes, but are not limited to, natural killer (NK) cells, macrophages, and other peripheral blood mononuclear cells (PBMC). Alternatively, or additionally, certain Fc effector functions may be assessed in vivo, for example, by employing an animal model described in Clynes et al. *PNAS.* 95:652-656, 1998.

Certain variant hybrid, or modified Fc regions may have altered stability or half-life relative to a corresponding, wild-type Fc sequence. In certain embodiments, such Fc regions may have increased half-life relative to a corresponding, wild-type Fc sequence. In other embodiments, variant hybrid, or modified Fc regions may have decreased half-life relative to a corresponding, wild-type Fc sequence. Half-life can be measured in vitro (e.g., under physiological conditions) or in vivo, according to routine techniques in the art, such as radiolabeling, ELISA, or other methods. In vivo measurements of stability or half-life can be measured in one or more bodily fluids, including blood, serum, plasma, urine, or cerebrospinal fluid, or a given tissue, such as the liver, kidneys, muscle, central nervous system tissues, bone, etc. As one example, modifications to an Fc region that alter its ability to bind the FcRn can alter its half-life in vivo. Assays for measuring the in vivo pharmacokinetic properties (e.g., in vivo mean elimination half-life) and non-limiting examples of Fc modifications that alter its binding to the FcRn are described, for example, in U.S. Pat. Nos. 7,217,797 and 7,732,570; and U.S. Application Nos. US 2010/0143254 and 2010/0143254.

Additional non-limiting examples of modifications to alter stability or half-life include substitutions/deletions at one or more of amino acid residues selected from 251-256, 285-290, and 308-314 in the $CH_2$ domain, and 385-389 and 428-436 in the $CH_3$ domain, according to the numbering system of Kabat et al. See U.S. Application No. 2003/0190311. Specific examples include substitution with leucine at position 251, substitution with tyrosine, tryptophan or phenylalanine at position 252, substitution with threonine or serine at position 254, substitution with arginine at position 255, substitution with glutamine, arginine, serine, threonine, or glutamate at position 256, substitution with threonine at position 308, substitution with proline at position 309, substitution with serine at position 311, substitution with aspartate at position 312, substitution with leucine at position 314, substitution with arginine, aspartate or serine at position 385, substitution with threonine or proline at position 386, substitution with arginine or proline at position 387, substitution with proline, asparagine or serine at position 389, substitution with methionine or threonine at position 428, substitution with tyrosine or phenylalanine at position 434, substitution with histidine, arginine, lysine or serine at position 433, and/or substitution with histidine, tyrosine, arginine or threonine at position 436, including any combination thereof. Such modifications optionally increase affinity of the Fc region for the FcRn and thereby increase half-life, relative to a corresponding, wild-type Fc region.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Additional examples of variants include IgG Fc regions having conservative or non-conservative substitutions (as described elsewhere herein) at one or more of positions 250, 314, or 428 of the heavy chain, or in any combination thereof, such as at positions 250 and 428, or at positions 250 and 314, or at positions 314 and 428, or at positions 250, 314, and 428 (see, e.g., U.S. Application No. 2011/0183412). In specific embodiments, the residue at position 250 is substituted with glutamic acid or glutamine, and/or the residue at position 428 is substituted with leucine or phenylalanine. As another illustrative example of an IgG Fc variant, any one or more of the amino acid residues at positions 214 to 238, 297 to 299, 318 to 322, and/or 327 to 331 may be used as a suitable target for modification (e.g., conservative or non-conservative substitution, deletion). In particular embodiments, the IgG Fc variant CH$_2$ domain contains amino acid substitutions at positions 228, 234, 235, and/or 331 (e g., human IgG4 with Ser228Pro and Leu235Ala mutations) to attenuate the effector functions of the Fc region (see U.S. Pat. No. 7,030,226). Here, the numbering of the residues in the heavy chain is that of the EU index (see Kabat et al., "Sequences of Proteins of Immunological Interest," 5$^{th}$ Ed., National Institutes of Health, Bethesda, Md. (1991)). Certain of these and related embodiments have altered (e.g., increased, decreased) FcRn binding and/or serum half-life, optionally without reduced effector functions such as ADCC or CDC-related activities.

Additional examples include variant Fc regions that comprise one or more amino acid substitutions at positions 279, 341, 343 or 373 of a wild-type Fc region, or any combination thereof (see, e.g., U.S. Application No. 2007/0224188). The wild-type amino acid residues at these positions for human IgG are valine (279), glycine (341), proline (343) and tyrosine (373). The substation(s) can be conservative or non-conservative, or can include non-naturally occurring amino acids or mimetics, as described herein. Alone or in combination with these substitutions, certain embodiments may also employ a variant Fc region that comprises at least 1, 2, 3, 4, 5, 6, 7, 8, 9, 10 or more amino acid substitutions selected from the following: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283P, 283R, 283T, 283W, 283Y, 285N, 286F, 288N, 288P, 292E, 292F, 292G, 292I, 292L, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343F, 343G, 343H, 343I, 343K, 343L, 343N, 343Q, 343R, 343S, 343T, 343V, 343W, 343Y, 373D, 373E, 373F, 373G, 373H, 373I, 373K, 373L, 373M, 373N, 373Q, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379Q, 379S, 379T, 380D, 380N, 380S, 380T, 382D, 382F, 382H, 382I, 382K, 382L, 382M, 382N, 382P, 382Q, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K. As above, the numbering of the residues in the heavy chain is that of the EU index (see Kabat et al., supra). Such variant Fc regions typically confer an altered effector function or altered serum half-life upon HRS polypeptide to which the variant Fc region is operably attached. Preferably the altered effector function is an increase in ADCC, a decrease in ADCC, an increase in CDC, a decrease in CDC, an increase in Clq binding affinity, a decrease in Clq binding affinity, an increase in FcR (preferably FcRn) binding affinity or a decrease in FcR (preferably FcRn) binding affinity as compared to a corresponding Fc region that lacks such amino acid substitution(s).

Additional examples include variant Fc regions that comprise an amino acid substitution at one or more of position(s) 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and/or 428 (see, e.g., U.S. Pat. No. 7,662,925). In specific embodiments, the variant Fc region comprises at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y. In other specific embodiments, the variant Fc region comprises at least one amino acid substitution selected from the group consisting of: V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/I332E, S239Q/V264I/I332E, S239E/V264I/A330Y/I332E, S239D/A330Y/I332E, S239N/A330Y/I332E, 5239D/A330L/I332E, 5239N/A330L/I332E, V264I/S298A/I332E, S239D/S298A/I332E, S239N/S298A/I332E, S239D/V264I/I332E, S239D/V264I/S298A/I332E, S239D/V264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/V264T, S239D/A330Y/I332E/K326E, and S239D/A330Y/

I332E/K326T, In more specific embodiments, the variant Fc region comprises a series of substitutions selected from the group consisting of: N297D/I332E, F241Y/F243YN262T/V264T/N297D/I332E, S239D/N297D/I332E, S239E/N297D/I332E, S239D/D265Y/N297D/I332E, S239D/D265H/N297D/I332E, V264E/N297D/I332E, Y296N/N297D/I332E, N297D/A330Y/I332E, S239D/D265V/N297D/I332E, S239D/D265I/N297D/I332E, and N297D/S298A/A330Y/I332E. In specific embodiments, the variant Fc region comprises an amino acid substitution at position 332 (using the numbering of the EU index, Kabat et al., supra). Examples of substitutions include 332A, 332D, 332E, 332F, 332G, 332H, 332K, 332L, 332M, 332N, 332P, 332Q, 332R, 332S, 332T, 332V, 332W and 332Y. The numbering of the residues in the Fc region is that of the EU index of Kabat et al. Among other properties described herein, such variant Fc regions may have increased affinity for an FcγR, increased stability, and/or increased solubility, relative to a corresponding, wild-type Fc region.

Further examples include variant Fc regions that comprise one or more of the following amino acid substitutions: 224N/Y, 225A, 228L, 230S, 239P, 240A, 241L, 243S/L/G/H/I, 244L, 246E, 247L/A, 252T, 254T/P, 258K, 261Y, 265V, 266A, 267G/N, 268N, 269K/G, 273A, 276D, 278H, 279M, 280N, 283G, 285R, 288R, 289A, 290E, 291L, 292Q, 297D, 299A, 300H, 301C, 304G, 305A, 306I/F, 311R, 312N, 315D/K/S, 320R, 322E, 323A, 324T, 325S, 326E/R, 332T, 333D/G, 335I, 338R, 339T, 340Q, 341E, 342R, 344Q, 347R, 351S, 352A, 354A, 355W, 356G, 358T, 361D/Y, 362L, 364C, 365Q/P, 370R, 372L, 377V, 378T, 383N, 389S, 390D, 391C, 393A, 394A, 399G, 404S, 408G, 409R, 411I, 412A, 414M, 421S, 422I, 426F/P, 428T, 430K, 431S, 432P, 433P, 438L, 439E/R, 440G, 441F, 442T, 445R, 446A, 447E, optionally where the variant has altered recognition of an Fc ligand and/or altered effector function compared with a parent Fc polypeptide, and wherein the numbering of the residues is that of the EU index as in Kabat et al. Specific examples of these and related embodiments include variant Fc regions that comprise or consist of the following sets of substitutions: (1) N276D, R292Q, V305A, I377V, T394A, V412A and K439E; (2) P244L, K246E, D399G and K409R; (3) S304G, K320R, S324T, K326E and M358T; (4) F243S, P247L, D265V, V266A, S383N and T411I; (5) H224N, F243L, T393A and H433P; (6) V240A, S267G, G341E and E356G; (7) M252T, P291L, P352A, R355W, N390D, S408G, S426F and A431S; (8) P228L, T289A, L365Q, N389S and S440G; (9) F241L, V273A, K340Q and L441F; (10) F241L, I299A, I332I and M428T; (11) E269K, Y300H, Q342R, V422I and G446A; (12) T225A, R301c, S304G, D312N, N315D, L351S and N421S; (13) S254T, L306I, K326R and Q362L; (14) H224Y, P230S, V323A, E333D, K338R and S364C; (15) I335I, K414M and P445R; (16) T335I and K414M; (17) P247A, E258K, D280N, K288R, N297D, T299A, K322E, Q342R, S354A and L365P; (18) H268N, V279M, A339T, N361D and S426P; (19) C261Y, K290E, L306F, Q311R, E333G and Q438L; (20) E283G, N315K, E333G, R344Q, L365P and S442T; (21) Q347R, N361Y and K439R; (22) S239P, S254P, S267N, H285R, N315S, F372L, A378T, N390D, Y391C, F404S, E430K, L432P and K447E; and (23) E269G, Y278H, N325S and K370R, wherein the numbering of the residues is that of the EU index as in Kabat et al. (see, e.g., U.S. Application No. 2010/0184959).

Another specific example of an Fc variant comprises an Fc sequence of Table H7, wherein Xaa at position 1 is Ala or absent; Xaa at position 16 is Pro or Glu; Xaa at position 17 is Phe, Val, or Ala; Xaa at position 18 is Leu, Glu, or Ala; Xaa at position 80 is Asn or Ala; and/or Xaa at position 230 is Lys or is absent (see, e.g., U.S. Application No. 2007/0253966). Certain of these Fc regions, and related HRS-Fc conjugates, have increased half-life, reduced effector activity, and/or are significantly less immunogenic than wild-type Fc sequences.

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

As noted above, HRS-Fc conjugates such as HRS-Fc fusion proteins typically have altered (e.g., improved, increased, decreased) pharmacokinetic properties relative to corresponding HRS polypeptides. Examples of pharmacokinetic properties include stability or half-life, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve (AUC or exposure; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state). In some aspects, these improved properties are achieved without significantly altering the secondary structure and/or reducing the non-canonical biological activity of the HRS polypeptide. Indeed, some HRS-Fc conjugates have increased non-canonical biological activity.

Hence, in some embodiments, the HRS-Fc conjugate or HRS-Fc fusion polypeptide has a plasma or sera pharmacokinetic AUC profile at least 2, 3, 4, 5, 6, 7, 8, 9, 10, 11, 12, 13, 14, 15, 16, 17, 18, 19, 20, 50, 100, 200, 300, 400, or 500-fold greater than a corresponding unmodified or differently modified HRS polypeptide when administered to a mammal under the same or comparable conditions. In certain embodiments, the HRS-Fc conjugate or HRS-Fc fusion polypeptide has a stability (e.g., as measured by half-life) which is at least 10%, 20%, 30%, 40%, 50%, 60%, 70%, 80%, 90%, 100%, 200%, 300%, 400%, or 500% greater than a corresponding unmodified or differently modified HRS polypeptide when compared under similar conditions at room temperature, for example, in PBS at pH 7.4 for about 1, 2, 3, 4, 5, 6, 7, 8, 9, 10, 11, 12, 13, 14 days, or 1, 2, 3, 4 weeks or so.

In particular embodiments, a HRS-Fc conjugate or HRS-Fc fusion polypeptide has a biological half life at pH 7.4, 25° C., e.g., a physiological pH, human body temperature (e.g., in vivo, in serum, in a given tissue, in a given species such as rat, mouse, monkey, or human), of about or at least about 30 minutes, about 1 hour, about 2 hour, about 3 hours, about 4 hours, about 5 hours, about 6 hours, about 12 hours, about 18 hours, about 20 hours, about 24 hours, about 30 hours, about 36 hours, about 40 hours, about 48 hours, about 50 hours, about 60 hours, about 70 hours, about 72 hours, about 80 hours, about 84 hours, about 90 hours, about 96 hours, about 120 hours, or about 144 hours or more or any intervening half-life.

In certain embodiments, the HRS-Fc conjugate or HRS-Fc fusion polypeptide has greater bioavailability after subcutaneous (SC) administration compared to a corresponding unmodified HRS-polypeptide. In certain embodiments, the HRS-Fc conjugate or HRS-Fc fusion polypeptide has at least about 20%, at least about 30%, at least about 40%, at least about 50%, at least about 60%, at least about 70%, at least about 80%, at least about 90%, or at least about 100%, or more bioavailability compared to the corresponding unmodified HRS polypeptide.

In certain embodiments, the HRS-Fc fusion polypeptide has substantially the same secondary structure as a corresponding unmodified or differently modified HRS polypeptide, as determined via UV circular dichroism analysis. In certain embodiments, the HRS-Fc fusion polypeptide has substantially the same activity of a corresponding unmodified or differently modified HRS polypeptide in an assay of anti-inflammatory activity. In other embodiments, the HRS-Fc fusion polypeptide has greater than 2, 3, 4, 5, 6, 7, 8, 9, 10, 11, 12, 13, 14, 15, 16, 17, 18, 19, or 20-fold the activity of a corresponding unmodified or differently modified HRS polypeptide in an assay of anti-inflammatory activity.

In certain embodiments, a peptide linker sequence may be employed to separate the HRS polypeptide(s) and the Fc region(s) or PEG(s) by a distance sufficient to ensure that each polypeptide folds into its desired secondary and tertiary structures. Such a peptide linker sequence can be incorporated into the conjugate or fusion protein using standard techniques well known in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, *J Protein Eng.* 15:871-879, 2002.

The linker sequence may generally be from 1 to about 200 amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16,17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA.* 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO:173), $[GGSG]_x$ (SEQ ID NO:174), $[GGGS]_x$ (SEQ ID NO:175), $[GGGGS]_x$ (SEQ ID NO:176), $[GN]_x$, $[GGN]_x$, $[GNN]_x$, $[GNGN]_x$ (SEQ ID NO:177), $[GGNG]_x$ (SEQ ID NO:178), $[GGGN]_x$ (SEQ ID NO:179), $[GGGGN]_x$ (SEQ ID NO:180) linkers, where $_x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

Additional examples of linker peptides include, but are not limited to the following amino acid sequences: Gly-Gly-Gly-Gly-Ser-Gly-Gly-Gly-Gly-Ser-Gly-Gly-Gly-Gly-Ser-(SEQ ID NO:181); Gly-Ser-Gly-Gly-Gly-Gly-Ser-Gly-Gly-Gly-Gly-Ser-Gly-Gly-Gly-Gly-Ser-Gly-Gly-Gly-Gly-Ser-(SEQ ID NO:182); Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-(SEQ ID NO:183); Asp-Ala-Ala-Ala-Lys-Glu-Ala-Ala-Ala-Lys-Asp-Ala-Ala-Ala-Arg-Glu-Ala-Ala-Ala-Arg-Asp-Ala-Ala-Ala-Lys-(SEQ ID NO:184); and Asn-Val-Asp-His-Lys-Pro-Ser-Asn-Thr-Lys-Val-Asp-Lys-Arg-(SEQ ID NO:185).

Further non-limiting examples of linker peptides include DGGGS (SEQ ID NO:186); TGEKP (SEQ ID NO:187) (see, e.g., Liu et al., *PNAS.* 94:5525-5530, 1997); GGRR (SEQ ID NO:188) (Pomerantz et al. 1995); $(GGGGS)_n$ (SEQ ID NO:176) (Kim et al., *PNAS.* 93:1156-1160, 1996); EGKSSGSGSESKVD (SEQ ID NO:189) (Chaudhary et al., *PNAS.* 87:1066-1070, 1990); KESGSVSSEQLAQFRSLD (SEQ ID NO:190) (Bird et al., *Science.* 242:423-426, 1988), GGRRGGGS (SEQ ID NO:191); LRQRDGERP (SEQ ID NO:192); LRQKDGGGSERP (SEQ ID NO:193); LRQKd $(GGGS)_2$ ERP (SEQ ID NO:194). In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, PNAS. 90:2256-2260, 1993; and PNAS. 91:11099-11103, 1994) or by phage display methods.

The peptide linkers may be physiologically stable or may include a releasable linker such as a physiologically degradable or enzymatically cleavable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of HRS polypeptides in the bloodstream, while also delivering a HRS polypeptide into the bloodstream that, subsequent to linker degradation, is substantially free of the Fc region(s). These aspects are especially useful in those cases where HRS polypeptides, when permanently conjugated to an Fc region, demonstrate reduced activity. By using the linkers as provided herein, such HRS polypeptides can maintain their therapeutic activity when in conjugated form. As another example, a large and relatively inert HRS-Fc conjugate polypeptide may be administered, which is then degraded in vivo (via the degradable linker) to generate a bioactive HRS polypeptide possessing a portion of the Fc region or lacking the Fc region entirely. In these and other ways, the properties of the HRS-Fc conjugate polypeptide can be more effectively tailored to balance the bioactivity and circulating half-life of the HRS polypeptide over time.

In particular embodiments, the linker peptide comprises an autocatalytic or self-cleaving peptide cleavage site. In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus. In certain embodiments, the self-cleaving polypeptide site comprises a 2A or 2A-like site, sequence or domain (Donnelly et al., *J. Gen. Virol.* 82:1027-1041, 2001). Exemplary 2A sites include the following sequences: LLNFDLLKLAGDVESNPGP (SEQ ID NO:195); TLNFDLLKLAGDVESNPGP (SEQ ID NO:196); LLKLAGDVESNPGP (SEQ ID NO:197); NFDLLKLAGDVESNPGP (SEQ ID NO:198); QLLNFDLLKLAGDVESNPGP (SEQ ID NO:199); APVKQTLNFDLLKLAGDVESNPGP (SEQ ID NO:200); VTELLYRMKRAETYCPRPLLAIHPTEAR-HKQKIVAPVKQT (SEQ ID NO:201); LNFDLLKLAGD-VESNPGP (SEQ ID NO:202); LLAIHP1EARHKQKIVAPVKQTLNFDLLKLAGDVESNPGP (SEQ ID NO:203); and EAR-HKQKIVAPVKQTLNFDLLKLAGDVESNPGP (SEQ ID NO:204). In some embodiments, the autocatalytic peptide cleavage site comprises a translational 2A signal sequence, such as, e.g., the 2A region of the aphthovirus foot-and-mouth disease virus (FMDV) polyprotein, which is an 18 amino acid sequence. Additional examples of 2A-like sequences that may be used include insect virus polyproteins, the NS34 protein of type C rotaviruses, and repeated sequences in *Trypanosoma* spp., as described, for example, in Donnelly et al., *Journal of General Virology.* 82:1027-1041, 2001.

Suitable protease cleavages sites and self-cleaving peptides are known to the skilled person (see, e.g., Ryan et al., *J. Gener. Virol.* 78:699-722, 1997; and Scymczak et al., *Nature Biotech.* 5:589-594, 2004). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase Due to its high cleavage stringency, 1EV (tobacco etch virus) protease cleavage sites are included in some embodiments, e.g., EXXYXQ(G/S) (SEQ ID NO:205), for example, ENLYFQG (SEQ ID NO:206) and ENLYFQS (SEQ ID NO:207), wherein X represents any amino acid (cleavage by TEV occurs between Q and G or Q and S).

Further examples of enzymatically degradable linkers suitable for use in particular embodiments include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp-(SEQ ID NO:208), -Gly-Gly-Arg-, -Gly-Arg-Gly-Asp-Asn-Pro-(SEQ ID NO:209), -Gly-Arg-Gly-Asp-Ser-(SEQ ID NO:210), -Gly-Arg-Gly-Asp-Ser-Pro-Lys-(SEQ ID NO:211), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val-(SEQ ID NO:212), -Ala-Ala-Pro-Leu-(SEQ ID NO:213), -Ala-Ala-Pro-Phe-(SEQ ID NO:214), -Ala-Ala-Pro-Ala-(SEQ ID NO:215), and -Ala-Tyr-Leu-Val-(SEQ ID NO:216).

Enzymatically degradable linkers also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO:217), -Gly-Pro-, Leu-Gly-Pro-Z-(SEQ ID NO:218), -Gly-Pro-Ile-Gly-Pro-Z-(SEQ ID NO:219), and -Ala-Pro-Gly-Leu-Z-(SEQ ID NO:220), where Y and Z are amino acids. Illustrative examples of collagenase-cleavable amino acid sequences include, but are not limited to: -Pro-Leu-Gly-Pro-D-Arg-Z-(SEQ ID NO:221), -Pro-Leu-Gly-Leu-Leu-Gly-Z-(SEQ ID NO:222), -Pro-Gln-Gly-Ile-Ala-Gly-Trp-(SEQ ID NO:223), -Pro-Leu-Gly-Cys(Me)-His-(SEQ ID NO:224), -Pro-Leu-Gly-Leu-Tyr-Ala-(SEQ ID NO:225), -Pro-Leu-Ala-Leu-Trp-Ala-Arg-(SEQ ID NO:226), and -Pro-Leu-Ala-Tyr-Trp-Ala-Arg-(SEQ ID NO:227), where Z is an amino acid. An illustrative example of a stromelysin-cleavable amino acid sequence is -Pro-Tyr-Ala-Tyr-Tyr-Met-Arg-(SEQ ID NO:228); and an example of a gelatinase-cleavable amino acid sequence is -Pro-Leu-Gly-Met-Tyr-Ser-Arg-(SEQ ID NO:229).

Enzymatically degradable linkers suitable for use in particular embodiments include amino acid sequences that can be cleaved by an angiotensin converting enzyme, such as, for example, -Asp-Lys-Pro-, -Gly-Asp-Lys-Pro-(SEQ ID NO:230), and -Gly-Ser-Asp-Lys-Pro-(SEQ ID NO:231).

Enzymatically degradable linkers suitable for use in particular embodiments include amino acid sequences that can be degraded by cathepsin B, such as, for example, Val-Cit, Ala-Leu-Ala-Leu-(SEQ ID NO:232), Gly-Phe-Leu-Gly-(SEQ ID NO:233) and Phe-Lys.

In particular embodiments, a releasable linker has a half life at pH 7.4, 25° C., e.g., a physiological pH, human body temperature (e.g., in vivo, in serum, in a given tissue), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a HRS-Fc conjugate polypeptide can be finely tailored by using a particular releasable linker.

In certain embodiments, however, any one or more of the peptide linkers are optional. For instance, linker sequences may not required when the first and second polypeptides have non-essential N-terminal and/or C-terminal amino acid regions that can be used to separate the functional domains and prevent steric interference.

The HRS polypeptides and polynucleotides, for example, expressible polynucleotides, can be used in any of the compositions, methods, and/or kits described herein.

Immunomodulatory Agents

Certain embodiments employ one or more immunomodulatory agents. Exemplary immunomodulatory agents include small molecules, polypeptides, for example, antibodies and antigen-binding fragments thereof, ligands, small peptides, antisense agents, RNAi agents, and mixtures thereof.

In some embodiments, the immunomodulatory agent is selected from one or more of a sphingosine-1-phosphate (S1P) and/or S1P receptor (S1PR) modulator, a steroid, a calcineurin inhibitor, a mechanistic target of rapamycin (mTOR) inhibitor, an indoleamine-pyrrole 2,3-dioxygenase (IDO) inhibitor, an inosine-5'-monophosphate dehydrogenase (IMPDH) inhibitor, a cytokine and/or cytokine receptor inhibitor, a B cell receptor inhibitor, a kinase inhibitor, and a cytostatic agent such as methotrexate.

In some embodiments, the immunomodulatory agent is pirfenidone, which is often used for the treatment of idiopathic pulmonary fibrosis (IPF). Pirfenidone has antifibrotic and anti-inflammatory properties in various in vitro systems and animal models of fibrosis. For example, cell-based studies have shown that pirfenidone reduces fibroblast proliferation, inhibits TGF-β stimulated collagen production, and reduces the production of fibrogenic mediators such as TGF-β. Pirfenidone has also been shown to reduce production of inflammatory mediators such as TNF-α and IL-1β in both cultured cells and isolated human peripheral blood mononuclear cells. In the United States, pirfenidone is approved for the treatment of IPF as an oral 801 mg dosage unit (three 267 mg capsules) taken orally 3× day, for a total oral dosage of 2403 mg/day. Additional exemplary dosages of pirfenidone are described herein.

In some embodiments, the immunomodulatory agent is nintedanib, which is also used for the treatment of IPF. Nintedanib inhibits certain growth factor receptors involved in pulmonary fibrosis, including platelet-derived growth factor receptor (PDGFR), fibroblast growth factor receptor (FGFR) and vascular endothelial growth factor receptor (VEGFR). It is believed that nintedanib reduces disease progression in IPF and slows the decline in lung function by blocking the signaling pathways that are involved in fibrotic processes. Nintedanib is formulated as salt with ethanesulfonic acid. In the United States, nintedanib is approved for the treatment of IPF as an oral 150 mg dosage unit taken 2× day for a total of 300 mg/day, which can be reduced for adverse effects to about 100 mg dosage taken 2× day for total of 200 mg/day. Additional exemplary dosages of nintedanib are described herein.

In some embodiments, the immunomodulatory agent is a sphingosine-1-phosphate (S1P) and/or a S1P receptor (S1PR) modulator. General examples of modulators include S1P and/or S1PR antagonists or inhibitors, and S1P and/or S1PR agonists or activators. S1P is a bioactive lipid with diverse biological functions, including cell proliferation, differentiation, angiogenesis, chemotaxis, and migration. Many of the activities of S1P are mediated through five closely related G-protein-coupled receptors of the sphingosine-1-phosphate receptor family (S1PR) which play a crucial role in sphingolipid metabolism. The S1PRs include $S1PR_1$, $S1PR_2$, $S1PR_3$, $S1PR_4$, and $S1PR_5$. The expression of these receptors varies: $S1PR_1$, $S1PR_2$, and $S1PR_3$ are expressed in a wide variety of cell types but mostly heavily on leukocytes, $S1PR_4$ is expressed mostly in lymphoid and hematopoietic tissues, and $S1PR_5$ is expressed mainly in the spleen and the white matter of the central nervous system (CNS).

Specific non-limiting examples of S1P or S1PR modulators include amiselimod (also MT-1303; a S1PR antagonist; see Kappos et al., Lancet Neurol 2016; 15: 1148-59, 2016), fingolimod ($S1PR_1$ functional antagonist), sonepcizumab (S1P-specific monoclonal antibody), KRP203 ($S1PR_1$ agonist), SEW2871 ($S1PR_1$ agonist), siponimod ($S1PR_1$ and $S1PR_5$ modulator), RPC1063 ($S1PR_1$ modulator), ONO-4641 ($S1PR_1$ and $S1PR_5$ agonist), JTE-013 ($S1PR_2$ antagonist), GSK2018682 ($S1PR_1$ agonist), ponesimod ($S1PR_1$ agonist), suramin (selective $S1PR_3$ and $S1PR_5$ antagonist), VPC23019 (aryl-amide analogs; competitive $S1PR_1$ and $S1PR_3$ antagonists); and W146 (selective $S1PR_1$ antagonist). In specific embodiments, the S1P or S1PR modulator is amiselimod.

Certain S1P or S1PR modulators include an antibody or antigen-binding fragment or small molecule that specifically binds to S1P or an S1PR (see, e.g., sonepcizumab, which binds to S1P). In some embodiments, the antibody or antigen-binding fragment thereof is an S1P and/or S1PR antagonist. In certain embodiments, the antibody or antigen-binding fragment thereof is an S1P and/or S1PR agonist.

Certain S1PR antagonists or inhibitors include antisense agents and RNAi agents that are directed against an S1PR coding sequence (see, e.g., Accession Nos. NM_001400.4; NM_004230.3). Certain antisense agents specifically hybridizes to a target region within a pre-mRNA or mRNA target sequence that encodes an S1PR, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes an S1PR, and optionally an antisense strand that is complementary or substantially complementary to the mRNA target sequence that encodes an S1PR.

In some embodiments, the immunomodulatory agent is a steroid or corticosteroid, for example, a glucocorticoid. In particular embodiments, the steroid is an anti-inflammatory steroid. Examples of steroids include betamethasone, budesonide, cortisol (hydrocortisone), cortisone, deflazacort, deoxycorticosterone, dexamethasone, fludrocortisone, hydrocortisone, methylprednisolone, prednisone, prednisolone, and triamcinolone, among others.

In some embodiments, the immunomodulatory agent is a calcineurin antagonist or inhibitor. Calcineurin is a calcium and calmodulin dependent serine/threonine protein phosphatase, which activates the T cells. Specifically, calcineurin activates nuclear factor of activated T cell (NFATc), which translocates into the nucleus to upregulate the expression of interleukin 2 (IL-2), which then stimulates the growth and differentiation of T cell responses. Specific examples of calcineurin antagonists or inhibitors include cyclosporin, pimecrolimus, and tacrolimus.

Certain calcineurin antagonists or inhibitors include an antibody or antigen-binding fragment or small molecule that specifically binds to calcineurin. Also included are antisense agents and RNAi agents that are directed against a calcineurin coding sequence, or a subunit thereof (see, e.g., Accession Nos. NM_000944; NM_021132; NM_005605; NM_000945; NM_147180). Certain antisense agents specifically hybridizes to a target region within a pre-mRNA or mRNA target sequence that encodes calcineurin or a subunit thereof, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes calcineurin or a subunit thereof, and optionally an antisense strand that is complementary or substantially complementary to the mRNA target sequence that encodes calcineurin or a subunit thereof.

In some embodiments, the immunomodulatory agent is a mechanistic target of rapamycin (mTOR) antagonist or inhibitor. mTOR is a member of the phosphatidylinositol 3-kinase-related kinase family of protein kinases, and is the catalytic subunit of two structurally distinct complexes: mTORC1 and mTORC2, which localize to different subcellular compartments, thus affecting their activation and function particular. As a core component of both complexes, mTOR functions as a serine/threonine protein kinase that regulates cell growth, cell proliferation, cell motility, cell survival, protein synthesis, autophagy, and transcription. As a core component of mTORC2, mTOR also functions as a tyrosine protein kinase that promotes the activation of insulin receptors and insulin-like growth factor 1 receptors. mTORC2 has also been implicated in the control and maintenance of the actin cytoskeleton. mTOR plays a role in fibrotic diseases and autoimmunity, and blockade of the mTORC pathway is under investigation as a treatment for such diseases.

Particular examples of mTOR inhibitors include everolimus, rapamycin, deforolimus, and temsirolimus. General examples of mTOR inhibitors include ATP-competitive mTOR kinase inhibitors, including mTORC1/mTORC2 dual inhibitors, and mTOR/PI3K dual inhibitors, which inhibit mTORC1, mTORC2, and the catalytic isoforms of PI3K. Specific examples include dactolisib, BGT226, SF1126, PKI-587, NVPBE235, sapanisertib, AZD8055, and AZD2014.

Certain mTOR antagonists or inhibitors include an antibody or antigen-binding fragment or small molecule that specifically binds to mTOR or a member of an mTOR complex. Also included are antisense agents and RNAi agents that are directed against a coding sequence of mTOR or a member of an mTOR complex (see, e.g., Ravichandran et al., Hum Mol Genet. 23:4919-31, 2014). Certain antisense agents specifically hybridizes to a target region within a pre-mRNA or mRNA target sequence that encodes mTOR or a member of an mTOR complex, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes mTOR or a member of an mTOR complex, and optionally an antisense strand that is complementary or substantially complementary to the mRNA target sequence that encodes mTOR or a member of an mTOR complex.

In some embodiments, the immunomodulatory agent is an IDO antagonist or inhibitor. IDO is a tryptophan catabolic enzyme with immune-inhibitory properties. For example, IDO is known to suppress T-cells and NK cells, generate and activate Tregs and myeloid-derived suppressor cells, and promote tumor angiogenesis. Specific examples of IDO antagonists or inhibitors include indoximod (NLG-8189), 1-methyl-tryptophan (1MT), β-Carboline (norharmane; 9H-pyrido[3,4-b]indole), rosmarinic acid, and epacadostat (see, e.g., Sheridan, Nature Biotechnology. 33:321-322, 2015). Certain IDO antagonists or inhibitors include an antibody or antigen-binding fragment or small molecule that specifically binds to IDO (see, e.g., Platten et al., Front Immunol. 5: 673, 2014). Also included are antisense agents and RNAi agents that are directed against an IDO coding sequence (see, e.g., Accession No. AH002828.2). Certain antisense agents specifically hybridizes to a target region within a pre-mRNA or mRNA target sequence that encodes IDO, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes IDO, and optionally an antisense strand that is complementary or substantially complementary to the mRNA target sequence that encodes IDO.

In some embodiments, the immunomodulatory agent is an inosine-5'-monophosphate dehydrogenase (IMPDH) antagonist or inhibitor. IMPDH is a purine biosynthetic enzyme that catalyzes the nicotinamide adenine dinucleotide (NAD+)-dependent oxidation of inosine monophosphate (IMP) to xanthosine monophosphate (XMP), the first committed and rate-limiting step towards the de novo biosynthesis of guanine nucleotides from IMP. Guanine nucleotide synthesis is essential for maintaining normal cell function and growth, and is also important for the maintenance of cell proliferation and immune responses. In particular, B and T cells display a dependence on IMPDH for normal activation and function, and demonstrate upregulated IMPDH expression.

Specific examples of IMPDH inhibitors include mycophenolic acid (mycophenolate mofetil), ribavirin, and 6TGMP (6-thioguanine monophosphate). Certain IMPDH antagonists or inhibitors include an antibody or antigen-binding fragment or small molecule that specifically binds to IMPDH. Also included are antisense agents and RNAi agents that are directed against an IMPDH coding sequence. Certain antisense agents specifically hybridizes to a target region within a pre-mRNA or mRNA target sequence that encodes IMPDH, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes IMPDH, and optionally an antisense strand that is complementary or substantially complementary to the mRNA target sequence that encodes IMPDH.

In some embodiments, the immunomodulatory agent is a cytokine and/or cytokine receptor antagonist or inhibitor. Cytokines are small (glyco)proteins (with molecular weights of 8-75 kDa) which play a role in hematopoiesis, immune reactions and inflammation Certain exemplary cytokine inhibitors decrease the synthesis of cytokines, decrease the concentration of cytokines in free active form, block the interaction between cytokines and their cognate receptors, and/or interfere with the signaling of cytokine receptors.

In some embodiments, the target cytokine or cytokine receptor is an inflammatory or pro-inflammatory cytokine or cytokine receptor. Examples of target cytokines include, without limitation, interleukin-1 (IL-1) including IL-1α and IL-1β, interleukin-5 (IL-5), interleukin-6 (IL-6), interleukin-8 (IL-8), interleukin-11 (IL-11), interleukin-12 (IL-12), interleukin-17 (IL-17), interleukin-18 (IL-18), interleukin-20 (IL-20), interleukin-33 (IL-33), tumor necrosis factor (TNF), interferon gamma (IFN-gamma), transforming growth factor-β (TGF-β), and granulocyte-macrophage colony stimulating factor (GM-CSF), and their cognate cytokine receptors, for example, IL-1R, IL-6R, IL-8R, IL-11R, IL-12R, IL-17R, IL-18R, IL-20R, ST2 (Interleukin 1 receptor-like 1, IL1RL1), a TNFR such as TNFR1, interferon-gamma receptor (IFNGR), a TGF-β receptor such as TGFβR1 (ALK5) or TGFβR2.

Specific examples of cytokine and/or cytokine receptor inhibitors include TNF-alpha inhibitors such as etanercept, which is a recombinant fusion protein of the soluble type II TNF receptor on a human IgG1 backbone, and infliximab, which is a chimeric anti-TNF-alpha monoclonal antibody containing a murine TNF-alpha binding region and human IgG1 backbone. Also included as TNF inhibitors are adalimumab, certolizumab, and golimumab.

Particular examples of interleukin inhibitors include, for example, IL-1R antagonists such as anakinra, IL-1 inhibitors such as rilonacept (a dimeric fusion protein consisting of the ligand-binding domains of the extracellular portions of the IL-1R1 component and IL-1 receptor accessory protein (IL-1RAcP) linked in-line to the fragment-crystallizable portion (Fc region) of human IgG1 that binds and neutralizes IL-1), IL-2 competitive inhibitors such as basiliximab (a chimeric mouse-human monoclonal antibody to the α chain (CD25) of the IL-2 receptor of T cells) and daclizumab (a humanized monoclonal antibody that binds to CD25), IL-10-specific inhibitors such as canakinumab (a human monoclonal antibody), IL-17 antagonists such as ixekizumab (a humanized monoclonal antibody that binds to IL-17) and secukinumab (a human IgG1κ monoclonal antibody that binds to the protein interleukin (IL)-17A), IL-5 inhibitors such as mepolizumab (a humanized monoclonal antibody that binds to IL-5 and prevents it from binding to the alpha subunit of the IL-5 receptor) and reslizumab, IL-6 inhibitors such as siltuximab (an antibody that binds to IL-6), sirukumab (an antibody that binds to IL-6), serilumab (an antibody that binds to the IL-6 receptor), an tocilizumab (an antibody that binds to the IL-6 receptor), and IL-12/IL-23 signaling inhibitors such as ustekinumab (an antibody that binds to the p-40 subunit of both IL-12 and IL-23).

Certain cytokine and/or cytokine receptor antagonists or inhibitors include an antibody or antigen-binding fragment or small molecule that specifically binds to the cytokine and/or cytokine receptor, for example, one or more of the foregoing cytokines and/or cytokine receptors. Also included are antisense agents and RNAi agents that are directed against a cytokine and/or cytokine receptor coding sequence, for example, one or more of the foregoing cytokines and/or cytokine receptors. Certain antisense agents specifically hybridizes to a target region within a pre-mRNA or mRNA target sequence that encodes a cytokine or a cytokine receptor, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes a cytokine or a cytokine receptor, and optionally an antisense strand that is complementary or substantially complementary to the mRNA target sequence that encodes a cytokine or a cytokine receptor.

In some embodiments, the immunomodulatory agent is a kinase antagonist or inhibitor, that is, an inhibitor that targets or is targeted against one or more kinases General examples include tyrosine kinase inhibitors (TK1s). Examples of target kinases include, without limitation, Janus kinase (JAK, including JAK1, JAK2, JAK3, TYK2), epidermal growth factor receptor (EGFR), Receptor tyrosine-protein kinase erbB-2 (Her2/neu, or ERBB2), Bcr-Abl, c-SRC, Mitogen-activated protein kinase (MAP) kinase, anaplastic lymphoma kinase (ALK), spleen tyrosine kinase (SYK), Bruton's tyrosine kinase (BTK), vascular endothelial growth factor (VEGF), vascular endothelial growth factor receptor (VEGFR, including VEGFR1, VEGFR2, VEGFR3), a fibroblast growth factor receptor (FGFR), B-Raf, RET proto-oncogene, platelet-derived growth factor receptors (PDGF-R), tropomyosin receptor kinase (Trk, including TrkA, TrkB, TrkC), and c-Met, among others. Thus, in certain embodiments, the kinase inhibitor is an inhibitor or antagonist of one or more of the foregoing kinases.

Specific examples of kinase inhibitors include JAK inhibitors such as baricitinib, fedratinib, filgotinib, gandotinib, lestaurtinib, momelotinib, pacritinib, peficitinib, ruxolitinib, tofacitinib, and padacitinib. Additional examples of kinase inhibitors include, without limitation, nintedanib, afatinib, axitinib, bosutinib, cetuximab, cobimetinib, crizotinib, cabozantinib, dasatinib, entrectinib, erlotinib, fostamatinib, gefitinib, ibrutinib, imatinib, lapatinib, lenvatinib, mubritinib, neratinib, nilotinib, pazopanib, pegaptanib, sorafenib, sunitinib, SU6656, toceranib, vandetanib, vatalanib, and vemurafenib.

Certain kinase antagonists or inhibitors include an antibody or antigen-binding fragment or small molecule that specifically binds to the kinase, for example, one or more of the foregoing kinases. Also included are antisense agents and RNAi agents that are directed against a kinase coding sequence, for example, one or more of the foregoing kinases Certain antisense agents specifically hybridizes to a target region within a pre-mRNA or mRNA target sequence that encodes a kinase, for example, wherein the target region is selected from one or more of an AUG start codon of the mRNA, a region upstream of the AUG start codon, a region downstream of the AUG codon, a 3' or 5' splice site of a pre-processed mRNA, a branch point, a 3' untranslated region (UTR), and a polyadenylation signal sequence. Certain RNAi agents comprise a sense strand that is substantially identical to an mRNA target sequence that encodes a kinase, and optionally an antisense strand that is complementary or substantially complementary to the mRNA target sequence that encodes the kinase.

In some embodiments, the immunomodulatory agent is a B cell receptor inhibitor, for example, an agent that is targeted against CD20. B lymphocyte antigen CD20 or CD20 is an activated-glycosylated phosphoprotein expressed on the surface of all B cells beginning at the pro-B phase (CD45R+, CD117+) and progressively increasing in concentration until maturity. The protein has no known natural ligand, and its function is to enable optimal B cell immune response, specifically against T-independent antigens. Exemplary immunomodulatory agents directed against CD20 include the monoclonal antibodies ibritumomab tiuxetan, obinutuzumab, ocaratuzumab, ocrelizumab, rituximab, tositumomab, and veltuzumab.

In some embodiments, the immunomodulatory agent is a cytostatic or cytotoxic agent. Examples of cytostatic or cytotoxic agents include azathioprine, chlorambucil, cyclophosphamide, cyclosporin A, methotrexate, and nitrogen mustard, among others.

In some embodiments, as noted above, the immunomodulatory agent is a "small molecule," which refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of about or less than about 1000-2000 Daltons, typically between about 300 and 700 Daltons, and including about or less than about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described herein. For instance, in some embodiments a small molecule specifically binds to a target (for example, S1P, S1PR, calcineurin, mTOR, IDO, IMPDH, a cytokine and/or cytokine receptor, a B cell receptor, a kinase) with a binding affinity (Kd) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In particular embodiments, the immunomodulatory agent is a polypeptide or peptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein. Antibodies are also included as polypeptides.

The binding properties of polypeptides can be quantified using methods well known in the art (see Davies et al., Annual Rev. Biochem. 59:439-473, 1990). In some embodiments, a polypeptide specifically binds to a target molecule (for example, S1P, S1PR, calcineurin, mTOR, IDO, IMPDH, a cytokine and/or cytokine receptor, a B cell receptor, a kinase or an epitope thereof) with an equilibrium dissociation constant that is about or ranges from about ≤10-7 to about 10-8 M. In some embodiments, the equilibrium dissociation constant is about or ranges from about ≤10-9 M to about ≤10-10 M. In certain illustrative embodiments, the polypeptide has an affinity (Kd) for a target described herein (to which it specifically binds, including, for example, S1P, S1PR, calcineurin, mTOR, IDO, IMPDH, a cytokine and/or cytokine receptor, a B cell receptor, or a kinase) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the immunomodulatory agent is an antibody or "antigen-binding fragment thereof" that specifically binds to a target described herein. The antibody or antigen-binding fragment can be of essentially any type. As is well known in the art, an antibody is an immunoglobulin molecule capable of specific binding to a target (for example, S1P, S1PR, calcineurin, mTOR, IDO, IMPDH, a cytokine and/or cytokine receptor, a B cell receptor, a kinase), through at least one epitope recognition site, located in the variable region of the immunoglobulin molecule.

As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. Certain features and characteristics of antibodies (and antigen-binding fragments thereof) are described in greater detail herein.

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise 1, 2, 3, 4, 5, or all 6 CDRs of a VH and VL sequence from antibodies that bind to a target molecule.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, for example, a polypeptide determinant, capable of specific binding to an immunoglobulin or T-cell receptor. An epitope is a region of an antigen or target protein that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

A molecule such as a polypeptide or antibody is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances, for example, by a statistically significant amount. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant (Kd) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant Kd.

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals) The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH:: VL heterodimer including an antigen-binding site which retains much of the antigen recognition and binding capabilities of the native antibody molecule. See Inbar et al., PNAS USA. 69:2659-2662, 1972; Hochman et al., Biochem. 15:2706-2710, 1976; and Ehrlich et al., Biochem. 19:4091-4096, 1980.

In certain embodiments, single chain Fv or scFV antibodies are contemplated. For example, Kappa bodies (Ill et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (sFv) polypeptide is a covalently linked VH::VL heterodimer which is expressed from a gene fusion including VH- and VL-encoding genes linked by a peptide-encoding linker. Huston et al. (PNAS USA. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., Nature 341:544-546, 1989). Diabodies and other multivalent or multispecific fragments can be constructed, for example, by gene fusion (see WO94/13804; and Holliger et al., PNAS USA. 90:6444-6448, 1993)).

Minibodies comprising a scFv joined to a CH3 domain are also included (see Hu et al., Cancer Res. 56:3055-3061, 1996). See also Ward et al., Nature. 341:544-546, 1989; Bird et al., Science. 242:423-426, 1988; Huston et al., PNAS USA. 85:5879-5883, 1988); PCT/US92/09965; WO94/13804; and Reiter et al., Nature Biotech. 14:1239-1245, 1996.

Where bispecific antibodies are to be used, these may be conventional bispecific antibodies, which can be manufactured in a variety of ways (Holliger and Winter, Current Opinion Biotechnol. 4:446-449, 1993), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., Protein Eng., 9:616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells.

In certain embodiments, the antibodies provided herein may take the form of a nanobody. Minibodies are encoded by single genes and are efficiently produced in almost all prokaryotic and eukaryotic hosts, for example, E. coli (see U.S. Pat. No. 6,765,087), molds (for example Aspergillus or Trichoderma) and yeast (for example Saccharomyces, Kluyvermyces, Hansenula or Pichia (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B cells.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of $CH_2$ and $CH_3$ domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In some embodiments, the immunomodulatory agent is or comprises a "ligand," for example, a natural ligand, of a target molecule. A "ligand" refers generally to a substance or molecule that forms a complex with a target molecule (e.g., biomolecule) to serve a biological purpose, and includes a "protein ligand," which generally produces a signal by binding to a site on a target molecule or target protein. Thus, certain agents are protein ligands that, in nature, bind to an target molecule and produce a signal. Also included are "modified ligands," for example, protein ligands that are fused to a pharmacokinetic modifier, for example, an Fc region derived from an immunoglobulin.

In some embodiments, the immunomodulatory agent or inhibitor is an antisense agent. Thus, in some embodiments, the target proteins, target sequences, and/or target genes described herein (for example, S1PR, calcineurin, mTOR, IDO, IMPDH, a cytokine and/or cytokine receptor, a B cell receptor, a kinase) are targeted by any variety of antisense agents, including oligonucleotide-based agents or methods. The antisense agents or oligonucleotides typically comprises a base sequence that targets (e.g., is sufficiently complementary to or specifically hybridizes to) a region within a target sequence which optionally includes one or more of the following: a region including or surrounding an AUG start codon of an mRNA (e.g., a region upstream of a start codon, a region downstream of a start codon, a region including a start codon), a 3' or 5' splice site of a pre-processed mRNA, pyrimidine-rich or polypyrimidine tracts upstream of splice acceptor sites, exon-intron boundaries, intron-exon boundaries, a branch sites, exonic splicing enhancer elements, 5' and 3' untranslated regions, and polyadenylation signal sequences.

In certain embodiments, the antisense agent is able to effectively modify expression (e.g., reduce expression, alter splicing) of the target gene upon administration to a subject in need thereof, or upon contact with a cell, for example, a muscle cell. This requirement is typically met when the antisense agent (a) has the ability to be actively taken up by mammalian cells (e.g., muscle cells), and (b) once taken up, forms a duplex with the target RNA with a Tm greater than about 45° C.

Certain "antisense agents" include "antisense oligonucleotides," "antisense oligomers," and "oligonucleotides," which refer to a linear sequence of nucleotides, or nucleotide analogs, which allows the nucleobase to hybridize to a target sequence in an RNA by Watson-Crick base pairing, to form an oligonucleotide:RNA heteroduplex within the target sequence. The terms "antisense oligonucleotide", "antisense oligomer," "oligomer" and "compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), tricyclo-DNA oligomers, tricyclo-phosphorothioate oligonucleotides, and 2'-O-Methyl oligonucleotides, among other antisense agents known in the art.

In certain embodiments, the "target sequence" includes a region including or surrounding an AUG start codon of an mRNA (e.g., a region upstream of a start codon, a region downstream of a start codon, a region including a start codon), a 3' or 5' splice site of a pre-processed mRNA, a branch point, or a 3' non-coding mRNA region such as a 3'-UTR or polyadenylation signal. The target sequence may be within an exon or within an intron. The target sequence for a splice site may include an mRNA sequence having its 5' end 1 to about 25 base pairs downstream of a normal splice acceptor junction in a preprocessed mRNA (pre-mRNA). An exemplary target sequence for a splice region is any region of a preprocessed mRNA that includes a splice site or is contained entirely within an exon coding sequence or spans a splice acceptor or donor site. An antisense agent is more generally said to be "targeted against" a biologically relevant target when it is targeted against, e.g., specifically hybridizes to or is complementary to the nucleic acid of the target in the manner described herein and known in the art. Other examples of target regions or target sequences are described herein.

The term "targeting sequence" is the sequence in the oligonucleotide that is complementary (meaning, in addition, substantially complementary) to the "target sequence" in the RNA. The entire sequence, or only a portion, of the antisense agent may be complementary to the target sequence. For example, in an antisense agent having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases in the oligonucleotide, but may alternatively be formed of non-contiguous sequences that when placed together, e.g., from opposite ends of the oligonucleotide, constitute sequence that spans the target sequence.

A target sequence may have "near" or "substantial" complementarity to the targeting sequence and still function for the purpose of the present disclosure, that is, still be "complementary." Preferably, the oligonucleotides employed in the present disclosure have at most one mismatch with the target sequence out of 10 nucleotides, and preferably at most one mismatch out of 20. Alternatively, the antisense oligonucleotide employed have at least 90% sequence homology or identity, at least 95% sequence homology or identity, or at least 98% sequence homology or identity with an exemplary targeting sequence.

Included are non-naturally-occurring oligonucleotides, or "oligonucleotide analogs," including oligonucleotides having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Particular examples of analogs include those having a substantially uncharged, phosphorus containing backbone.

A "nuclease-resistant" oligonucleotide refers to one whose backbone is substantially resistant to nuclease cleavage, in non-hybridized or hybridized form; by common extracellular and intracellular nucleases in the body (for example, by exonucleases such as 3'-exonucleases, endonucleases, RNase H); that is, the oligonucleotide shows little or no nuclease cleavage under normal nuclease conditions in the body to which the oligonucleotide is exposed. A "nuclease-resistant heteroduplex" refers to a heteroduplex formed by the binding of an antisense oligonucleotide to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligonucleotide and the complementary portion of a target RNA.

In certain embodiments, the antisense oligonucleotide is recognized as a substrate for active or facilitated transport across the cell membrane, for example, the muscle cell membrane. The ability of the oligonucleotide to form a stable duplex with the target RNA may also relate to other features of the oligonucleotide backbone, including the length and degree of complementarity of the antisense oligonucleotide with respect to the target, the ratio of G:C to A:T base matches, and the positions of any mismatched bases. The ability of the antisense oligonucleotide to resist cellular nucleases may promote survival and ultimate delivery of the agent to the cell cytoplasm. Thus, certain embodiments include non-naturally-occurring antisense oligonucleotides that are nuclease resistant or substantially nuclease resistant.

In certain embodiments, the antisense oligonucleotide comprises a non-natural chemical backbone selected from a phosphoramidate or phosphorodiamidate morpholino oligonucleotides (PMO), a peptide nucleic acid (PNA), a locked nucleic acid (LNA), a phosphorothioate oligonucleotide, a tricyclo-DNA oligonucleotide, a tricyclo-phosphorothioate oligonucleotide, a 2'O-Me-modified oligonucleotide (e.g., 2' O-methyl phosphorothioate oligonucleotide), or any combination of the foregoing.

An antisense oligonucleotide "specifically hybridizes" to a target sequence or polynucleotide (e.g., pre-mRNA, mRNA) if the oligonucleotide hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligonucleotide to the target sequence, as well as with exact complementarity.

As used herein, "sufficient length" refers to an antisense oligonucleotide that is complementary to at least 8, more typically 8-40, contiguous nucleobases in a target sequence or gene described herein. An antisense oligonucleotide of sufficient length has at least a minimal number of nucleotides to be capable of specifically hybridizing to a region of a target sequence or gene. Preferably an oligonucleotide of sufficient length is from 8 to 30 nucleotides in length. More preferably, an oligonucleotide of sufficient length is from 9 to 27 nucleotides in length.

Antisense oligonucleotides generally comprise a plurality of nucleotide subunits each bearing a nucleobase which taken together form or comprise a targeting sequence. Accordingly, in some embodiments, the antisense oligonucleotides range in length from about 10 to about 40 subunits, or about 10 to 30 subunits, and typically 15-25 subunits. For example, in some embodiments an antisense oligonucleotide is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subunits in length, or ranges from 10 subunits to 40 subunits, 10 subunits to 30 subunits, 14 subunits to 25 subunits, 15 subunits to 30 subunits, 17 subunits to 30 subunits, 17 subunits to 27 subunits, 10 subunits to 27 subunits, 10 subunits to 25 subunits, and 10 subunits to 20 subunits. In certain embodiments, the antisense oligonucleotide is about 10 to about 40 or about 5 to about 30 nucleotides in length. In some embodiments, the antisense oligonucleotide is about 14 to about 25 or about 17 to about 27 nucleotides in length.

In some embodiments, the backbone of the antisense oligonucleotide is substantially uncharged, and is optionally recognized as a substrate for active or facilitated transport across the cell membrane. In some embodiments, all the internucleotide linkages are uncharged. The ability of the oligonucleotide to form a stable duplex with the target RNA may also relate to other features of the backbone, including the length and degree of complementarity of the antisense oligonucleotide with respect to the target, the ratio of G:C to A:T base matches, and the positions of any mismatched bases. The ability of the antisense oligonucleotide to resist cellular nucleases may promote survival and ultimate delivery of the agent to the cell cytoplasm.

In certain embodiments, the antisense oligonucleotide has at least one internucleoside linkage that is positively charged or cationic at physiological pH. In some embodiments, the antisense oligonucleotide has at least one internucleoside linkage that exhibits a pKa between about 5.5 and about 12. Optionally, the antisense oligonucleotide has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. While not being bound by any one theory, it is believed that the presence of a cationic linkage or linkages (e.g., APN group or APN derivative) in the oligonucleotide facilitates binding to the negatively charged phosphates in the target nucleotide. Thus, the formation of a heteroduplex between mutant RNA and the cationic linkage-containing oligonucleotide may be held together by both an ionic attractive force and Watson-Crick base pairing.

In some embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In specific embodiments, an oligonucleotide of about 19-20 subunits may have 2-10, e.g., 4-8, cationic linkages, and the remainder uncharged linkages. In other specific embodiments, an oligonucleotide of 14-15 subunits may have 2-7, e.g., 2, 3, 4, 5, 6, or 7 cationic linkages and the remainder uncharged linkages. The total number of cationic linkages in the oligonucleotide can thus vary from about 1 to 10 to 15 to 20 to 30 or more (including all integers in between), and can be interspersed throughout the oligonucleotide.

In some embodiments, an antisense oligonucleotide may have about or up to about 1 cationic linkage per every 2-5 or 2, 3, 4, or 5 uncharged linkages, such as about 4-5 or 4 or 5 per every 10 uncharged linkages.

Certain embodiments include antisense oligonucleotides that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the backbone linkages are cationic. In certain embodiments, enhancement may be seen with a small number e.g., 10-20% cationic linkages, or where the number of cationic linkages are in the range 50-80%, such as about 60%.

In some embodiments, the cationic linkages are interspersed along the backbone. Such oligonucleotides optionally contain at least two consecutive uncharged linkages; that is, the oligonucleotide optionally does not have a strictly alternating pattern along its entire length. In specific instances, each one or two cationic linkage(s) is/are separated along the backbone by at least 1, 2, 3, 4, or 5 uncharged linkages.

Also included are oligonucleotides having blocks of cationic linkages and blocks of uncharged linkages. For example, a central block of uncharged linkages may be flanked by blocks of cationic linkages, or vice versa. In some embodiments, the oligonucleotide has approximately equal-length 5', 3' and center regions, and the percentage of cationic linkages in the center region is greater than about 50%, 60%, 70%, or 80% of the total number of cationic linkages.

In certain antisense oligonucleotides, the bulk of the cationic linkages (e.g., 70, 75%, 80%, 90% of the cationic linkages) are distributed close to the "center-region" backbone linkages, e.g., the 6, 7, 8, 9, 10, 11, 12, 13, 14, or 15 centermost linkages. For example, a 16, 17, 18, 19, 20, 21, 22, 23, or 24-mer oligonucleotide with may have at least 50%, 60%, 70%, or 80% of the total cationic linkages localized to the 8, 9, 10, 11, or 12 centermost linkages.

As noted above, the antisense oligonucleotides can employ a variety of antisense chemistries. Examples of oligonucleotide chemistries include, without limitation, peptide nucleic acid (PNA), locked nucleic acid (LNA), phosphorothioate, 2'-O-Me-modified oligonucleotides, morpholino, PMO, PPMO, PMOplus, and PMO-X chemistries, including combinations of any of the foregoing. In general, PNA and LNA chemistries can utilize shorter targeting sequences because of their relatively high target binding strength relative to PMO and 2'-O-Me oligonucleotides. Phosphorothioate and 2'-O-Me-modified chemistries are often combined to generate a 2'O-Me-phosphorothioate backbone. See, e.g., PCT Publication Nos. WO/2013/112053 and WO/2009/008725, incorporated herein by reference in their entireties.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed Bts PNA monomers (Bts; benzothiazole-2-sulfonyl group) and an oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Antisense oligonucleotide compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability. The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230.

Compounds of the disclosure may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990). The latter methods avoid the problem of elemental sulfur's insolubility in most organic solvents and the toxicity of carbon disulfide. The TETD and BDTD methods also yield higher purity phosphorothioates.

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in International Patent Application Publication No. WO 2010/115993. Compounds of the disclosure may incorporate one or more tricycle-DNA nucleotides; in some cases, the compounds may be entirely composed of tricycle-DNA nucleotides.

Tricyclo-phosphorothioate nucleotides are tricyclo-DNA nucleotides with phosphorothioate intersubunit linkages. Tricyclo-phosphorothioate nucleotides and their synthesis are described in International Patent Application Publication No. WO 2013/053928. Compounds of the disclosure may incorporate one or more tricycle-DNA nucleotides; in some cases, the compounds may be entirely composed of tricycle-DNA nucleotides.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligonucleotides (PTOs) for further stabilization. 2'O-Me oligonucleotides (phosphodiester or phosphothioate) can be synthesized according to routine techniques in the art (see, e.g., Yoo et al., Nucleic Acids Res. 32:2008-16, 2004). In some instances, 2'O-Me oligonucleotides comprise a phosphorothioate linkage (2'O-Me phosphorothioate oligonucleotides).

A "morpholino oligonucleotide" or "PMO" refers to an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligonucleotide comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligonucleotides (including antisense oligonucleotides) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication numbers WO/2009/064471 and WO/2012/043730, all of which are incorporated herein by reference in their entirety.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMO-X oligonucleotides described herein, one nitrogen is always pendant to the backbone chain. The second nitrogen, in a phosphorodiamidate linkage, is typically the ring nitrogen in a morpholino ring structure.

"PMO-X" refers to phosphorodiamidate morpholino oligonucleotides (PMOs) having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl. Exemplary PMO-X oligonucleotides are disclosed in PCT application No. PCT/US2011/38459 and PCT Publication No. WO/2013/074834, each of which is herein incorporated by reference in its entirety. "PMO-apn" or "APN" refers to a PMO-X oligonucleotide which comprises at least one internucleoside linkage where a phosphorus atom is linked to a morpholino group and to the ring nitrogen of a 4-aminopiperdin-1-yl (i.e., APN). In specific embodiments, an antisense oligonucleotide comprising a targeting sequence described herein comprises at least one APN-containing linkage or APN derivative-containing linkage. Specific embodiments include PMOs that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

Additional antisense oligonucleotides/chemistries that can be used in accordance with the methods and compositions provided herein include those described in the following patents and patent publications, the contents of which are incorporated herein by reference: PCT Publication Nos. WO/2007/002390; WO/2010/120820; and WO/2010/148249; U.S. Pat. No. 7,838,657; and U.S. Application No. 2011/0269820.

In some embodiments, the immunomodulatory agent or inhibitor is an RNA interference (RNAi) agent. Thus, in some embodiments, the target proteins, target sequences, and/or target genes described herein (for example, S1PR, calcineurin, mTOR, IDO, IMPDH, a cytokine and/or cytokine receptor, a B cell receptor, a kinase) are targeted by any variety of RNA interference-based agents or methods. RNA interference (RNAi) is an evolutionarily conserved gene-silencing mechanism, originally discovered in studies of the nematode Caenorhabditis elegans (Lee et al, Cell 75:843, 1993; Reinhart et al., Nature 403:901, 2000). It can be triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (see Ruvkun, Science 2294:797, 2001).

In certain embodiments, an RNA agent is more generally said to be "targeted against" a biologically relevant target (gene) when it comprises a sense strand that corresponds to the "target sequence" of the target gene, in a manner described herein and known in the art.

RNAi agents include RNAi nucleic acid molecules and RNAi nucleic acid analogue molecules, such as short interfering nucleic acids and short interfering nucleic acid analogues (siNA), including short interfering RNA and short interfering RNA nucleic acid analogues (siRNA), and including, for example, double-stranded RNA and double-stranded RNA analogues (dsRNA), micro-RNA and micro-RNA analogues (miRNA), and short hairpin RNA and short hairpin RNA analogues (shRNA).

Certain embodiments employ double-stranded ribonucleic acid (dsRNA) molecules as RNAi agents. dsRNAs generally comprise two single strands. One strand of the dsRNA comprises a nucleotide sequence that is substantially identical to a portion of the target gene or target sequence (the "sense" strand), and the other strand (the "complementary" or "antisense" strand) comprises a sequence that is complementary or substantially complementary to a portion of the target region. Substantially identical sequences include those that are at least about 80, 85, 90, 95, 97, 98, 99% identical to the target sequence. The strands are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length. In certain embodiments, the sense strand of the RNAi agent is substantially identical to a portion of a target sequence described herein. In some embodiments, the antisense strand is complementary or substantially complementary to a portion of target sequence described herein. In certain embodiments, said portion comprises, consists, or consists essentially of about, at least about, or no more than about 6, 7, 8, 9, 10, 11, 12, 13, 14, 15, 16, 17, 18, 19, 20, 21, 22, 23, 24, or 25 contiguous nucleotides of a target sequence described herein.

Suitable siRNA sequences can be identified using any means known in the art. In some instances, using the exemplary target sequences described herein, the methods described in Elbashir et al., Nature, 411:494-498 (2001) and Elbashir et al., EMBO J., 20:6877-6888 (2001) are combined with rational design rules set forth in Reynolds et al., Nature Biotech., 22:326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., EMBO J., 20:6877-6888 (2001)). The nucleotides immediately 3' to the dinucleotide sequences are identified as potential siRNA sequences (i.e., a target sequence or a sense strand sequence). In some instances, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as a potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA are known. One of skill in the art will appreciate that sequences with one or more of the foregoing characteristics may be selected for further analysis and testing as potential siRNA sequences.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., Cell, 115:209-216 (2003); and Schwarz et al., Cell, 115:199-208 (2003). In certain embodiments, potential siRNA target sequences may be further analyzed based on secondary structure at the mRNA target site as described in, e.g., Luo et al., Biophys. Res. Commun., 318:303-310 (2004). For example, mRNA secondary structure can be modeled using the Mfold algorithm to select siRNA sequences which favor accessibility at the mRNA target site where less secondary structure in the form of base-pairing and stem-loops is present.

A potential siRNA sequence can also be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naive mammal (i e, a mammal that has not previously been in contact with the siRNA sequence). The mammalian responder cell may be, e.g., a peripheral blood mononuclear cell (PBMC), a macrophage, and the like. The detectable immune response may comprise production of a cytokine or growth factor such as, e.g., TNF-alpha, IFN-alpha, IFN-beta, IFN-gamma, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

An RNAi agent typically includes a double stranded portion (notwithstanding the optional and potentially preferred presence of any single-stranded overhands) comprising at least 16 bases, optionally at least 17 bases, more optionally at least 18 bases and still more optionally at least 19 bases, and usually between 18 and 35 bases, optionally between 19 and 30 bases, more optionally between 20 and 25 bases and even more optionally between 21 and 23 bases which are identical or almost identical to (e.g., showing 90% or more, e.g., at least 95%, sequence identity to, or showing maximum 2 and optionally only 1 mismatch with) an mRNA whose silencing is desired and which is thus targeted by said RNAi agent.

In certain embodiments, at least one of the RNA strands comprises a nucleotide overhang of 1 to 4 nucleotides in length. In some embodiments, the dsRNA comprises at least one chemically modified nucleotide. In certain aspects, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In some embodiments, the last complementary nucleotide pairs on both ends of a dsRNA are a G-C pair, or, at least two of the last four terminal nucleotide pairs are G-C pairs.

Certain embodiments RNAi agents include microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (see V. Ambros et al., Current Biology 13:807, 2003). Micro-RNAs are not translated into proteins, but instead bind to specific messenger RNAs, thereby blocking translation. It is thought that micro-RNAs base-pair imprecisely with their targets to inhibit translation. Certain micro-RNAs may be transcribed as hairpin RNA precursors, which are then processed to their mature forms by Dicer enzyme.

In certain embodiments, the RNAi agent or oligonucleotide is single stranded. In some embodiments, the RNAi agent or oligonucleotide is double stranded. Certain embodiments include short-interfering RNAs (siRNA). In certain embodiments, the first strand of the double-stranded oligonucleotide contains two more nucleoside residues than the second strand. In other embodiments, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In some instances where the modulating agent comprises siRNA, the agent includes a region of sufficient homology to the target region, and is of sufficient length in terms of nucleotides, such that the siRNA agent, or a fragment thereof, mediates down-regulation of the target gene or RNA. It will be understood that the term "ribonucleotide" or "nucleotide" can, in the case of a modified RNA or nucleotide surrogate, also refer to a modified nucleotide, or surrogate replacement moiety at one or more positions. Thus, an siRNA agent is or includes a region which is at least partially complementary to the target sequence. It is not necessary that there be perfect complementarity between the siRNA agent and the target sequence, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired, some embodiments include one or more but preferably 10, 8, 6, 5, 4, 3, 2, or fewer mismatches with respect to the target sequence. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In some embodiments, an RNAi agent or oligonucleotide, e.g., an siRNA oligonucleotide, is modified or includes nucleoside surrogates. Single stranded regions of an siRNA agent may be modified or include nucleoside surrogates, e.g., the unpaired region or regions of a hairpin structure, e.g., a region which links two complementary regions, can have modifications or nucleoside surrogates. Modifications to stabilize one or more 3'- or 5'-terminus of an siRNA agent, e.g., against exonucleases, or to favor the antisense siRNA agent to enter into RISC, are also included. Exemplary modifications include C3 (or C6, C7, C12) amino linkers, thiol linkers, carboxyl linkers, non-nucleotidic spacers (C3, C6, C9, C12, abasic, triethylene glycol, hexaethylene glycol), and special biotin or fluorescein reagents that come as phosphoramidites and that have another DMT-protected hydroxyl group, allowing multiple couplings during RNA synthesis.

Certain siRNA agents include, for example, molecules that are long enough to trigger an interferon response (which can be cleaved by Dicer (Bernstein et al. 2001. Nature, 409:363-366) and enter a RISC (RNAi-induced silencing complex)). Also included are molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter RNAi agents herein. "siRNA agent or shorter RNAi agent" as used refers to an siRNA agent that is sufficiently short that it does not induce a deleterious interferon response in a human cell, e.g., it has a duplexed region of less than 60 but preferably less than 50, 40, or 30 nucleotide pairs. An siRNA modulating agent, or a cleavage product thereof, can down regulate a target gene, e.g., by inducing RNAi with respect to a target RNA.

In some instances, each strand of an siRNA agent is about or less than about 35, 34, 33, 32, 31, 30, 29, 28, 27, 26, 25, 24, 23, 22, 21, 20, 19, 18, 17, 16, or 15 nucleotides in length. For example, each strand can be between about 21 and 25 nucleotides in length. Specific siRNA agents have a duplex region of about 17, 18, 19, 29, 21, 22, 23, 24, or 25 nucleotide pairs, and one or more overhangs, for example, one or two 3' overhangs, of 1-3 nucleotides.

In addition to homology to target RNA and the ability to down regulate a target gene, an siRNA agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a C3'-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In some aspects, RNAi agents include an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In some embodiments, the RNAi agent is an oligonucleotide tethered to a ligand for the purposes of improving cellular targeting and uptake. For example, an RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In certain embodiments, the RNAi agent comprises a non-natural nucleobase. In some embodiments, the non-natural nucleobase is difluorotolyl, nitroimidazolyl, nitroindolyl, or nitropyrrolyl. In certain embodiments, the modulating agents provided herein relate to a double-stranded oligonucleotide sequence, wherein only one of the two strands contains a non-natural nucleobase. In certain embodiments, the modulating agents as used herein relate to a double-stranded oligonucleotide sequence, wherein both of the strands independently comprise at least one non-natural nucleobase.

In certain instances, the ribose sugar moiety that naturally occurs in nucleosides is replaced with a hexose sugar. In certain aspects, the hexose sugar is an allose, altrose, glucose, mannose, gulose, idose, galactose, talose, or a derivative thereof. In a preferred embodiment, the hexose is a D-hexose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane. In certain embodiments, the backbone of the oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands are complementary, partially complementary, or chimeric oligonucleotides.

Examples of modified RNAi agents include oligonucleotides containing modified backbones or non-natural internucleoside linkages. As defined herein, oligonucleotides having modified backbones or internucleoside linkages include those that retain a phosphorus atom in the backbone and those that do not have a phosphorus atom in the backbone. Modified oligonucleotides that do not have a phosphorus atom in their intersugar backbone can also be considered to be oligonucleotides. Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative U.S. patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleotides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative U.S. patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other examples of oligonucleotide mimetics, both the sugar and the internucleoside linkage, i.e., the backbone, of the nucleoside units may be replaced with other groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Also included are oligonucleotides that employ ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.). The cleavage reactions are catalyzed by the RNA molecules themselves. In naturally occurring RNA molecules, the sites of self-catalyzed cleavage are located within highly conserved regions of RNA secondary structure (Buzayan et al., PNAS USA. 83:8859, 1986). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes described herein.

In certain instances, the RNAi agents may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the literature. Examples of non-ligand moieties include lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-mc-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Certain exemplary RNAi agents are provided for delivery in a vector. The term "vector" generally refers to a nucleic acid molecule, typically DNA, to which nucleic acid segments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, viral vectors, etc., as appropriate. Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

Exemplary vectors for use herein include viral vectors, which are well known and include vectors derived from for example, but without limitation, retroviruses, vaccinia viruses, poxviruses, adenoviruses, and adeno-associated viruses (AAV). Such viral vectors may me be engineered by recombinant techniques as known per se to introduce thereto nucleic acid sequence(s) encoding any one of the antisense or RNAi agents disclosed herein.

For example, a retroviral vector may be used herein to deliver an RNAi agent. Generally, retroviral vectors may comprise the retroviral genomic sequences encoding components necessary for the integration of the recombinant viral genome (randomly) into the host cell genome and the nucleic acid sequence(s) of interest, such as in particular the nucleic acid sequence(s) encoding any one of the antisense or RNAi agents disclosed herein. Such retroviral vectors may be readily constructed using standard recombinant techniques (e.g., Sambrook et al., Molecular Cloning: A Laboratory Manual, 2d ed., Cold Spring Harbor Laboratory Press, 1989) from a wide variety of retroviruses, including for example, B, C, and D type retroviruses as well as spumaviruses and lentiviruses (see RNA Tumor Viruses, Second Edition, Cold Spring Harbor Laboratory, 1985).

Recombinant adenoviral vectors may also be contemplated for delivery and expression of RNAi agents as disclosed herein in a host cell. Adenovirus-based viral vectors have the advantage of being capable of infecting non-dividing host cells, but the recombinant viral genome is not integrated into the host cell genome. For example, a suitable adenoviral vector, a method for constructing a recombinant adenoviral vector thereof, and a method for delivering the recombinant vector into host cells, are described in Xia H et al. (2002) (Nat. Biotech 20: 1006-1010). Use of recombinant AAV (RAAV) vectors is also contemplated herein. RAAV vectors can infect both dividing and non-dividing cells and may incorporate its recombinant viral genome into that of the host cell. RAAV vectors may be generated from a variety of adeno-associated viruses, including for example, serotypes 1 through 6. Generally, RAAV vectors may comprise, in order, a 5' adeno-associated virus inverted terminal repeat (ITR), a nucleic acid of interest, such as in particular a nucleic acid sequence encoding any one of the antisense or RNAi agents disclosed herein, operatively linked to a sequence which regulates its expression in a host cell or host organism, and a 3' adeno-associated virus ITR. In addition, the rAAV vector may preferably have a polyadenylation signal. Suitable RAAV vectors are described inter alia in WO 1994/13788, WO 1993/24641, and in Goyenvalle et al. 2004 (Science 306: 1796-1799) where antisense sequences are linked to a modified U7 small nuclear RNA.

Other exemplary viral vectors for use herein are vectors derived from a pox virus such as a vaccinia virus, for example an attenuated vaccinia virus such as Modified Virus Ankara (MVA) or NYVAC, an avipox virus such as fowl pox virus or canary pox virus.

Additional examples of modulating agents, such as RNAi oligonucleotides including siRNA oligonucleotides, may be found in U.S. Application Publication Nos. 2009/0312531; 2009/0318676; 2011/0117125; 2011/0269814; 2007/0275465, 2007/0054279; 2006/0287260; 2006/0035254; and 2006/0008822, which are incorporated by reference.

Methods of Use

Certain embodiments include the use of the HRS polypeptides/expressible polynucleotides and compositions described herein for treating lung inflammation, either alone or in combination with immunotherapy agents. Included is the treatment of interstitial lung diseases (ILDs) and related disorders. In some embodiments, the HRS polypeptides/expressible polynucleotides and compositions, methods, and/or combination therapies are employed to reduce lung inflammation, treat one or more ILDs, and/or improve clinical symptoms or parameters of the disease in a subject in need thereof.

Thus, some embodiments include methods of treating lung inflammation in a subject in need thereof, comprising administering to the subject a histidyl-tRNA synthetase (HRS) polypeptide (for example, an HRS-Fc fusion polypeptide), or an expressible polynucleotide that encodes the HRS polypeptide.

Certain embodiments include methods of treating lung inflammation in a subject in need thereof, comprising administering to the subject (a) a histidyl-tRNA synthetase (HRS) polypeptide, or an expressible polynucleotide that encodes the HRS polypeptide; and (b) an immunomodulatory agent, for example, as described herein. In some embodiments, (a) and (b) are administered separately, and are optionally defined as described herein. In certain embodiments, (a) and (b) are administered together, optionally as a therapeutic composition described herein.

In particular embodiments, the immunomodulatory agent is pirfenidone or nintedanib. In some methods or compositions, the pirfenidone is administered at an individual dosage unit that ranges from about 50 to about 1000 mg, or an individual dosage unit of about no more than about, or at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg, for example, in about 1, 2, or 3 capsules for oral dosing.

In some embodiments, the pirfenidone is administered at a daily dosage unit that ranges from about 100 to about 4000 mg/day, or a daily dosage unit of about, no more than about, or at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1200, 1300, 1400, 1500, 1600, 1700, 1800, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day, for example, in about 1, 2, 3, 4, 5, 6, 7, 8, 9 capsules for oral dosing.

In specific embodiments, the pirfenidone is administered at an individual dosage unit of about 800 mg (e.g., 801 mg), for example, as three ~267 mg capsules for oral dosing, taken as three capsules per individual dosage, or the pirfenidone is administered at daily dosage unit of about 2400 mg/day (e.g., 2403 mg/day), for example, as nine ~267 mg capsules for oral dosing three times daily, taken as three capsules per individual dosage.

In some methods or compositions, the nintedanib is administered at an individual dosage unit that ranges from about 10 to about 500 mg, or an individual dosage unit of about, no more than about, or at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg, for example, in about 1, 2, or 3 capsules.

In some embodiments, the nintedanib is administered at a daily dosage unit that ranges from about 20 to about 1000 mg/day, or a daily dosage unit of about, no more than about, or at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg/day, for example, in about 1, 2, 3, 4, 5, or 6 capsules.

In specific embodiments, the nintedanib is administered at a daily dosage unit that ranges from about 100 to 150 mg, or ranges from about 200 to 300 mg/day, for example, for a once or twice daily dosage, or the nintedanib is administered at a daily dosage unit of about 100 or 150 mg, or about 200 to 300 mg/day, for example, for a once or twice daily dosage.

In some embodiments, the immunomodulatory agent alters or improves one or more pharmacokinetic characteristics of the HRS polypeptide relative to the HRS polypeptide alone. Examples of pharmacokinetic characteristics include stability or half-life, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve of a concentration-time graph (AUC or exposure; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state). In specific embodiments, the one or more altered pharmacokinetic characteristics of the HRS polypeptide are increased serum half-life, increased bioavailability, increased exposure (AUC), increased serum concentration, and/or decreased clearance.

In some embodiments, the immunomodulatory agent increases the half-life or serum half-life of the HRS polypeptide in the subject by at least about 10, 20, 30, 40, 50, 60, 70, 80, 90, 100, 150, or 200% or more relative to the HRS polypeptide alone. In some embodiments, the immunomodulatory agent increases the bioavailability of the HRS polypeptide in the subject by at least about 10, 20, 30, 40, 50, 60, 70, 80, 90, 100, 150, or 200% or more relative to the HRS polypeptide alone. In some embodiments, the immunomodulatory agent increases the exposure (AUC) of the HRS polypeptide in the subject by at least about 10, 20, 30, 40, 50, 60, 70, 80, 90, 100, 150, or 200% or more relative to the HRS polypeptide alone. In some embodiments, the immunomodulatory agent increases the serum concentration of the HRS polypeptide in the subject by at least about 10, 20, 30, 40, 50, 60, 70, 80, 90, 100, 150, or 200% or more relative to the HRS polypeptide alone. In some embodiments, the immunomodulatory agent decreases the clearance of the HRS polypeptide in the subject by at least about 10, 20, 30, 40, 50, 60, 70, 80, 90, 100, 150, or 200% or more relative to the HRS polypeptide alone. In particular embodiments, the HRS polypeptide comprises, consists, or consists essentially of SEQ ID NO:157 (Fc-HRS(2-60) or $HRS^{FC1}$), and the immunomodulatory agent is pirfenidone. In specific embodiments, the pirfenidone increases the serum concentration of the HRS polypeptide (for example, $HRS^{FC1}$) in the subject by at least about 10, 20, 30, 40, 50, 60, 70, 80, 90, 100, 150, or 200% or more relative to the HRS polypeptide alone.

Certain embodiments therefore include methods of altering one or more pharmacokinetic characteristics of an HRS-Fc fusion polypeptide in a subject, comprising administering to the subject the HRS-Fc fusion polypeptide, or an expressible polynucleotide that encodes the HRS-Fc fusion polypeptide, in combination with pirfenidone. In particular embodiments, the HRS-Fc fusion polypeptide comprises, consists, or consists essentially of an amino acid sequence that is at least 80%, 85%, 90%, 95%, 96%, 97%, 98%, 99%, or 100% identical to a sequence selected from Table H8. In specific embodiments, the HRS polypeptide comprises, consists, or consists essentially of SEQ ID NO:157 (Fc-HRS (2-60) or $HRS^{FC1}$).

In certain embodiments, the subject in need thereof has or is risk for having an inflammatory lung disease or an interstitial lung disease. Interstitial lung disease (ILD) refers to a broad category of lung diseases that includes more than 130 disorders characterized by scarring (i.e., "fibrosis") and/or inflammation of the lungs. ILD accounts for 15 percent of the cases seen by pulmonologists. In some instances, ILD is idiopathic. However, in some instances, ILD can develop from or associate with a variety of sources or conditions, ranging from other diseases to environmental factors. Some of the causes of, or associations with, ILD include, for example, connective tissue diseases, autoimmune disease, including for example, scleroderma/progressive systemic sclerosis, Lupus (systemic lupus erythematosus), rheumatoid arthritis, and polymyositis/dermatomyositis. Also included are occupational and environmental exposures, including for example, exposure to inhaled substances such as dust, gases, allergens, or toxins/poisons; exposure to drugs such as antibiotics, chemotherapeutic agents, antiarrhythmic agents, and statins; exposure to infections such as pneumonia (e.g., atypical pneumonia), pneumocystis pneumonia (PCP), tuberculosis,

*Chlamydia trachomatis*, Respiratory Syncytial Virus (RSV), and cryptogenic organizing pneumonia; exposure to radiation therapy; and malignancies such as lymphangitic carcinomatosis and lymphoma. In certain embodiments, the subject in need thereof has acute respiratory distress syndrome (ARDS).

In ILD, the tissue in the lungs becomes inflamed and/or scarred. The interstitium of the lung includes the area in and around the small blood vessels and alveoli (air sacs) where the exchange of oxygen and carbon dioxide takes place. Inflammation and scarring of the interstitium disrupts this tissue and leads to a decrease in the ability of the lungs to extract oxygen from the air.

The progression of ILD varies from disease to disease and from person to person. Because interstitial lung disease disrupts the transfer of oxygen and carbon dioxide in the lungs, its symptoms typically manifest as problems with breathing. The two most common symptoms of ILD are shortness of breath with exercise and a non-productive cough.

In certain embodiments, the ILD is selected from, or is associated with, one or more of idiopathic interstitial pneumonia, idiopathic pulmonary fibrosis, sarcoidosis, Hammann-Rich syndrome, Antisynthetase syndrome, idiopathic eosinophilic pneumonia, alveolar hemorrhage syndrome, pulmonary alveolar proteinosis, asbestosis, silicosis, berylliosis, rheumatoid arthritis, lupus erythematosus, chronic graft vs host disease with pulmonary involvement, sclerosis (systemic) or scleroderma, polymyositis, dermatomyositis, chronic pulmonary disease, asthma, bronchitis (respiratory bronchitis), pneumonia, hypersensitivity pneumonitis, chronic hypersensitivity pneumonia, respiratory distress syndrome, Still's disease, acute lung injury, microscopic polyangitis, pulmonary edema, pulmonary Langerhans cell histiocytosis, acute inhalational exposures, drug-induced lung disease, desquamative interstitial pneumonia, and/or cystic fibrosis.

Certain genetic deficiencies or mutations also associate with ILDs. For example, in certain embodiments, the ILD is associated with one or more of Surfactant-Protein-B Deficiency (Mutations in SFTPB), Surfactant-Protein-C Deficiency (Mutations in SFTPC), ABCA3-Deficiency (Mutations in ABCA3), Brain Lung Thyroid Syndrome (Mutations in TTF1), or Congenital Pulmonary Alveolar Proteinosis (Mutations in CSFR2A, CSFR2B), Alveolar Capillary Dysplasia (Mutations in FoxF1), Mutations in telomerase reverse transcriptase (TERT), Mutations in telomerase RNA component (TERC), Mutations in the regulator of telomere elongation helicase 1 (RTEL1), and/or Mutations in poly (A)-specific ribonuclease (PARN).

In some embodiments, the subject in need thereof has a condition selected from one or more of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema.

In some embodiments, the subject in need thereof has an obstructive or inflammatory airway disease. Examples include chronic eosinophilic pneumonia, chronic obstructive pulmonary disease (COPD), COPD that includes chronic bronchitis, pulmonary emphysema or dyspnea, COPD that is characterized by irreversible, progressive airways obstruction, and acute respiratory distress syndrome (ARDS). In some embodiments, the subject in need thereof has a condition related to exacerbation of airways hyper-reactivity consequent to other drug therapy, airway disease that is associated with pulmonary hypertension, bronchitis or acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis, vesicular bronchitis, acute lung injury, bronchiectasis or cylindric bronchiectasis, sacculated bronchiectasis, fusiform bronchiectasis, capillary bronchiectasis, cystic bronchiectasis, dry bronchiectasis, or follicular bronchiectasis.

In certain embodiments, as noted herein, the subject in need thereof has fibrosis, or pulmonary fibrosis. The severity of pulmonary fibrosis can be measured on a numerical scale, referred to as an Ashcroft score (see, e.g., Ashcroft et al., J. Clin. Path. 41:467-470, 1988). The Ashcroft score can range from minimal fibrous thickening of the alveolar or bronchioloar walls, moderate thickening of walls without obvious to lung architecture, increased fibrosis with definite damage to lung structure and formation of fibrous bands or small fibrous masses, severe distortion of structure and large fibrous areas (including "honeycomb lung"), and total fibrous obliteration of the field. An Ashcroft score of 0 refers to normal lung. In some embodiments, for example, prior to treatment, the subject in need thereof has an Ashcroft score of 1, 2, 3, 4, 5, 6, 7, or 8 (1 being the best and 8 being the worst score on the scale).

In certain embodiments, the lung inflammation has an autoimmune component. For instance, lung and peripheral blood T cells in patients with severe emphysema secrete Th1 cytokines and chemokines when stimulated with elastin peptides in vitro, and these patients have increased anti-elastin antibody as compared to controls (see Goswami et al, The Journal of Immunology. 178: 130.41, 2007). Also, IgG autoantibodies with avidity for pulmonary epithelium, and the potential to mediate cytotoxicity, are prevalent in patients with COPD (see Feghali-Bostwick et al., Am J Respir Crit Care Med. 177: 156-63, 2008). Since autoreactive immune responses may be important in the etiology of this disease, including, for example, auto-reactive responses to self-antigens such as elastin, may play a role in COPD, the combination therapies described herein can be used to desensitize immune cells to these antigens and thereby reduce pulmonary inflammation.

In some embodiments, the methods and compositions increase the life expectancy of the subject in need thereof, for example, by about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more years.

In some embodiments, the methods and compositions improve one or more of the clinical symptoms or parameters of the lung inflammation in the subject in need thereof. Exemplary clinical symptoms or parameters include lung fibrosis, inflammatory cell infiltrates in the lung, respiratory function, and body weight.

Thus, in some embodiments, the methods and compositions improve lung fibrosis in the subject in need thereof by about or at least about 10, 20, 30, 40, 50, 60, 70, 80, 90, 100, 200, 300, 400, 500, 600, 700, 800, 900, 1000% or more, for example, as measured over a period of about 1, 2, 3, 4, 5, 6, 7, 8, 9, 10, 11, 12, 13, 14, 15, 16, 17, 18, 19, 20, 21, 22, 23, or 24 months or more. Particular embodiments improve lung fibrosis in the subject in need thereof as measured by a reduced Ashcroft score, for example, an Ashcroft score that is reduced by 1, 2, 3, 4, 5, 6, 7, or 8 grades relative to an earlier score. In some embodiments, the methods and compositions result in an Ashcroft score of 0, 1, 2, or 3 or less.

In some embodiments, the methods and compositions reduce inflammatory cell infiltrates in the lung by about or at least about 10, 20, 30, 40, 50, 60, 70, 80, 90, 100, 200, 300, 400, 500, 600, 700, 800, 900, 1000% or more, for example, as measured over a period of about 1, 2, 3, 4, 5, 6, 7, 8, 9, 10, 11, 12, 13, 14, 15, 16, 17, 18, 19, 20, 21, 22, 23, or 24 months or more.

In some embodiments, the methods and compositions improve respiratory function by about or at least about 10, 20, 30, 40, 50, 60, 70, 80, 90, 100, 200, 300, 400, 500, 600, 700, 800, 900, 1000% or more, for example, as measured over a period of about 1, 2, 3, 4, 5, 6, 7, 8, 9, 10, 11, 12, 13, 14, 15, 16, 17, 18, 19, 20, 21, 22, 23, or 24 months or more. In some embodiments, respiratory function is selected from one or more of increased expiration time, increased inspiration time, decreased peak expiratory flow, decreased peak inspiratory flow, decreased respiratory minute volume (RMV), and decreased respiratory rate. Exemplary methods for measuring such symptoms or parameters are known in the art or described herein (see the Examples).

Pharmaceutical Compositions and Kits

Certain embodiments include pharmaceutical compositions, therapeutic compositions, and formulations suitable for the therapeutic delivery of the HRS polypeptides/expressible polynucleotides and immunomodulatory agents described herein. Some embodiments therefore include pharmaceutically acceptable compositions that comprise a therapeutically-effective amount of one or more of the HRS polypeptides/expressible polynucleotides and immunomodulatory agents described herein, formulated together with one or more pharmaceutically acceptable carriers and/or diluents.

The compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the HRS polypeptides/expressible polynucleotides and immunomodulatory agents include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999).

Also included are compositions comprising surface-modified liposomes containing poly (ethylene glycol) lipids (PEG-modified, branched and unbranched or combinations thereof, or long-circulating liposomes or stealth liposomes). HRS polypeptides/expressible polynucleotides and/or immunomodulatory agents can also comprise covalently attached PEG molecules of various molecular weights. These formulations offer a method for increasing the accumulation of drugs in target tissues. Long-circulating liposomes are also likely to protect drugs from nuclease degradation to a greater extent compared to cationic liposomes, based on their ability to avoid accumulation in metabolically aggressive MPS tissues such as the liver and spleen.

Also included are compositions prepared for delivery as described in U.S. Pat. Nos. 6,692,911, 7,163,695 and 7,070, 807. In this regard, certain embodiments include compositions comprising copolymers of lysine and histidine (HK) as described in U.S. Pat. Nos. 7,163,695, 7,070,807, and 6,692, 911 either alone or in combination with PEG (e.g., branched or unbranched PEG or a mixture of both), in combination with PEG and a targeting moiety or any of the foregoing in combination with a crosslinking agent. Some embodiments provide HRS polypeptides/expressible polynucleotides and/or immunomodulatory agents in compositions comprising gluconic-acid-modified polyhistidine or gluconylated-polyhistidine/transferrin-polylysine. One skilled in the art will also recognize that amino acids with properties similar to His and Lys may be substituted within the composition.

Certain agents described herein may contain a basic functional group, such as amino or alkylamino, which is capable of forming pharmaceutically-acceptable salts with pharmaceutically-acceptable acids. The term "pharmaceutically-acceptable salts" in this respect, refers to the relatively non-toxic, inorganic and organic acid addition salts of an agent. These salts can be prepared in situ in the administration vehicle or the dosage form manufacturing process, or by separately reacting a purified agent in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the agents described herein include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the agents described herein contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of an agent. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of include those suitable for intravenous, intramuscular, oral, nasal, pulmonary, topical (including buccal and sublingual), rectal, vaginal, and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a composition or formulation comprises an excipient selected from cyclodextrins, celluloses, liposomes, micelle forming agents, e.g., bile acids, and polymeric carriers, e.g., polyesters and polyanhydrides; and an HRS polypeptide/expressible polynucleotide and immunomodulatory agent.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an HRS polypeptide/expressible polynucleotide and/or immunomodulatory agent as an active ingredient. The compositions or agents may also be administered as a bolus, electuary, or paste.

In solid dosage forms for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the HRS polypeptides/expressible polynucleotides and immunomodulatory agents include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations or dosage forms for the topical or transdermal administration of the HRS polypeptides/expressible polynucleotides and immunomodulatory agents include powders, sprays, ointments, pastes, creams, lotions, gels, solutions, patches and inhalants. The active HRS polypeptides/expressible polynucleotides and/or immunomodulatory agents may be mixed under sterile conditions with a pharmaceutically-acceptable carrier, and with any preservatives, buffers, or propellants which may be required. The ointments, pastes, creams and gels may contain, in addition to the HRS polypeptides/expressible polynucleotides and/or immunomodulatory agents, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the HRS polypeptides/expressible polynucleotides and/or immunomodulatory agents to the body. Such dosage forms can be made by dissolving or dispersing the agent in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more HRS polypeptides/expressible polynucleotides and/or immunomodulatory agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject may be ensured by the inclusion of various antibacterial and antifungal agents, for example, paraben, chlorobutanol, phenol sothic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject HRS polypeptides/expressible polynucleotides and/or immunomodulatory agents in biodegradable polymers such as polylactide-polyglycolide. Depending on the ratio of agent to polymer, and the nature of the particular polymer employed, the rate of release can be controlled. Examples of other biodegradable polymers include poly(orthoesters) and poly(anhydrides). Depot injectable formulations may also prepared by entrapping the drug in liposomes or microemulsions that are compatible with body tissues.

When the HRS polypeptides/expressible polynucleotides and/or immunomodulatory agents are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the HRS polypeptides/expressible polynucleotides and/or immunomodulatory agents may be formulated into pharmaceutically-acceptable dosage forms by conventional methods known to those of skill in the art. Actual dosage levels of the active ingredients in the pharmaceutical compositions may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular HRS polypeptides/expressible polynucleotides and/or immunomodulatory agents employed, or the ester, salt or amide thereof, the route of administration, the time of administration, the rate of excretion or metabolism of the particular agent being employed, the rate and extent of absorption, the duration of the treatment, other drugs, compounds and/or materials used in combination with the particular agent employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could start doses of the HRS polypeptides/expressible polynucleotides and/or immunomodulatory agents employed in the pharmaceutical composition at levels lower than that required in order to achieve the desired therapeutic effect and gradually increase the dosage until the desired effect is achieved. In general, a suitable daily dose of HRS polypeptides/expressible polynucleotides and/or immunomodulatory agents will be that amount of the compound which is the lowest dose effective to produce a therapeutic effect. Such an effective dose will generally depend upon the factors described herein. Generally, oral, intravenous, intramuscular, intracerebroventricular and subcutaneous doses of the HRS polypeptides/expressible polynucleotides and/or immunomodulatory agents for a subject or patient, when used for the indicated effects, will range from about 0.0001 to about 100 mg per dosage, or about 0.0001 to about 100 mg per kilogram of body weight per dosage.

If desired, the effective daily dose of the active agent(s) may be administered as one, two, three, four, five, six or more sub-doses administered separately at appropriate intervals throughout the day or week, for example, in unit dosage forms. In certain situations, dosing is one administration per day. In certain situations, dosing is one, two, or three administration per week. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to treat the desired condition.

HRS polypeptides/expressible polynucleotides and/or immunomodulatory agents can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In some embodiments, the compositions or formulations contain micelles which are formed from the HRS polypeptides/expressible polynucleotides and/or immunomodulatory agents and at least one amphiphilic carrier, in which the micelles have an average diameter of less than about 100 nm. Exemplary embodiments provide micelles having an average diameter less than about 50 nm, and even certain embodiments provide micelles having an average diameter less than about 30 nm, or even less than about 20 nm. While all suitable amphiphilic carriers are contemplated, the presently preferred carriers are generally those that have Generally-Recognized-as-Safe (GRAS) status, and that can both solubilize the active ingredient and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or monounsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc. (produced and distributed by a number of companies in USA and worldwide).

In certain embodiments, the delivery may occur by use of liposomes, nanocapsules, microparticles, microspheres, lipid particles, vesicles, and the like, for the introduction of the HRS polypeptides/expressible polynucleotides and/or immunomodulatory agents into suitable host cells. In particular, the compositions may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG (750)). Polymers may also be defined by the number of monomers therein.

Other hydrophilic polymers which may be suitable include polyvinylpyrrolidone, polymethoxazoline, polyethyloxazoline, polyhydroxypropyl methacrylamide, polymethacrylamide, polydimethylaciylamide, and derivatized celluloses such as hydroxymethylcellulose or hydroxyethylcellulose.

In certain embodiments, a composition or formulation comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β, and γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. The physicochemical properties of the cyclodextrin derivatives depend on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Some embodiments relate to formulations comprising liposomes containing HRS polypeptides/expressible polynucleotides and/or immunomodulatory agents, where the liposome membrane is formulated to provide a liposome with increased carrying capacity. Alternatively or in addition, the active ingredients may be contained within, or adsorbed onto, the liposome bilayer of the liposome. The HRS polypeptides/expressible polynucleotides and/or immunomodulatory agents may be aggregated with a lipid surfactant and carried within the liposome's internal space; in these cases, the liposome membrane is formulated to resist the disruptive effects of the active agent-surfactant aggregate.

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several non-concentric membranes, i.e., several smaller vesicles contained within a larger vesicle, are termed multivesicular vesicles.

In some embodiments, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Liposomes maybe prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993. For example, liposomes may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the HRS polypeptides/expressible polynucleotides and/or immunomodulatory agents are first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT™ and Lipofectamine™ may be utilized to introduce polynucleotides or proteins into cells.

The release characteristics of a formulation depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™ Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The HRS polypeptides/expressible polynucleotides and/or immunomodulatory agents may be formulated to be contained within, or, adapted to release by a surgical or medical device or implant. In certain aspects, an implant may be coated or otherwise treated with an agent. For example, hydrogels, or other polymers, such as biocompatible and/or biodegradable polymers, may be used to coat an implant with the HRS polypeptides/expressible polynucleotides and/or immunomodulatory agents (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

The HRS polypeptides/expressible polynucleotides and/or immunomodulatory agents may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

Also included are kits, for example, patient care kits, comprising one or more containers filled with one or more of the therapeutic compositions, HRS polypeptides/expressible polynucleotides and/or immunomodulatory agents described herein. In some embodiments, the kits include written instructions on how to use such compositions, for example, in the treatment of one or more diseases.

Certain embodiments therefore include a patient care kit, comprising: (a) a histidyl-tRNA synthetase (HRS) polypeptide, or an expressible polynucleotide that encodes the HRS polypeptide; and (b) an immunomodulatory agent. In some kits, (a) and (b) are in separate compositions, and are optionally defined as described herein. In some kits, (a) and (b) are in the same composition, optionally as a therapeutic composition as described herein.

In particular embodiments, the immunomodulatory agent in a therapeutic composition and/or patient care kit is pirfenidone or nintedanib.

In some embodiments, the pirfenidone is at an individual dosage unit that ranges from about 50 to about 1000 mg (optionally in about 1, 2, or 3 capsules for oral dosing), or an individual dosage unit of about no more than about, or at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg (optionally in 1, 2, or 3 capsules for oral dosing).

In some embodiments, the pirfenidone is at a daily dosage unit that ranges from about 100 to about 4000 mg/day (optionally in about 3, 4, 5, 6, 7, 8, 9 capsules for oral dosing), or a daily dosage unit of about, no more than about, or at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1200, 1300, 1400, 1500, 1600, 1700, 1800, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day (optionally in about 3, 4, 5, 6, 7, 8, 9 capsules for oral dosing).

In specific embodiments, the pirfenidone is at an individual dosage unit of about 800 mg (e.g., 801 mg), for example, as three ~267 mg capsules for oral dosing, taken as three capsules per individual dosage. In specific embodiments, the pirfenidone is at daily dosage unit of about 2400 mg/day (e.g., 2403 mg/day), for example, as nine ~267 mg capsules for oral dosing three times daily, taken as three capsules per individual dosage.

In some embodiments, the nintedanib is at an individual dosage unit that ranges from about 10 to about 500 mg (optionally in about 1, 2, or 3 capsules), or an individual dosage unit of about, no more than about, or at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg (optionally in about 1, 2, or 3 capsules).

In some embodiments, the nintedanib is at a daily dosage unit that ranges from about 20 to about 1000 mg/day (optionally in about 1, 2, 3, 4, 5, or 6 capsules), or a daily dosage unit of about, no more than about, or at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg/day (optionally in about 1, 2, 3, 4, 5, or 6 capsules).

In some embodiments, the nintedanib is at a daily dosage unit that ranges from about 100 to 150 mg, or ranges from about 200 to 300 mg/day, optionally for a once or twice daily dosage. In some embodiments, the nintedanib is at a dosage unit of about 100 or 150 mg, or about 200 to 300 mg/day, optionally for a once or twice daily dosage.

The kits and compositions described herein may also include a one or more additional therapeutic agents or other components suitable or desired for the indication being treated. An additional therapeutic agent may be contained in a second container, if desired. Examples of additional therapeutic agents include, but are not limited to anti-inflammatory agents, anticancer agents, antibacterial agents, antiviral agents, etc.

The kits herein can also include one or more syringes (e.g., injectable syringes) or other components necessary or desired to facilitate an intended mode of delivery (e.g., stents, implantable depots, etc.).

EXAMPLES

Histidyl-tRNA synthetase (HRS) polypeptides were tested for activity in a bleomycin-induced pulmonary fibrosis model in mice or rats. Intratracheal administration of bleomycin (BLM) induces sequential changes in lung similar to those of certain ILDs, including for example, lung inflammation, and fibrosis seen in various ILDs in humans, suggesting that it may be used as a general model for the investigation for the evaluation of therapeutic agents for the treatment of ILDs, pulmonary injury, inflammation and fibrosis (see, e.g., Adamson and Bowden. The American J. Path. 77:185-197, 1974; Wynn, J Exp Med. 208:1339-1350, 2011; Williamson et al., Exp. Lung Res. 41:57-73, 2015).

Example 1

Evaluation of HRS Polypeptides for the Treatment of Bleomycin-Induced Interstitial Lung Disease Studies were performed to determine if an exemplary HRS polypeptide (HisRS1$^{N8}$) reduces respiratory impairment and/or lung fibrosis in a mouse model of bleomycin-induced the lung fibrosis. The effects of the HRS polypeptide on inflammatory and fibrotic processes were determined by measuring the cellular content of the bronchoalveolar lavage (BAL), histological fibrosis score, and lung collagen content.

Protocol and Methods.

Lung inflammation and fibrosis were induced in male C57Bl/6J mice by oropharyngeal administration of BLM. After the habituation phase mice were randomized based on body weight over the different groups. Under isoflurane anesthesia, 50 µl PBS or BLM was dripped onto the vocal cords facilitating aspiration. Mice were sacrificed at day 21 using a terminal bleed under isoflurane anesthesia. Animals were treated as shown in Table E1 below.

TABLE E1

| Day | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| control | ↓ saline | | | | | | | | | | | | | | | | | | | | | |
| untreated | ↓ | | | | | | | | | | | | | | | | | | | | | |
| Vehicle PO | ↓↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ |
| Nintedanib 60 mg/kg PO | ↓↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ |
| Dexamethasone 0.25 mg/kg PO | ↓↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ | ↓ |
| Vehicle IV | ↓ | | | | | | | | ↓ | ↓ | ↓ | ↓ | ↓ | ↓ | ↓ | ↓ | ↓ | ↓ | ↓ | | | ↓ |
| Test Article 1 mg/kg IV | ↓ | | | | | | | | ↓ | ↓ | ↓ | ↓ | ↓ | ↓ | ↓ | ↓ | ↓ | ↓ | ↓ | | | ↓ |
| Test Article 3 mg/kg IV | ↓ | | | | | | | | ↓ | ↓ | ↓ | ↓ | ↓ | ↓ | ↓ | ↓ | ↓ | ↓ | ↓ | | | ↓ |

TABLE E1-continued

| Day | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| Test Article 10 mg/kg IV | ✣ | | | | | | | | | ✣ | ✣ | ✣ | ✣ | ✣ | ✣ | ✣ | ✣ | ✣ | ✣ | | | ✣ |
| | | | | | | | | | B | # | # | # | # | # | # | # | # | # | # | # | # | X |

Male C57bl/6 mice, monitor BW
✣ Bleomycin 0.04 mg/mouse oropharyngeal admin.
Test Article lot # S0613043
D2O administration (new collagen measure) B = bolus IP; # = present in drinking water
X takedown - serum, BALF cell counts, frozen pellets, fluid, collagen content, lung histology, frozen lung Animals receiving PBS on day 0 served as non-diseased controls Animals receiving BLM oropharangeally on day 0 received either no therapeutic treatment, oral vehicle (0.5% Natrosol), oral Nintedanib (60 mg/kg in Natrosol), oral dexamethasone (0.25 mg/kg in water), intravenous (IV) vehicle (50 mM His, 140 mM NaCl, 0.05% polysorbate 20, pH 7.3), or Test Article (HisRS1$^{N8}$; Lot #S0613043) diluted in the IV vehicle at 1, 3 or 10 mg/kg. Daily oral treatments commenced on Day 0, while daily IV treatments commenced on Day 8. Dosing was planned to continue until the day of termination (Day 21), however, due to high mortality in IV treated groups (see results), IV dosing was skipped on Day 19 and Day 20. In order to determine new collagen formation, mice were given an IP bolus injection of 100% deuterated (D2O) water/0.9% NaCl (35 μl/gram bodyweight) at day 7; one day before starting treatment with Test Article. Subsequently, the mice received 8% D2O (Kinemed, Emeryville) drinking water until sacrifice to maintain labeling of newly formed collagen. Body weight was monitored three times a week.

At termination, mice were sacrificed using isoflurane and exsanguination via heart puncture one day after the last dosing (non-diseased controls, dexamethasone and vehicle groups) or 2 hours after the last IV administration of Test Article. Blood samples were processed to plasma (new collagen assay) or serum and stored frozen (<−70° C.).

The lungs were flushed two times with 750 μl PBS, combined into one bronchoalveolar lavage (BAL) sample, and stored on ice until centrifugation. The supernatant was collected and stored frozen (<−70° C.). The erythrocytes in the cell pellet were lysed and the remaining cells were resuspended in 100 μl PBS. 20 μl was diluted in trypan blue solution and used for counting the live cells using a hemocytometer.

The five lung lobes were collected and isolated. Wet weight of the medial and accessory lung lobes was recorded. The lobes were then snap frozen and stored at <−70° C. until use for hydroxyproline analysis. The left lung lobe was inflated and fixed for 48 hours in 4% formaldehyde and embedded in paraffin for histological analysis. The cranial lung lobe was snap frozen and stored at −80° C. until shipment to Kinemed for the determination of new collagen formation.

Sections of the left lung lobe were stained using Masson's Trichrome and were scored in a blinded fashion using a modified Ashcroft score (Hubner et al., BioTechniques. 44:507-511, 514-507, 2008). Hydroxyproline content was determined in the medial and accessory lung lobes using acid hydrolysis followed by a chromogenic assay (QuickZyme Biosciences, Leiden, Netherlands). Newly formed collagen was measured in the cranial lung lobe by Kinemed Inc., Emeryville, USA using the fraction of body water enriched in 2H for normalization.

All statistical analyses were performed using the SPSS 22 for Windows statistical software package (SPPS Inc., Chicago, Ill., USA). First, the equality of error variances was tested using Levene's test; equal variances were assumed at $p>0.01$. In the case of equality of error variances, groups were compared using the one-way ANOVA test, followed, when appropriate by a post-hoc Dunnett test versus the BLM+appropriate vehicle group. In the case of inequality of error variances, groups were compared using the Kruskall-Wallis test, followed by a Mann-Whitney test.

Results—Survival.

The study commenced with 7 animals in the non-diseased control group and 12 animals in the BLM-induced groups. Survival is show in Table E2 below.

TABLE E2

| | | Survival | | | | | | | |
|---|---|---|---|---|---|---|---|---|---|
| | Saline | BLM | | | | | | | |
| Day of | | | | | | | Test Article (mg/kg) | | |
| Study | IT | No tx | Veh PO | Ninte. | Dex. | Veh IV | 1 | 3 | 10 |
| 11 | 7 | 12 | 12 | 12 | 12 | 12 | 12 | 12 | 12 |
| 12 | 7 | 12 | 12 | 12 | 12 | 10 | 12 | 12 | 12 |
| 13 | 7 | 12 | 12 | 12 | 11 | 10 | 12 | 12 | 12 |
| 14 | 7 | 12 | 12 | 12 | 10 | 10 | 11 | 10 | 7 |
| 15 | 7 | 12 | 12 | 12 | 10 | 9 | 10 | 9 | 7 |
| 16 | 7 | 12 | 12 | 12 | 10 | 7 | 10 | 9 | 6 |
| 17 | 7 | 12 | 12 | 12 | 10 | 7 | 9 | 6 | 6 |
| 18 | 7 | 12 | 12 | 12 | 9 | 7 | 9 | 6 | 5 |
| 19 | 7 | 12 | 12 | 12 | 9 | 7 | 9 | 6 | 5 |
| 20 | 7 | 12 | 12 | 12 | 9 | 7 | 9 | 6 | 5 |
| 21 | 7 | 10 | 12 | 11 | 9 | 7 | 8 | 5 | 5 |

The number in each square indicates the number of animals surviving to each study day
Ninte. = Nintedanib (60 mg/kg), Dex. = Dexamethasone (0.25 mg/kg)

All animals in the non-diseased control (saline IT) group and in the BLM-treated PO-vehicle group survived the experimental period. The survival rate in the BLM untreated group was 83%. In the oral treated groups the survival rates were 75% after dexamethasone treatment and 92% Nintedanib treatment group. Survival rates dropped to 58% in the IV Vehicle and to a similar range in the Test Article treated groups (see Table E2).

Results—Body Weights.

Based on data from animals which survived to scheduled necropsy, administration of BLM in the lungs resulted in a decrease of body weight of the mice during the initial phase (first eight to ten days) of the experiment which is a characteristic of this model. After this phase the body weights of BLM-induced mice stabilized and started to increase slowly over the remaining experimental period. In the PBS-induced non-treated group, body weights remained stable and slowly increased (in total 6%) over the entire experimental period. When animals are treated orally on daily basis with vehicle, dexamethasone, or Nintedanib the body weights were comparable to untreated BLM-induced animals and stayed around 90% of their initial body weights. Until start of the IV treatment, body weight was comparable in all IV groups. After starting IV treatment with Test Article at day 8, body weights of the 1 and 3 mg/kg treatment dropped below or followed the trend line of the BLM untreated group. Daily IV treatment with the Test Article at 10 mg/kg had a positive effect on the BW when compared to the lower dose groups.

Results—Cell Counts in BAL Fluid.

The total number of cells in the BAL per sample was 19.8 times higher after induction of lung fibrosis by BLM (see FIG. 1). Oral treatment with dexamethasone or Nintedanib did not significantly affect live cells counted in BAL fluid at termination. In the Test Article-treated groups the cell number in BAL fluid compared with the IV-vehicle treated group was reduced by about 46%, 38% and 45% after IV treatment with Test Article at 1, 3 or 10 mg/kg, respectively.

Results—Lung Mass, Collagen Content and New Collagen Content.

BLM induction significantly affected the lung wet and dry weight of the BLM-induced non-treated mice resulting in a 1.8-fold increase in wet weight and a 2.1-fold increase in lung dry weight compared to PBS-induced mice. Dexamethasone decreased lung wet weight 15.6% when compared to the PO vehicle treated group. No significant changes in lung wet or dry weight were observed with other treatments.

Induction with BLM resulted in a significant 1.97-fold increase in collagen content in the medial and accessory lung lobes compared to PBS-induced mice. No significant changes in collagen content in the medial and accessory lung lobes were observed with any treatment.

A significant, 5.4-fold increase in new collagen synthesis after BLM administration was observed compared to mice receiving PBS IT. No significant changes in new collagen synthesis were observed with any treatment.

Results—Histological Fibrosis (Ashcroft) Score.

The extent of fibrosis in the lungs was determined by Ashcroft scoring of Masson's Trichrome stained paraffin sections of the left lung lobe. BLM induction resulted in a significant 8.3-fold increase in fibrosis score in the left lung lobe in comparison to PBS-induced animals Oral treatment with dexamethasone or Nintedanib did not result in a significant decrease of group mean histological score in comparison to the PO vehicle group, although dexamethasone treatment showed a decrease of the histological score of 11.7%. Similarly, treatment with Test Article did not result in a significant decrease of the histological score in comparison with the IV vehicle group although the Test Article 10 mg/kg dose showed a decrease of the histological score of 12.3%.

Figure 2:
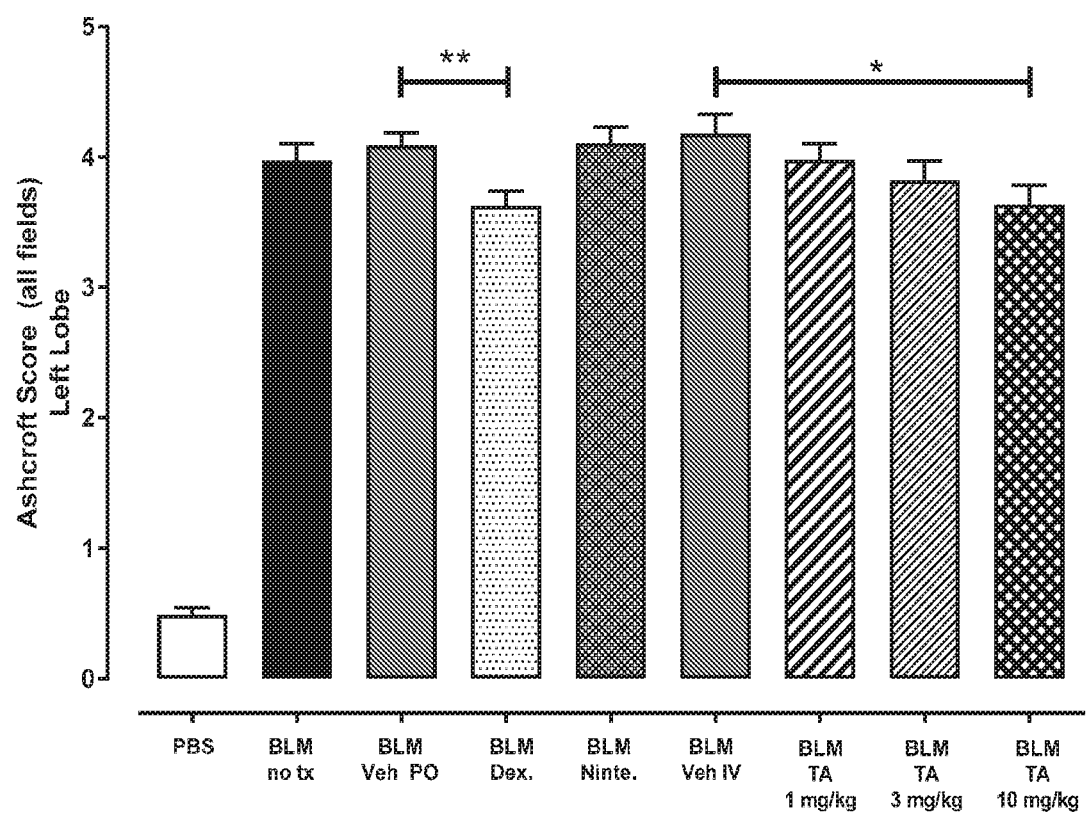
FIG. 2 shows Histological Fibrosis (Ashcroft) Scores. Mean data from all fields scored within each group are shown (+SEM): "no tx" indicates no treatment, "Veh" indicates treatment with Vehicle, "Dex." indicates treatment with dexamethasone, "Ninte." indicates treatment with Nintedanib, and "TA" indicates treatment with Test Article. Statistical comparisons were conducted by 1-way ANOVA within PO or IV treatment groups followed by Dunnett's post-hoc test. $*p<0.05$, $**p<0.01$ vs. respective vehicle.

Having noted the high variability in mean Ashcroft Index Scores within groups and also in lung pathology within each individual due to the focal nature of the model, Ashcroft scores were analyzed from all fields scored (13-20 per animal), which increased the number of observations to 84-182 in BLM-induced groups. Using this comprehensive analysis, treatment with dexamethasone at 0.25 mg/kg and Test Article at 10 mg/kg significantly reduced lung fibrosis in comparison to vehicle-treated controls (see FIG. 2).

Summary

The goal of this study was to investigate the therapeutic dose response effects of treatment with Test Article on lung fibrosis in the mouse induced by oropharyngeal administration of BLM. Lung fibrosis was induced by a single oropharyngeal instillation of BLM into the lungs of male C57Bl/6J mice. Animals receiving PBS instead of BLM were used as control. The induction of the fibrotic process in the lung was demonstrated by a 19.8-fold increase in BAL cell count and an 8.3-fold increase in fibrosis score in the left lung lobe. An increase of 1.97-fold in total collagen was observed. In addition, also a significant increase in lung wet and dry weights was observed. Taken together, these data support the conclusion that fibrosis was significantly induced in the lungs.

The combination of intravenous injection combined with BLM resulted in a marked loss of animals in all IV injected groups. Although the exact reason for this loss in survival could not be determined, we suspect that the increase in body temperature induced by placing the animals on a heating pad to facilitate IV injections combined with the damage to the lungs by BLM played a role.

Treatment with Test Article resulted in a significant decrease of the total cells in the BAL fluid (i.e., 46%, 38% and 45% for 1, 3 and 10 mg/kg, respectively). Treatment with Test Article starting eight days after the instillation of BLM into the lungs also improved Ashcroft fibrosis score in a dose-related manner (i.e., 4.9%, 8.6%, and 13.1% for 1, 3 and 10 mg/kg, respectively), reaching statistical significance in animals treated with Test Article at 10 mg/kg.

Treatment with dexamethasone (0.25 mg/kg/dose) starting on the day of instillation of BLM into the lungs resulted in a significant decrease in lung wet weight and significant improvement in Ashcroft fibrosis score (11.3%).

Treatment with Nintedanib (60 mg/kg/dose) starting on the day of instillation of BLM into the lungs showed no significant effects in this experiment. The lack of effect is likely a reflection of the high hurdle to ameliorating fibrosis under the conditions of this experiment. Induction in the model is known to vary between and within experimental replicates and Nintedanib has been shown to improve fibrosis at a similar dose level and dosing paradigm in the literature (see Wollin et al., The Journal of Pharmacology and Experimental Therapeutics 349:209-220, 2014).

Conclusions.

Overall, Test Article showed strong disease-ameliorating activity in the BLM-induced lung inflammation and fibrosis model when dosed therapeutically, that is beginning 8 days after BLM instillation Cell counts obtained in the BAL fluid are thought to reflect the degree of immune cell infiltration of the lungs. Test Article significantly decreased these cells, strongly suggesting that it decreased immune cell infiltration of the lungs. In contrast, neither the anti-fibrotic, Nintedanib, nor the immunosuppressant, dexamethasone, had any effect, despite their prophylactic administration.

Therapeutic intervention with Test Article also improved (decreased) histological fibrosis 21 days after BLM instillation, demonstrating the anti-fibrotic potential of the molecule. Dexamethasone had a similar effect on this endpoint, but Nintedanib was without effect. In this study the Test Article outperformed Nintedanib, which is marketed for the treatment of idiopathic pulmonary fibrosis. These results suggest that HRS Polypeptides such as the Test Article display significant therapeutic utility for the treatment of lung inflammation and fibrosis in a broad range of ILDs.

Example 2

Evaluation of HRS Polypeptide-Fc Fusion Proteins for the Treatment of Bleomycin-Induced Interstitial Lung Disease Studies were performed to determine if an exemplary HRS-Fc fusion protein ($HRS^{FC1}$) reduces respiratory impairment and/or lung fibrosis in a rat model of bleomycin-induced the lung fibrosis. The effects of the HRS-Fc fusion protein on the inflammatory and fibrotic processes were determined by measuring histological fibrosis and inflammation scores, and lung collagen content.

Protocol and Methods.

Lung inflammation and fibrosis were induced in male Sprague Dawley (Crl:CD(SD)) rats by oropharyngeal administration of bleomycin (BLM) at a dose level of approximately 1 mg/kg in 100 µl for up to 7 consecutive days. PBS or BLM was administered under isoflurane anesthesia. The first day of BLM administration was defined as Day 1. Rats were sacrificed at day 22 using a terminal bleed after carbon dioxide administration Animals were treated as shown in Table E3 below.

Due to large body weight loss in animals receiving BLM, oropharyngeal administrations were skipped on Days 4 and 5 Animals receiving PBS on Days 1, 2, 3, 6 and 7 served as non-diseased controls Animals receiving BLM oropharangeally on Days 1, 2, 3, 6 and 7 received either no therapeutic treatment, oral vehicle (water), oral Nintedanib (60 mg/kg in water), intravenous (IV) vehicle (20 mM His, 150 mM NaCl, pH 6.9), or Test Article ($HRS^{FC1}$; Lot #H-Fcv3-N4-921) diluted in the IV vehicle at 0.1, 0.3, 1, or 3 mg/kg. Daily oral treatments commenced on Day 1, while weekly IV treatments commenced on Day 9 (all dose levels) or Day 2 (1 mg/kg).

In-life, body weights were measured and clinical observations were conducted daily. On Day 8 and Day 15, animals were removed from their home cages and placed individually into whole body plethysmography chambers. After a 20-minute acclimatization phase, respiratory parameters were recorded for 10 minutes.

At termination, rats were sacrificed using carbon dioxide and exsanguination via heart puncture one day after the last oral dosing (non-diseased controls, nintedanib and oral vehicle groups) or 6 days after the last IV administration of Test Article.

The five lung lobes were collected and weighed. The right lung lobes were inflated and fixed in 10% neutral buffered formalin and embedded in paraffin for histological analysis. An approximately 50 mg piece of the left lung lobe was snap frozen and stored at −80° C. for potential RNA analysis. The remainder of the lobe was also snap frozen until analyzed for collagen content.

Sections for histology were stained using picrosirius red and were scored in a blinded fashion (1 score for each of the 4 lobes) by a veterinary pathologist using a modified Ashcroft score (Hubner et al., 2008). Hydroxyproline content was determined in the left lung lobe using a mass spectrometry method.

All statistical analyses were performed using GmphPad Prism (GraphPad Software, San Diego, Calif.). Groups were compared using the one way ANOVA test, followed, when appropriate by a post-hoc Dunnett t-test versus the BLM+ appropriate vehicle group.

TABLE E3

| Day | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| control | ↓ saline IT | ↓ | ↓ | | | ↓ | ↓ | | PS | | | | | | | PS | | | | | | X |
| Vehicle PO | ⁂V | ⁂V | ⁂V | V | V | ⁂V | ⁂V | V | PSV | V | V | V | V | V | V | PSV | V | V | V | V | V | X |
| Nintedanib or Pirfenidone | ⁂↓ | ⁂↓ | ⁂↓ | ↓ | ↓ | ⁂↓ | ⁂↓ | ↓ | PS↓ | ↓ | ↓ | ↓ | ↓ | ↓ | ↓ | PS↓ | ↓ | ↓ | ↓ | ↓ | ↓ | X |
| Vehicle IV | ⁂ | ⁂⁂ | ⁂ | | | ⁂ | ⁂ | | PSV | | | | | | | PSV | | | | | | X |
| $HRS^{FC1}$ 0.1 mg/kg IV | ⁂ | ⁂⁂ | ⁂ | | | ⁂ | ⁂ | | PS⁂ | | | | | | | PS⁂ | | | | | | X |
| $HRS^{FC1}$ 0.3 mg/kg IV | ⁂ | ⁂⁂ | ⁂ | | | ⁂ | ⁂ | | PS⁂ | | | | | | | PS⁂ | | | | | | X |
| $HRS^{FC1}$ 1 mg/kg IV | ⁂ | ⁂⁂ | ⁂ | | | ⁂ | ⁂ | | PS⁂ | | | | | | | PS⁂ | | | | | | X |
| $HRS^{FC1}$ 3 mg/kg IV | ⁂ | ⁂⁂ | ⁂ | | | ⁂ | ⁂ | | PS⁂ | | | | | | | PS⁂ | | | | | | X |
| $HRS^{FC1}$ 1 mg/kg IV | ⁂ | ⁂⁂ | ⁂ | | | ⁂ | ⁂ | | PS⁂ | | | | | | | PS⁂ | | | | | | X | n = 8/group male SD rats; Daily BWs and survival

⁂ Bleomycin to lung
V—vehicle
↓—dose administration
P—whole body plethsmography (prior to dose administration)
S—serum (post-plethsmography, prior to dose adminstration)
X takedown - serum, BALF, lung histology, lung collagen, frozen lung, quadriceps and liver Results—Survival.

Several animals required euthanasia for humane reasons due to severe body weight loss induced by BLM induction. There were 2 animals in groups 3 and 8, respectively. Three of the euthanasias were conducted prior to Test Article administration. The remaining euthanasia was conducted in group 8 (Test Article at 3 mg/kg) on Day 13. Since this animal had lost 11% of its body weight prior to the commencement of treatment, the euthanasia was not attributed to an adverse effect of the Test Article.

Results—Body Weights.

Based on data from animals which survived to scheduled necropsy, administration of BLM in the lungs resulted in a decrease of body weight of the rats versus non-diseased controls throughout the experiment which is a characteristic of this model. None of the groups treated with Nintedanib or Test Article had body weight curves that significantly differed from their respective controls.

Results—Respiratory Measurements.

Respiratory measurements were conducted on Day 8 and showed a clear impairment induced by BLM. The results are shown in Table E4 below.

Significant decreases in expiration and inspiration time were observed, whereas peak expiratory flow, peak inspiratory flow, respiratory minute volume (RMV), and respiratory rate were significantly increased. Tidal volumes were similar between BLM- and non-induced animals on Day 8.

Respiratory measurements conducted on Day 15 (Table E4) show continued impairment in BLM-induced vehicle treated groups. Treatment with Nintedanib did not significantly impact BLM-induced alterations in respiratory parameters. Test Article, in contrast, significantly reversed all respiratory measurements impaired by BLM induction (expiration and inspiration time were increased towards non-diseased controls, and peak expiratory flow, peak inspiratory flow, RMV, and respiratory rate were decreased towards non-diseased controls). Interestingly, tidal volume, which was not significantly elevated by BLM exposure, was decreased by Test Article treatment.

TABLE E4

Respiratory Measurements

| | | | BLM | | | | | | |
|---|---|---|---|---|---|---|---|---|---|
| | | | | | Test Article (mg/kg)/Treatment Days | | | | |
| | Disease Control | Veh PO | Ninte. | Veh IV | 0.1 D 9, 16 | 0.3 D 9, 16 | 1 D 9, 16 | 3 D 9, 16 | 1 D 2, 9, 16 |
| DAY 8 | | | | | | | | | |
| Expiratory Time | 0.25 (0.017) | 0.12 (0.008) | 0.12 (0.008) | 0.11 (0.008) | 0.14 (0.012) | 0.12 (0.011) | 0.15 (0.014) | 0.13 (0.014) | 0.13 (0.007) |
| Inspiratory Time | 0.18 (0.016) | 0.10 (0.004) | 0.09 (0.005) | 0.09 (0.005) | 0.10 (0.005) | 0.10 (0.007) | 0.11 (0.008) | 0.11 (0.006) | 0.10 (0.005) |
| Peak Expiratory Flow | 10.3 (1.5) | 25.6 (2.5) | 28.4 (1.9) | 28.2 (1.8) | 20.3 (2.1) | 25.6 (3.5) | 22.2 (4.0) | 20.5 (2.7) | 23.6 (3.1) |
| Peak Inspiratory Flow | 13.4 (1.5) | 22.9 (1.1) | 26.7 (2.1) | 24.1 (1.4) | 19.6 (1.8) | 21.6 (1.8) | 203 (3.2) | 18.1 (2.2) | 23.3 (2.7) |
| Respiratory Minute Volume | 230.5 (28.0) | 423.0 (33.4) | 477.5 (36.3) | 456.3 (28.7) | 342.4 (33.5) | 400 (39.3) | 351.2 (55.5) | 329.9 (42.5) | 391.9 (44.3) |
| Respiratory Rate | 164.4 (20.2) | 298.9 (15.9) | 313.0 (17.8) | 318.2 (16.6) | 270.8 (17.4) | 288.6 (18.2) | 259.5 (21.0) | 274.7 (23.2) | 279.3 (13.5) |
| Tidal Volume | 1.5 (0.06) | 1.4 (0.05) | 1.5 (0.05) | 1.4 (0.05) | 1.2 (0.05) | 1.4 (0.09) | 1.3 (0.11) | 1.2 (0.07) | 1.3 (0.11) |
| DAY 15 | | | | | | | | | |
| Expiratory Time | 0.26 (0.016) | 0.13 (0.013) | 0.12 (0.006) | 0.16 (0.012) | 0.19 (0.015) | 0.18 (0.010) | 0.22* (0.021) | 0.18 (0.013) | 0.21* (0.010) |
| Inspiratory Time | 0.19 (0.016) | 0.09 (0.004) | 0.09 (0.002) | 0.11 (0.010) | 0.13 (0.010) | 0.13 (0.009) | 0.15* (0.011) | 0.16** (0.014) | 0.15* (0.008) |
| Peak Expiratory Flow | 11.8 (1.1) | 26.4 (2.8) | 28.8 (1.2) | 21.6 (2.1) | 12.3** (1.1) | 15.5* (1.5) | 12.8** (2.0) | 13.3** (2.3) | 11.4*** (0.5) |
| Peak Inspiratory Flow | 14.0 (1.5) | 27.9 (1.8) | 29.0 (1.0) | 21.3 (2.1) | 13.8** (1.4) | 15.4* (1.4) | 13.1** (2.0) | 10.8** (1.6) | 11.7*** (0.7) |
| Respiratory Minute Volume | 241.1 (23.6) | 501.2 (39.6) | 534.6 (20.1) | 378.4 (39.0) | 233.5** (26.2) | 262.2* (23.5) | 222.1 (33.3) | 195*** (20.9) | 198*** (13.3) |
| Respiratory Rate | 163.1 (17.1) | 312.5 (20.0) | 317.3 (10.5) | 255.5 (20.0) | 204.2 (14.8) | 213.5 (15.5) | 178** (15.1) | 183.1* (14.5) | 175.1** (8.5) |
| Tidal Volume | 1.6 (0.06) | 1.6 (0.04) | 1.6 (0.04) | 1.4 (0.05) | 1.1** (0.06) | 1.2 (0.05) | 1.2 (0.08) | 1.1** (0.08) | 1.1** (0.04) |

Data shown are mean + SEM in (brackets). Significant differences from disease control is shown by bold font, asterisks marks significant differences from respective vehicle treated controls. IV groups were compared by 1-way ANOVA, PO groups by t test.
*$p < 0.05$,
** $p < 0.01$,
***$p < 0.001$.

Figure 3:
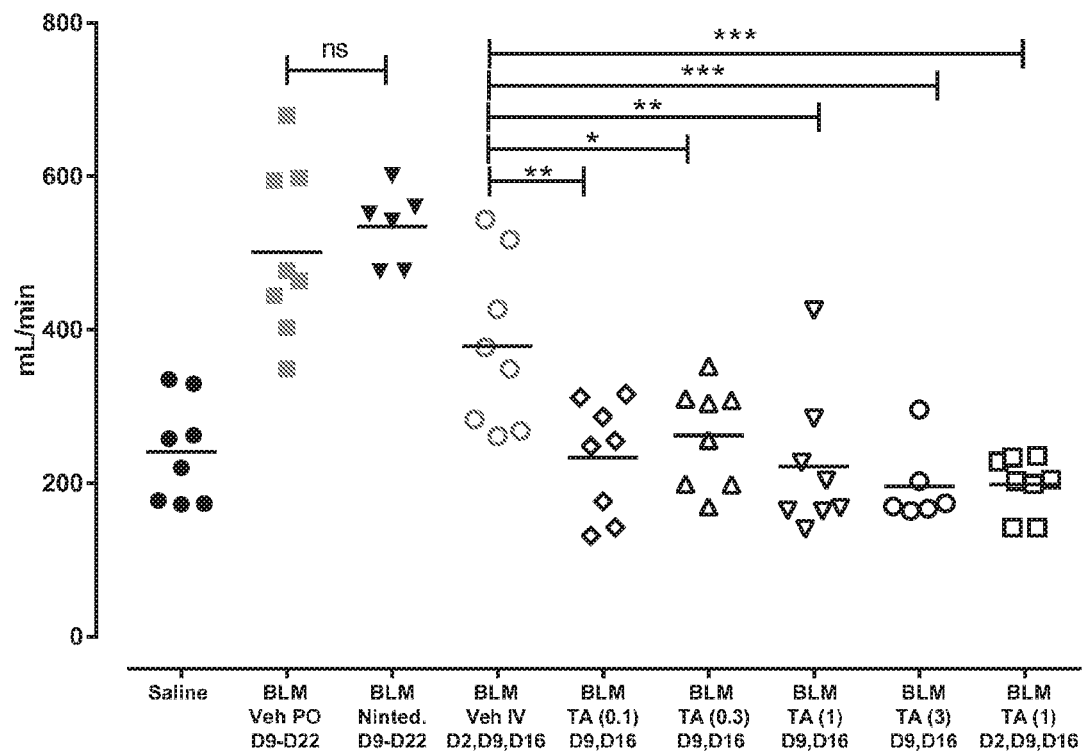
FIG. 3 shows Respiratory Minute Volume (RMV) on Day 15. Individual RMVs are shown with a line indicating the group mean: "Veh" indicates treatment with Vehicle, "Ninted." indicates treatment with Nintedanib, and "TA" indicates treatment with Test Article. Test Article dose is indicated in parentheses. IV groups were compared by 1-way ANOVA, PO groups by t test. $*p<0.05$, $p<0.01$, $*p<0.001$.

Graphical representation of RMV is shown in FIG. 3. RMV is the volume of gas inspired or expired per minute. As shown in FIG. 3, RMV is significantly elevated by BLM induction (compare Vehicle groups to group which received Saline IT), likely reflecting physiological compensation for impaired gas exchange between the alveolar space and the blood. Gas exchange is likely poor due to ongoing tissue edema secondary to the high level of immune cell infiltration and release of cytokines described in the model by others. Nintedanib has no impact on RMV (or any other respiratory measures). Test Article beginning on Day 9 or on Day 2., in contrast, significantly decreased this endpoint at all dose levels, In fact, RMV is normalized (i.e., not different than oropharyngeal Saline) by Test Article treatment.

Results—Lung Mass and Collagen Content.

Lung mass (wet weight) obtained at necropsy on Day 22 and collagen content were significantly elevated by BLM induction on Days 1, 2, 3, 4, 6 and 7. None of the treatment groups significantly changed lung wet weight or collagen content.

Results—Histological Scores.

Slides were read by a veterinary pathologist and each of the 4 lobes evaluated was assigned 4 scores [Ashcroft for fibrosis (scores range from 0 to 8), perivascular/peribronchiolar inflammatory cell infiltrate (scores range from 0 to 5), interstitial/alveolar inflammatory cell infiltrate (scores range from 0 to 5), type II pneumocyte hyperplasia (scores range from 0 to 5)].

Ashcroft scores assigned to PBS-induced animals were uniformly scored 0, while BLM-induced vehicle treated animals had scores ranging from 2 to 6 on the 8-point scale, confirming significant fibrosis had been induced. Oral treatment with Nintedanib decreased group mean histological scores 5% in comparison to the PO vehicle group, which did not meet statistical criteria. Similarly, treatment with Test Article did not result in a significant decrease of the histological score in comparison with the IV vehicle group although the group receiving Test Article at 1 mg/kg on Days 2, 9 and 16 showed a decrease of the Ashcroft score of 15.3%.

Figure 4:
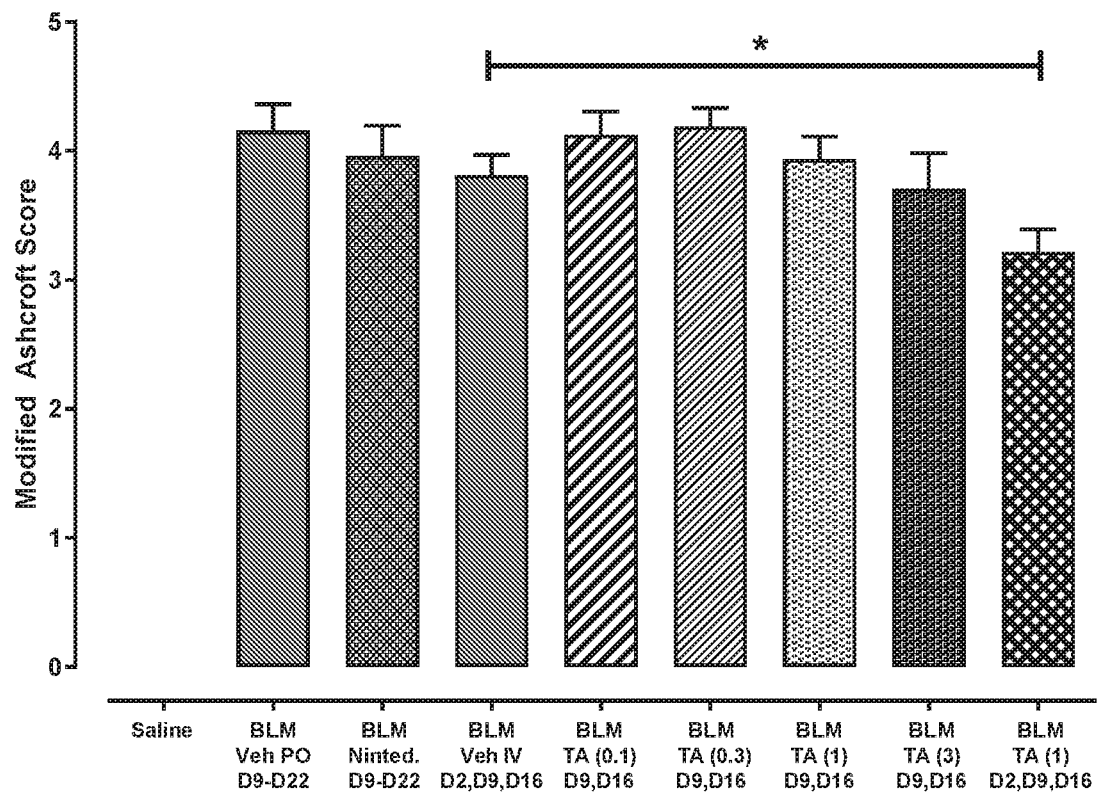
FIG. 4 shows Histological Fibrosis (Ashcroft) Scores. Mean data from all fields scored within each group are shown (+SEM): "Veh" indicates treatment with Vehicle, "Ninted." indicates treatment with Nintedanib, and "TA" indicates treatment with Test Article. Test Article dose is indicated in parentheses. Statistical comparisons were conducted by t-test within PO or IV treatment groups. $*p<0.05$ vs. IV vehicle.

Having noted the high variability in mean Ashcroft Index Scores within groups and also in lung pathology within each individual due to the focal nature of the model, we analyzed Ashcroft scores from all fields scored (4 per animal), which increased the number of observations to 24-32 in BLM-induced groups. Using this comprehensive analysis, treatment with Test Article at 1 mg/kg on Days 2, 9 and 16 significantly reduced lung fibrosis in comparison to vehicle-treated controls (see FIG. 4).

Perivascular/peribronchiolar inflammatory cell infiltrate and type II pneumoycte hyperplasia was absent in all of the sections from Saline-induced non-diseased controls. Perivascular/peribronchiolar inflammatory cell infiltrate was absent in all but 2 animals receiving Vehicle PO and 1 animal receiving Vehicle IV, in which minimal to mild (score=1-2) infiltrate was observed. No statistical evaluation was done on this endpoint since BLM had little effect. Similarly, minimal (score=1) type II pneumocyte hyperplasia was observed in some sections from BLM-induced animals, but was not affected by treatment.

Figure 5:
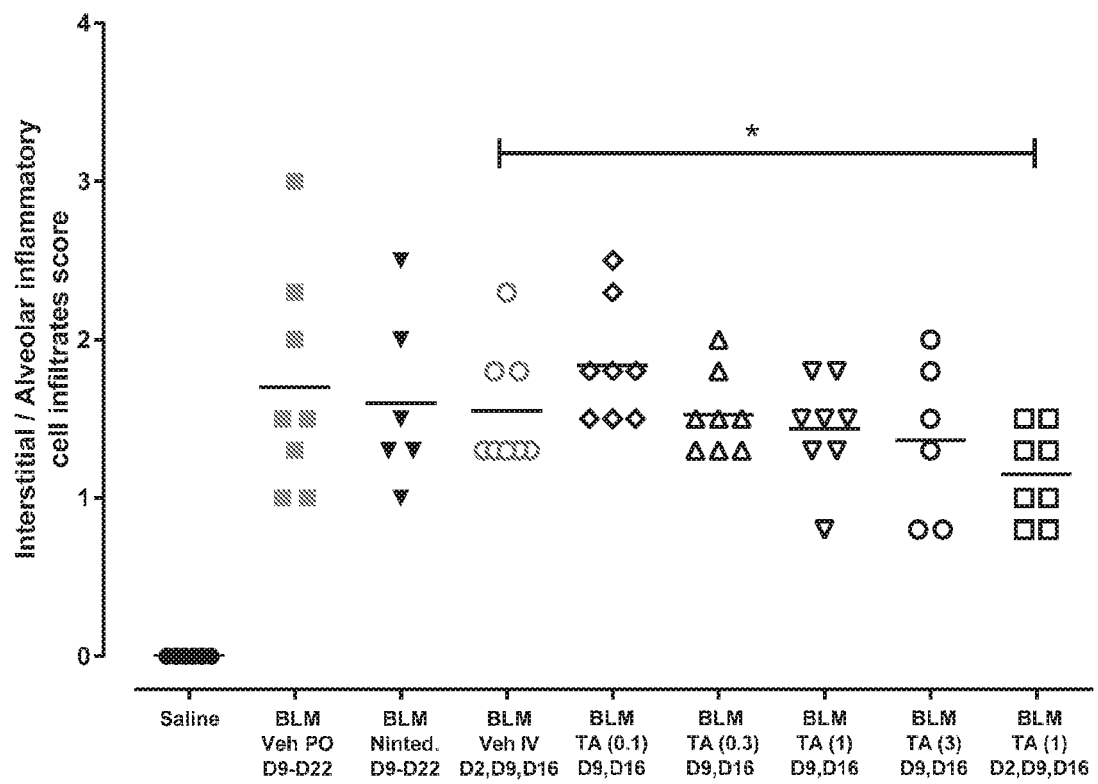
FIG. 5 shows Interstitial/Alveolar Inflammatory Cell Infiltrates. Individual mean scores within each group are shown: "Veh" indicates treatment with Vehicle, "Ninted." indicates treatment with Nintedanib, and "TA" indicates treatment with Test Article. Test Article dose is indicated in parentheses. Statistical comparisons were conducted by t-test within PO or IV treatment groups. $*p<0.05$ vs. IV vehicle.

Interstitial/alveolar inflammatory cell infiltrate was absent (score=0) in all sections from Saline-induced lungs. In animals induced with BLM, minimal to moderate (score=1-3) interstitial inflammatory cell infiltrate was observed as shown in FIG. 5. Oral treatment with Nintedanib had no effect on interstitial inflammatory cell infiltrate whereas treatment with Test Article at 1 mg/kg on Days 2, 9, and 16 significantly reduced interstitial inflammatory cell infiltrate in comparison to vehicle-treated controls.

Summary

The overall objective of this study was to determine whether the Test Article reduces the extent of respiratory impairment and/or lung fibrosis in a rat model of bleomycin-induced the lung fibrosis. Lung fibrosis was induced by five oropharyngeal instillations of BLM into the lungs of male Sprague Dawley rats during the first 7 days of the experiment Animals receiving Saline instead of BLM were used as control. The induction of inflammation and fibrotic processes in the lung was demonstrated by histological observation of minimal to moderate interstitial/alveolar inflammatory cell infiltrate and Ashcroft fibrosis scores of 2 to 6 in BLM-induced animals Respiratory measures conducted at Day 8 and Day 15 showed significant changes induced by BLM, persisting in animals that received Vehicles, supporting the hypothesis that gas exchange was impaired, likely by inflammation-associated lung edema. Taken together, these data support the conclusion that inflammation and fibrosis were significantly induced in the lungs, with pathological changes present by at least Day 8.

Treatment with Test Article resulted in a striking resolution of respiratory measures conducted on Day 15. Whereas Vehicle-treated animals had stable values between Day 8 and Day 15, Test Article treatment elicited significant changes in all measures towards (and in many cases matching) the measures obtained in Saline-induced non-diseased controls. The activity of Test Article was observed across dose levels (0.1-3 mg/kg). Treatment of Test Article also resulted in a significant decrease (improvement) in Ashcroft score and interstitial inflammation measured on Day 22 in rats that received 1 mg/kg on Days 2, 9 and 16.

Treatment with Nintedanib (50 mg/kg/dose) starting on Day 9 showed no significant effects in this experiment. The lack of effect is likely a reflection of the high hurdle to ameliorating fibrosis under the conditions of this experiment. Induction in the model is known to vary between and within experimental replicates and Nintedanib has been shown to improve fibrosis at a similar dose level in the literature (see Chaudhary et al., The European Respiratory Journal: Official Journal of the European Society for Clinical Respiratory Physiology. 29:976-985, 2007).

Conclusions.

Overall, Test Article showed strong disease-ameliorating activity in the BLM-induced lung inflammation and fibrosis model when dosed therapeutically, that is beginning 2 or 9 days after starting BLM instillation Respiratory measures were the most sensitive endpoint in this study, showing significant effects at all doses and paradigms tested (0.1-3 mg/kg administered weekly). In contrast, but not surprisingly given the likely reliance of respiratory measures on immune-driven interstitial edema in this model, the anti-fibrotic, Nintedanib had no effect.

Therapeutic intervention with Test Article also improved (decreased) histological fibrosis and interstitial immune cell infiltration measured on Day 22, further substantiating the immune modulatory potential and demonstrating the anti-fibrotic potential of the molecule. The Test Article outperformed Nintedanib, which had no significant effects in the study, but is marketed for the treatment of idiopathic pulmonary fibrosis. These results suggest that HRS Polypeptides such as the Test Article display significant therapeutic utility for the treatment of lung inflammation and fibrosis in a broad range of ILDs.

Example 3

Evaluation of HRS Polypeptide-Fc Fusion Protein in Combination with Nintedanib or Pirfenidone for the Treatment of Bleomycin-Induced Interstitial Lung Disease Studies were performed to determine if an exemplary HRS-Fc fusion protein ($HRS^{FC1}$) in combination with Nintedanib or Pirfenidone, which are marketed for treatment of IPF, reduces respiratory impairment and/or lung fibrosis in a rat model of bleomycin-induced the lung fibrosis. The effects of the HRS-Fc fusion protein on the inflammatory and fibrotic processes were determined by measuring respiratory measures, histological fibrosis and inflammation scores, and lung collagen content. The circulating levels of $HRS^{FC1}$ were also determined.

Protocol and Methods.

In the same laboratory using methods identical to those described in Example 2, lung inflammation and fibrosis were induced in male Sprague Dawley (Crl:CD(SD)) rats by oropharyngeal administration of bleomycin (BLM) at a dose level of approximately 1 mg/kg in 100 µl for up to 7 consecutive days. PBS or BLM was administered under isoflurane anesthesia. Excess rats were induced with BLM and used to replace any animals with excessive body weight loss. The first day of BLM administration was defined as Day 1. Rats were sacrificed at Day 17 or 22 using a terminal bleed after carbon dioxide administration Animals were treated as shown in Table E5-A and E5-B below.

TABLE E5-A

| Day | | −1 | 1 | 2 | 3 | 4 | 5 | 6 | 7 | 8 | 9 | 10 | 11 | 12 | 13 |
|---|---|---|---|---|---|---|---|---|---|---|---|---|---|---|---|
| 1 | disease control, procedures | S | ↓sal IT | ↓ | ↓ | | ↓ | ↓ | | WBP | | S | | | |
| 2-7 | induction, procedures | S | ↓ | ↓ | ↓ | | ↓ | ↓ | | WBP | | S | | | |
| 2 | Vehicle PO (TID) + Vehicle IV | | | | | | | | | | VVV V | VVV | VVV | VVV | VVV |
| 3 | Nintedanib PO + Vehicle PO + Vehicle IV | | | | | | | | | | VNV V | VNV | VNV | VNV | VNV |
| 4 | Pirfenidone PO (TID) + Vehicle IV | | | | | | | | | | PPP V | PPP | PPP | PPP | PPP |
| 5 | Vehicle PO + $HRS^{FC1}$ 3 mg/kg IV | | | | | | | | | | VVV ATYR | VVV | VVV | VVV | VVV |
| 6 | Nintedanib PO + Vehicle PO + $HRS^{FC1}$ 3 mg/kg IV | | | | | | | | | | VNV ATYR | VNV | VNV | VNV | VNV |
| 7 | Pirfenidone PO (TID) + $HRS^{FC1}$ 3 mg/kg IV | | | | | | | | | | PPP ATYR | PPP | PPP | PPP | PPP |

TABLE E5-B

| Day | | 14 | 15 | 16 | 17 | 18 | 19 | 20 |
|---|---|---|---|---|---|---|---|---|
| 1 | disease control, procedures | | WBP | | X (A) | | | |
| 2-7 | induction, procedures | | WBP | | X (A) | | | |
| 2 | Vehicle PO (TID) + Vehicle IV | VVV | VVV | VVV V (B) | VVV | VVV | VVV | VVV |
| 3 | Nintedanib PO + Vehicle PO + Vehicle IV | VNV | VNV | VNV V (B) | VNV | VNV | VNV | VNV |
| 4 | Pirfenidone PO (TID) + Vehicle IV | PPP | PPP | PPP V (B) | PPP | PPP | PPP | PPP |
| 5 | Vehicle PO + $HRS^{FC1}$ 3 mg/kg IV | VVV | VVV | VVV ATYR (B) | VVV | VVV | VVV | VVV |
| 6 | Nintedanib PO + Vehicle PO + $HRS^{FC1}$ 3 mg/kg IV | VNV | VNV | VNV ATYR (B) | VNV | VNV | VNV | VNV |
| 7 | Pirfenidone PO (TID) + $HRS^{FC1}$ 3 mg/kg IV | PPP | PPP | PPP ATYR (B) | PPP | PPP | PPP | PPP |
| | | 21 | 22 | 23 | 24 | 25 | 26 | 27 | 28 |
| 1 | | | WBP | S | | | | | WBP, X (B) |
| 2-7 | | | WBP | S | | | | | WBP, X (B) |
| 2 | | VVV | VVV | VVV V | VVV | VVV | VVV | VV | |
| 3 | | VNV | VNV | VNV V | VNV | VNV | VNV | VNV | |
| 4 | | PPP | PPP | PPP V | PPP | PPP | PPP | PPP | |
| 5 | | VVV | VVV | VVV ATYR | VVV | VVV | VVV | VVV | |
| 6 | | VNV | VNV | VNV ATYR | VNV | VNV | VNV | VNV | |
| 7 | | PPP | PPP | PPP ATYR | PPP | PPP | PPP | PPP | | n=12/group male SD rats in two cohorts, A (n=4, term Day 16) and B (n=8, term Day 30); 3×/week BWs and daily survival
↓ Bleomycin to lung
V—vehicle—super convenient if we can use the same vehicle for nintedanib and pirfenidone
N—nintendanib, 60 mg/kg/day PO
P—pirfenidone, 100 mg/kg/does×3 doses/day PO
ATYR—HRS$^{FC1}$ 3 mg/kg IV
WBP—whole body plethsmography
S—serum
X(A) takedown—serum, lung wet and dry weight, lung histology (1 lobe), tissues in RNALater: lung, quadriceps
X(B) takedown—serum, lung histology, lung collage content, tissues in RNALater: lung quadriceps Due to large body weight loss in animals receiving BLM, oropharyngeal administrations were skipped on Days 4 and 7 Animals receiving PBS on Days 1, 2, 3, 5 and 6 served as non-diseased controls (group 1) Animals receiving BLM oropharangeally on Days 1, 2, 3, 5 and 6 received either oral vehicle (0.5% CMC and 0.5% Tween-80) 3 times daily plus IV vehicle (20 mM His, 125 mM NaCl, 10 mM Methionine, 3% Sucrose, 0.02% PS20, pH 6.9) once weekly (group 2), oral Nintedanib (60 mg/kg) once daily at midday plus oral vehicle twice daily in the morning and evening plus IV vehicle once weekly (group 3); oral Pirfenidone (70 mg/kg per dose) three times daily plus IV vehicle once weekly (group 4), oral vehicle three times daily plus Test Article (HRS$^{FC1}$; 3 mg/kg; Lot #H-Fcv3-N4-1005) once weekly (group 5), oral Nintedanib once daily at midday plus oral vehicle twice daily in the morning and evening plus IV Test Article once weekly (group 6), or oral Pirfenidone three times daily plus IV Test Article once weekly (group 4). All treatments commenced on Day 9.

In-life, body weights were measured and clinical observations were conducted daily. On Days 8, 15 and 21, animals were removed from their home cages and placed individually into whole body plethysmography chambers. After a 20-minute acclimatization phase, respiratory parameters were recorded for 10 minutes. Pre-study and on Days 10 and Day 17, whole blood was obtained from the tail vein and processed to serum for measurement of HRS$^{FC1}$.

At termination on either Day 17 (n=4) or Day 22 (n=8), rats were sacrificed using carbon dioxide and exsanguination via heart puncture one day after the last oral dosing (non-diseased controls, nintedanib and oral vehicle groups) or 6 days after the last IV administration of Test Article.

The five lung lobes were collected and weighed. On Day 17, the right accessory lobe was retained and desiccated to obtain dry weight. The remaining right lung lobes were inflated and fixed in 10% neutral buffered formalin and embedded in paraffin for histological analysis. An approximately 50 mg piece of the left lung lobe was snap frozen and stored at −80° C. for potential RNA analysis. The remainder of the lobe was also snap frozen until analyzed for collagen content.

Sections for histology were stained using picrosirius red and were scored in a blinded fashion (1 score for each of the 3-4 lobes) by a veterinary pathologist using a modified Ashcroft score (Hubner et al., 2008). Hydroxyproline content was determined in the left lung lobe using a mass spectrometry method.

Serum samples from animals treated with HRS$^{FC1}$ were used to determine levels of the protein in systemic circulation using standard sandwich ELISA techniques with antibodies that capture the HRS moiety and detect the Fc portion of the fusion protein.

All statistical analyses were performed using GraphPad Prism (GraphPad Software, San Diego, Calif.). Groups were compared using the one-way ANOVA test (histology, lung weights, collagen content) or two-way repeated measures ANOVA test (pharmacokinetics), followed, when appropriate by a post-hoc Dunnett test.

Results—Survival.

All animals that initiated treatments on Day 9 survived to scheduled necropsy.

Results—Body Weights.

Administration of BLM in the lungs resulted in a decrease of body weight of the rats versus non-diseased controls throughout the experiment which is a characteristic of this model. None of the groups treated with Nintedanib, Pirfenidone or Test Article alone or in combination had body weight curves that significantly differed from their respective controls.

Results—Respiratory Measurements.

Respiratory measurements were conducted on Day 8 and showed a clear impairment induced BLM (Table E6).

TABLE E6

Respiratory Measurements

| | Disease | Vehicle IV (BLM) | | | Test Article (3 mg/kg) (BLM) | | |
|---|---|---|---|---|---|---|---|
| | Control | Veh PO | Ninte. PO | Pirf. PO | Veh PO | Ninte. PO | Pirf. PO |
| DAY 8 | | | | | | | |
| Expiratory Time | 0.263 | 0.158 | 0.151 | 0.153 | 0.146 | 0.148 | 0.148 |
| | (0.016) | (0.013) | (0.012) | (0.014) | (0.009) | (0.011) | (0.011) |
| Inspiratory Time | 0.180 | 0.113 | 0.115 | 0.114 | 0.117 | 0.117 | 0.113 |
| | (0.014) | (0.006) | (0.007) | (0.006) | (0.008) | (0.007) | (0.006) |
| Peak Expiratory Flow | 10.4 | 19.1 | 18.4 | 19.5 | 19.7 | 22.6 | 18.0 |
| | (1.2) | (2.0) | (1.7) | (2.0) | (1.6) | (2.4) | (1.7) |
| Peak Inspiratory Flow | 13.5 | 18.3 | 17.2 | 17.5 | 18.0 | 19.8 | 16.9 |
| | (1.7) | (1.8) | (1.5) | (1.5) | (1.6) | (2.0) | (1.7) |

TABLE E6-continued

Respiratory Measurements

|  | Disease Control | BLM | | | | | |
|---|---|---|---|---|---|---|---|
|  |  | Vehicle IV | | | Test Article (3 mg/kg) | | |
|  |  | Veh PO | Ninte. PO | Pirf. PO | Veh PO | Ninte. PO | Pirf. PO |
| Respiratory Minute Volume | 218.1 (28.1) | 313.1 (32.9) | 304.5 (28.7) | 314.8 (29.6) | 310.9 (26.8) | 341.0 (35.8) | 304.5 (28.9) |
| Respiratory Rate | 170.2 (16.1) | 244.6 (15.7) | 249.0 (16.0) | 247.6 (16.3) | 247.8 (14.1) | 251.3 (16.1) | 250.9 (15.5) |
| Tidal Volume | 1.32 (0.059) | 1.23 (0.060) | 1.19 (0.066) | 1.24 (0.051) | 1.22 (0.049) | 1.31 (0.071) | 1.19 (0.065) |

DAY 15

| | | | | | | | |
|---|---|---|---|---|---|---|---|
| Expiratory Time | 0.288 (0.014) | 0.201 (0.019) | 0.205 (0.016) | 0.193 (0.014) | 0.179 (0.016) | 0.192 (0.018) | 0.191 (0.010) |
| Inspiratory Time | 0.183 (0.012) | 0.138 (0.009) | 0.122 (0.007) | 0.135 (0.009) | 0.126 (0.009) | 0.129 (0.011) | 0.128 (0.006) |
| Peak Expiratory Flow | 9.5 (0.5) | 14.2 (1.8) | 16.5 (1.3) | 15.0 (1.5) | 17.5 (2.1) | 18.1 (2.3) | 14.2 (1.2) |
| Peak Inspiratory Flow | 13.2 (1.0) | 15.2 (1.7) | 19.0 (1.6) | 15.6 (1.7) | 18.1 (2.0) | 19.1 (1.9) | 15.8 (1.2) |
| Respiratory Minute Volume | 203.4 (14.7) | 262.7 (31.9) | 309.5 (27.5) | 260.2 (26.8) | 309.2 (39.9) | 307.6 (36.9) | 260.1 (20.4) |
| Respiratory Rate | 153.6 (10.5) | 203.1 (19.3) | 223.4 (14.6) | 206.2 (14.5) | 229.1 (19.3) | 220.4 (16.5) | 205.6 (12.0) |
| Tidal Volume | 1.41 (0.03) | 1.27 (0.05) | 1.35 (0.06) | 1.23 (0.06) | 1.30 (0.06) | 1.33 (0.07) | 1.27 (0.05) |

DAY 21

| | | | | | | | |
|---|---|---|---|---|---|---|---|
| Expiratory Time | 0.247 (0.020) | 0.199 (0.027) | 0.231 (0.018) | 0.234 (0.020) | 0.211 (0.019) | 0.210 (0.019) | 0.223 (0.018) |
| Inspiratory Time | 0.145 (0.011) | 0.120 (0.010) | 0.127 (0.006) | 0.148 (0.011) | 0.137 (0.011) | 0.160 (0.017) | 0.135 (0.010) |
| Peak Expiratory Flow | 12.5 (1.2) | 15.4 (1.6) | 13.9 (1.3) | 13.0 (1.1) | 14.6 (2.1) | 14.9 (2.1) | 12.5 (0.9) |
| Peak Inspiratory Flow | 17.3 (1.4) | 20.3 (1.6) | 18.1 (1.2) | 15.8 (1.5) | 17.1 (2.3) | 15.9 (2.5) | 16.5 (1.2) |
| Respiratory Minute Volume | 274.5 (26.4) | 334.5 (36.2) | 286.0 (22.0) | 259.6 (25.2) | 282.4 (44.8) | 264.1 (46.1) | 263.7 (22.2) |
| Respiratory Rate | 199.0 (18.8) | 231.7 (20.3) | 203.7 (12.7) | 186.5 (17.9) | 199.6 (20.8) | 192.9 (23.0) | 199.3 (13.5) |
| Tidal Volume | 1.50 (0.040) | 1.48 (0.052) | 1.44 (0.071) | 1.43 (0.048) | 1.39 (0.065) | 1.33 (0.087) | 1.37 (0.068) |

Data shown are mean ± SEM (in brackets). Significant differences from animals receiving vehicle both PO and IV is shown by bold font (2-way ANOVA followed by Dunnett's post-hoc)

On Day 8, prior to any treatments, significant decreases in expiration and inspiration time were observed, whereas peak expiratory flow and respiratory rate were significantly increased. Tidal volumes, peak inspiratory flow, and respiratory minute volume (RMV) were similar between BLM- and non-induced animals on Day 8 in this experiment.

Respiratory measurements conducted on Day 15 and Day 21 (Table E6) showed declined impairment in BLM-induced vehicle treated groups, suggesting rapid spontaneous resolution, which has been reported in bleomycin models. Treatment with Nintedanib, Pirfenidone or Test Article did not significantly impact BLM-induced alterations in respiratory parameters, in this study—likely because of this rapid spontaneous resolution of disease.

Results—Lung Mass and Collagen Content.

Lung mass (wet weight) obtained at necropsy on Day 17 or Day 22 and collagen content measured on Day 22 were significantly elevated by BLM induction on Days 1, 2, 3, 5 and 6. None of the treatment groups significantly changed lung wet weight or collagen content (data not shown).

Results—Histological Scores.

Slides were read by a veterinary pathologist and each of the 3 lobes evaluated was assigned 4 score types [Ashcroft for fibrosis (scores range from 0 to 8), perivascular/peribronchiolar inflammatory cell infiltrate (scores range from 0 to 5), interstitial/alveolar inflammatory cell infiltrate (scores range from 0 to 5), type II pneumocyte hyperplasia (scores range from 0 to 5)].

Ashcroft scores assigned to PBS-induced animals were uniformly scored 0, while BLM-induced vehicle treated animals had scores ranging from 1 to 5 on the 8-point scale, confirming significant fibrosis had been induced, albeit more moderate that observed in example 2. Intervention with Nintedanib, Pirfenidone or Test Article, alone or in combination had no significant effect on interstitial inflammatory cell infiltrate in comparison to controls receiving PO plus IV vehicles (data not shown).

Interstitial/alveolar inflammatory cell infiltrate was absent (score=0) in all sections from Saline-induced lungs. In animals induced with BLM, minimal to moderate (score=1-3) interstitial inflammatory cell infiltrate was observed. Intervention with Nintedanib, Pirfenidone or Test Article, alone or in combination had no significant effect on interstitial inflammatory cell infiltrate in comparison to controls receiving PO plus IV vehicles (data not shown).

Results: PK.

Figure 6:
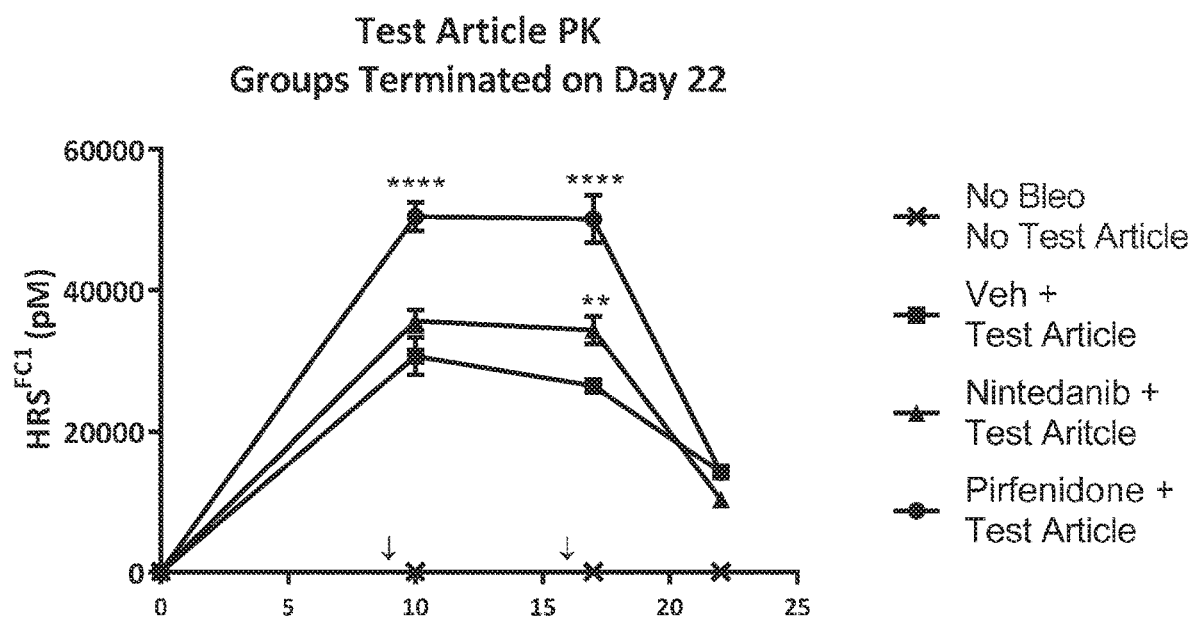
FIG. 6 shows mean serum $HRS^{FC1}$ levels in pMol (+SEM): for each group terminated on Day 22 of the study: Statistical comparisons were conducted by t-test $p<0.01$, $*p<0.001$, $****p<0.0005$ between vehicle (Veh) in combination with the Test Article, compared to the groups treated with Nintedanib in combination with the Test Article, or Pirfenidone in combination with the Test Article respectively.

Serum levels of $HRS^{FC1}$ were detectable on Days 10, 17 and 22 in animals receiving Test Article $HRS^{FC1}$ on Days 9 and 16. As expected, levels of $HRS^{FC1}$ decreased between Days 17 and 22, demonstrating clearance of the Test Article over time. $HRS^{FC1}$ was also measurable in animals that were also receiving Nintedanib or Pirfenidone. Surprisingly, however, the levels of $HRS^{FC1}$, measured ~24 hours post dose were significantly increased by the concomitant treatment with the small molecules marketed for the treatment of IPF in this rodent model of lung inflammation and fibrosis induced by oropharyngeal administration of BLM (FIG. 6).

Summary

The overall objective of this study was to determine whether the Test Article reduces the extent of respiratory impairment and/or lung fibrosis in a rat model of bleomycin-induced the lung fibrosis. Lung fibrosis was induced by five oropharyngeal instillations of BLM into the lungs of male Sprague Dawley rats during the first 7 days of the experiment Animals receiving Saline instead of BLM were used as control. The induction of inflammation and fibrotic processes in the lung was demonstrated by histological observation of minimal to moderate interstitial/alveolar inflammatory cell infiltrate and Ashcroft fibrosis scores of 1 to 5 in BLM-induced animals Respiratory measures conducted at Day 8 showed significant changes induced by BLM, although these declined in animals that received Vehicles. Taken together, these data support the conclusion that inflammation was transiently induced in the lungs, with pathological changes present by at least Day 8 and that moderate inflammation and fibrosis persisted until Day 22.

Intervention beginning on Day 9 with Nintedanib, Pirfenidone or Test Article was without significant effect in this experiment, in contrast to the experiment summarized in Example 2, which was likely related to the rapid spontaneous resolution and transient nature of the response in this study.

Conclusions.

Overall, none of the interventions (Nintedanib, Pirfenidone or Test Article) tested were effective in ameliorating disease measures in this experiment, alone or in combination. These results are potentially secondary to the milder phenotype elicited in this experimental cohort, since both Nintedanib and Pirfenidone have been reported as efficacious in this model.

Although the Test Article and small molecules did not affect model efficacy endpoints, the $HRS^{FC1}$ data clearly demonstrate that both Nintedanib and Pirfenidone interact with pharmacokinetic characteristics of the Test Article, which is an engineered protein.

To confirm the observation that Nintedanib and Pirfenidone altered the PK of $HRS^{FC1}$, we evaluated a second study conducted in the same laboratory using methods identical to those described in Example 3. Surprisingly, concomitant administration of both Nintedanib and Pirfenidone increased the amount of $HRS^{FC1}$ measured in serum 24 hours after IV injection (data not shown) confirming the initial observation. In both cases, the effect is more marked after the $2^{nd}$ injection. This novel and unexpected observation of altered PK of $HRS^{FC1}$, an engineered HRS polypeptide, in the presence of two small molecule therapies for IPF with distinct mechanisms of action, suggests that these molecules interact either directly or on shared pathways in the context of inflammatory and fibrotic diseases.

The invention claimed is:

1. A method of increasing serum concentration of a histidyl-tRNA synthetase (HRS)-Fc fusion polypeptide in a subject, comprising administering to the subject the HRS-Fc fusion polypeptide in combination with pirfenidone, wherein the HRS-Fc fusion polypeptide comprises, consists, or consists essentially of SEQ ID NO: 157.

2. The method of claim 1, wherein the pirfenidone increases the serum concentration of the HRS-Fc fusion polypeptide in the subject by at least about 10, 20, 30, 40, 50, 60, 70, 80, 90, 100, 150, or 200% or more relative to the HRS-Fc fusion polypeptide alone.

3. The method of claim 1, wherein the pirfenidone is administered at an individual dosage unit that ranges from about 50 to about 1000 mg, or an individual dosage unit of about no more than about, or at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg, optionally in 1, 2, or 3 capsules for oral dosing.

4. The method of claim 1, wherein the pirfenidone is administered at a daily dosage unit that ranges from about 100 to about 4000 mg/day, or a daily dosage unit of about, no more than about, or at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 10, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1200, 1300, 1400, 1500, 1600, 1700, 1800, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day, optionally in about 1, 2, 3, 4, 5, 6, 7, 8, 9 capsules for oral dosing.

5. The method of claim 1, wherein the pirfenidone is administered at an individual dosage unit of about 800 mg (e.g., 801 mg), optionally as three approximately 267 mg capsules for oral dosing, taken as three capsules per individual dosage.

6. The method of claim 1, wherein the pirfenidone is administered at daily dosage unit of about 2400 mg/day (e.g., 2403 mg/day), optionally as nine approximately 267 mg capsules for oral dosing three times daily, taken as three capsules per individual dosage.

7. The method of claim 1, wherein the subject has lung inflammation.

8. The method of claim 7, which improves one or more of the clinical symptoms or parameters of the lung inflammation in the subject in need thereof.

9. The method of claim 8, wherein the one or more clinical symptoms or parameters are selected from one or more of lung fibrosis, inflammatory cell infiltrates in the lung, respiratory function, and body weight.

10. The method of claim 7, wherein the subject has or is risk for having an interstitial lung disease (ILD).

11. The method of claim 10, wherein the ILD is idiopathic or associated with a connective tissue disease, an autoimmune disease, exposure to inhaled substances or drug(s), an infection, or a malignancy.

12. The method of claim 11, wherein the ILD is selected from or is associated with one or more of idiopathic interstitial pneumonia, idiopathic pulmonary fibrosis, sarcoidosis, Hammann-Rich syndrome, Antisynthetase syndrome, idiopathic eosinophilic pneumonia, alveolar hemorrhage syndrome, pulmonary alveolar proteinosis, asbestosis, silicosis, berylliosis, rheumatoid arthritis, lupus erythematosus, chronic graft vs host disease with pulmonary involvement, sclerosis (systemic) or scleroderma, polymyositis, dermatomyositis, chronic pulmonary disease, asthma, bronchitis (respiratory bronchitis), pneumonia, hypersensitivity pneumonitis, chronic hypersensitivity pneumonia, respiratory distress syndrome, Still's disease, acute lung injury, microscopic polyangitis, pulmonary edema, pulmonary Langerhans cell histiocytosis, acute inhalational exposures, drug-induced lung disease, desquamative interstitial pneumonia, and/or cystic fibrosis.

\* \* \* \* \*